US007262280B1

(12) United States Patent
Stormann et al.

(10) Patent No.: US 7,262,280 B1
(45) Date of Patent: Aug. 28, 2007

(54) G-PROTEIN FUSION RECEPTORS AND CONSTRUCTS ENCODING SAME

(75) Inventors: Thomas M. Stormann, Salt Lake City, UT (US); Lance G. Hammerland, Salt Lake City, UT (US); Laura L. Storjohann, Salt Lake City, UT (US); James G. Busby, Simi Valley, CA (US); James E. Garrett, Salt Lake City, UT (US); Rachel T. Simin, Durham, NC (US)

(73) Assignee: NPS Pharmaceuticals, Inc., Salt Lake City, UT (US)

( * ) Notice: Subject to any disclaimer, the term of this patent is extended or adjusted under 35 U.S.C. 154(b) by 0 days.

(21) Appl. No.: 09/679,664

(22) Filed: Oct. 3, 2000

Related U.S. Application Data

(63) Continuation-in-part of application No. PCT/US99/07333, filed on Apr. 2, 1999.

(60) Provisional application No. 60/080,671, filed on Apr. 3, 1998.

(51) Int. Cl.
*C07K 1/00* (2006.01)
*C08H 1/00* (2006.01)
*C07H 21/04* (2006.01)
*C12P 21/06* (2006.01)
*C12N 1/20* (2006.01)

(52) U.S. Cl. ..................... 530/402; 530/350; 536/23.4; 536/23.5; 435/69.1; 435/252.3; 435/320.1; 435/325; 435/471

(58) Field of Classification Search ............... 435/69.1, 435/70.1, 71.1, 71.2, 252.3, 320.1, 325, 471; 536/23.5; 530/350, 402
See application file for complete search history.

(56) References Cited

U.S. PATENT DOCUMENTS

| 4,859,609 A | 8/1989 | Dull et al. .................. 436/501 |
| 5,030,576 A | 7/1991 | Dull et al. .................. 435/69.7 |
| 5,385,831 A | 1/1995 | Mulvihill et al. .......... 435/69.1 |
| 5,688,938 A | 11/1997 | Brown et al. .............. 536/23.5 |
| 5,831,047 A | 11/1998 | Segerson et al. .......... 536/23.5 |
| 5,981,195 A | 11/1999 | Fuller et al. ................. 435/7.1 |
| 6,051,688 A | 4/2000 | Stormann et al. ........... 530/350 |
| 6,077,675 A | 6/2000 | Stormann et al. ............ 435/7.1 |
| 6,084,084 A | 7/2000 | Stormann et al. .......... 536/23.5 |

FOREIGN PATENT DOCUMENTS

| EP | 569 240 A1 | 11/1993 |
| EP | 711 832 A2 | 5/1996 |
| EP | 816 498 A2 | 1/1998 |
| WO | 92/05244 | 4/1992 |
| WO | 92/10583 | 6/1992 |
| WO | 94/29449 | 12/1994 |
| WO | 95/08627 | 3/1995 |
| WO | 95/22609 | 8/1995 |
| WO | 96/06167 | 2/1996 |
| WO | 96/29404 | 9/1996 |
| WO | 97/05252 | 2/1997 |
| WO | 97/37967 | 10/1997 |
| WO | 97/46675 | 12/1997 |
| WO | 97/48724 | 12/1997 |
| WO | 97/48820 | 12/1997 |
| WO | 99/20751 | 4/1999 |
| WO | WO 99/51641 | 10/1999 |
| WO | WO99/51641 | 10/1999 |

OTHER PUBLICATIONS

Rock EP., et al. Vaccine 14:1560-1568, 1996.*
Skolnick et al. Trends in Biotech. 18:34-39, 2000.*
Bork P. Genome Research 10:398-400, 2000.*
Doerks et al. Trends in Genetics 14:248-250, 1998.*
Smith et al. Nature Biotechnology 15:1222-1223, 1997.*
Brenner SE. Trends in Genetics 15:132-133, 1999.*
Bork, et al. Trends in Genetics 12:425-427, 1996.*
Cunningham BV and Wells JA. Science 244:1081-1085, 1989.*
Brown E. M. et al., "Cloning and Characterization of an Extracellular Ca2+ -Sensing Receptor From Bovine Parathyroid," *Nature* 366:575 (1993).
C.J. Marcus-Sekura and M.J.M. Hitchcock, "Guide to Molecular Cloning Techniques," *Methods in Enzymology*, vol. 152 (1987).
Conklin, et al., "Substitution of Three Amino Acids Switches Receptor Specificity of Gqα to That of Gia," *Nature*, 363:274-277 (1993).
Cotecchia et al., "Regions of the $\alpha_1$-Adrenergic Receptor Involved in Coupling to Phosphatidylinositol Hydrolysis and Enhanced Sensitivity of Biological Function," *Proc. Natl. Acad. Sci.*, USA 87-2896-2900 (1990).
Cunningham et al., "Excitatory Amino Acid Receptors: A Gallery of New Targets for Pharmacological Intervention," *Life Sci.* 54:135 (1994).
*Current Protocols in Molecular Biology*, Frederick et al., John Wiley & Sons, Inc. (1995).
Duvoisin et al., "A Novel Metabotropic Glutamate Receptor Expressed in the Retina and Olfactory Bulb," *J. Neurosci.* 15:3075-3083 (1995).
Garrett J.E., et al., "Molecular Cloning and Functional Expression of Human Parathyroid Calcium Receptor cDNAs," *J. Biol. Chem.* 31:12919-12925 (1995).
Hille, B., *Ionic Channels of Excitable Membranes*, pp. 30-34, Sinnauer Associates, Inc. , Sunderland MA (1992).
Jones et al., "$GABA_B$ Receptors Function as a Heteromeric Assembly of the Subunits $GABA_BR1$ and $GABA_BR2$," *Nature* 396-674-679 (1998).

(Continued)

*Primary Examiner*—Robert S. Landsman
(74) *Attorney, Agent, or Firm*—TraskBritt

(57) ABSTRACT

The present invention features G-protein fusion receptors and chimeric $GABA_B$ receptors ($GABA_BRs$), nucleic acid encoding such receptors, and the use of such receptors and nucleic acid. G-protein fusion receptors comprise at least one domain from a CaR, an mGluR, and/or a $GABA_B$ receptor fused directly or through a linker to a guanine nucleotide-binding protein (G-protein). Chimeric $GABA_BRs$ comprise at least one of a $GABA_BR$ extracellular domain, a $GABA_BR$ transmembrane domain, or a $GABA_BR$ intracellular domain and one or more domains from a mGluR subtype 8 (mGluR8) and/or a CaR.

28 Claims, 116 Drawing Sheets

OTHER PUBLICATIONS

Kaupmann et al., "Expression Cloning of GABA Receptors Uncovers Similarity to Metabotropic Glutamate Receptors," *Nature,* 386:239-246 (1997).

Kerr and Ong, "GABA$_B$ Receptors: Targets for Drug Development," *Drug Discovery Today,* 1:371-380 (1996).

Knopfel et al., "Metabotropic Glutamate Receptors: Novel Targets for Drug DEvelopment," *J. Med. Chem.* 38:1417 (1995).

Kobilka et al., "Chimeric α2-β2-Adrenergic Receptors: Delineation of Domains Involved in Effector Coupling And Ligand Binding Specificity," *Science* 240:1310-1316 (1988).

Lechleiter, "Distinct Sequence Elements Control the Specificity of G Protein Activation by Muscarinic Acetylcholine Receptor Subtypes," *EMBO J.* 9:4831-4390 (1990).

Nakanishi, "Metabotropic Glutamate Receptors: Synaptic Transmission, Modulation, and Plasticity," *Neuron* 13:1031 (1994).

Nemeth, "Ca$^{2+}$ Receptor-Dependent Regulation of Cellular Functions," *NIPS* 10:1-5 (1995).

Pin et al., "Domains Involved in the specificity of G Protein Activation in Phospholipasse C-coupled Metabotropic Glutamate Receptors," *EMBO J.* 13:342-348 (1994).

Pin and Duvoisin, "Review: Neurotransmitter Receptors I. The Metabotropic Glutamate Receptors: Structure and Functions," *Neuropharmacology,* 34:1 (1995).

*Remington's Pharmaceutical Sciences,* 18th ed., Mack Publishing Co., Easton PA (1990).

Riccardi D., et al., "Cloning and Functional Expression of a Rat Kidney Extracellular Calcium/Polyvalent Cation-sensing Receptor," *Proc. Nat'l Acad. Sci. USA* 92:131-135 (1995).

Sambrook et al., *Molecular Cloning,* Cold Spring Harbor Laboratory Press, (1989) Chapter 15.

Schoepp et al., "Pharmacological and Functional Characteriestics of Metabotropic Excitatory amino Acid Receptors," *Trends Pharmacol. Sci.* 11:508 (1990).

Schoepp and Conn, "Metabotropic Glutamate Receptors in Brain Function and Pathology," *Trends Pharmacol. Sci.* 14:13 (1993).

Schoepp, "Novel Functions for Subtypes of Metabotropic Glutamate Receptors," *Neurochem, Int.* 24:439 (1994).

Wise and Milligan, "Rescue of Functional Interactions Between the α$_{2a}$-Adrenoreceptors and Acylation-Resistant Forms of G$_{i1}$α by Expressing the Proteins . . . " *J. Biological Chemistry* 39:24673-24678 (1997).

Wess et al., "Identification of a Small Intracellular Region of the Muscarinic m3 Receptor as a Determinant of Selective Coupling to PI Turnover," *FEBS Lett.* 258:133-136 (1989).

Wess et al, "Delineation of Muscarinic Receptor Domains Conferring Selectivity of Coupling to Guanine Nucleotide-Binding Proteins and Second Messengers," *Mol. Pharmacol.* 38:517-523 (1990).

Altschul et al., "Basic Local Alignment Search Tool," *J. Mol. Biol* 215:403-410 (1990).

Bertin et al., "Cellular Signaling by an Agonist-Activated Receptor/Gsα Fusion Protein," *Proc Acad. Sci. USA* 91:8827-831 (1994).

Bertin et al., "Activation of a β2-Adrenergic Receptor/Gsα Fusion Protein Elicites a Desensitization-Resistant cAMP Signal Capable of Inhibiting Proliferation of Two Cancer . . . " *Receptors and Channels* 5:41-51 (1997).

Bittiger et al., "GABA$_B$ Receptor Anatagonists: From Synthesis to Therapeutic Applications," *TIPS* 14:391-394 (1993).

Bowery, "GABA$_B$ Receptor Pharmacology," Annu. Rev. Pharmacol. *Annu. Rev. Pharmacol. Toxicol.* 33:109-147 (1993).

Cotecchia et al., Discrete Amino Acid Sequences of the α1-Adrenergic Receptor Determine the Selectivity of Coupling to Phosphatidylinositol Hydrolysis, *J. Biol. Chem.* 267:1633-1639 (1992).

Ferguson et al., "Cell-Surface Anchoring of Proteins Via Glycosylphosphatidylinositol Structures", *Ann. Rev. Biochem.* 57:285-320 (1988).

Liggett et al., "Sites in the Third Intracellular Loop of the α$_{α2A}$-Adrenergic Receptor Confer Short Term Agonist-Promoted Desensitization", *J. Biol. Chem.* 267:4740-4746 (1992).

Okamoto et al., "Identification of a G$_s$ Activator Region of the β2-Adrenergic Receptor that is Autoregulated via Protein Kinase A-Dependent Phosphorylation", *Cell* 67:723-730 (1991).

Wang et al. "Identification of a Domain in the Angiotensin II Type I Receptor Determining G$_q$ Coupling by the Use of Receptor Chimeras", *J. Biol. Chem.* 270:16677-16682 (1995).

Wong et al., "Chimeric Muscarinic Cholinergic:β-Adrenergic Receptors That Activate G$_s$ in Response to Muscarinic Agonists", *J. Biol. Chem,* 265:6219-6224 (1990).

Database GSP Online!, Jan. 7, 2000 retrieved from EBI, Database Accession No. AAY49131 XP002220593 abstract.

Database GSP Online!, Jan. 7, 2000 retrieved from EBI, Database Accession No. AAY49134 XP002220594 abstract.

Database SWALL Online!, Nov. 1, 1997 retrieved from EBI, Database Accession NO. 014832, XP002220590 abstract.

Database SWALL Online!, Nov. 1. 1997 retrieved from EBI, Database Accession No. 014833, XP002220591 abstract.

Couve Andres et al., "GABAB receptors: A new paradigm in G protein signaling." Molecular and Cellular Neuroscience, 16(4):296-312, 2000.

Jones et al., "Signal transduction by GABA(B) receptor heterodimers." Neuropsychopharmacology, 23(4 supp.):541-549, 2000.

Bourne, H., "How Receptors Talk to Trimeric G Proteins," Current Opinion in Cell Biology, vol. 9 (1997) pp. 134-142.

Gomeza, J., "Coupling of Metabotropic Ghutamate Receptors 2 and 4 to G alpha 15, G alpha 16, and Chimeric G alpha q/i Proteins: Characterization of New Antagonists," Molecular Pharmacology, vol. 50 (1996); pp. 923-930.

Underwood, et al., "Getting It Together. Signal Transduction in G-Protein Coupled Receptors by Association of Receptor Domains," Chemistry & Biology, vol. 4 (Apr. 1997), pp. 239-248.

Database GSP Online!, Jan. 7, 2000 retrieved from EBI, Database Accession No. AAY49131 XP002220593 abstract.

Database GSP Online!, Jan. 7, 2000 retrieved from EBI, Database Accession No. AAY49134 XP002220594 abstract.

Database SWALL Online!, Nov. 1, 1997 retrieved from EBI, Database Accession No. 014832, XP002220590 abstract.

Database SWALL Online!, Nov. 1, 1997 retrieved from EBI, Database Accession No. 014833, XP002220591 abstract.

Couve Andres et al., "GABAB receptors: A new paradigm in G protein signaling." Molecular and Cellular Neuroscience, 16(4): 296-312, 2000.

* cited by examiner

ClustalW Formatted Alignments

```
SEQ ID 1   M A F Y S C C W V L L A L T W H T S A Y G P D Q R
SEQ ID 2   M L L L L L L A P L F L R P P G A G G A Q T P N A
SEQ ID 3   M G P G A P F A R V G W P L P L L V V M A A G V A
SEQ ID 4   M A S P R S S G Q P G P X P P P P P P A R L L L
SEQ ID 5   M V C E G K R S A S C P C F F L L T A K F Y W I L

SEQ ID 1   A Q K K G D I I L G G L F P I H F G V A A K D Q D
SEQ ID 2   T S E G C Q I I H P P W E G G I R Y R G L T R D Q
SEQ ID 3   P V W A S H S P H L P R P H S R V P P H P S S E R
SEQ ID 4   L L L L P L L L P L A P G A W G W A R G A P R P P
SEQ ID 5   T M M Q R T H S Q E Y A H S I R V D G D I I L G G

SEQ ID 1   L K S R P E S V E C I R Y N F R G F R W L Q A M I
SEQ ID 2   V K A I N F L P V D Y E I E Y V C R G E R E V V G
SEQ ID 3   R A V Y I G A L F P M S G G W P G G Q A C Q P A V
SEQ ID 4   P S S P P L S I M G L M P L T K E V A K G S I G R
SEQ ID 5   L F P V H A K G E R G V P C G E L K K E K G I H R

SEQ ID 1   F A I E E I N S S P A L L P N L T L G Y R I F D T
SEQ ID 2   P K V R K C L A N G S W T D M D T P S R C V R I C
SEQ ID 3   E M A L E D V N S R R D I L P D Y E L K L I H H D
SEQ ID 4   G V L P A V E L A I E Q I R N E S L L R P Y F L D
SEQ ID 5   L E A M L Y A I D Q I N K D P D L L S N I T L G V

SEQ ID 1   C N T V S K A L E A T L S F V A Q N K I D S L N L
SEQ ID 2   S K S Y L T L E N G K V F L T G G D L P A L D G A
SEQ ID 3   S K C D P G Q A T K Y L Y E L L Y N D P I K I I L
SEQ ID 4   L R L Y D T E C D N A K G L K A F Y D A I K Y G P
SEQ ID 5   R I L D T C S R D T Y A L E Q S L T F V Q A L I E

SEQ ID 1   D E F C N C S E H I P S T I A V V G A T G S G V S
SEQ ID 2   R V D F R C D P D F H L V G S S R S I C S Q G Q W
SEQ ID 3   M P G C S S V S T L V A E A A R M W N L I V L S Y
SEQ ID 4   N H L M V F G G V C P S V T S I I A E S L Q G W N
SEQ ID 5   K D A S D V K C A N G D P P I F T K P D K I S G V

SEQ ID 1   T A V A N L L G L F Y I P Q V S Y A S S S R L L S
SEQ ID 2   S T P K P H C Q V N R T P H S E R R A V Y I G A L
SEQ ID 3   G S S S P A L S N R Q R F P T F F R T H P S A T L
SEQ ID 4   L V Q L S F A A T T P V L A D K K K Y P Y F F R T
SEQ ID 5   I G A A A S S V S I M V A N I L R L F K I P Q I S
```

Figure 1a

```
SEQ ID 1  N K N Q F K S F L R T I P N D E H Q A T A M A D I
SEQ ID 2  F P M S G G W P G G Q A C Q P A V E M A L E D V N
SEQ ID 3  H N P T R V K L F E K W G W K K I A T I Q Q T T E
SEQ ID 4  V P S D N A V N P A I L K L L K H Y Q W K R V G T
SEQ ID 5  Y A S T A P E L S D N T R Y D F F S R V V P P D S

SEQ ID 1  I E Y F R W N W V G T I A A D D D Y G R P G I E K
SEQ ID 2  S R R D I L P D Y E L K L I H H D S K C D P G Q A
SEQ ID 3  V F T S T L D D L E E R V K E A G I E I T F R Q S
SEQ ID 4  L T Q D V Q R F S E V R N D L T G V L Y G E D I E
SEQ ID 5  Y Q A Q A M V D I V T A L G W N Y V S T L A S E G

SEQ ID 1  F R E E A E E R D I C I D F S E L I S Q Y S D E E
SEQ ID 2  T K Y L Y E L L Y N D P I K I I L M P G C S S V S
SEQ ID 3  F F S D P A V P V K N L K R Q D A R I I V G L F Y
SEQ ID 4  I S D T E S F S N D P C T S V K K L K G N D V R I
SEQ ID 5  N Y G E S G V E A F T Q I S R E I G G V C I A Q S

SEQ ID 1  E I Q H V V E V I Q N S T A K V I V V F S S G P D
SEQ ID 2  T L V A E A A R M W N L I V L S Y G S S S P A L S
SEQ ID 3  E T E A R K V F C E V Y K E R L F G K K Y V W F L
SEQ ID 4  I L G Q F D Q N M A A K V F C C A Y E E N M Y G S
SEQ ID 5  Q K I P R E P R P G E F E K I I K R L L E T P N A

SEQ ID 1  L E P L I K E I V R R N I T G K I W L A S E A W A
SEQ ID 2  N R Q R F P T F F R T H P S A T L H N P T R V K L
SEQ ID 3  I G W Y A D N W F K I Y D P S I N C T V D E M T E
SEQ ID 4  K Y Q W I I P G W Y E P S W W E Q V H T E A N S S
SEQ ID 5  R A V I M F A N E D D I R R I L E A A K K L N Q S

SEQ ID 1  S S S L I A M P Q Y F H V V G G T I G F A L K A G
SEQ ID 2  F E K W G W K K I A T I Q Q T T E V F T S T L D D
SEQ ID 3  A V E G H I T T E I V M L N P A N T R S I S N M T
SEQ ID 4  R C L R K N L L A A M E G Y I G V D F E P L S S K
SEQ ID 5  G H F L W I G S D S W G S K I A P V Y Q Q E E I A

SEQ ID 1  Q I P G F R E F L K K V H P R K S V H N G F A K E
SEQ ID 2  L E E R V K E A G I E I T F R Q S F F S D P A V P
SEQ ID 3  S Q E F V E K L T K R L K R H P E E T G G F Q E A
SEQ ID 4  Q I K T I S G K T P Q Q Y E R E Y N N K R S G V G
SEQ ID 5  E G A V T I L P K R A S I D G F D R Y F R S R T L
```

Figure 1b

```
SEQ ID 1   F W E E T F N C H L Q E G A K G P L P V D T F L R
SEQ ID 2   V K N L K R Q D A R I I V G L F Y E T B A R K V F
SEQ ID 3   P L A Y D A I W A L A L A L N K T S G G G G R S G
SEQ ID 4   P S K F H G Y A Y D G I W V I A K T L Q R A M E T
SEQ ID 5   A N N R R N V W F A E F W E E N F G C K L G S H G

SEQ ID 1   G H E E S G D R F S N S S T A F R P L C T G D E N
SEQ ID 2   C E V Y K E R L F G K K Y V W F L I G W Y A D N W
SEQ ID 3   V R L E D F N Y N N Q T I T D Q I Y R A M N S S S
SEQ ID 4   L H A S S R H Q R I Q D F N Y T D H T L G R I I L
SEQ ID 5   K R N S H I K K C T G L E R I A R D S S Y E Q E G

SEQ ID 1   I S S V E T P Y I D Y T H L R I S Y N V Y L A V Y
SEQ ID 2   F K I Y D P S I N C T V D E M T E A V E G H I T T
SEQ ID 3   F E G V S G H V V F D A S G S R M A W T L I E Q L
SEQ ID 4   N A M N E T N F F G V T G Q V V F R N G E R M G T
SEQ ID 5   K V Q F V I D A V Y S M A Y A L H N M H K D L C P

SEQ ID 1   S I A H A L Q D I Y T C L P G R G L F T N G S C A
SEQ ID 2   E I V M L N P A N T R S I S N M T S Q E F V E K L
SEQ ID 3   Q G G S Y K K I G Y Y D S T K D D L S W S K T D K
SEQ ID 4   I K F T Q F Q D S R E V K V G E Y N A V A D T L E
SEQ ID 5   G Y I G L C P R M S T I D G K E L L G Y I R A V N

SEQ ID 1   D I K K V E A W Q V L K H L R H L N F T N N M G E
SEQ ID 2   T K R L K R H P E E T G G F Q E A P L A Y D A I W
SEQ ID 3   W I G G S P P A D Q T L V I K T F R F L S Q K
SEQ ID 4   I I N D T I R F Q G S E P P K D K T I I L E Q L R
SEQ ID 5   P N G S A G T P V T F N E N G D A P G R Y D I F Q

SEQ ID 1   Q V T F D E C G D L V G N Y S I I N W H L S P E D
SEQ ID 2   A L A L A L N K T S G G G G R S G V R L E D F N Y
SEQ ID 3
SEQ ID 4   K I S L P
SEQ ID 5   Y Q I T N K S T E Y K V I G H W T N Q L H L K V E

SEQ ID 1   G S I V F K E V G Y Y N V Y A K K G E R L F I N E
SEQ ID 2   N N Q T I T D Q I Y R A M N S S S F E G V S G H V
SEQ ID 3
SEQ ID 4
SEQ ID 5   D M Q W A H R E H T H P A S V C S L P C K P G E R
```

Figure 1c

```
SEQ ID 1  E K I L W S G F S R E V P F S N C S R D C L A G T
SEQ ID 2  V F D A S G S R M A W T L I E Q L Q G G S Y K K I
SEQ ID 3
SEQ ID 4
SEQ ID 5  K K T V K G V P C C W H C E R C E G Y N Y Q V D E

SEQ ID 1  R K G I I E G E P T C C F E C V E C P D G E Y S D
SEQ ID 2  G Y Y D S T K D D L S W S K T D K W I G G S P P A
SEQ ID 3
SEQ ID 4
SEQ ID 5  L S C E L C P L D Q R P N M N R T G C Q L I P I I

SEQ ID 1  E T D A S A C N K C P D D F W S N E N H T S C I A
SEQ ID 2  D Q T L V I K T F R F L S Q K
SEQ ID 3
SEQ ID 4
SEQ ID 5  K L E W H S P W

SEQ ID 1  K E I E F L S W T E P F
SEQ ID 2
SEQ ID 3
SEQ ID 4
SEQ ID 5
```

Figure 1d

```
SEQ ID 6   G I A L T L F A V L G I F L T A F V L G V F I K F R N T P I
SEQ ID 7   L F I S V S V L S S L G I V L A V V C L S F N I Y N S H V R
SEQ ID 8   L F I S V S V L S S L G I V L A V V C L S F N I Y N S H V R
SEQ ID 9   L Y S I L S A L T I L G M I M A S A F L F F N I K N R N Q K
SEQ ID 10  A V V P V F V A I L G I I A T T F V I V T F V R Y N D T P I

SEQ ID 6   V K A T N R E L S Y L L L F S L L C C F S S S L F F I G E P
SEQ ID 7   Y I Q N S Q P N L N N L T A V G C S L A L A A V F P L G L D
SEQ ID 8   Y I Q N S Q P N L N N L T A V G C S L A L A A V F P L G L D
SEQ ID 9   L I K M S S P Y M N N L I I L G G M L S Y A S I F L F G L D
SEQ ID 10  V R A S G R E L S Y V L L T G I F L C Y S I T F L M I A A P

SEQ ID 6   Q Q W T C R L R Q P A F G I S F V L C I S C I L V K T N R V
SEQ ID 7   G Y H I G R N Q F P F V C Q A R L W L L G L G F S L G Y G S
SEQ ID 8   G Y H I G R N Q F P F V C Q A R L W L L G L G F S L G Y G S
SEQ ID 9   G S F V S E K T F E T L C T V R T W I L T V G Y T T A F G A
SEQ ID 10  D T I I C S R R V F L G L G M C F S Y A A L L T K T N R I

SEQ ID 6   L L V F E A K I P T S F H R K W W G L N L Q F L L V F L C T
SEQ ID 7   M F T K I W W V H T V F T K K E E K K E W R K T L E P W K L
SEQ ID 8   M F T K I W W V H T V F T K K E E K K E W R K T L E P W K L
SEQ ID 9   M F A K T W R V H A I F K N V K M K K K I I K Q Q K L L V I
SEQ ID 10  H R I F E Q G K K S V T A P K F I S P A S Q L V I T F S L I

SEQ ID 6   F M Q I V I C V I W L Y T A P P S S Y R N Q E L E Q E I I F
SEQ ID 7   Y A T V G L L V G M D V L T L A I W Q I V D P L H R T I E T
SEQ ID 8   Y A T V G L L V G M D V L T L A I W Q I V D P L H R T I E T
SEQ ID 9   V G G M L L L D L C I L I C W Q A V D P L R R T V E K Y S M
SEQ ID 10  S V Q L L G V F V W F V V Q P P H I I I Q Y G E Q R T L Q P

SEQ ID 6   I T C H E G S L M A L G F L I G Y T C L L A A I C F F F A F
SEQ ID 7   F A K E E P K E D I Q V S I L P Q L E H C S S R K M N T W L
SEQ ID 8   F A K E E P K E D I Q V S I L P Q L E H C S S R K M N T W L
SEQ ID 9   E P Q P A G R D I S I R P L L E H C E N T H M T I W L G I V
SEQ ID 10  E K A R G V L K C D I S D L S L I C S L G Y S I L L M V T C

SEQ ID 6   K S R K L P E N F N E A K F I T F S M L I F F I V W I S F I
SEQ ID 7   G I F Y G Y K G L L L L L G I F L A Y E T K S V S T E K I N
SEQ ID 8   G I F Y G Y K G L L L L L G I F L A Y E T K S V S T E K I N
SEQ ID 9   Y A Y K G L L M L F G C F L A W E T R N V S I P A L N D S K
SEQ ID 10  T V Y A I K T R G V P E T F N E A K P I G F T M Y T T C I I
```

Figure 2a

```
SEQ ID 6   P A Y A S T Y G K F V S A V E V I A I L A A S F G L L A C I
SEQ ID 7   D H R A V G M A I Y N V A V L C L I T A P V T M I L S S Q Q
SEQ ID 8   D H R A V G M A I Y N V A V L C L I T A P V T M I L S S Q Q
SEQ ID 9   Y I G M S V Y N V G I M C I I G A A V S F L T R D Q P N V Q
SEQ ID 10  W L A F I P I F F G T A Q S A E K M Y I Q T T T L T V S M S

SEQ ID 6   F F N K I Y I I L F
SEQ ID 7   D A A F A F A S L A I V F S S Y I T L V V L F V P K M
SEQ ID 8   D A A F A F A S L A I V F S S Y I T L V V L F V P K M
SEQ ID 9   F C I V A L V I I F C S T I T L C L V F V P K L
SEQ ID 10  L S A S V S L G M L Y M P K V Y I I I F
```

Figure 2b

```
SEQ ID 11   K P S R N T I E E V R C S T A A H A F K V A A R A T L R R S
SEQ ID 12   R R L I T R G E W Q S E A Q D T M K T G S S T N N N E E E K
SEQ ID 13   R R L I T R G E W Q S E A Q D T M K T G S S T N N N E E E K
SEQ ID 14   I T L R T N P D A A T Q N R R F Q F T Q N Q K K E D S K T S
SEQ ID 15   H P E Q N V Q K R K R S F K A V V T A A T M Q S K L I Q K G

SEQ ID 11   N V S R K R S S S L G G S T G S T P S S S I S S K S N S E Q
SEQ ID 12   S R L L E K E N R E L E K I I A E K E E R V S E L R H Q L Q
SEQ ID 13   S R L L E K E N R E L E K I I A E K E E R V S E L R H Q L Q
SEQ ID 14   T S V T S V N Q A S T S R L E G L Q S E N H R L R M K I T E
SEQ ID 15   N Q R P N G E V K S E L C E S L E T N S K S S V E F P M V K

SEQ ID 11   P F P Q P E R Q K Q Q Q P L A L T Q Q E Q Q Q Q P L T L P Q
SEQ ID 12   S R Q Q L R S R R H P P T P P E P S G G L P R G P P E P P D
SEQ ID 13   S R Q Q L R S R R H P P T P P E P S G G L P R G P P E P P D
SEQ ID 14   L D K D L E E V T M Q L Q D T P E K T T Y I K Q N H Y Q E L
SEQ ID 15   S G S T S

SEQ ID 11   Q Q R S Q Q Q P R C K Q K V I F G S G T V T F S L S F D E P
SEQ ID 12   R L S C D G S R V H L L Y K
SEQ ID 13   R L S C D G S R V H L L Y K
SEQ ID 14   N D I L N L G N F T E S T D G G K A I L K N H L D Q N P Q L
SEQ ID 15

SEQ ID 11   Q K N A M A H G N S T H Q N S L E A Q K S S Q T L T R H Q P
SEQ ID 12
SEQ ID 13
SEQ ID 14   Q W N T T E P S R T C K D P I E D I N S P E H I Q R R L S L
SEQ ID 15

SEQ ID 11   L L P L Q C G E T D L D L T V Q E T G L Q G P V G G Q Q R P
SEQ ID 12
SEQ ID 13
SEQ ID 14   Q L P I L H H A Y L P S I G G V D A S C V S P C V S P T A S
SEQ ID 15

SEQ ID 11   E V E D P E E L S P A L V V S S S Q S F V I S G G G S T V T
SEQ ID 12
SEQ ID 13
SEQ ID 14   P R H R H V P P S F R V M V S G L
SEQ ID 15
```

Figure 3a

SEQ ID 11  E N V V N S
SEQ ID 12
SEQ ID 13
SEQ ID 14
SEQ ID 15

Figure 3b

SEQ.ID.NO.16  M A R S L T W G C C P W C L T E E E K T A A R I Q Q E I N R
SEQ.ID.NO.17  M A R S L T W R C C P W C L T E Q E K A A A R V Q Q E I N R

SEQ.ID.NO.16  I L L E Q K K Q E R E E L K L L L L G P G E S G K S T F I K
SEQ.ID.NO.17  I L L E Q K K Q D R G E L K L L L L G P G E S G K S T F I K

SEQ.ID.NO.16  Q M R I I H G V G Y S E E D R R A F R L L I Y Q N I F V S M
SEQ.ID.NO.17  Q M R I I H G A G Y S E E E R K G F R P L V Y Q N I F V S M

SEQ.ID.NO.16  Q A M I D A M Q R L Q I P F S R P D S K Q H A S L V M T Q D
SEQ.ID.NO.17  R A M I E A M E R L Q I P F S R P E S K H H A S L V M S Q D

SEQ.ID.NO.16  P Y K V S T F E K P Y A V A M Q Y L W R D A G I R A C Y E R
SEQ.ID.NO.17  P Y K V T T F E K R Y A A A M Q W L W R D A G I R A C Y E R

SEQ.ID.NO.16  R R E F H L L D S A V Y Y L S H L E R I S E D S Y I P T A Q
SEQ.ID.NO.17  R R E F H L L D S A V Y Y L S H L E R I T E E G Y V P T A Q

SEQ.ID.NO.16  D V L R S R M P T T G I N E Y C F S V K K T K L R I V D V G
SEQ.ID.NO.17  D V L R S R M P T T G I N E Y C F S V Q K T N L R I V D V G

SEQ.ID.NO.16  G Q R S E R R K W I H C F E N V I A L I Y L A S L S E Y D Q
SEQ.ID.NO.17  G Q K S E R R K W I H C F E N V I A L I Y L A S L S E Y D Q

SEQ.ID.NO.16  C L E E N D Q E N R M E E S L A L F S T I L E L P W F K S T
SEQ.ID.NO.17  C L E E N N Q E N R M K E S L A L F G T I L E L P W F K S T

SEQ.ID.NO.16  S V I L F L N K T D I L E D K I H T S H L A T Y F P S F Q G
SEQ.ID.NO.17  S V I L F L N K T D I L E E K I P T S H L A T Y F P S F Q G

SEQ.ID.NO.16  P R R D A E A A K S F I L D M Y A R V Y A S C A E P Q Q G G
SEQ.ID.NO.17  P K Q D A E A A K R F I L D M Y T R M Y T G C V Q G P E G S

SEQ.ID.NO.16  R K G S R A R R F F A H F T C A T D T Q S V R S V F K D V R
SEQ.ID.NO.17  K K G A R S R R L F S H Y T C A T D T Q N I R K V F K D V R

Figure 4a

SEQ. ID. NO. 16  D S V L A R Y L D E I N L L
SEQ. ID. NO. 17  D S V L A R Y L D E I N L L

Figure 4b

ClustalW Formatted Alignments

```
SEQ. ID. NO. 18   A T G G C A T T T T A T A G C T G C T G C T G G G
SEQ. ID. NO. 19   A T G T T G C T G C T G C T G C T A C T G G C G C
SEQ. ID. NO. 20   A T G G G G C C C G G G G C C C C T T T T G C C C
SEQ. ID. NO. 21   A T G G C T T C C C C G C G G A G C T C C G G G C

SEQ. ID. NO. 18   T C C T C T T G G C A C T C A C C T G G C A C A C
SEQ. ID. NO. 19   C A C T C T T C C T C C G C C C C C G G G C G C
SEQ. ID. NO. 20   G G G T G G G G T G G C C A C T G C C G C T T C T
SEQ. ID. NO. 21   A G C C C G G G C C G C - G C C G C C G C C G C C

SEQ. ID. NO. 18   C T C T G C C T A C G G G C C A G A C C A G C G A
SEQ. ID. NO. 19   G G G C G G G G C G C A G A C C C C C A A C G C C
SEQ. ID. NO. 20   G G T T G T G A T G G C G G C A G G G G T G G C T
SEQ. ID. NO. 21   A C C G C C G C C C G C G C G C C T G C T A C T G

SEQ. ID. NO. 18   G C C C A A A A G A A G G G G G A C A T T A T C C
SEQ. ID. NO. 19   A C C T C A G A A G G T T G C C A G A T C A T A C
SEQ. ID. NO. 20   C C G G T G T G G G C C T C C C A C T C C C C C C
SEQ. ID. NO. 21   C T A C T G C T G C T G C C G C T G C T G C T G C

SEQ. ID. NO. 18   T T G G G G G G C T C T T T C C T A T T C A T T T
SEQ. ID. NO. 19   A C C C G C C C T G G G A A G G G G G C A T C A G
SEQ. ID. NO. 20   A T C T C C G C G G C C T C A C T C G C G G G T
SEQ. ID. NO. 21   C T C T G G C G C C C G G G G C C T G G G G C T G

SEQ. ID. NO. 18   T G G A G T A G C A G C T A A A G A T C A A G A T
SEQ. ID. NO. 19   G T A C C G G G G C C T G A C T C G G A C C A G
SEQ. ID. NO. 20   C C C C C C G C A C C C C T C C T C A G A A C G G
SEQ. ID. NO. 21   G G C G C G G G G C G C C C C C G G C C G C C G

SEQ. ID. NO. 18   C T C A A A T C A A G G C C G G A G T C T G T G G
SEQ. ID. NO. 19   G T G A A G G C T A T C A A C T T C C T G C C A G
SEQ. ID. NO. 20   C G C G C A G T G T A C A T C G G G G C A C T G T
SEQ. ID. NO. 21   C C C A G C A G C C C G C C G C T C T C C A T C A

SEQ. ID. NO. 18   A A T G T A T C A G G T A T A A T T T C C G T G G
SEQ. ID. NO. 19   T G G A C T A T G A G A T T G A G T A T G T G T G
SEQ. ID. NO. 20   T T C C C A T G A G C G G G G C T G G C C A G G
SEQ. ID. NO. 21   T G G G C C T C A T G C C G C T C A C C A A G G A
```

Figure 5a

SEQ. ID. NO. 18  G T T T C G C T G G T T A C A G G C T A T G A T A
SEQ. ID. NO. 19  C C G G G G G G A G C G C G A G G T G G T G G G G
SEQ. ID. NO. 20  G G G C C A G G C C T G C C A G C C C G C G G T G
SEQ. ID. NO. 21  G G T G G C C A A G G G C A G C A T C G G G C G C

SEQ. ID. NO. 18  T T T G C C A T A G A G G A G A T A A A C A G C A
SEQ. ID. NO. 19  C C C A A G G T C C G C A A G T G C C T G G C C A
SEQ. ID. NO. 20  G A G A T G G C G C T G G A G G A C G T G A A T A
SEQ. ID. NO. 21  G G T G T G C T C C C C G C C G T G G A A C T G G

SEQ. ID. NO. 18  G C C C A G C C C T T C T T C C C A A C T T G A C
SEQ. ID. NO. 19  A C G G C T C C T G G A C A G A T A T G G A C A C
SEQ. ID. NO. 20  G C C G C A G G G A C A T C C T G C C G G A C T A
SEQ. ID. NO. 21  C C A T C G A G C A G A T C C G C A A C G A G T C

SEQ. ID. NO. 18  G C T G G G A T A C A G G A T A T T T G A C A C T
SEQ. ID. NO. 19  A C C C A G C C G C T G T G T C C G A A T C T G C
SEQ. ID. NO. 20  T G A G C T C A A G C T C A T C C A C C A C G A C
SEQ. ID. NO. 21  A C T C C T G C G C C C C T A C T T C C T C G A C

SEQ. ID. NO. 18  T G C A A C A C C G T T T C T A A G G C C T T G G
SEQ. ID. NO. 19  T C C A A G T C T T A T T T G A C C C T G G A A A
SEQ. ID. NO. 20  A G C A A G T G T G A T C C A G G C C A A G C C A
SEQ. ID. NO. 21  C T G C G G C T C T A T G A C A C G G A G T G C G

SEQ. ID. NO. 18  A A G C C A C C C T G A G T T T T G T T G C T C A
SEQ. ID. NO. 19  A T G G G A A G G T T T T C C T G A C G G G T G G
SEQ. ID. NO. 20  C C A A G T A C C T A T A T G A G C T G C T C T A
SEQ. ID. NO. 21  A C A A C G C A A A A G G G T T G A A A G C C T T

SEQ. ID. NO. 18  A A A C A A A A T T G A T T C T T T G A A C C T T
SEQ. ID. NO. 19  G G A C C T C C C A G C T C T G G A C G G A G C C
SEQ. ID. NO. 20  C A A C G A C C C T A T C A A G A T C A T C C T T
SEQ. ID. NO. 21  C T A C G A T G C A A T A A A A T A C G G G C C G

SEQ. ID. NO. 18  G A T G A G T T C T G C A A C T G C T C A G A G C
SEQ. ID. NO. 19  C G G G T G G A T T T C C G G T G T G A C C C C G
SEQ. ID. NO. 20  A T G C C T G G C T G C A G C T C T G T C T C C A
SEQ. ID. NO. 21  A A C C A C T T G A T G G T G T T T G G A G G C G

Figure 5b

```
SEQ. ID. NO. 18   A C A T T C C C T C T A C G A T T G C T G T G G T
SEQ. ID. NO. 19   A C T T C C A T C T G G T G G G C A G C T C C C G
SEQ. ID. NO. 20   C G C T G G T G G C T G A G G C T G C T A G G A T
SEQ. ID. NO. 21   T C T G T C C A T C C G T C A C A T C C A T C A T

SEQ. ID. NO. 18   G G G A G C A A C T G G C T C A G G C G T C T C C
SEQ. ID. NO. 19   G A G C A T C T G T A G T C A G G G C C A G T G G
SEQ. ID. NO. 20   G T G G A A C C T C A T T G T G C T T T C C T A T
SEQ. ID. NO. 21   T G C A G A G T C C C T C C A A G G C T G G A A T

SEQ. ID. NO. 18   A C G G C A G T G G C A A A T C T G C T G G G G C
SEQ. ID. NO. 19   A G C A C C C C C A A G C C C C A C T G C C A G G
SEQ. ID. NO. 20   G G C T C C A G C T C A C C A G C C C T G T C A A
SEQ. ID. NO. 21   C T G G T G C A G C T T T C T T T T G C T G C A A

SEQ. ID. NO. 18   T C T T C T A C A T T C C C C A G G T C A G T T A
SEQ. ID. NO. 19   T G A A T C G A A C G C C A C A C T C A G A A C G
SEQ. ID. NO. 20   A C C G G C A G C G T T T C C C C A C T T T C T T
SEQ. ID. NO. 21   C C A C G C C T G T T C T A G C C G A T A A G A A

SEQ. ID. NO. 18   T G C C T C C T C C A G C A G A C T C C T C A G C
SEQ. ID. NO. 19   G C G C G C A G T G T A C A T C G G G G C A C T G
SEQ. ID. NO. 20   C C G A A C G C A C C C A T C A G C C A C A C T C
SEQ. ID. NO. 21   A A A A T A C C C T T A T T T C T T T C G G A C C

SEQ. ID. NO. 18   A A C A A G A A T C A A T T C A A G T C T T T C C
SEQ. ID. NO. 19   T T T C C C A T G A G C G G G G G C T G G C C A G
SEQ. ID. NO. 20   C A C A A C C C T A C C C G C G T G A A A C T C T
SEQ. ID. NO. 21   G T C C A T C A G A C A A T G C G G T G A A T C

SEQ. ID. NO. 18   T C C G A A C C A T C C C C A A T G A T G A G C A
SEQ. ID. NO. 19   G G G G C C A G G C C T G C C A G C C C G C G G T
SEQ. ID. NO. 20   T T G A A A A G T G G G G C T G G A A G A A G A T
SEQ. ID. NO. 21   C A G C C A T T C T G A A G T T G C T C A A G C A

SEQ. ID. NO. 18   C C A G G C C A C T G C C A T G G C A G A C A T C
SEQ. ID. NO. 19   G G A G A T G G C G C T G G A G G A C G T G A A T
SEQ. ID. NO. 20   T G C T A C C A T C C A G C A G A C C A C T G A G
SEQ. ID. NO. 21   C T A C C A G T G G A A G C G C C T G G G C A C G
```

Figure 5c

SEQ. ID. NO. 18  A T C G A G T A T T T C C G C T G G A A C T G G G
SEQ. ID. NO. 19  A G C C G C A G G G A C A T C C T G C C G G A C T
SEQ. ID. NO. 20  G T C T T C A C T T C G A C T C T G G A C G A C C
SEQ. ID. NO. 21  C T G A C G C A A G A C G T T C A G A G G T T C T

SEQ. ID. NO. 18  T G G G C A C A A T T G C A G C T G A T G A C G A
SEQ. ID. NO. 19  A T G A G C T C A A G C T C A T C C A C C A C G A
SEQ. ID. NO. 20  T G G A G G A A C G A G T G A A G G A G G C T G G
SEQ. ID. NO. 21  C T G A G G T G C G G A A T G A C C T G A C T G G

SEQ. ID. NO. 18  C T A T G G G C G G C C G G G G A T T G A G A A A
SEQ. ID. NO. 19  C A G C A A G T G T G A T C C A G G C C A A G C C
SEQ. ID. NO. 20  A A T T G A G A T T A C T T T C C G C C A G A G T
SEQ. ID. NO. 21  A G T T C T G T A T G G C G A G G A C A T T G A G

SEQ. ID. NO. 18  T T C C G A G A G G A A G C T G A G G A A A G G G
SEQ. ID. NO. 19  A C C A A G T A C C T A T A T G A G C T G C T C T
SEQ. ID. NO. 20  T T C T T C T C A G A T C C A G C T G T G C C C G
SEQ. ID. NO. 21  A T T T C A G A C A C C G A G A G C T T C T C C A

SEQ. ID. NO. 18  A T A T C T G C A T C G A C T T C A G T G A A C T
SEQ. ID. NO. 19  A C A A C G A C C C T A T C A A G A T C A T C C T
SEQ. ID. NO. 20  T C A A A A A C C T G A A G C G C C A G G A T G C
SEQ. ID. NO. 21  A C G A T C C C T G T A C C A G T G T C A A A A A

SEQ. ID. NO. 18  C A T C T C C C A G T A C T C T G A T G A G G A A
SEQ. ID. NO. 19  T A T G C C T G G C T G C A G C T C T G T C T C C
SEQ. ID. NO. 20  C C G A A T C A T C G T G G A C T T T T C T A T
SEQ. ID. NO. 21  G C T G A A G G G G A A T G A T G T G C G G A T C

SEQ. ID. NO. 18  G A G A T C C A G C A T G T G G T A G A G G T G A
SEQ. ID. NO. 19  A C G C T G G T G G C T G A G G C T G C T A G G A
SEQ. ID. NO. 20  G A G A C T G A A G C C C G G A A A G T T T T T T
SEQ. ID. NO. 21  A T C C T T G G C C A G T T T G A C C A G A A T A

SEQ. ID. NO. 18  T T C A A A A T T C C A C G G C C A A A G T C A T
SEQ. ID. NO. 19  T G T G G A A C C T C A T T G T G C T T T C C T A
SEQ. ID. NO. 20  G T G A G G T G T A C A A G G A G C G T C T C T T
SEQ. ID. NO. 21  T G G C A G C A A A A G T G T T C T G T T G T G C

Figure 5d

```
SEQ. ID. NO. 18   C G T G G T T T T C T C C A G T G G C C C A G A T
SEQ. ID. NO. 19   T G G C T C C A G C T C A C C A G C C C T G T C A
SEQ. ID. NO. 20   T G G G A A G A A G T A C G T C T G G T T C C T C
SEQ. ID. NO. 21   A T A C G A G G A G A A C A T G T A T G G T A G T

SEQ. ID. NO. 18   C T T G A G C C C C T C A T C A A G G A G A T T G
SEQ. ID. NO. 19   A A C C G G C A G C G T T T C C C C A C T T T C T
SEQ. ID. NO. 20   A T T G G G T G G T A T G C T G A C A A T T G G T
SEQ. ID. NO. 21   A A A T A T C A G T G G A T C A T T C C G G G C T

SEQ. ID. NO. 18   T C C G G C G C A A T A T C A C G G G C A A G A T
SEQ. ID. NO. 19   T C C G A A C G C A C C C A T C A G C C A C A C T
SEQ. ID. NO. 20   T C A A G A T C T A C G A C C C T T C T A T C A A
SEQ. ID. NO. 21   G G T A C G A G C C T T C T T G G T G G G A G C A

SEQ. ID. NO. 18   C T G G C T G G C C A G C G A G G C C T G G G C C
SEQ. ID. NO. 19   C C A C A A C C C T A C C C G C G T G A A A C T C
SEQ. ID. NO. 20   C T G C A C A G T G G A T G A G A T G A C T G A G
SEQ. ID. NO. 21   G G T G C A C A C G G A A G C C A A C T C A T C C

SEQ. ID. NO. 18   A G C T C C T C C C T G A T C G C C A T G C C T C
SEQ. ID. NO. 19   T T T G A A A A G T G G G G C T G G A A G A A G A
SEQ. ID. NO. 20   G C G G T G G A G G G C C A C A T C A C A A C T G
SEQ. ID. NO. 21   C G C T G C C T C C G G A A G A A T C T G C T T G

SEQ. ID. NO. 18   A G T A C T T C C A C G T G G T T G G C G G C A C
SEQ. ID. NO. 19   T T G C T A C C A T C C A G C A G A C C A C T G A
SEQ. ID. NO. 20   A G A T T G T C A T G C T G A A T C C T G C C A A
SEQ. ID. NO. 21   C T G C C A T G G A G G G C T A C A T T G G C G T

SEQ. ID. NO. 18   C A T T G G A T T C G C T C T G A A G G C T G G G
SEQ. ID. NO. 19   G G T C T T C A C T T C G A C T C T G G A C G A C
SEQ. ID. NO. 20   T A C C C G C A G C A T T T C C A A C A T G A C A
SEQ. ID. NO. 21   G G A T T T C G A G C C C C T G A G C T C C A A G

SEQ. ID. NO. 18   C A G A T C C C A G G C T T C C G G G A A T T C C
SEQ. ID. NO. 19   C T G G A G G A A C G A G T G A A G G A G G C T G
SEQ. ID. NO. 20   T C C C A G G A A T T T G T G G A G A A A C T A A
SEQ. ID. NO. 21   C A G A T C A A G A C C A T C T C A G G A A A G A
```

Figure 5e

```
SEQ. ID. NO. 18   T G A A G A A G G T C C A T C C C A G G A A G T C
SEQ. ID. NO. 19   G A A T T G A G A T T A C T T T C C G C C A G A G
SEQ. ID. NO. 20   C C A A G C G A C T G A A A A G A C A C C C T G A
SEQ. ID. NO. 21   C T C C A C A G C A G T A T G A G A G A G T A

SEQ. ID. NO. 18   T G T C C A C A A T G G T T T T G C C A A G G A G
SEQ. ID. NO. 19   T T T C T T C T C A G A T C C A G C T G T G C C C
SEQ. ID. NO. 20   G G A G A C A G G A G G C T T C C A G G A G G C A
SEQ. ID. NO. 21   C A A C A A C A A G C G G T C A G G C G T G G G G

SEQ. ID. NO. 18   T T T T G G G A A G A A A C A T T T A A C T G C C
SEQ. ID. NO. 19   G T C A A A A A C C T G A A G C G C C A G G A T G
SEQ. ID. NO. 20   C C G C T G G C C T A T G A T G C C A T C T G G
SEQ. ID. NO. 21   C C C A G C A A G T T C C A C G G G T A C G C C T

SEQ. ID. NO. 18   A C C T C C A A G A A G G T G C A A A A G G A C C
SEQ. ID. NO. 19   C C C G A A T C A T C G T G G G A C T T T T C T A
SEQ. ID. NO. 20   C C T T G G C A C T G G C C C T G A A C A A G A C
SEQ. ID. NO. 21   A C G A T G G C A T C T G G G T C A T C G C C A A

SEQ. ID. NO. 18   T T T A C C T G T G G A C A C C T T T C T G A G A
SEQ. ID. NO. 19   T G A G A C T G A A G C C C G G A A A G T T T T T
SEQ. ID. NO. 20   A T C T G G A G G A G G C G G C C G T T C T G G T
SEQ. ID. NO. 21   G A C A C T G C A G A G G G C C A T G G A G A C A

SEQ. ID. NO. 18   G G T C A C G A A G A A A G T G G C G A C A G G T
SEQ. ID. NO. 19   T G T G A G G T G T A C A A G G A G C G T C T C T
SEQ. ID. NO. 20   G T G C G C C T G G A G G A C T T C A A C T A C A
SEQ. ID. NO. 21   C T G C A T G C C A G C A G C C G G C A C C A G C

SEQ. ID. NO. 18   T T A G C A A C A G C T C G A C A G C C T T C C G
SEQ. ID. NO. 19   T T G G G A A G A A G T A C G T C T G G T T C C T
SEQ. ID. NO. 20   A C A A C C A G A C C A T T A C C G A C C A A A T
SEQ. ID. NO. 21   G G A T C C A G G A C T T C A A C T A C A C G G A

SEQ. ID. NO. 18   A C C C C T C T G T A C A G G G G A T G A G A A C
SEQ. ID. NO. 19   C A T T G G G T G G T A T G C T G A C A A T T G G
SEQ. ID. NO. 20   C T A C C G G G C A A T G A A C T C T T C G T C C
SEQ. ID. NO. 21   C C A C A C G C T G G G C A G G A T C A T C C T C
```

Figure 5f

```
SEQ. ID. NO. 18  A T C A G C A G T G T C G A G A C C C C T T A C A
SEQ. ID. NO. 19  T T C A A G A T C T A C G A C C C T T C T A T C A
SEQ. ID. NO. 20  T T T G A G G G T G T C T C T G G C C A T G T G G
SEQ. ID. NO. 21  A A T G C C A T G A A C G A G A C C A A C T T C T

SEQ. ID. NO. 18  T A G A T T A C A C G C A T T T A C G G A T A T C
SEQ. ID. NO. 19  A C T G C A C A G T G G A T G A G A T G A C T G A
SEQ. ID. NO. 20  T G T T T G A T G C C A G C G G C T C T C G G A T
SEQ. ID. NO. 21  T C G G G G T C A C G G G T C A A G T T G T A T T

SEQ. ID. NO. 18  C T A C A A T G T G T A C T T A G C A G T C T A C
SEQ. ID. NO. 19  G G C G G T G G A G G G C C A C A T C A C A A C T
SEQ. ID. NO. 20  G G C A T G G A C G C T T A T C G A G C A G C T T
SEQ. ID. NO. 21  C C G G A A T G G G G A G A G A A T G G G G A C C

SEQ. ID. NO. 18  T C C A T T G C C C A C G C C T T G C A A G A T A
SEQ. ID. NO. 19  G A G A T T G T C A T G C T G A A T C C T G C C A
SEQ. ID. NO. 20  C A G G G T G G C A G C T A C A A G A A G A T T G
SEQ. ID. NO. 21  A T T A A A T T T A C T C A A T T T C A A G A C A

SEQ. ID. NO. 18  T A T A T A C C T G C T T A C C T G G G A G A G G
SEQ. ID. NO. 19  A T A C C C G C A G C A T T T C C A A C A T G A C
SEQ. ID. NO. 20  G C T A C T A T G A C A G C A C C A A G G A T G A
SEQ. ID. NO. 21  G C A G G G A G G T G A A G G T G G G A G A G T A

SEQ. ID. NO. 18  G C T C T T C A C C A A T G G C T C C T G T G C A
SEQ. ID. NO. 19  A T C C C A G G A A T T T G T G G A G A A A C T A
SEQ. ID. NO. 20  T C T T T C C T G G T C C A A A A C A G A T A A A
SEQ. ID. NO. 21  C A A C G C T G T G G C C G A C A C A C T G G A G

SEQ. ID. NO. 18  G A C A T C A A G A A A G T T G A G G C G T G G C
SEQ. ID. NO. 19  A C C A A G C G A C T G A A A A G A C A C C C T G
SEQ. ID. NO. 20  T G G A T T G G A G G G T C C C C C C C A G C T G
SEQ. ID. NO. 21  A T C A T C A A T G A C A C C A T C A G G T T C C

SEQ. ID. NO. 18  A G G T C C T G A A G C A C C T A C G G C A T C T
SEQ. ID. NO. 19  A G G A G A C A G G A G G C T T C C A G G A G G C
SEQ. ID. NO. 20  A C C A G A C C C T G G T C A T C A A G A C A T T
SEQ. ID. NO. 21  A A G G A T C C G A A C C A C C A A A A G A C A A
```

Figure 5g

```
SEQ. ID. NO. 18  A A A C T T T A C A A A C A A T A T G G G G G A G
SEQ. ID. NO. 19  A C C G C T G G C C T A T G A T G C C A T C T G G
SEQ. ID. NO. 20  C C G C T T C C T G T C A C A G A A A C T C T T T
SEQ. ID. NO. 21  G A C C A T C A T C C T G G A G C A G C T G C G G

SEQ. ID. NO. 18  C A G G T G A C C T T T G A T G A G T G T G G T G
SEQ. ID. NO. 19  G C C T T G G C A C T G G C C C T G A A C A A G A
SEQ. ID. NO. 20  A T C T C C G T C T C A G T T C T C T C C A G C C
SEQ. ID. NO. 21  A A G A T C T C C C T A C C T C T C T A C A G C A

SEQ. ID. NO. 18  A C C T G G T G G G G A A C T A T T C C A T C A T
SEQ. ID. NO. 19  C A T C T G G A G G A G G C G G C C G T T C T G G
SEQ. ID. NO. 20  T G G G C A T T G T C C T A G C T G T T G T C T G
SEQ. ID. NO. 21  T C C T C T C T G C C C T C A C C A T C C T C G G

SEQ. ID. NO. 18  C A A C T G G C A C C T C T C C C A G A G G A T
SEQ. ID. NO. 19  T G T G C G C C T G G A G G A C T T C A A C T A C
SEQ. ID. NO. 20  T C T G T C C T T T A A C A T C T A C A A C T C A
SEQ. ID. NO. 21  G A T G A T C A T G G C C A G T G C T T T T C T C

SEQ. ID. NO. 18  G G C T C C A T C G T G T T T A A G G A A G T C G
SEQ. ID. NO. 19  A A C A A C C A G A C C A T T A C C G A C C A A A
SEQ. ID. NO. 20  C A T G T C C G T T A T A T C C A G A A C T C A C
SEQ. ID. NO. 21  T T C T T C A A C A T C A A G A A C C G G A A T C

SEQ. ID. NO. 18  G G T A T T A C A A C G T C T A T G C C A A G A A
SEQ. ID. NO. 19  T C T A C C G G G C A A T G A A C T C T T C G T C
SEQ. ID. NO. 20  A G C C C A A C C T G A A C A A C C T G A C T G C
SEQ. ID. NO. 21  A G A A G C T C A T A A A G A T G T C G A G T C C

SEQ. ID. NO. 18  G G G A G A A A G A C T C T T C A T C A A C G A G
SEQ. ID. NO. 19  C T T T G A G G G T G T C T C T G G C C A T G T G
SEQ. ID. NO. 20  T G T G G G C T G C T C A C T G G C T T T A G C T
SEQ. ID. NO. 21  A T A C A T G A A C A A C C T T A T C A T C C T T

SEQ. ID. NO. 18  G A G A A A A T C C T G T G G A G T G G G T T C T
SEQ. ID. NO. 19  G T G T T T G A T G C C A G C G G C T C T C G G A
SEQ. ID. NO. 20  G C T G T C T T C C C C C T G G G G C T C G A T G
SEQ. ID. NO. 21  G G A G G G A T G C T C T C C T A T G C T T C C A
```

Figure 5h

SEQ. ID. NO. 18  C C A G G G A G G T G C C C T T C T C C A A C T G
SEQ. ID. NO. 19  T G G C A T G G A C G C T T A T C G A G C A G C T
SEQ. ID. NO. 20  G T T A C C A C A T T G G G A G G A A C C A G T T
SEQ. ID. NO. 21  T A T T T C T C T T T G G C C T T G A T G G A T C

SEQ. ID. NO. 18  C A G C C G A G A C T G C C T G G C A G G G A C C
SEQ. ID. NO. 19  T C A G G G T G G C A G C T A C A A G A A G A T T
SEQ. ID. NO. 20  T C C T T T C G T C T G C C A G G C C C G C C T C
SEQ. ID. NO. 21  C T T T G T C T C T G A A A A G A C C T T T G A A

SEQ. ID. NO. 18  A G G A A A G G G A T C A T T G A G G G G G A G C
SEQ. ID. NO. 19  G G C T A C T A T G A C A G C A C C A A G G A T G
SEQ. ID. NO. 20  T G G C T C C T G G G C C T G G G C T T T A G T C
SEQ. ID. NO. 21  A C A C T T T G C A C C G T C A G G A C C T G G A

SEQ. ID. NO. 18  C C A C C T G C T G C T T T G A G T G T G T G G A
SEQ. ID. NO. 19  A T C T T T C C T G G T C C A A A A C A G A T A A
SEQ. ID. NO. 20  T G G G C T A C G G T T C C A T G T T C A C C A A
SEQ. ID. NO. 21  T T C T C A C C G T G G G C T A C A C G A C C G C

SEQ. ID. NO. 18  G T G T C C T G A T G G G G A G T A T A G T G A T
SEQ. ID. NO. 19  A T G G A T T G G A G G G T C C C C C C A G C T
SEQ. ID. NO. 20  G A T T T G G T G G G T C C A C A C G G T C T T C
SEQ. ID. NO. 21  T T T T G G G G C C A T G T T T G C A A A G A C C

SEQ. ID. NO. 18  G A G A C A G A T G C C A G T G C C T G T A A C A
SEQ. ID. NO. 19  G A C C A G A C C C T G G T C A T C A A G A C A T
SEQ. ID. NO. 20  A C A A A G A A G G A A G A A A G A A G G A G T
SEQ. ID. NO. 21  T G G A G A G T C C A C G C C A T C T T C A A A A

SEQ. ID. NO. 18  A G T G C C C A G A T G A C T T C T G G T C C A A
SEQ. ID. NO. 19  T C C G C T T C C T G T C A C A G A A A C T C T T
SEQ. ID. NO. 20  G G A G G A A G A C T C T G G A A C C C T G G A A
SEQ. ID. NO. 21  A T G T G A A A A T G A A G A A G A A G A T C A T

SEQ. ID. NO. 18  T G A G A A C C A C A C C T C C T G C A T T G C C
SEQ. ID. NO. 19  T A T C T C C G T C T C A G T T C T C T C C A G C
SEQ. ID. NO. 20  G C T G T A T G C C A C A G T G G G C C T G C T G
SEQ. ID. NO. 21  C A A G G A C C A G A A A C T G C T T G T G A T C

Figure 5i

SEQ. ID. NO. 18  A A G G A G A T C G A G T T T C T G T C G T G G A
SEQ. ID. NO. 19  C T G G G C A T T G T C C T A G C T G T T G T C T
SEQ. ID. NO. 20  G T G G G C A T G G A T G T C C T C A C T C T C G
SEQ. ID. NO. 21  G T G G G G G G C A T G C T G C T G A T C G A C C

SEQ. ID. NO. 18  C G G A G C C C T T T G G G A T C G C A C T C A C
SEQ. ID. NO. 19  G T C T G T C C T T T A A C A T C T A C A A C T C
SEQ. ID. NO. 20  C C A T C T G G C A G A T C G T G G A C C C T C T
SEQ. ID. NO. 21  T G T G T A T C C T G A T C T G C T G G C A G G C

SEQ. ID. NO. 18  C C T C T T T G C C G T G C T G G G C A T T T T C
SEQ. ID. NO. 19  A C A T G T C C G T T A T A T C C A G A A C T C A
SEQ. ID. NO. 20  G C A C C G G A C C A T T G A G A C A T T G C C
SEQ. ID. NO. 21  T G T G G A C C C C C T G C G A A G G A C A G T G

SEQ. ID. NO. 18  C T G A C A G C C T T T G T G C T G G G T G T G T
SEQ. ID. NO. 19  C A G C C C A A C C T G A A C A A C C T G A C T G
SEQ. ID. NO. 20  A A G G A G G A A C C T A A G G A A G A T A T T G
SEQ. ID. NO. 21  G A G A A G T A C A G C A T G G A G C C G G A C C

SEQ. ID. NO. 18  T T A T C A A G T T C C G C A A C A C A C C C A T
SEQ. ID. NO. 19  C T G T G G G C T G C T C A C T G G C T T T A G C
SEQ. ID. NO. 20  A C G T C T C T A T T C T G C C C C A G C T G G A
SEQ. ID. NO. 21  C A G C A G G A C G G G A T A T C T C C A T C C G

SEQ. ID. NO. 18  T G T C A A G G C C A C C A A C C G A G A G C T C
SEQ. ID. NO. 19  T G C T G T C T T C C C C C T G G G G C T C G A T
SEQ. ID. NO. 20  G C A T T G C A G C T C C A G G A A G A T G A A T
SEQ. ID. NO. 21  C C C T C T C C T G G A G C A C T G T G A G A A C

SEQ. ID. NO. 18  T C C T A C C T C C T C C T C T T C T C C C T G C
SEQ. ID. NO. 19  G G T T A C C A C A T T G G G A G G A A C C A G T
SEQ. ID. NO. 20  A C A T G G C T T G G C A T T T T C T A T G G T T
SEQ. ID. NO. 21  A C C C A T A T G A C C A T C T G G C T T G G C A

SEQ. ID. NO. 18  T C T G C T G C T T C T C C A G C T C C C T G T T
SEQ. ID. NO. 19  T T C C T T T C G T C T G C C A G G C C C G C C T
SEQ. ID. NO. 20  A C A A G G G G C T G C T G C T G C T G C T G G G
SEQ. ID. NO. 21  T C G T C T A T G C C T A C A A G G G A C T T C T

Figure 5j

```
SEQ. ID. NO. 18  C T T C A T C G G G G A G C C C C A G G A C T G G
SEQ. ID. NO. 19  C T G G C T C C T G G G C C T G G G C T T T A G T
SEQ. ID. NO. 20  A A T C T T C C T T G C T T A T G A G A C C A A G
SEQ. ID. NO. 21  C A T G T T G T T C G G T T G T T T C T T A G C T

SEQ. ID. NO. 18  A C G T G C C G C C T G C G C C A G C C G G C C T
SEQ. ID. NO. 19  C T G G G C T A C G G T T C C A T G T T C A C C A
SEQ. ID. NO. 20  A G T G T G T C C A C T G A G A A G A T C A A T G
SEQ. ID. NO. 21  T G G G A G A C C C G C A A C G T C A G C A T C C

SEQ. ID. NO. 18  T T G G C A T C A G C T T C G T G C T C T G C A T
SEQ. ID. NO. 19  A G A T T T G G T G G G T C C A C A C G G T C T T
SEQ. ID. NO. 20  A T C A C C G G G C T G T G G G C A T G G C T A T
SEQ. ID. NO. 21  C C G C A C T C A A C G A C A G C A A G T A C A T

SEQ. ID. NO. 18  C T C A T G C A T C C T G G T G A A A A C C A A C
SEQ. ID. NO. 19  C A C A A A G A A G G A A G A A A G A A G G A G
SEQ. ID. NO. 20  C T A C A A T G T G G C A G T C C T G T G C C T C
SEQ. ID. NO. 21  C G G G A T G A G T G T C T A C A A C G T G G G G

SEQ. ID. NO. 18  C G T G T C C T C C T G G T G T T T G A G G C C A
SEQ. ID. NO. 19  T G G A G G A A G A C T C T G G A A C C C T G G A
SEQ. ID. NO. 20  A T C A C T G C T C C T G T C A C C A T G A T T C
SEQ. ID. NO. 21  A T C A T G T G C A T C A T C G G G G C C G C T G

SEQ. ID. NO. 18  A G A T C C C C A C C A G C T T C C A C C G C A A
SEQ. ID. NO. 19  A G C T G T A T G C C A C A G T G G G C C T G C T
SEQ. ID. NO. 20  T G T C C A G C C A G C A G G A T G C A G C C T T
SEQ. ID. NO. 21  T C T C C T T C C T G A C C C G G G A C C A G C C

SEQ. ID. NO. 18  G T G G T G G G G G C T C A A C C T G C A G T T C
SEQ. ID. NO. 19  G G T G G G C A T G G A T G T C C T C A C T C T C
SEQ. ID. NO. 20  T G C C T T T G C C T C T C T T G C C A T A G T T
SEQ. ID. NO. 21  C A A T G T G C A G T T C T G C A T C G T G G C T

SEQ. ID. NO. 18  C T G C T G G T T T T C C T C T G C A C C T T C A
SEQ. ID. NO. 19  G C C A T C T G G C A G A T C G T G G A C C C T C
SEQ. ID. NO. 20  T T C T C C T C C T A T A T C A C T C T T G T T G
SEQ. ID. NO. 21  C T G G T C A T C A T C T T C T G C A G C A C C A

Figure 5k
```

SEQ. ID. NO. 18    T G C A G A T T G T C A T C T G T G T G A T C T G
SEQ. ID. NO. 19    T G C A C C G G A C C A T T G A G A C A T T T G C
SEQ. ID. NO. 20    T G C T C T T T G T G C C C A A G A T G C G C A G
SEQ. ID. NO. 21    T C A C C C T C T G C C T G G T A T T C G T G C C

SEQ. ID. NO. 18    G C T C T A C A C C G C G C C C C C T C A A G C
SEQ. ID. NO. 19    C A A G G A G G A A C C T A A G G A A G A T A T T
SEQ. ID. NO. 20    G C T G A T C A C C C G A G G G G A A T G G C A G
SEQ. ID. NO. 21    G A A G C T C A T C A C C C T G A G A A C A A A C

SEQ. ID. NO. 18    T A C C G C A A C C A G G A G C T G G A G G A T G
SEQ. ID. NO. 19    G A C G T C T C T A T T C T G C C C C A G C T G G
SEQ. ID. NO. 20    T C G G A G G C G C A G G A C A C C A T G A A G A
SEQ. ID. NO. 21    C C A G A T G C A G C A A C G C A G A A C A G G C

SEQ. ID. NO. 18    A G A T C A T C T T C A T C A C G T G C C A C G A
SEQ. ID. NO. 19    A G C A T T G C A G C T C C A G G A A G A T G A A
SEQ. ID. NO. 20    C A G G G T C A T C G A C C A A C A A C A A C G A
SEQ. ID. NO. 21    G A T T C C A G T T C A C T C A G A A T C A G A A

SEQ. ID. NO. 18    G G G C T C C C T C A T G G C C C T G G G C T T C
SEQ. ID. NO. 19    T A C A T G G C T T G G C A T T T T C T A T G G T
SEQ. ID. NO. 20    G G A G G A G A A G T C C C G G C T G T T G G A G
SEQ. ID. NO. 21    G A A A G A A G A T T C T A A A A C G T C C A C C

SEQ. ID. NO. 18    C T G A T C G G C T A C A C C T G C C T G C T G G
SEQ. ID. NO. 19    T A C A A G G G G C T G C T G C T G C T G C T G G
SEQ. ID. NO. 20    A A G G A G A A C C G T G A A C T G G A A A A G A
SEQ. ID. NO. 21    T C G G T C A C C A G T G T G A A C C A A G C C A

SEQ. ID. NO. 18    C T G C C A T C T G C T T C T T C T T T G C C T T
SEQ. ID. NO. 19    G A A T C T T C C T T G C T T A T G A G A C C A A
SEQ. ID. NO. 20    T C A T T G C T G A G A A A G A G G A G C G T G T
SEQ. ID. NO. 21    G C A C A T C C C G C C T G G A G G G C C T A C A

SEQ. ID. NO. 18    C A A G T C C C G G A A G C T G C C G G A G A A C
SEQ. ID. NO. 19    G A G T G T G T C C A C T G A G A A G A T C A A T
SEQ. ID. NO. 20    C T C T G A A C T G C G C C A T C A A C T C C A G
SEQ. ID. NO. 21    G T C A G A A A A C C A T C G C C T G C G A A T G

Figure 51

SEQ. ID. NO. 18 TTCAATGAAGCCAAGTTCATCACCT
SEQ. ID. NO. 19 GATCACCGGGCTGTGGGCATGGCTA
SEQ. ID. NO. 20 TCTCGGCAGCAGCTCCGCTCCCGGC
SEQ. ID. NO. 21 AAGATCACAGAGCTGGATAAAGACT

SEQ. ID. NO. 18 TCAGCATGCTCATCTTCTTCATCGT
SEQ. ID. NO. 19 TCTACAATGTGGCAGTCCTGTGCCT
SEQ. ID. NO. 20 GCCACCCACCGACACCCCAGAACC
SEQ. ID. NO. 21 TGGAAGAGGTCACCATGCAGCTGCA

SEQ. ID. NO. 18 CTGGATCTCCTTCATTCCAGCCTAT
SEQ. ID. NO. 19 CATCACTGCTCCTGTCACCATGATT
SEQ. ID. NO. 20 CTCTGGGGGCCTGCCCAGGGGACCC
SEQ. ID. NO. 21 GGACACACCAGAAAGACCACCTAC

SEQ. ID. NO. 18 GCCAGCACCTATGGCAAGTTTGTCT
SEQ. ID. NO. 19 CTGTCCAGCCAGCAGGATGCAGCCT
SEQ. ID. NO. 20 CCTGAGCCCCCCGACCGGCTTAGCT
SEQ. ID. NO. 21 ATTAAACAGAACCACTACCAAGAGC

SEQ. ID. NO. 18 CTGCCGTAGAGGTGATTGCCATCCT
SEQ. ID. NO. 19 TTGCCTTTGCCTCTCTTGCCATAGT
SEQ. ID. NO. 20 GTGATGGGAGTCGAGTGCATTTGCT
SEQ. ID. NO. 21 TCAATGACATCCTCAACCTGGGAAA

SEQ. ID. NO. 18 GGCAGCCAGCTTTGGCTTGCTGGCG
SEQ. ID. NO. 19 TTTCTCCTCCTATATCACTCTTGTT
SEQ. ID. NO. 20 TTATAAGTGAGGGTAGGGTGAGGGA
SEQ. ID. NO. 21 CTTCACTGAGAGCACAGATGGAGGA

SEQ. ID. NO. 18 TCAATCTTCTTCAACAAGATCTACA
SEQ. ID. NO. 19 GTGCTCTTTGTGCCCAAGATGCGCA
SEQ. ID. NO. 20 GGACAGGCCAGTAGGGGGAGGGAAA
SEQ. ID. NO. 21 AAGGCCATTTTAAAAAATCACCTCG

SEQ. ID. NO. 18 TCATTCTCTTCAAGCCATCCCGCAA
SEQ. ID. NO. 19 GGCTGATCACCCGAGGGGAATGGCA
SEQ. ID. NO. 20 GGGAGAGGGGAAGGGCAGGGGACTC
SEQ. ID. NO. 21 ATCAAAATCCCCAGCTACAGTGGAA

Figure 5m

SEQ. ID. NO. 18   C A C C A T C G A G G A G G T G C G T T G C A G C
SEQ. ID. NO. 19   G T C G G A G G C G C A G G A C A C C A T G A A G
SEQ. ID. NO. 20   A G G A A G C A G G G G G T C C C C A T C C C C A
SEQ. ID. NO. 21   C A C A A C A G A G C C T C T C G A A C A T G C

SEQ. ID. NO. 18   A C C G C A G C T C A C G C T T T C A A G G T G G
SEQ. ID. NO. 19   A C A G G G T C A T C G A C C A A C A A C A A C G
SEQ. ID. NO. 20   G C T G G G A A G A A C A T G C T A T C C A A T C
SEQ. ID. NO. 21   A A A G A T C C T A T A G A A G A T A T A A A C T

SEQ. ID. NO. 18   C T G C C C G G G C C A C G C T G C G C C G C A G
SEQ. ID. NO. 19   A G G A G G A G A A G T C C C G G C T G T T G G A
SEQ. ID. NO. 20   T C A T C T C T T G T A A A T A C A T G T C C C C
SEQ. ID. NO. 21   C T C C A G A A C A C A T C C A G C G T C G G C T

SEQ. ID. NO. 18   C A A C G T C T C C C G C A A G C G G T C C A G C
SEQ. ID. NO. 19   G A A G G A G A A C C G T G A A C T G G A A A A G
SEQ. ID. NO. 20   C T G T G A G T T C T G G G C T G A T T T G G G T
SEQ. ID. NO. 21   G T C C T C C A G C T C C C C A T C C T C C A C

SEQ. ID. NO. 18   A G C C T T G G A G G C T C C A C G G G A T C C A
SEQ. ID. NO. 19   A T C A T T G C T G A G A A A G A G G A G C G T G
SEQ. ID. NO. 20   C T C T C A T A C C T C T G G G A A A C A G A C C
SEQ. ID. NO. 21   C A C G C C T A C C T C C C A T C C A T C G G A G

SEQ. ID. NO. 18   C C C C C T C C T C C T C C A T C A G C A G C A A
SEQ. ID. NO. 19   T C T C T G A A C T G C G C C A T C A G C T C C A
SEQ. ID. NO. 20   T T T T T C T C T C T T A C T G C T T C A T G T A
SEQ. ID. NO. 21   G C G T G G A C G C C A G C T G T G T C A G C C C

SEQ. ID. NO. 18   G A G C A A C A G C G A A G A C C C A T T C C C A
SEQ. ID. NO. 19   G T C T C G G C A G C A G C T C C G C T C C C G G
SEQ. ID. NO. 20   A T T T T G T A T C A C C T C T T C A C A A T T T
SEQ. ID. NO. 21   C T G C G T C A G C C C C A C C G C C A G C C C C

SEQ. ID. NO. 18   C A G C C C G A G A G G C A G A A G C A G C A G C
SEQ. ID. NO. 19   C G C C A C C C A C C G A C A C C C C A G A A C
SEQ. ID. NO. 20   A G T T C G T A C C T G G C T T G A A G C T G C T
SEQ. ID. NO. 21   C G C C A C A G A C A T G T G C C A C C C T C C T

Figure 5n

SEQ. ID. NO. 18  A G C C G C T G G C C C T A A C C C A G C A A G A
SEQ. ID. NO. 19  C C T C T G G G G G C C T G C C C A G G G G A C C
SEQ. ID. NO. 20  C A C T G C T C A C A C G C T G C C T C C T C A G
SEQ. ID. NO. 21  T C C G A G T C A T G G T C T C G G G C C T G T A

SEQ. ID. NO. 18  G C A G C A G C A G C A G C C C C T G A C C C T C
SEQ. ID. NO. 19  C C C T G A G C C C C C C G A C C G G C T T A G C
SEQ. ID. NO. 20  C A G C C T C A C T G C A T C T T T C T C T T C C
SEQ. ID. NO. 21  A G G G T G G G A G G C C T G G G C C C G G G G C

SEQ. ID. NO. 18  C C A C A G C A G C A A C G A T C T C A G C A G C
SEQ. ID. NO. 19  T G T G A T G G G A G T C G A G T G C A T T T G C
SEQ. ID. NO. 20  C A T G C A A C A C C C T C T T C T A G T T A C C
SEQ. ID. NO. 21  C T C C C C C G T G A C A G A A C C A C A C T G G

SEQ. ID. NO. 18  A G C C C A G A T G C A A G C A G A A G G T C A T
SEQ. ID. NO. 19  T T T A T A A G T G A G G G T A G G G T G A G G G
SEQ. ID. NO. 20  A C G G C A A C C C C T
SEQ. ID. NO. 21  G C A G A G G G G T C T G C T G C A G A A A C A C

SEQ. ID. NO. 18  C T T T G G C A G C G G C A C G G T C A C C T T C
SEQ. ID. NO. 19  A G G A C A G G C C A G T A G G G G C A G G G A A
SEQ. ID. NO. 20
SEQ. ID. NO. 21  T G T C G G C T C T G G C T G C G G A G A A G C T

SEQ. ID. NO. 18  T C A C T G A G C T T T G A T G A G C C T C A G A
SEQ. ID. NO. 19  A G G G A G A G G G G A A G G G C A G G G A C T
SEQ. ID. NO. 20
SEQ. ID. NO. 21  G G G C A C C A T G G C T G G C C T C T C A G G A

SEQ. ID. NO. 18  A G A A C G C C A T G G C C C A C G G G A A T T C
SEQ. ID. NO. 19  C A G G A A G C A G G G G T C C C C A T C C C C
SEQ. ID. NO. 20
SEQ. ID. NO. 21  C C A C T C G G A T G G C A C T C A G G T G G A C

SEQ. ID. NO. 18  T A C G C A C C A G A A C T C C C T G G A G G C C
SEQ. ID. NO. 19  A G C T G G G A A G A A C A T G C T A T C C A A T
SEQ. ID. NO. 20
SEQ. ID. NO. 21  A G G A C G G G G C A G G G G G A G A C T T G G C

Figure 5o

SEQ. ID. NO. 18  C A G A A A A G C A G C G A T A C G C T G A C C C
SEQ. ID. NO. 19  C T C A T C T C T T G T A A A T A C A T G T C C C
SEQ. ID. NO. 20
SEQ. ID. NO. 21  A C C T G A C C T C G A G C C T T A T T T G T G A

SEQ. ID. NO. 18  G A C A C C A G C C A T T A C T C C C G C T G C A
SEQ. ID. NO. 19  C C T G T G A G T T C T G G G C T G A T T T G G G
SEQ. ID. NO. 20
SEQ. ID. NO. 21  A G T C C T T A T T T C T T C A C A A A G A A G A

SEQ. ID. NO. 18  G T G C G G G G A A A C G G A C T T A G A T C T G
SEQ. ID. NO. 19  T C T C T C A T A C C T C T G G G A A A C A G A C
SEQ. ID. NO. 20
SEQ. ID. NO. 21  G G A A C G G A A A T G G G A C G T C T T C C T T

SEQ. ID. NO. 18  A C C G T C C A G G A A A C A G G T C T G C A A G
SEQ. ID. NO. 19  C T T T T T C T C T C T T A C T G C T T C A T G T
SEQ. ID. NO. 20
SEQ. ID. NO. 21  A A C A T C T G C A A A C A A G G A G G C G C T G

SEQ. ID. NO. 18  G A C C T G T G G G T G G A G A C C A G C G G C C
SEQ. ID. NO. 19  A A T T T T G T A T C A C C T C T T C A C A A T T
SEQ. ID. NO. 20
SEQ. ID. NO. 21  G G A T A T C A A A C T T G C A A A A A A A A A A

SEQ. ID. NO. 18  A G A G G T G G A G G A C C C T G A A G A G T T G
SEQ. ID. NO. 19  T A G T T C G T A C C T G G C T T G A A G C T G C
SEQ. ID. NO. 20
SEQ. ID. NO. 21  A A A A A A A A A A A A

SEQ. ID. NO. 18  T C C C C A G C A C T T G T A G T G T C C A G T T
SEQ. ID. NO. 19  T C A C T G C T C A C A C G C T G C C T C C T C A
SEQ. ID. NO. 20
SEQ. ID. NO. 21

SEQ. ID. NO. 18  C A C A G A G C T T T G T C A T C A G T G G T G G
SEQ. ID. NO. 19  G C A G C C T C A C T G C A T C T T T C T C T T C
SEQ. ID. NO. 20
SEQ. ID. NO. 21

Figure 5p

SEQ. ID. NO. 18  A G G C A G C A C T G T T A C A G A A A A C G T A
SEQ. ID. NO. 19  C C A T G C A A C A C C C T C T T C T A G T T A C
SEQ. ID. NO. 20
SEQ. ID. NO. 21

SEQ. ID. NO. 18  G T G A A T T C A
SEQ. ID. NO. 19  C A C G G C A A C C C C T G C A G C T C C T C T G
SEQ. ID. NO. 20
SEQ. ID. NO. 21

SEQ. ID. NO. 18
SEQ. ID. NO. 19  C C T T T G T G C T C T G T T C C T G T C C A G C
SEQ. ID. NO. 20
SEQ. ID. NO. 21

SEQ. ID. NO. 18
SEQ. ID. NO. 19  A G G G G T C T C C C A A C A A G T G C T C T T T
SEQ. ID. NO. 20
SEQ. ID. NO. 21

SEQ. ID. NO. 18
SEQ. ID. NO. 19  C C A C C C C A A A G G G G C C T C T C C T T T T
SEQ. ID. NO. 20
SEQ. ID. NO. 21

SEQ. ID. NO. 18
SEQ. ID. NO. 19  C T C C A C T G T C A T A A T C T C T T T C C A T
SEQ. ID. NO. 20
SEQ. ID. NO. 21

SEQ. ID. NO. 18
SEQ. ID. NO. 19  C T T A C T T G C C C T T C T A T A C T T T C T C
SEQ. ID. NO. 20
SEQ. ID. NO. 21

SEQ. ID. NO. 18
SEQ. ID. NO. 19  A C A T G T G G C T C C C C C T G A A T T T T G C
SEQ. ID. NO. 20
SEQ. ID. NO. 21

Figure 5q

SEQ. ID. NO. 18
SEQ. ID. NO. 19    T T C C T T T G G G G A G C T C A T T C T T T C G
SEQ. ID. NO. 20
SEQ. ID. NO. 21

SEQ. ID. NO. 18
SEQ. ID. NO. 19    C C A A G G T C A C A T G C T C C C T T G C C T C
SEQ. ID. NO. 20
SEQ. ID. NO. 21

SEQ. ID. NO. 18
SEQ. ID. NO. 19    T G G C T C C G T G C A
SEQ. ID. NO. 20
SEQ. ID. NO. 21

Figure 5r

SEQ. ID. NO. 22  A T G C T G C T G C T G C T G G T G C C T C T C T T C
SEQ. ID. NO. 23  A T G G G C C C G G G G G G A C C C T G T A C C C C A G T G

SEQ. ID. NO. 22  C T C C G C C C C C T G G G C G C T G G C G G G G C G C A G
SEQ. ID. NO. 23  G G G T G G C C G C T G C C T C T T C T G C T G G T G A T G

SEQ. ID. NO. 22  A C C C C A A C G C C A C C T C G G A A G G T T G C C A G
SEQ. ID. NO. 23  G C G G C T G G G G T G G C T C C G G T G T G G G C C T C T

SEQ. ID. NO. 22  A T T A T A C A T C C G C C C T G G G A A G G T G G C A T C
SEQ. ID. NO. 23  C A C T C C C C T C A T C T C C C G C G G C C T C A C C C G

SEQ. ID. NO. 22  A G G T A C C G T G G C T T G A C T C G C G A C C A G G T G
SEQ. ID. NO. 23  A G G G T C C C C C C G C A C C C C T C C T C A G A A C G G

SEQ. ID. NO. 22  A A G G C C A T C A A C T T C C T G C C T G T G G A C T A T
SEQ. ID. NO. 23  C G T G C A G T A T A C A T C G G G G C G C T G T T T C C C

SEQ. ID. NO. 22  G A G A T C G A A T A T G T G T G C C G A G G G G A G C G C
SEQ. ID. NO. 23  A T G A G C G G G G G C T G G C C G G G G G G C C A G G C C

SEQ. ID. NO. 22  G A G G T G G T G G G G C C C A A G G T G C G C A A A T G C
SEQ. ID. NO. 23  T G C C A G C C C G C G G T G G A G A T G G C G C T G G A G

SEQ. ID. NO. 22  C T G G C C A A C G G C T C C T G G A C G G A T A T G G A C
SEQ. ID. NO. 23  G A C G T T A A C A G C C G C A G A G A C A T C C T G C C G

SEQ. ID. NO. 22  A C A C C C A G C C G C T G T G T C C G A A T C T G C T C C
SEQ. ID. NO. 23  G A C T A C G A G C T C A A G C T T A T C C A C C A C G A C

SEQ. ID. NO. 22  A A G T C T T A T T T G A C C C T G G A A A A T G G G A A G
SEQ. ID. NO. 23  A G C A A G T G T G A C C C A G G G C A A G C C A C C A A G

SEQ. ID. NO. 22  G T T T T C C T G A C G G G T G G G G A C C T C C C A G C T
SEQ. ID. NO. 23  T A C T T G T A C G A A C T A C T C T A C A A T G A C C C C

Figure 6a

SEQ. ID. NO. 22  C T G G A T G G A G C C C G G G T G G A G T T C C G A T G T
SEQ. ID. NO. 23  A T C A A G A T C A T T C T C A T G C C T G G C T G T A G T

SEQ. ID. NO. 22  G A C C C C G A C T T C C A T C T G G T G G G C A G C T C C
SEQ. ID. NO. 23  T C T G T C T C C A C A C T T G T A G C T G A G G C T G C C

SEQ. ID. NO. 22  C G G A G C G T C T G T A G T C A G G G C C A G T G G A G C
SEQ. ID. NO. 23  C G G A T G T G G A A C C T T A T T G T G C T C T C A T A T

SEQ. ID. NO. 22  A C C C C C A A G C C C C A C T G C C A G G T G A A T C G A
SEQ. ID. NO. 23  G G C T C C A G T T C A C C A G C C T T G T C A A A C C G A

SEQ. ID. NO. 22  A C G C C A C A C T C A G A A C G G C G T G C A G T A T A C
SEQ. ID. NO. 23  C A G C G G T T T C C C A C G T T C T T C C G G A C G C A T

SEQ. ID. NO. 22  A T C G G G G C G C T G T T T C C C A T G A G C G G G G G C
SEQ. ID. NO. 23  C C A T C C G C C A C A C T C C A C A A T C C C A C C C G G

SEQ. ID. NO. 22  T G G C C G G G G G G C C A G G C C T G C C A G C C C G C G
SEQ. ID. NO. 23  G T G A A A C T C T T C G A A A A G T G G G G C T G G A A G

SEQ. ID. NO. 22  G T G G A G A T G G C G C T G G A G G A C G T T A A C A G C
SEQ. ID. NO. 23  A A G A T C G C T A C C A T C C A A C A G A C C A C C G A G

SEQ. ID. NO. 22  C G C A G A G A C A T C C T G C C G G A C T A C G A G C T C
SEQ. ID. NO. 23  G T C T T C A C C T C A A C G C T G G A T G A C C T G G A G

SEQ. ID. NO. 22  A A G C T T A T C C A C C A C G A C A G C A A G T G T G A C
SEQ. ID. NO. 23  G A G C G A G T G A A A G A G G C T G G G A T C G A G A T C

SEQ. ID. NO. 22  C C A G G G C A A G C C A C C A A G T A C T T G T A C G A A
SEQ. ID. NO. 23  A C T T T C C G A C A G A G T T T C T T C T C G G A T C C A

SEQ. ID. NO. 22  C T A C T C T A C A A T G A C C C C A T C A A G A T C A T T
SEQ. ID. NO. 23  G C T G T G C C T G T T A A A A A C C T G A A G C G T C A A

SEQ. ID. NO. 22  C T C A T G C C T G G C T G T A G T T C T G T C T C C A C A
SEQ. ID. NO. 23  G A T G C T C G A A T C A T C G T G G G A C T T T T C T A T

Figure 6b

SEQ. ID. NO. 22  C T T G T A G C T G A G G C T G C C C G G A T G T G G A A C
SEQ. ID. NO. 23  G A G A C G G A A G C C C G G A A A G T T T T T G T G A G

SEQ. ID. NO. 22  C T T A T T G T G C T C T C A T A T G G C T C C A G T T C A
SEQ. ID. NO. 23  G T C T A T A A G G A A A G G C T C T T T G G G A A G A A G

SEQ. ID. NO. 22  C C A G C C T T G T C A A A C C G A C A G C G G T T T C C C
SEQ. ID. NO. 23  T A C G T C T G G T T C C T C A T C G G G T G G T A T G C T

SEQ. ID. NO. 22  A C G T T C T T C C G G A C G C A T C C A T C C G C C A C A
SEQ. ID. NO. 23  G A C A A C T G G T T C A A G A C C T A T G A C C C G T C A

SEQ. ID. NO. 22  C T C C A C A A T C C C A C C C G G G T G A A A C T C T T C
SEQ. ID. NO. 23  A T C A A T T G T A C A G T G G A A G A A A T G A C C G A G

SEQ. ID. NO. 22  G A A A A G T G G G G C T G G A A G A A G A T C G C T A C C
SEQ. ID. NO. 23  G C G G T G G A G G G C C A C A T C A C C A C G G A G A T T

SEQ. ID. NO. 22  A T C C A A C A G A C C A C C G A G G T C T T C A C C T C A
SEQ. ID. NO. 23  G T C A T G C T G A A C C C T G C C A A C A C C C G A A G C

SEQ. ID. NO. 22  A C G C T G G A T G A C C T G G A G G A G C G A G T G A A A
SEQ. ID. NO. 23  A T T T C C A A C A T G A C G T C A C A G G A A T T T G T G

SEQ. ID. NO. 22  G A G G C T G G G A T C G A G A T C A C T T T C C G A C A G
SEQ. ID. NO. 23  G A G A A A C T A A C C A A G C G G C T G A A A A G A C A C

SEQ. ID. NO. 22  A G T T T C T T C T C G G A T C C A G C T G T G C C T G T T
SEQ. ID. NO. 23  C C C G A G G A G A C T G G A G G C T T C C A G G A G G C A

SEQ. ID. NO. 22  A A A A A C C T G A A G C G T C A A G A T G C T C G A A T C
SEQ. ID. NO. 23  C C A C T G G C C T A T G A T G C T A T C T G G G C C T T G

SEQ. ID. NO. 22  A T C G T G G G A C T T T T C T A T G A G A C G G A A G C C
SEQ. ID. NO. 23  G C T T T G G C C T T G A A C A A G A C G T C T G G A G G A

SEQ. ID. NO. 22  C G G A A A G T T T T T T G T G A G G T C T A T A A G G A A
SEQ. ID. NO. 23  G G T G G T C G T T C C G G C G T G C G C C T G G A G G A C

Figure 6c

SEQ. ID. NO. 22   A G G C T C T T T G G G A A G A A G T A C G T C T G G T T C
SEQ. ID. NO. 23   T T T A A C T A C A A C A A C C A G A C C A T T A C A G A C

SEQ. ID. NO. 22   C T C A T C G G G T G G T A T G C T G A C A A C T G G T T C
SEQ. ID. NO. 23   C A G A T C T A C C G G C C A T G A A C T C C T C C T C C

SEQ. ID. NO. 22   A A G A C C T A T G A C C C G T C A A T C A A T T G T A C A
SEQ. ID. NO. 23   T T T G A G G G C G T T T C T G G C C A T G T G G T C T T T

SEQ. ID. NO. 22   G T G G A A G A A A T G A C C G A G G C G G T G G A G G G C
SEQ. ID. NO. 23   G A T G C C A G C G G C T C C C G G A T G G C A T G G A C A

SEQ. ID. NO. 22   C A C A T C A C C A C G G A G A T T G T C A T G C T G A A C
SEQ. ID. NO. 23   C T T A T C G A G C A G C T A C A G G G C G G C A G C T A C

SEQ. ID. NO. 22   C C T G C C A A C A C C C G A A G C A T T T C C A A C A T G
SEQ. ID. NO. 23   A A G A A G A T C G G C T A C T A C G A C A G C A C C A A G

SEQ. ID. NO. 22   A C G T C A C A G G A A T T T G T G G A G A A A C T A A C C
SEQ. ID. NO. 23   G A T G A T C T T T C C T G G T C C A A A A C G G A C A A G

SEQ. ID. NO. 22   A A G C G G C T G A A A A G A C A C C C C G A G G A G A C T
SEQ. ID. NO. 23   T G G A T T G G A G G G T C T C C C C A G C T G A C C A G

SEQ. ID. NO. 22   G G A G G C T T C C A G G A G G C A C C A C T G G C C T A T
SEQ. ID. NO. 23   A C C T T G G T C A T C A A G A C A T T C C G T T T C C T G

SEQ. ID. NO. 22   G A T G C T A T C T G G G C C T T G G C T T T G G C C T T G
SEQ. ID. NO. 23   T C T C A G A A A C T C T T T A T C T C C G T C T C A G T T

SEQ. ID. NO. 22   A A C A A G A C G T C T G G A G G A G G T G G T C G T T C C
SEQ. ID. NO. 23   C T C T C C A G C C T G G G C A T T G T T C T T G C T G T T

SEQ. ID. NO. 22   G G C G T G C G C C T G G A G G A C T T T A A C T A C A A C
SEQ. ID. NO. 23   G T C T G T C T G T C C T T T A A C A T C T A C A A C T C C

SEQ. ID. NO. 22   A A C C A G A C C A T T A C A G A C C A G A T C T A C C G G
SEQ. ID. NO. 23   C A C G T T C G T T A T A T C C A G A A C T C C C A G C C C

Figure 6d

SEQ. ID. NO. 22  G C C A T G A A C T C C T C C T C C T T T G A G G G C G T T
SEQ. ID. NO. 23  A A C C T G A A C A A T C T G A C T G C T G T G G G C T G C

SEQ. ID. NO. 22  T C T G G C C A T G T G G T C T T T G A T G C C A G C G G C
SEQ. ID. NO. 23  T C A C T G G C A C T G G C T G C T G T C T T C C C T C T C

SEQ. ID. NO. 22  T C C C G G A T G G C A T G G A C A C T T A T C G A G C A G
SEQ. ID. NO. 23  G G G C T G G A T G G T T A C C A C A T A G G G A G A A G C

SEQ. ID. NO. 22  C T A C A G G G C G G C A G C T A C A A G A A G A T C G G C
SEQ. ID. NO. 23  C A G T T C C C G T T T G T C T G C C A G G C C C G C C T T

SEQ. ID. NO. 22  T A C T A C G A C A G C A C C A A G G A T G A T C T T T C C
SEQ. ID. NO. 23  T G G C T C T T G G G C T T G G G C T T T A G T C T G G C

SEQ. ID. NO. 22  T G G T C C A A A A C G G A C A A G T G G A T T G G A G G G
SEQ. ID. NO. 23  T A T G G C T C T A T G T T C A C C A A G A T C T G G T G G

SEQ. ID. NO. 22  T C T C C C C A G C T G A C C A G A C C T T G G T C A T C
SEQ. ID. NO. 23  G T C C A C A C A G T C T T C A C G A A G A A G G A G G A G

SEQ. ID. NO. 22  A A G A C A T T C C G T T T C C T G T C T C A G A A A C T C
SEQ. ID. NO. 23  A A G A A G G A G T G G A G G A A G A C C C T A G A G C C C

SEQ. ID. NO. 22  T T T A T C T C C G T C T C A G T T C T C T C C A G C C T G
SEQ. ID. NO. 23  T G G A A A C T C T A T G C C A C T G T G G G C C T G C T G

SEQ. ID. NO. 22  G G C A T T G T T C T T G C T G T T G T C T G T C T G T C C
SEQ. ID. NO. 23  G T G G G C A T G G A T G T C C T G A C T C T T G C C A T C

SEQ. ID. NO. 22  T T T A A C A T C T A C A A C T C C C A C G T T C G T T A T
SEQ. ID. NO. 23  T G G C A G A T T G T G G A C C C C T T G C A C C G A A C C

SEQ. ID. NO. 22  A T C C A G A A C T C C C A G C C C A A C C T G A A C A A T
SEQ. ID. NO. 23  A T T G A G A C T T T T G C C A A G G A G G A A C C A A A G

SEQ. ID. NO. 22  C T G A C T G C T G T G G G C T G C T C A C T G G C A C T G
SEQ. ID. NO. 23  G A A G A C A T C G A T G T C T C C A T T C T G C C C C A G

Figure 6e

SEQ. ID. NO. 22   G C T G C T G T C T T C C C T C T C G G G C T G G A T G G T
SEQ. ID. NO. 23   T T G G A G C A C T G C A G C T C C A A G A A G A T G A A T

SEQ. ID. NO. 22   T A C C A C A T A G G G A G A A G C C A G T T C C C G T T T
SEQ. ID. NO. 23   A C G T G G C T T G G C A T T T T C T A T G G T T A C A A G

SEQ. ID. NO. 22   G T C T G C C A G G C C C G C C T T T G G C T C T T G G G C
SEQ. ID. NO. 23   G G G C T G C T G C T G C T G C T G G G A A T C T T T C T T

SEQ. ID. NO. 22   T T G G G C T T T A G T C T G G G C T A T G G C T C T A T G
SEQ. ID. NO. 23   G C T T A C G A A A C C A A G A G C G T G T C C A C T G A A

SEQ. ID. NO. 22   T T C A C C A A G A T C T G G T G G G T C C A C A C A G T C
SEQ. ID. NO. 23   A A G A T C A A T G A C C A C A G G G C C G T G G G C A T G

SEQ. ID. NO. 22   T T C A C G A A G A A G G A G G A G A A G A A G G A G T G G
SEQ. ID. NO. 23   G C T A T C T A C A A T G T C G C G G T C C T G T G T C T C

SEQ. ID. NO. 22   A G G A A G A C C C T A G A G C C C T G G A A A C T C T A T
SEQ. ID. NO. 23   A T C A C T G C T C C T G T G A C C A T G A T C C T T T C C

SEQ. ID. NO. 22   G C C A C T G T G G G C C T G C T G G T G G G C A T G G A T
SEQ. ID. NO. 23   A G T C A G C A G G A C G C A G C C T T T G C C T T T G C C

SEQ. ID. NO. 22   G T C C T G A C T C T T G C C A T C T G G C A G A T T G T G
SEQ. ID. NO. 23   T C T C T G G C C A T C G T G T T C T C T T C C T A C A T C

SEQ. ID. NO. 22   G A C C C C T T G C A C C G A A C C A T T G A G A C T T T T
SEQ. ID. NO. 23   A C T C T G G T T G T G C T C T T T G T G C C C A A G A T G

SEQ. ID. NO. 22   G C C A A G G A G G A A C C A A A G G A A G A C A T C G A T
SEQ. ID. NO. 23   C G C A G G C T G A T C A C C C G A G G G G A A T G G C A G

SEQ. ID. NO. 22   G T C T C C A T T C T G C C C C A G T T G G A G C A C T G C
SEQ. ID. NO. 23   T C T G A A A C G C A G G A C A C C A T G A A A A C A G G A

SEQ. ID. NO. 22   A G C T C C A A G A A G A T G A A T A C G T G G C T T G G C
SEQ. ID. NO. 23   T C A T C C A C C A A C A A C A A C G A G G A A G A G A A G

Figure 6f

SEQ. ID. NO. 22  A T T T T C T A T G G T T A C A A G G G G C T G C T G C T G
SEQ. ID. NO. 23  T C C C G A C T G T T G G A G A A G G A A A A C C G A G A A

SEQ. ID. NO. 22  C T G C T G G G A A T C T T T C T T G C T T A C G A A A C C
SEQ. ID. NO. 23  C T G G A A A A G A T C A T C G C T G A G A A A G A G G A G

SEQ. ID. NO. 22  A A G A G C G T G T C C A C T G A A A A G A T C A A T G A C
SEQ. ID. NO. 23  C G C G T C T C T G A A C T G C G C C A T C A G C T C C A G

SEQ. ID. NO. 22  C A C A G G G C C G T G G G C A T G G C T A T C T A C A A T
SEQ. ID. NO. 23  T C T C G G C A G C A A C T C C G C T C A C G G C G C C A C

SEQ. ID. NO. 22  G T C G C G G T C C T G T G T C T C A T C A C T G C T C C T
SEQ. ID. NO. 23  C C C C C A A C A C C C C A G A T C C C T C T G G G G G C

SEQ. ID. NO. 22  G T G A C C A T G A T C C T T T C C A G T C A G C A G G A C
SEQ. ID. NO. 23  C T T C C C A G G G G A C C C T C T G A G C C C C T G A C

SEQ. ID. NO. 22  G C A G C C T T T G C C T T T G C C T C T C T G G C C A T C
SEQ. ID. NO. 23  C G G C T T A G C T G T G A T G G G A G T C G A G T A C A T

SEQ. ID. NO. 22  G T G T T C T C T T C C T A C A T C A C T C T G G T T G T G
SEQ. ID. NO. 23  T T G C T T T A C A A G

SEQ. ID. NO. 22  C T C T T T G T G C C C A A G A T G C G C A G G C T G A T C
SEQ. ID. NO. 23

SEQ. ID. NO. 22  A C C C G A G G G G A A T G G C A G T C T G A A A C G C A G
SEQ. ID. NO. 23

SEQ. ID. NO. 22  G A C A C C A T G A A A A C A G G A T C A T C C A C C A A C
SEQ. ID. NO. 23

SEQ. ID. NO. 22  A A C A A C G A G G A A G A G A A G T C C C G A C T G T T G
SEQ. ID. NO. 23

SEQ. ID. NO. 22  G A G A A G G A A A A C C G A G A A C T G G A A A A G A T C
SEQ. ID. NO. 23

Figure 6g

SEQ. ID. NO. 22  A T C G C T G A G A A A G A G G A G C G C G T C T C T G A A
SEQ. ID. NO. 23

SEQ. ID. NO. 22  C T G C G C C A T C A G C T C C A G T C T C G G C A G C A A
SEQ. ID. NO. 23

SEQ. ID. NO. 22  C T C C G C T C A C G G C G C C A C C C C C A A C A C C C
SEQ. ID. NO. 23

SEQ. ID. NO. 22  C C A G A T C C C T C T G G G G G C C T T C C C A G G G G A
SEQ. ID. NO. 23

SEQ. ID. NO. 22  C C C T C T G A G C C C C C T G A C C G G C T T A G C T G T
SEQ. ID. NO. 23

SEQ. ID. NO. 22  G A T G G G A G T C G A G T A C A T T T G C T T T A C A A G
SEQ. ID. NO. 23

Figure 6h

SEQ. ID. NO. 24  M L L L L L V P L F L R P L G A G G A Q T P N A T S E G C Q
SEQ. ID. NO. 25  M G P G G P C T P V G W P L P L L L V M A A G V A P V W A S

SEQ. ID. NO. 24  I I H P P W E G G I R Y R G L T R D Q V K A I N F L P V D Y
SEQ. ID. NO. 25  H S P H L P R P H P R V P P H P S S E R R A V Y I G A L F P

SEQ. ID. NO. 24  E I E Y V C R G E R E V V G P K V R K C L A N G S W T D M D
SEQ. ID. NO. 25  M S G G W P G G Q A C Q P A V E M A L E D V N S R R D I L P

SEQ. ID. NO. 24  T P S R C V R I C S K S Y L T L E N G K V F L T G G D L P A
SEQ. ID. NO. 25  D Y E L K L I H H D S K C D P G Q A T K Y L Y E L L Y N D P

SEQ. ID. NO. 24  L D G A R V E F R C D P D F H L V G S S R S V C S Q G Q W S
SEQ. ID. NO. 25  I K I I L M P G C S S V S T L V A E A A R M W N L I V L S Y

SEQ. ID. NO. 24  T P K P H C Q V N R T P H S E R R A V Y I G A L F P M S G G
SEQ. ID. NO. 25  G S S S P A L S N R Q R F P T F F R T H P S A T L H N P T R

SEQ. ID. NO. 24  W P G G Q A C Q P A V E M A L E D V N S R R D I L P D Y E L
SEQ. ID. NO. 25  V K L F E K W G W K K I A T I Q Q T T E V F T S T L D D L E

SEQ. ID. NO. 24  K L I H H D S K C D P G Q A T K Y L Y E L L Y N D P I K I I
SEQ. ID. NO. 25  E R V K E A G I E I T F R Q S F F S D P A V P V K N L K R Q

SEQ. ID. NO. 24  L M P G C S S V S T L V A E A A R M W N L I V L S Y G S S S
SEQ. ID. NO. 25  D A R I I V G L F Y E T E A R K V F C E V Y K E R L F G K K

SEQ. ID. NO. 24  P A L S N R Q R F P T F F R T H P S A T L H N P T R V K L F
SEQ. ID. NO. 25  Y V W F L I G W Y A D N W F K T Y D P S I N C T V E E M T E

SEQ. ID. NO. 24  E K W G W K K I A T I Q Q T T E V F T S T L D D L E E R V K
SEQ. ID. NO. 25  A V E G H I T T E I V M L N P A N T R S I S N M T S Q E F V

SEQ. ID. NO. 24  E A G I E I T F R Q S F F S D P A V P V K N L K R Q D A R I
SEQ. ID. NO. 25  E K L T K R L K R H P E E T G G F Q E A P L A Y D A I W A L

Figure 7a

SEQ. ID. NO. 24  I V G L F Y E T E A R K V F C E V Y K E R L F G K K Y V W F
SEQ. ID. NO. 25  A L A L N K T S G G G G R S G V R L E D F N Y N N Q T I T D

SEQ. ID. NO. 24  L I G W Y A D N W F K T Y D P S I N C T V E E M T E A V E G
SEQ. ID. NO. 25  Q I Y R A M N S S S F E G V S G H V V F D A S G S R M A W T

SEQ. ID. NO. 24  H I T T E I V M L N P A N T R S I S N M T S Q E F V E K L T
SEQ. ID. NO. 25  L I E Q L Q G G S Y K K I G Y Y D S T K D D L S W S K T D K

SEQ. ID. NO. 24  K R L K R H P E E T G G F Q E A P L A Y D A I W A L A L A L
SEQ. ID. NO. 25  W I G G S P P A D Q I L V I K T F R F L S Q K L F I S V S V

SEQ. ID. NO. 24  N K T S G G G G R S G V R L E D F N Y N N Q T I T D Q I Y R
SEQ. ID. NO. 25  L S S L G I V L A V V C L S F N I Y N S H V R Y I Q N S Q P

SEQ. ID. NO. 24  A M N S S S F E G V S G H V V F D A S G S R M A W T L I E Q
SEQ. ID. NO. 25  N L N N L T A V G C S L A L A A V F P L G L D G Y H I G R S

SEQ. ID. NO. 24  L Q G G S Y K K I G Y Y D S T K D D L S W S K T D K W I G G
SEQ. ID. NO. 25  Q F P F V C Q A R L W L L G L G F S L G Y G S M F T K I W W

SEQ. ID. NO. 24  S P P A D Q I L V I K T F R F L S Q K L F I S V S V L S S L
SEQ. ID. NO. 25  V H T V F T K K E E K K E W R K T L E P W K L Y A T V G L L

SEQ. ID. NO. 24  G I V L A V V C L S F N I Y N S H V R Y I Q N S Q P N L N N
SEQ. ID. NO. 25  V G M D V L T L A I W Q I V D P L H R T I E T F A K E E P K

SEQ. ID. NO. 24  L T A V G C S L A L A A V F P L G L D G Y H I G R S Q F P F
SEQ. ID. NO. 25  E D I D V S I L P Q L E H C S S K K M N T W L G I F Y G Y K

SEQ. ID. NO. 24  V C Q A R L W L L G L G F S L G Y G S M F T K I W W V H T V
SEQ. ID. NO. 25  G L L L L L G I F L A Y E T K S V S T E K I N D H R A V G M

SEQ. ID. NO. 24  F T K K E E K K E W R K T L E P W K L Y A T V G L L V G M D
SEQ. ID. NO. 25  A I Y N V A V L C L I T A P V T M I L S S Q Q D A A F A F A

SEQ. ID. NO. 24  V L T L A I W Q I V D P L H R T I E T F A K E E P K E D I D
SEQ. ID. NO. 25  S L A I V F S S Y I T L V V L F V P K M R R L I T R G E W Q

Figure 7b

SEQ. ID. NO. 24  V S I L P Q L E H C S S K K M N T W L G I F Y G Y K G L L L
SEQ. ID. NO. 25  S E T Q D T M K T G S S T N N N E E E K S R L L E K E N R E

SEQ. ID. NO. 24  L L G I F L A Y E T K S V S T E K I N D H R A V G M A I Y N
SEQ. ID. NO. 25  L E K I I A E K E E R V S E L R H Q L Q S R Q Q L R S R R H

SEQ. ID. NO. 24  V A V L C L I T A P V T M I L S S Q Q D A A F A F A S L A I
SEQ. ID. NO. 25  P P T P P D P S G G L P R G P S E P P D R L S C D G S R V H

SEQ. ID. NO. 24  V F S S Y I T L V V L F V P K M R R L I T R G E W Q S E T Q
SEQ. ID. NO. 25  L L Y K

SEQ. ID. NO. 24  D T M K T G S S T N N N E E E K S R L L E K E N R E L E K I
SEQ. ID. NO. 25

SEQ. ID. NO. 24  I A E K E E R V S E L R H Q L Q S R Q Q L R S R R H P P T P
SEQ. ID. NO. 25

SEQ. ID. NO. 24  P D P S G G L P R G P S E P P D R L S C D G S R V H L L Y K
SEQ. ID. NO. 25

Figure 7c

ClustalW Formatted Alignments

```
SEQ. ID. NO. 38   A T G G T A T G C G A G G G A A A G C G A T C A G
SEQ. ID. NO. 34   A T G G G A T C G C T G C T T G C G C T C C C G G
SEQ. ID. NO. 30   A T G G C A T T T T A T A G C T G C T G C T G G G
SEQ. ID. NO. 26   A T G G G A T C G C T G C T T G C G C T C C T G G

SEQ. ID. NO. 38   C C T C T T G C C C T T G T T T C T T C C T C T T
SEQ. ID. NO. 34   C A C T G C T G C T G C T G T G G G G T G C T G T
SEQ. ID. NO. 30   T C C T C T T G G C A C T C A C C T G G C A C A C
SEQ. ID. NO. 26   C A C T G C T G C C G C T G T G G G G T G C T G T

SEQ. ID. NO. 38   G A C C G C C A A G T T C T A C T G G A T C C T C
SEQ. ID. NO. 34   G G C T G A G G G C C C A G C C A A G A A G G T G
SEQ. ID. NO. 30   C T C T G C C T A C G G G C C A G A C C A G C G A
SEQ. ID. NO. 26   G G C T G A G G G C C C A G C C A A G A A G G T G

SEQ. ID. NO. 38   A C A A T G A T G C A A A G A A C T C A C A G C C
SEQ. ID. NO. 34   C T G A C C C T G G A G G G A G A C T T G G T G C
SEQ. ID. NO. 30   G C C C A A A A G A A G G G G G A C A T T A T C C
SEQ. ID. NO. 26   C T G A C C C T G G A G G G A G A C T T G G T G C

SEQ. ID. NO. 38   A G G A G T A T G C C C A T T C C A T A C G G G T
SEQ. ID. NO. 34   T G G G T G G G C T G T T C C C A G T G C A C C A
SEQ. ID. NO. 30   T T G G G G G G C T C T T T C C T A T T C A T T T
SEQ. ID. NO. 26   T G G G T G G G C T G T T C C C A G T G C A C C A

SEQ. ID. NO. 38   G G A T G G G G A C A T T A T T T T G G G G G G T
SEQ. ID. NO. 34   G A A G G G C G G C C C A G C A G A G G A C T G T
SEQ. ID. NO. 30   T G G A G T A G C A G C T A A A G A T C A A G A T
SEQ. ID. NO. 26   G A A G G G C G G C C C A G C A G A G G A C T G T

SEQ. ID. NO. 38   C T C T T C C C T G T C C A C G C A A A G G G A G
SEQ. ID. NO. 34   G G T C C T G T C A A T G A G C A C C G T G G C A
SEQ. ID. NO. 30   C T C A A A T C A A G G C C G G A G T C T G T G G
SEQ. ID. NO. 26   G G T C C T G T C A A T G A G C A C C G T G G C A

SEQ. ID. NO. 38   A G A G A G G G G T G C C T T G T G G G G A G C T
SEQ. ID. NO. 34   T C C A G C G C C T G G A G G C C A T G C T T T T
SEQ. ID. NO. 30   A A T G T A T C A G G T A T A A T T T C C G T G G
SEQ. ID. NO. 26   T C C A G C G C C T G G A G G C C A T G C T T T T
```

Figure 9a

SEQ. ID. NO. 38  G A A G A A G G A A A A G G G G A T T C A C A G A
SEQ. ID. NO. 34  T G C A C T G G A C C G C A T C A A C C G T G A C
SEQ. ID. NO. 30  G T T T C G C T G G T T A C A G G C T A T G A T A
SEQ. ID. NO. 26  T G C A C T G G A C C G C A T C A A C C G T G A C

SEQ. ID. NO. 38  C T G G A G G C C A T G C T T T A T G C A A T T G
SEQ. ID. NO. 34  C C G C A C C T G C T G C C T G G C G T G C G C C
SEQ. ID. NO. 30  T T T G C C A T A G A G G A G A T A A A C A G C A
SEQ. ID. NO. 26  C C G C A C C T G C T G C C T G G C G T G C G C C

SEQ. ID. NO. 38  A C C A G A T T A A C A A G G A C C C T G A T C T
SEQ. ID. NO. 34  T G G G T G C A C A C A T C C T C G A C A G T T G
SEQ. ID. NO. 30  G C C C A G C C C T T C T T C C C A A C T T G A C
SEQ. ID. NO. 26  T G G G T G C A C A C A T C C T C G A C A G T T G

SEQ. ID. NO. 38  C C T T T C C A A C A T C A C T C T G G G T G T C
SEQ. ID. NO. 34  C T C C A A G G A C A C A C A T G C G C T G G A G
SEQ. ID. NO. 30  G C T G G G A T A C A G G A T A T T T G A C A C T
SEQ. ID. NO. 26  C T C C A A G G A C A C A C A T G C G C T G G A G

SEQ. ID. NO. 38  C G C A T C C T C G A C A C G T G C T C T A G G G
SEQ. ID. NO. 34  C A G G C A C T G G A C T T T G T G C G T G C C T
SEQ. ID. NO. 30  T G C A A C A C C G T T T C T A A G G C C T T G G
SEQ. ID. NO. 26  C A G G C A C T G G A C T T T G T G C G T G C C T

SEQ. ID. NO. 38  A C A C C T A T G C T T T G G A G C A G T C T C T
SEQ. ID. NO. 34  C A C T C A G C C G T G G T G C T G A T G G C T C
SEQ. ID. NO. 30  A A G C C A C C C T G A G T T T T G T T G C T C A
SEQ. ID. NO. 26  C A C T C A G C C G T G G T G C T G A T G G A T C

SEQ. ID. NO. 38  A A C A T T C G T G C A G G C A T T A A T A G A G
SEQ. ID. NO. 34  A C G C C A C A T C T G C C C C G A C G G C T C T
SEQ. ID. NO. 30  A A A C A A A A T T G A T T C T T T G A A C C T T
SEQ. ID. NO. 26  A C G C C A C A T C T G C C C C G A C G G C T C T

SEQ. ID. NO. 38  A A A G A T G C T T C G G A T G T G A A G T G T G
SEQ. ID. NO. 34  T A T G C G A C C C A T G G T G A T G C T C C C A
SEQ. ID. NO. 30  G A T G A G T T C T G C A A C T G C T C A G A G C
SEQ. ID. NO. 26  T A T G C G A C C C A T G G T G A T G C T C C C A

Figure 9b

| | |
|---|---|
| SEQ. ID. NO. 38 | C T A A T G G A G A T C C A C C C A T T T T C A C |
| SEQ. ID. NO. 34 | C T G C C A T C A C T G G T G T T A T T G G C G G |
| SEQ. ID. NO. 30 | A C A T T C C C T C T A C G A T T G C T G T G G T |
| SEQ. ID. NO. 26 | C T G C C A T C A C T G G T G T T A T T G G C G G |
| | |
| SEQ. ID. NO. 38 | C A A G C C C G A C A A G A T T T C T G G C G T C |
| SEQ. ID. NO. 34 | T T C C T A C A G T G A T G T C T C C A T C C A G |
| SEQ. ID. NO. 30 | G G G A G C A A C T G G C T C A G G C G T C T C C |
| SEQ. ID. NO. 26 | T T C C T A C A G T G A T G T C T C C A T C C A G |
| | |
| SEQ. ID. NO. 38 | A T A G G T G C T G C A G C A A G C T C C G T G T |
| SEQ. ID. NO. 34 | G T G G C C A A C C T C T T G A G G C T A T T T C |
| SEQ. ID. NO. 30 | A C G G C A G T G G C A A A T C T G C T G G G G C |
| SEQ. ID. NO. 26 | G T G G C C A A C C T C T T G A G G C T A T T T C |
| | |
| SEQ. ID. NO. 38 | C C A T C A T G G T T G C T A A C A T T T T A A G |
| SEQ. ID. NO. 34 | A G A T C C C A C A G A T T A G C T A C G C C T C |
| SEQ. ID. NO. 30 | T C T T C T A C A T T C C C C A G G T C A G T T A |
| SEQ. ID. NO. 26 | A G A T C C C A C A G A T T A G C T A C G C C T C |
| | |
| SEQ. ID. NO. 38 | A C T T T T T A A G A T A C C T C A A A T C A G C |
| SEQ. ID. NO. 34 | T A C C A G T G C C A A G C T G A G T G A C A A G |
| SEQ. ID. NO. 30 | T G C C T C C T C C A G C A G A C T C C T C A G C |
| SEQ. ID. NO. 26 | T A C C A G T G C C A A G C T G A G T G A C A A G |
| | |
| SEQ. ID. NO. 38 | T A T G C A T C C A C A G C C C A G A G C T A A |
| SEQ. ID. NO. 34 | T C C C G C T A T G A C T A C T T T G C C C G C A |
| SEQ. ID. NO. 30 | A A C A A G A A T C A A T T C A A G T C T T T C C |
| SEQ. ID. NO. 26 | T C C C G C T A T G A C T A C T T T G C C C G C A |
| | |
| SEQ. ID. NO. 38 | G T G A T A A C A C C A G G T A T G A C T T T T T |
| SEQ. ID. NO. 34 | C A G T G C C T C C T G A C T T C T T C C A A G C |
| SEQ. ID. NO. 30 | T C C G A A C C A T C C C A A T G A T G A G C A |
| SEQ. ID. NO. 26 | C A G T G C C T C C T G A C T T C T T C C A A G C |
| | |
| SEQ. ID. NO. 38 | C T C T C G A G T G G T T C C G C C T G A C T C C |
| SEQ. ID. NO. 34 | C A A G G C C A T G G C T G A G A T T C T C C G C |
| SEQ. ID. NO. 30 | C C A G G C C A C T G C C A T G G C A G A C A T C |
| SEQ. ID. NO. 26 | C A A G G C C A T G G C T G A G A T T C T C C G C |

Figure 9c

SEQ. ID. NO. 38   T A C C A A G C C C A A G C C A T G G T G G A C A
SEQ. ID. NO. 34   T T C T T C A A C T G G A C C T A T G T G T C C A
SEQ. ID. NO. 30   A T C G A G T A T T T C C G C T G G A A C T G G G
SEQ. ID. NO. 26   T T C T T C A A C T G G A C C T A T G T G T C C A

SEQ. ID. NO. 38   T C G T G A C A G C A C T G G G A T G G A A T T A
SEQ. ID. NO. 34   C T G T G G C G T C T G A G G G C G A C T A T G G
SEQ. ID. NO. 30   T G G G C A C A A T T G C A G C T G A T G A C G A
SEQ. ID. NO. 26   C T G A G G C C T C T G A G G G C G A C T A T G G

SEQ. ID. NO. 38   T G T T T C G A C A C T G G C T T C T G A G G G G
SEQ. ID. NO. 34   C G A G A C A G G C A T T G A G G C C T T T G A G
SEQ. ID. NO. 30   C T A T G G G C G G C C G G G G A T T G A G A A A
SEQ. ID. NO. 26   C G A G A C A G G C A T T G A G G C C T T T G A G

SEQ. ID. NO. 38   A A C T A T G G T G A G A G C G G T G T G G A G G
SEQ. ID. NO. 34   C T A G A G G C T C G T G C C C G C A A C A T C T
SEQ. ID. NO. 30   T T C C G A G A G G A A G C T G A G G A A A G G G
SEQ. ID. NO. 26   C T A G A G G C T C G T G C C C G C A A C A T C T

SEQ. ID. NO. 38   C C T T C A C C C A G A T C T C G A G G G A G A T
SEQ. ID. NO. 34   G T G T G G C C A C C T C G G A G A A A G T G G G
SEQ. ID. NO. 30   A T A T C T G C A T C G A C T T C A G T G A A C T
SEQ. ID. NO. 26   G T G T G G C C A C C T C G G A G A A A G T G G G

SEQ. ID. NO. 38   T G G T G G T G T T T G C A T T G C T C A G T C A
SEQ. ID. NO. 34   C C G T G C C A T G A G C C G C G C G G C C T T T
SEQ. ID. NO. 30   C A T C T C C C A G T A C T C T G A T G A G G A A
SEQ. ID. NO. 26   C C G T G C C A T G A G C C G C G C G G C C T T T

SEQ. ID. NO. 38   C A G A A A A T C C C A C G T G A A C C A A G A C
SEQ. ID. NO. 34   G A G G G T G T G G T G C G A G C C C T G C T G C
SEQ. ID. NO. 30   G A G A T C C A G C A T G T G G T A G A G G T G A
SEQ. ID. NO. 26   G A G G G T G T G G T G C G A G C C C T G C T G C

SEQ. ID. NO. 38   C T G G A G A A T T T G A A A A A A T T A T C A A
SEQ. ID. NO. 34   A G A A G C C C A G T G C C C G C G T G G C T G T
SEQ. ID. NO. 30   T T C A A A A T T C C A C G G C C A A A G T C A T
SEQ. ID. NO. 26   A G A A G C C C A G T G C C C G C G T G G C T G T

Figure 9d

SEQ. ID. NO. 38  A C G C C T G C T A G A A A C A C C T A A T G C T
SEQ. ID. NO. 34  C C T G T T C A C C C G T T C T G A G G A T G C C
SEQ. ID. NO. 30  C G T G G T T T T C T C C A G T G G C C C A G A T
SEQ. ID. NO. 26  C C T G T T C A C C C G T T C T G A G G A T G C C

SEQ. ID. NO. 38  C G A G C A G T G A T T A T G T T T G C C A A T G
SEQ. ID. NO. 34  C G G G A G C T G C T T G C T G C C A G C C A G C
SEQ. ID. NO. 30  C T T G A G C C C C T C A T C A A G G A G A T T G
SEQ. ID. NO. 26  C G G G A G C T G C T T G C T G C C A G C C A G C

SEQ. ID. NO. 38  A G G A T G A C A T C A G G A G G A T A T T G G A
SEQ. ID. NO. 34  G C C T C A A T G C C A G C T T C A C C T G G G T
SEQ. ID. NO. 30  T C C G G C G C A A T A T C A C G G G C A A G A T
SEQ. ID. NO. 26  G C C T C A A T G C C A G C T T C A C C T G G G T

SEQ. ID. NO. 38  A G C A G C A A A A A A C T A A A C C A A A G T
SEQ. ID. NO. 34  G G C C A G T G A T G G T T G G G G G G C C C T G
SEQ. ID. NO. 30  C T G G C T G G C C A G C G A G G C C T G G G C C
SEQ. ID. NO. 26  G G C C A G T G A T G G T T G G G G G G C C C T G

SEQ. ID. NO. 38  G G G C A T T T T C T C T G G A T T G G C T C A G
SEQ. ID. NO. 34  G A G A G T G T G G T G G C A G G C A G T G A G G
SEQ. ID. NO. 30  A G C T C C T C C C T G A T C G C C A T G C C T C
SEQ. ID. NO. 26  G A G A G T G T G G T G G C A G G C A G T G A G G

SEQ. ID. NO. 38  A T A G T T G G G G A T C C A A A A T A G C A C C
SEQ. ID. NO. 34  G G G C T G C T G A G G G T G C T A T C A C C A T
SEQ. ID. NO. 30  A G T A C T T C C A C G T G G T T G G C G G C A C
SEQ. ID. NO. 26  G G G C T G C T G A G G G T G C T A T C A C C A T

SEQ. ID. NO. 38  T G T C T A T C A G C A A G A G G A G A T T G C A
SEQ. ID. NO. 34  C G A G C T G G C C T C C T A C C C C A T C A G T
SEQ. ID. NO. 30  C A T T G G A T T C G C T C T G A A G G C T G G G
SEQ. ID. NO. 26  C G A G C T G G C C T C C T A C C C C A T C A G T

SEQ. ID. NO. 38  G A A G G G G C T G T G A C A A T T T T G C C C A
SEQ. ID. NO. 34  G A C T T T G C C T C C T A C T T C C A G A G C C
SEQ. ID. NO. 30  C A G A T C C C A G G C T T C C G G G A A T T C C
SEQ. ID. NO. 26  G A C T T T G C C T C C T A C T T C C A G A G C C

Figure 9e

SEQ. ID. NO. 38  A A C G A G C A T C A A T T G A T G G A T T T G A
SEQ. ID. NO. 34  T G G A C C C T T G G A A C A A C A G C C G G A A
SEQ. ID. NO. 30  T G A A G A A G G T C C A T C C C A G G A A G T C
SEQ. ID. NO. 26  T G G A C C C T T G G A A C A A C A G C C G G A A

SEQ. ID. NO. 38  T C G A T A C T T T A G A A G C C G A A C T C T T
SEQ. ID. NO. 34  C C C C T G G T T C C G T G A A T T C T G G G A G
SEQ. ID. NO. 30  T G T C C A C A A T G G T T T T G C C A A G G A G
SEQ. ID. NO. 26  C C C C T G G T T C C G T G A A T T C T G G G A G

SEQ. ID. NO. 38  G C C A A T A A T C G A A G A A A T G T G T G G T
SEQ. ID. NO. 34  C A G A G G T T C C G C T G C A G C T T C C G G C
SEQ. ID. NO. 30  T T T T G G G A A G A A A C A T T T A A C T G C C
SEQ. ID. NO. 26  C A G A G G T T C C G C T G C A G C T T C C G G C

SEQ. ID. NO. 38  T T G C A G A A T T C T G G G A G G A G A A T T T
SEQ. ID. NO. 34  A G C G A G A C T G C G C A G C C C A C T C T C T
SEQ. ID. NO. 30  A C C T C C A A G A A G G T G C A A A A G G A C C
SEQ. ID. NO. 26  A G C G A G A C T G C G C A G C C C A C T C T C T

SEQ. ID. NO. 38  T G G C T G C A A G T T A G G A T C A C A T G G G
SEQ. ID. NO. 34  C C G G G C T G T G C C C T T T G A G C A G G A G
SEQ. ID. NO. 30  T T T A C C T G T G G A C A C C T T T C T G A G A
SEQ. ID. NO. 26  C C G G G C T G T G C C C T T T G A A C A G G A G

SEQ. ID. NO. 38  A A A A G G A A C A G T C A T A T A A A G A A A T
SEQ. ID. NO. 34  T C C A A G A T C A T G T T T G T G G T C A A T G
SEQ. ID. NO. 30  G G T C A C G A A G A A A G T G G C G A C A G G T
SEQ. ID. NO. 26  T C C A A G A T C A T G T T T G T G G T C A A T G

SEQ. ID. NO. 38  G C A C A G G G C T G G A G C G A A T T G C T C G
SEQ. ID. NO. 34  C A G T G T A C G C C A T G G C C C A T G C G C T
SEQ. ID. NO. 30  T T A G C A A C A G C T C G A C A G C C T T C C G
SEQ. ID. NO. 26  C A G T G T A C G C C A T G G C C C A T G C G C T

SEQ. ID. NO. 38  G G A T T C A T C T T A T G A A C A G G A A G G A
SEQ. ID. NO. 34  C C A C A A C A T G C A C C G T G C C C T C T G C
SEQ. ID. NO. 30  A C C C C T C T G T A C A G G G G A T G A G A A C
SEQ. ID. NO. 26  C C A C A A C A T G C A C C G T G C C C T C T G C

Figure 9f

SEQ. ID. NO. 38  A A G G T C C A A T T T G T A A T T G A T G C T G
SEQ. ID. NO. 34  C C C A A C A C C A C C C G G C T C T G T G A C G
SEQ. ID. NO. 30  A T C A G C A G T G T C G A G A C C C C T T A C A
SEQ. ID. NO. 26  C C C A A C A C C A C C C G G C T C T G T G A C G

SEQ. ID. NO. 38  T A T A T T C C A T G G C T T A C G C C C T G C A
SEQ. ID. NO. 34  C G A T G C G G C C A G T T A A C G G G C G C C G
SEQ. ID. NO. 30  T A G A T T A C A C G C A T T T A C G G A T A T C
SEQ. ID. NO. 26  C G A T G C G G C C A G T T A A C G G G C G C C G

SEQ. ID. NO. 38  C A A T A T G C A C A A A G A T C T C T G C C C T
SEQ. ID. NO. 34  C C T C T A C A A G G A C T T T G T G C T C A A C
SEQ. ID. NO. 30  C T A C A A T G T G T A C T T A G C A G T C T A C
SEQ. ID. NO. 26  C C T C T A C A A G G A C T T T G T G C T C A A C

SEQ. ID. NO. 38  G G A T A C A T T G G C C T T T G T C C A C G A A
SEQ. ID. NO. 34  G T C A A G T T T G A T G C C C C C T T T C G C C
SEQ. ID. NO. 30  T C C A T T G C C C A C G C C T T G C A A G A T A
SEQ. ID. NO. 26  G T C A A G T T T G A T G C C C C C T T T C G C C

SEQ. ID. NO. 38  T G A G T A C C A T T G A T G G G A A A G A G C T
SEQ. ID. NO. 34  C A G C T G A C A C C C A C A A T G A G G T C C G
SEQ. ID. NO. 30  T A T A T A C C T G C T T A C C T G G G A G A G G
SEQ. ID. NO. 26  C A G C T G A C A C C C A C A A T G A G G T C C G

SEQ. ID. NO. 38  A C T T G G T T A T A T T C G G G C T G T A A A T
SEQ. ID. NO. 34  C T T T G A C C G C T T T G G T G A T G G T A T T
SEQ. ID. NO. 30  G C T C T T C A C C A A T G G C T C C T G T G C A
SEQ. ID. NO. 26  C T T T G A C C G C T T T G G T G A T G G T A T T

SEQ. ID. NO. 38  T T T A A T G G C A G T G C T G G C A C T C C T G
SEQ. ID. NO. 34  G G C C G C T A C A A C A T C T T C A C C T A T C
SEQ. ID. NO. 30  G A C A T C A A G A A A G T T G A G G C G T G G C
SEQ. ID. NO. 26  G G C C G C T A C A A C A T C T T C A C C T A T C

SEQ. ID. NO. 38  T C A C T T T T A A T G A A A A C G G A G A T G C
SEQ. ID. NO. 34  T G C G T G C A G G C A G T G G G C G C T A T C G
SEQ. ID. NO. 30  A G G T C C T G A A G C A C C T A C G G C A T C T
SEQ. ID. NO. 26  T G C G T G C A G G C A G T G G G C G C T A T C G

Figure 9g

SEQ. ID. NO. 38  T C C T G G A C G T T A T G A T A T C T T C C A G
SEQ. ID. NO. 34  C T A C C A G A A G G T G G G C T A C T G G G C A
SEQ. ID. NO. 30  A A A C T T T A C A A A C A A T A T G G G G G A G
SEQ. ID. NO. 26  C T A C C A G A A G G T G G G C T A C T G G G C A

SEQ. ID. NO. 38  T A T C A A A T A A C C A A C A A A A G C A C A G
SEQ. ID. NO. 34  G A A G G C T T G A C T C T G G A C A C C A G C C
SEQ. ID. NO. 30  C A G G T G A C C T T T G A T G A G T G T G G T G
SEQ. ID. NO. 26  G A A G G C T T G A C T C T G G A C A C C A G C C

SEQ. ID. NO. 38  A G T A C A A A G T C A T C G G C C A C T G G A C
SEQ. ID. NO. 34  T C A T C C C A T G G G C C T C A C C C T C A G C
SEQ. ID. NO. 30  A C C T G G T G G G G A A C T A T T C C A T C A T
SEQ. ID. NO. 26  T C A T C C C A T G G G C C T C A C C G T C A G C

SEQ. ID. NO. 38  C A A T C A G C T T C A T C T A A A A G T G G A A
SEQ. ID. NO. 34  C G G C C C C C T G C C C G C C T C T C G C T G C
SEQ. ID. NO. 30  C A A C T G G C A C C T C T C C C A G A G G A T
SEQ. ID. NO. 26  C G G C C C C C T G G C C G C C T C T C G C T G C

SEQ. ID. NO. 38  G A C A T G C A G T G G G C T C A T A G A G A A C
SEQ. ID. NO. 34  A G T G A G C C C T G C C T C C A G A A T G A G G
SEQ. ID. NO. 30  G G C T C C A T C G T G T T T A A G G A A G T C G
SEQ. ID. NO. 26  A G T G A G C C C T G C C T C C A G A A T G A G G

SEQ. ID. NO. 38  A T A C T C A C C C G G C G T C T G T C T G C A G
SEQ. ID. NO. 34  T G A A G A G T G T G C A G C C G G G C G A A G T
SEQ. ID. NO. 30  G G T A T T A C A A C G T C T A T G C C A A G A A
SEQ. ID. NO. 26  T G A A G A G T G T G C A G C C G G G C G A A G T

SEQ. ID. NO. 38  C C T G C C G T G T A A G C C A G G G G A G A G G
SEQ. ID. NO. 34  C T G C T G C T G G C T C T G C A T T C C G T G C
SEQ. ID. NO. 30  G G G A G A A A G A C T C T T C A T C A A C G A G
SEQ. ID. NO. 26  C T G C T G C T G G C T C T G C A T T C C G T G C

SEQ. ID. NO. 38  A A G A A A A C G G T G A A A G G G G T C C C T T
SEQ. ID. NO. 34  C A G C C C T A T G A G T A C C G A T T G G A C G
SEQ. ID. NO. 30  G A G A A A A T C C T G T G G A G T G G G T T C T
SEQ. ID. NO. 26  C A G C C C T A T G A G T A C C G A T T G G A C G

Figure 9h

SEQ. ID. NO. 38  G C T G C T G G C A C T G T G A A C G C T G T G A
SEQ. ID. NO. 34  A A T T C A C T T G C G C T G A T T G T G G C C T
SEQ. ID. NO. 30  C C A G G G A G G T G C C C T T C T C C A A C T G
SEQ. ID. NO. 26  A A T T C A C T T G C G C T G A T T G T G G C C T

SEQ. ID. NO. 38  A G G T T A C A A C T A C C A G G T G G A T G A G
SEQ. ID. NO. 34  G G G C T A C T G G C C C A A T G C C A G C C T G
SEQ. ID. NO. 30  C A G C C G A G A C T G C C T G G C A G G G A C C
SEQ. ID. NO. 26  G G G C T A C T G G C C C A A T G C C A G C C T G

SEQ. ID. NO. 38  C T G T C C T G T G A A C T T T G C C C T C T G G
SEQ. ID. NO. 34  A C T G G C T G C T T C G A A C T G C C C C A G G
SEQ. ID. NO. 30  A G G A A A G G G A T C A T T G A G G G G A G C
SEQ. ID. NO. 26  A C T G G C T G C T T C G A A C T G C C C C A G G

SEQ. ID. NO. 38  A T C A G A G A C C C A A C A T G A A C C G C A C
SEQ. ID. NO. 34  A G T A C A T C C G C T G G G G C G A T G C C T G
SEQ. ID. NO. 30  C C A C C T G C T G C T T T G A G T G T G T G G A
SEQ. ID. NO. 26  A G T A C A T C C G C T G G G G C G A T G C C T G

SEQ. ID. NO. 38  A G G C T G C C A G C T T A T C C C C A T C A T C
SEQ. ID. NO. 34  G G C T G T G G G A C C T G T C A C C A T C G C C
SEQ. ID. NO. 30  G T G T C C T G A T G G G G A G T A T A G T G A T
SEQ. ID. NO. 26  G G C T G T G G G A C C T G T C A C C A T C G C C

SEQ. ID. NO. 38  A A A T T G G A G T G G C A T T C T C C C T G G G
SEQ. ID. NO. 34  T G C C T C G G T G C C C T G G C C A C C C T C T
SEQ. ID. NO. 30  G A G A C A G A T G C C A G T G C C T G T A A C A
SEQ. ID. NO. 26  T G C C T C G G T G C C C T G G C C A C C C T G T

SEQ. ID. NO. 38  C T G T G G T G C C T G T G T T T G T T G C A A T
SEQ. ID. NO. 34  T T G T G C T G G G T G T C T T T G T G C G G C A
SEQ. ID. NO. 30  A G T G C C C A G A T G A C T T C T G G T C C A A
SEQ. ID. NO. 26  T T G T G C T G G G T G T C T T T G T G C G G C A

SEQ. ID. NO. 38  A T T G G G A A T C A T C G C C A C C A C C T T T
SEQ. ID. NO. 34  C A A T G C C A C A C C A G T G G T C A A G G C C
SEQ. ID. NO. 30  T G A G A A C C A C A C C T C C T G C T T C G A A
SEQ. ID. NO. 26  C A A T G C C A C A C C A G T G G T C A A G G C C

Figure 9i

| | |
|---|---|
| SEQ. ID. NO. 38 | G T G A T C G T G A C C T T T G T C C G C T A T A |
| SEQ. ID. NO. 34 | T C A G G T C G G G A G C T C T G C T A C A T C C |
| SEQ. ID. NO. 30 | C T G C C C C A G G A G T A C A T C C G C T G G G |
| SEQ. ID. NO. 26 | T C A G G T C G G G A G C T C T G C T A C A T C C |

| | |
|---|---|
| SEQ. ID. NO. 38 | A T G A C A C C T A T C G T G A G G G C T T C |
| SEQ. ID. NO. 34 | T G C T G G G T G G T G T C T T C C T C T G C T A |
| SEQ. ID. NO. 30 | G C G A T G C C T G G G C T G T G G G A C C T G T |
| SEQ. ID. NO. 26 | T G C T G G G T G G T G T C T T C C T C T G C T A |

| | |
|---|---|
| SEQ. ID. NO. 38 | A G G A C G C G A A C T A G T T A C G T G C T C |
| SEQ. ID. NO. 34 | C T G C A T G A C C T T C A T C T T C A T T G C C |
| SEQ. ID. NO. 30 | C A C C A T C G C C T G C C T C G G T G C C C T G |
| SEQ. ID. NO. 26 | C T G C A T G A C C T T C A T C T T C A T T G C C |

| | |
|---|---|
| SEQ. ID. NO. 38 | C T A A C G G G G A T T T T T C T C T G T T A T T |
| SEQ. ID. NO. 34 | A A G C C A T C C A C G G C A G T G T G T A C C T |
| SEQ. ID. NO. 30 | G C C A C C C T G T T T G T G C T G G G T G T C T |
| SEQ. ID. NO. 26 | A A G C C A T C C A C G G C A G T G T G T A C C T |

| | |
|---|---|
| SEQ. ID. NO. 38 | C A A T C A C G T T T T T A A T G A T T G C A G C |
| SEQ. ID. NO. 34 | T A C G G C G T C T T G G T T T G G G C A C T G C |
| SEQ. ID. NO. 30 | T T G T G C G G C A C A A T G C C A C A C C A G T |
| SEQ. ID. NO. 26 | T A C G G C G T C T T G G T T T G G G C A C T G C |

| | |
|---|---|
| SEQ. ID. NO. 38 | A C C A G A T A C A A T C A T A T G C T C C T T C |
| SEQ. ID. NO. 34 | C T T C T C T G T C T G C T A C T C A G C C C T G |
| SEQ. ID. NO. 30 | G G T C A A G G C C T C A G G T C G G G A G C T C |
| SEQ. ID. NO. 26 | C T T C T C T G T C T G C T A C T C A G C C C T G |

| | |
|---|---|
| SEQ. ID. NO. 38 | C G A C G G G T C T T C C T A G G A C T T G G C A |
| SEQ. ID. NO. 34 | C T C A C C A A G A C C A A C C G C A T T G C A C |
| SEQ. ID. NO. 30 | T G C T A C A T C C T G C T G G G T G G T G T C T |
| SEQ. ID. NO. 26 | C T C A C C A A G A C C A A C C G C A T T G C A C |

| | |
|---|---|
| SEQ. ID. NO. 38 | T G T G T T T C A G C T A T G C A G C C C T T C T |
| SEQ. ID. NO. 34 | G C A T C T T C G G T G G G G C C C G G G A G G G |
| SEQ. ID. NO. 30 | T C C T C T G C T A C T G C A T G A C C T T C A T |
| SEQ. ID. NO. 26 | G C A T C T T C G G T G G G G C C C G G G A G G G |

Figure 9j

SEQ. ID. NO. 38  G A C C A A A A C A A A C C G T A T C C A C C G A
SEQ. ID. NO. 34  T G C C C A G C G G C C A C G C T T C A T C A G T
SEQ. ID. NO. 30  C T T C A T T G C C A A G C C A T C C A C G G C A
SEQ. ID. NO. 26  T G C C C A G C G G C C A C G C T T C A T C A G T

SEQ. ID. NO. 38  A T A T T T G A G C A G G G G A A G A A A T C T G
SEQ. ID. NO. 34  C C T G C C T C A C A G G T G G C C A T C T G C C
SEQ. ID. NO. 30  G T G T G T A C C T T A C G G C G T C T T G G T T
SEQ. ID. NO. 26  C C T G C C T C A C A G G T G G C C A T C T G C C

SEQ. ID. NO. 38  T C A C A G C G C C C A A G T T C A T T A G T C C
SEQ. ID. NO. 34  T G G C A C T T A T C T C G G C C A G C T G C T
SEQ. ID. NO. 30  T G G G C A C T G C C T T C T C T G T C T G C T A
SEQ. ID. NO. 26  T G G C A C T T A T C T C G G C C A G C T G C T

SEQ. ID. NO. 38  A G C A T C T C A G C T G G T G A T C A C C T T C
SEQ. ID. NO. 34  C A T C G T G G T C G C C T G G C T G G T G G T G
SEQ. ID. NO. 30  C T C A G C C C T G C T C A C C A A G A C C A A C
SEQ. ID. NO. 26  C A T C G T G G T C G C C T G G C T G G T G G T G

SEQ. ID. NO. 38  A G C C T C A T C T C C G T C C A G C T C C T T G
SEQ. ID. NO. 34  G A G G C A C C G G G C A C A G G C A A G G A G A
SEQ. ID. NO. 30  C G C A T T G C A C G C A T C T T C G G T G G G G
SEQ. ID. NO. 26  G A G G C A C C G G G C A C A G G C A A G G A G A

SEQ. ID. NO. 38  G A G T G T T T G T C T G G T T T G T T G T G G A
SEQ. ID. NO. 34  C A G C C C C C G A A C G G C G G G A G G T G G T
SEQ. ID. NO. 30  C C C G G G A G G G T G C C C A G C G G C C A C G
SEQ. ID. NO. 26  C A G C C C C C G A A C G G C G G G A G G T G G T

SEQ. ID. NO. 38  T C C C C C C C A C A T C A T C A T T G A C T A T
SEQ. ID. NO. 34  G A C A C T G C G C T G C A A C C A C C G C G A T
SEQ. ID. NO. 30  C T T C A T C A G T C C T G C C T C A C A G G T G
SEQ. ID. NO. 26  G A C A C T G C G C T G C A A C C A C C G C G A T

SEQ. ID. NO. 38  G G A G A G C A G C G G A C A C T A G A T C C A G
SEQ. ID. NO. 34  G C A A G T A T G T T G G G C T C G C T G G C C T
SEQ. ID. NO. 30  G C C A T C T G C C T G G C A C T T A T C T C G G
SEQ. ID. NO. 26  G C A A G T A T G T T G G G C T C G C T G G C C T

Figure 9k

```
SEQ. ID. NO. 38  AGAAGGCCAGGGGAGTGCTCAAGTG
SEQ. ID. NO. 34  ACAATGTGCTCCTCATCGCGCTCTG
SEQ. ID. NO. 30  GCCAGCTGCTCATCGTGGTCGCCTG
SEQ. ID. NO. 26  ACAATGTGCTCCTCATCGCGCTCTG

SEQ. ID. NO. 38  TGACATTTCTGATCTCTCACTCATT
SEQ. ID. NO. 34  CACGCTTTATGCCTTCAAGACTCGC
SEQ. ID. NO. 30  GCTGGTGGTGGAGGCACCGGCACA
SEQ. ID. NO. 26  CACGCTTTATGCCTTCAATACTCGC

SEQ. ID. NO. 38  TGTTCACTTGGATACAGTATCCTCT
SEQ. ID. NO. 34  AAGTGCCCCGAAAACTTCAACGAGG
SEQ. ID. NO. 30  GGCAAGGAGACAGCCCCCGAACGGC
SEQ. ID. NO. 26  AAGTGCCCCGAAAACTTCAACGAGG

SEQ. ID. NO. 38  TGATGGTCACTTGTACTGTTTATGC
SEQ. ID. NO. 34  CCAAGTTCATTGGCTTCACCATGTA
SEQ. ID. NO. 30  GGGAGGTGGTGACACTGCGCTGCAA
SEQ. ID. NO. 26  CCAAGTTCATTGGCTTCACCATGTA

SEQ. ID. NO. 38  CATTAAAACGAGAGGTGTCCCAGAG
SEQ. ID. NO. 34  CACCACCTGCATCATCTGGCTGGCA
SEQ. ID. NO. 30  CCACCGCGATGCAAGTATGTTGGGC
SEQ. ID. NO. 26  CACCACCTGCATCATCTGGCTGGCA

SEQ. ID. NO. 38  ACTTTCAATGAAGCCAAACCTATTG
SEQ. ID. NO. 34  TTCCTGCCCATCTTCTATGTCACCT
SEQ. ID. NO. 30  TCGCTGGCCTACAATGTGCTCCTCA
SEQ. ID. NO. 26  TTGTTGCCCATCTTCTATGTCACCT

SEQ. ID. NO. 38  GATTTACCATGTATACCACCTGCAT
SEQ. ID. NO. 34  CCAGTGACTACCGGGTACAGACCAC
SEQ. ID. NO. 30  TCGCGCTCTGCACGCTTTATGCCTT
SEQ. ID. NO. 26  CCAGTGACTACCGGGTACAGACCAC

SEQ. ID. NO. 38  CATTTGGTTAGCTTTCATCCCCATC
SEQ. ID. NO. 34  CACCATGTGCGTGTCAGTCAGCCTC
SEQ. ID. NO. 30  CAATACTCGCAAGTGCCCCGAAAAC
SEQ. ID. NO. 26  CACCATGTGCGTGTCAGTCAGCCTC
```

Figure 91

SEQ. ID. NO. 38    T T T T T T G G T A C A G C C C A G T C A G C A G
SEQ. ID. NO. 34    A G C G G C T C C G T G G T G C T T G G C T G C C
SEQ. ID. NO. 30    T T C A A C G A G G C C A A G T T C A T T G G C T
SEQ. ID. NO. 26    A G C G G C T C C G T G G T G C T T G G C T G C C

SEQ. ID. NO. 38    A A A A G A T G T A C A T C C A G A C A A C A A C
SEQ. ID. NO. 34    T C T T T G C G C C C A A G C T G C A C A T C A T
SEQ. ID. NO. 30    T C A C C A T G T A C A C C A C C T G C A T C A T
SEQ. ID. NO. 26    T C T T T G C G C C C A A G C T G C A C A T C A T

SEQ. ID. NO. 38    A C T T A C T G T C T C C A T G A G T T T A A G T
SEQ. ID. NO. 34    C C T C T T C C A G C C G C A G A A G A A C A C C
SEQ. ID. NO. 30    C T G G C T G G C A T T G T T G C C C A T C T T C
SEQ. ID. NO. 26    C C T C T T C C A G C C G C A G A A G A A C G T G

SEQ. ID. NO. 38    G C T T C A G T A T C T C T G G G C A T G C T C T
SEQ. ID. NO. 34    A T C G A G G A G G T G C G T T G C A G C A C C G
SEQ. ID. NO. 30    T A T G T C A C C T C C A G T G A C T A C C G G G
SEQ. ID. NO. 26    G T T A G C C A C C G G G C A C C C A C C A G C C

SEQ. ID. NO. 38    A T A T G C C C A A G G T T T A T A T T A T A A T
SEQ. ID. NO. 34    C A G C T C A C G C T T T C A A G G T G G C T G C
SEQ. ID. NO. 30    T A C A G A C C A C C A C C A T G T G C G T G T C
SEQ. ID. NO. 26    G C T T T G G C A G T G C T G C T G C C A G G G C

SEQ. ID. NO. 38    T T T T C A T C C A G A A C A G A A T A C C A T C
SEQ. ID. NO. 34    C C G G G C C A C G C T G C G C C G C A G C A A C
SEQ. ID. NO. 30    A G T C A G C C T C A G C G G C T C C G T G G T G
SEQ. ID. NO. 26    C A G C T C C A G C C T T G G C C A A G G G T C T

SEQ. ID. NO. 38    G A G G A G G T G C G T T G C A G C A C C G C A G
SEQ. ID. NO. 34    G T C T C C C G C A A G C G G T C C A G C A G C C
SEQ. ID. NO. 30    C T T G G C T G C C T C T T T G C G C C C A A G C
SEQ. ID. NO. 26    G G C T C C C A G T T T G T C C C C A C T G T T T

SEQ. ID. NO. 38    C T C A C G C T T T C A A G G T G G C T G C C C G
SEQ. ID. NO. 34    T T G G A G G C T C C A C G G G A T C C A C C C C
SEQ. ID. NO. 30    T G C A C A T C A T C C T C T T C C A G C C G C A
SEQ. ID. NO. 26    G C A A T G G C C G T G A G G T G G T G G A C T C

Figure 9m

| | |
|---|---|
| SEQ. ID. NO. 38 | G G C C A C G C T G C G C C G C A G C A A C G T C |
| SEQ. ID. NO. 34 | C T C C T C C T C C A T C A G C A G C A A G A G C |
| SEQ. ID. NO. 30 | G A A G A A C G T G G T T A G C C A C C G G G C A |
| SEQ. ID. NO. 26 | G A C A A C G T C A T C G C T T |

| | |
|---|---|
| SEQ. ID. NO. 38 | T C C C G C A A G C G G T C C A G C A G C C T T G |
| SEQ. ID. NO. 34 | A A C A G C G A A G A C C C A T T C C C A C A G C |
| SEQ. ID. NO. 30 | C C C A C C A G C C G C T T T G G C A G T G C T G |
| SEQ. ID. NO. 26 | |

| | |
|---|---|
| SEQ. ID. NO. 38 | G A G G C T C C A C G G G A T C C A C C C C C T C |
| SEQ. ID. NO. 34 | C C G A G A G G C A G A A G C A G C A G C A G C C |
| SEQ. ID. NO. 30 | C T G C C A G G G C C A G C T C C A G C C T T G G |
| SEQ. ID. NO. 26 | |

| | |
|---|---|
| SEQ. ID. NO. 38 | C T C C T C C A T C A G C A G C A A G A G C A A C |
| SEQ. ID. NO. 34 | G C T G G C C C T A A C C C A G C A A G A G C A G |
| SEQ. ID. NO. 30 | C C A A G G G T C T G G C T C C C A G T T T G T C |
| SEQ. ID. NO. 26 | |

| | |
|---|---|
| SEQ. ID. NO. 38 | A G C G A A G A C C C A T T C C C A C A G C C C G |
| SEQ. ID. NO. 34 | C A G C A G C A G C C C C T G A C C C T C C C A C |
| SEQ. ID. NO. 30 | C C C A C T G T T T G C A A T G G C C G T G A G G |
| SEQ. ID. NO. 26 | |

| | |
|---|---|
| SEQ. ID. NO. 38 | A G A G G C A G A A G C A G C A G C A G C C G C T |
| SEQ. ID. NO. 34 | A G C A G C A A C G A T C T C A G C A G C A G C C |
| SEQ. ID. NO. 30 | T G G T G G A C T C G A C A A C G T C A T C G C T |
| SEQ. ID. NO. 26 | |

| | |
|---|---|
| SEQ. ID. NO. 38 | G G C C C T A A C C C A G C A A G A G C A G C A G |
| SEQ. ID. NO. 34 | C A G A T G C A A G C A G A A G G T C A T C T T T |
| SEQ. ID. NO. 30 | T |
| SEQ. ID. NO. 26 | |

| | |
|---|---|
| SEQ. ID. NO. 38 | C A G C A G C C C C T G A C C C T C C C A C A G C |
| SEQ. ID. NO. 34 | G G C A G C G G C A C G G T C A C C T T C T C A C |
| SEQ. ID. NO. 30 | |
| SEQ. ID. NO. 26 | |

Figure 9n.

SEQ. ID. NO. 38   A G C A A C G A T C T C A G C A G C A G C C C A G
SEQ. ID. NO. 34   T G A G C T T T G A T G A G C C T C A G A A G A A
SEQ. ID. NO. 30
SEQ. ID. NO. 26

SEQ. ID. NO. 38   A T G C A A G C A G A A G G T C A T C T T T G G C
SEQ. ID. NO. 34   C G C C A T G G C C C A C G G G A A T T C T A C G
SEQ. ID. NO. 30
SEQ. ID. NO. 26

SEQ. ID. NO. 38   A G C G G C A C G G T C A C C T T C T C A C T G A
SEQ. ID. NO. 34   C A C C A G A A C T C C C T G G A G G C C C A G A
SEQ. ID. NO. 30
SEQ. ID. NO. 26

SEQ. ID. NO. 38   G C T T T G A T G A G C C T C A G A A G A A C G C
SEQ. ID. NO. 34   A A A G C A G C G A T A C G C T G A C C C G A C A
SEQ. ID. NO. 30
SEQ. ID. NO. 26

SEQ. ID. NO. 38   C A T G G C C C A C G G G A A T T C T A C G C A C
SEQ. ID. NO. 34   C C A G C C A T T A C T C C C G C T G C A G T G C
SEQ. ID. NO. 30
SEQ. ID. NO. 26

SEQ. ID. NO. 38   C A G A A C T C C C T G G A G G C C C A G A A A A
SEQ. ID. NO. 34   G G G G A A A C G G A C T T A G A T C T G A C C G
SEQ. ID. NO. 30
SEQ. ID. NO. 26

SEQ. ID. NO. 38   G C A G C G A T A C G C T G A C C C G A C A C C A
SEQ. ID. NO. 34   T C C A G G A A A C A G G T C T G C A A G G A C C
SEQ. ID. NO. 30
SEQ. ID. NO. 26

SEQ. ID. NO. 38   G C C A T T A C T C C C G C T G C A G T G C G G G
SEQ. ID. NO. 34   T G T G G G T G G A G A C C A G C G G C C A G A G
SEQ. ID. NO. 30
SEQ. ID. NO. 26

Figure 9o

SEQ. ID. NO. 38 G A A A C G G A C T T A G A T C T G A C C G T C C
SEQ. ID. NO. 34 G T G G A G G A C C C T G A A G A G T T G T C C C
SEQ. ID. NO. 30
SEQ. ID. NO. 26

SEQ. ID. NO. 38 A G G A A A C A G G T C T G C A A G G A C C T G T
SEQ. ID. NO. 34 C A G C A C T T G T A G T G T C C A G T T C A C A
SEQ. ID. NO. 30
SEQ. ID. NO. 26

SEQ. ID. NO. 38 G G G T G G A G A C C A G C G G C C A G A G G T G
SEQ. ID. NO. 34 G A G C T T T G T C A T C A G T G G T G G A G G C
SEQ. ID. NO. 30
SEQ. ID. NO. 26

SEQ. ID. NO. 38 G A G G A C C C T G A A G A G T T G T C C C C A G
SEQ. ID. NO. 34 A G C A C T G T T A C A G A A A C G T A G T G A
SEQ. ID. NO. 30
SEQ. ID. NO. 26

SEQ. ID. NO. 38 C A C T T G T A G T G T C C A G T T C A C A G A G
SEQ. ID. NO. 34 A T T C A
SEQ. ID. NO. 30
SEQ. ID. NO. 26

SEQ. ID. NO. 38 C T T T G T C A T C A G T G G T G G A G G C A G C
SEQ. ID. NO. 34
SEQ. ID. NO. 30
SEQ. ID. NO. 26

SEQ. ID. NO. 38 A C T G T T A C A G A A A C G T A G T G A A T T
SEQ. ID. NO. 34
SEQ. ID. NO. 30
SEQ. ID. NO. 26

SEQ. ID. NO. 38 C A
SEQ. ID. NO. 34
SEQ. ID. NO. 30
SEQ. ID. NO. 26

Figure 9p

ClustalW Formatted Alignments

```
SEQ. ID. NO. 39   M V C E G K R S A S C P C F F L L T A K F Y W I L
SEQ. ID. NO. 35   M G S L L A L P A L L L L W G A V A E G P A K K V
SEQ. ID. NO. 31   M A F Y S C C W V L L A L T W H T S A Y G P D Q R
SEQ. ID. NO. 27   M G S L L A L L A L L P L W G A V A E G P A K K V

SEQ. ID. NO. 39   T M M Q R T H S Q E Y A H S I R V D G D I I L G G
SEQ. ID. NO. 35   L T L E G D L V L G G L F P V H Q K G G P A E D C
SEQ. ID. NO. 31   A Q K K G D I I L G G L F P I H F G V A A K D Q D
SEQ. ID. NO. 27   L T L E G D L V L G G L F P V H Q K G G P A E D C

SEQ. ID. NO. 39   L F P V H A K G E R G V P C G E L K K E K G I H R
SEQ. ID. NO. 35   G P V N E H R G I Q R L E A M L F A L D R I N R D
SEQ. ID. NO. 31   L K S R P E S V E C I R Y N F R G F R W L Q A M I
SEQ. ID. NO. 27   G P V N E H R G I Q R L E A M L F A L D R I N R D

SEQ. ID. NO. 39   L E A M L Y A I D Q I N K D P D L L S N I T L G V
SEQ. ID. NO. 35   P H L L P G V R L G A H I L D S C S K D T H A L E
SEQ. ID. NO. 31   F A I E E I N S S P A L L P N L T L G Y R I F D T
SEQ. ID. NO. 27   P H L L P G V R L G A H I L D S C S K D T H A L E

SEQ. ID. NO. 39   R I L D T C S R D T Y A L E Q S L T F V Q A L I E
SEQ. ID. NO. 35   Q A L D F V R A S L S R G A D G S R H I C P D G S
SEQ. ID. NO. 31   C N T V S K A L E A T L S F V A Q N K I D S L N L
SEQ. ID. NO. 27   Q A L D F V R A S L S R G A D G S R H I C P D G S

SEQ. ID. NO. 39   K D A S D V K C A N G D P P I F T K P D K I S G V
SEQ. ID. NO. 35   Y A T H G D A P T A I T G V I G G S Y S D V S I Q
SEQ. ID. NO. 31   D E F C N C S E H I P S T I A V V G A T G S G V S
SEQ. ID. NO. 27   Y A T H G D A P T A I T G V I G G S Y S D V S I Q

SEQ. ID. NO. 39   I G A A A S S V S I M V A N I L R L F K I P Q I S
SEQ. ID. NO. 35   V A N L L R L F Q I P Q I S Y A S T S A K L S D K
SEQ. ID. NO. 31   T A V A N L L G L F Y I P Q V S Y A S S S R L L S
SEQ. ID. NO. 27   V A N L L R L F Q I P Q I S Y A S T S A K L S D K

SEQ. ID. NO. 39   Y A S T A P E L S D N T R Y D F F S R V V P P D S
SEQ. ID. NO. 35   S R Y D Y F A R T V P P D F F Q A K A M A E I L R
SEQ. ID. NO. 31   N K N Q F K S F L R T I P N D E H Q A T A M A D I
SEQ. ID. NO. 27   S R Y D Y F A R T V P P D F F Q A K A M A E I L R
```

Figure 10a

```
SEQ. ID. NO. 39   Y Q A Q A M V D I V T A L G W N Y V S T L A S E G
SEQ. ID. NO. 35   F F N W T Y V S T V A S E G D Y G E T G I E A F E
SEQ. ID. NO. 31   I E Y F R W N W V G T I A A D D D Y G R P G I E K
SEQ. ID. NO. 27   F F N W T Y V S T E A S E G D Y G E T G I E A F E

SEQ. ID. NO. 39   N Y G E S G V E A F T Q I S R E I G G V C I A Q S
SEQ. ID. NO. 35   L E A R A R N I C V A T S E K V G R A M S R A A F
SEQ. ID. NO. 31   F R E E A E E R D I C I D F S E L I S Q Y S D E E
SEQ. ID. NO. 27   L E A R A R N I C V A T S E K V G R A M S R A A F

SEQ. ID. NO. 39   Q K I P R E P R P G E F E K I I K R L L E T P N A
SEQ. ID. NO. 35   E G V V R A L L Q K P S A R V A V L F T R S E D A
SEQ. ID. NO. 31   E I Q H V V E V I Q N S T A K V I V V F S S G P D
SEQ. ID. NO. 27   E G V V R A L L Q K P S A R V A V L F T R S E D A

SEQ. ID. NO. 39   R A V I M F A N E D D I R R I L E A A K K L N Q S
SEQ. ID. NO. 35   R E L L A A S Q R L N A S F T W V A S D G W G A L
SEQ. ID. NO. 31   L E P L I K E I V R R N I T G K I W L A S E A W A
SEQ. ID. NO. 27   R E L L A A S Q R L N A S F T W V A S D G W G A L

SEQ. ID. NO. 39   G H F L W I G S D S W G S K I A P V Y Q Q E E I A
SEQ. ID. NO. 35   E S V V A G S E G A A E G A I T I E L A S Y P I S
SEQ. ID. NO. 31   S S S L I A M P Q Y F H V V G G T I G F A L K A G
SEQ. ID. NO. 27   E S V V A G S E G A A E G A I T I E L A S Y P I S

SEQ. ID. NO. 39   E G A V T I L P K R A S I D G F D R Y F R S R T L
SEQ. ID. NO. 35   D F A S Y F Q S L D P W N N S R N P W F R E F W E
SEQ. ID. NO. 31   Q I P G F R E F L K K V H P R K S V H N G F A K E
SEQ. ID. NO. 27   D F A S Y F Q S L D P W N N S R N P W F R E F W E

SEQ. ID. NO. 39   A N N R R N V W F A E F W E E N F G C K L G S H G
SEQ. ID. NO. 35   Q R F R C S F R Q R D C A A H S L R A V P F E Q E
SEQ. ID. NO. 31   F W E E T F N C H L Q E G A K G P L P V D T F L R
SEQ. ID. NO. 27   Q R F R C S F R Q R D C A A H S L R A V P F E Q E

SEQ. ID. NO. 39   K R N S H I K K C T G L E R I A R D S S Y E Q E G
SEQ. ID. NO. 35   S K I M F V V N A V Y A M A H A L H N M H R A L C
SEQ. ID. NO. 31   G H E E S G D R F S N S S T A F R P L C T G D E N
SEQ. ID. NO. 27   S K I M F V V N A V Y A M A H A L H N M H R A L C

Figure 10b
```

```
SEQ. ID. NO. 39  K V Q F V I D A V Y S M A Y A L H N M H K D L C P
SEQ. ID. NO. 35  P N T T R L C D A M R P V N G R R L Y K D F V L N
SEQ. ID. NO. 31  I S S V E T P Y I D Y T H L R I S Y N V Y L A V Y
SEQ. ID. NO. 27  P N T T R L C D A M R P V N G R R L Y K D F V L N

SEQ. ID. NO. 39  G Y I G L C P R M S T I D G K E L L G Y I R A V N
SEQ. ID. NO. 35  V K F D A P F R P A D T H N E V R F D R F G D G I
SEQ. ID. NO. 31  S I A H A L Q D I Y T C L P G R G L F T N G S C A
SEQ. ID. NO. 27  V K F D A P F R P A D T H N E V R F D R F G D G I

SEQ. ID. NO. 39  F N G S A G T P V T F N E N G D A P G R Y D I F Q
SEQ. ID. NO. 35  G R Y N I F T Y L R A G S G R Y R Y Q K V G Y W A
SEQ. ID. NO. 31  D I K K V E A W Q V L K H L R H L N F T N N M G E
SEQ. ID. NO. 27  G R Y N I F T Y L R A G S G R Y R Y Q K V G Y W A

SEQ. ID. NO. 39  Y Q I T N K S T E Y K V I G H W T N Q L H L K V E
SEQ. ID. NO. 35  E G L T L D T S L I P W A S P S A G P L P A S R C
SEQ. ID. NO. 31  Q V T F D E C G D L V G N Y S I I N W H L S P E D
SEQ. ID. NO. 27  E G L T L D T S L I P W A S P S A G P L A A S R C

SEQ. ID. NO. 39  D M Q W A H R E H T H P A S V C S L P C K P G E R
SEQ. ID. NO. 35  S E P C L Q N E V K S V Q P G E V C C W L C I P C
SEQ. ID. NO. 31  G S I V F K E V G Y Y N V Y A K K G E R L F I N E
SEQ. ID. NO. 27  S E P C L Q N E V K S V Q P G E V C C W L C I P C

SEQ. ID. NO. 39  K K T V K G V P C C W H C E R C E G Y N Y Q V D E
SEQ. ID. NO. 35  Q P Y E Y R L D E F T C A D C G L G Y W P N A S L
SEQ. ID. NO. 31  E K I L W S G F S R E V P F S N C S R D C L A G T
SEQ. ID. NO. 27  Q P Y E Y R L D E F T C A D C G L G Y W P N A S L

SEQ. ID. NO. 39  L S C E L C P L D Q R P N M N R T G C Q L I P I I
SEQ. ID. NO. 35  T G C F E L P Q E Y I R W G D A W A V G P V T I A
SEQ. ID. NO. 31  R K G I I E G E P T C C F E C V E C P D G E Y S D
SEQ. ID. NO. 27  T G C F E L P Q E Y I R W G D A W A V G P V T I A

SEQ. ID. NO. 39  K L E W H S P W A V V P V F V A I L G I I A T T F
SEQ. ID. NO. 35  C L G A L A T L F V L G V F V R H N A T P V V K A
SEQ. ID. NO. 31  E T D A S A C N K C P D D F W S N E N H T S C F E
SEQ. ID. NO. 27  C L G A L A T L F V L G V F V R H N A T P V V K A
```

Figure 10c

```
SEQ. ID. NO. 39  V I V T F V R Y N D T P I V R A S G R E L S Y V L
SEQ. ID. NO. 35  S G R E L C Y I L L G G V F L C Y C M T F I F I A
SEQ. ID. NO. 31  L P Q E Y I R W G D A W A V G P V T I A C L G A L
SEQ. ID. NO. 27  S G R E L C Y I L L G G V F L C Y C M T F I F I A

SEQ. ID. NO. 39  L T G I F L C Y S I T F L M I A A P D T I I C S F
SEQ. ID. NO. 35  K P S T A V C T L R R L G L G T A F S V C Y S A L
SEQ. ID. NO. 31  A T L F V L G V F V R H N A T P V V K A S G R E L
SEQ. ID. NO. 27  K P S T A V C T L R R L G L G T A F S V C Y S A L

SEQ. ID. NO. 39  R R V F L G L G M C F S Y A A L L T K T N R I H R
SEQ. ID. NO. 35  L T K T N R I A R I F G G A R E G A Q R P R F I S
SEQ. ID. NO. 31  C Y I L L G G V F L C Y C M T F I F I A K P S T A
SEQ. ID. NO. 27  L T K T N R I A R I F G G A R E G A Q R P R F I S

SEQ. ID. NO. 39  I F E Q G K K S V T A P K F I S P A S Q L V I T F
SEQ. ID. NO. 35  P A S Q V A I C L A L I S G Q L L I V V A W L V V
SEQ. ID. NO. 31  V C T L R R L G L G T A F S V C Y S A L L T K T N
SEQ. ID. NO. 27  P A S Q V A I C L A L I S G Q L L I V V A W L V V

SEQ. ID. NO. 39  S L I S V Q L L G V F V W F V V D P P H I I I D Y
SEQ. ID. NO. 35  E A P G T G K E T A P E R R E V V T L R C N H R D
SEQ. ID. NO. 31  R I A R I F G G A R E G A Q R P R F I S P A S Q V
SEQ. ID. NO. 27  E A P G T G K E T A P E R R E V V T L R C N H R D

SEQ. ID. NO. 39  G E Q R T L D P E K A R G V L K C D I S D L S L I
SEQ. ID. NO. 35  A S M L G S L A Y N V L L I A L C T L Y A F K T R
SEQ. ID. NO. 31  A I C L A L I S G Q L L I V V A W L V V E A P G T
SEQ. ID. NO. 27  A S M L G S L A Y N V L L I A L C T L Y A P N T R

SEQ. ID. NO. 39  C S L G Y S I L L M V T C T V Y A I K T R G V P E
SEQ. ID. NO. 35  K C P E N F N E A K F I G F T M Y T T C I I W L A
SEQ. ID. NO. 31  G K E T A P E R R E V V T L R C N H R D A S M L G
SEQ. ID. NO. 27  K C P E N F N E A K F I G F T M Y T T C I I W L A

SEQ. ID. NO. 39  T F N E A K P I G F T M Y T T C I I W L A F I P I
SEQ. ID. NO. 35  F L P I F Y V T S S D Y R V Q T T T M C V S V S L
SEQ. ID. NO. 31  S L A Y N V L L I A L C T L Y A F N T R K C P E N
SEQ. ID. NO. 27  L L P I F Y V T S S D Y R V Q T T T M C V S V S L
```

Figure 10d

SEQ. ID. NO. 39   F F G T A Q S A E K M Y I Q T T T L T V S M S L S
SEQ. ID. NO. 35   S G S V V L G C L F A P K L H I I L F Q P Q K N T
SEQ. ID. NO. 31   F N E A K F I G F T M Y T T C I I W L A L L P I F
SEQ. ID. NO. 27   S G S V V L G C L F A P K L H I I L F Q P Q K N

SEQ. ID. NO. 39   A S V S L G M L Y M P K V Y I I I F H P E Q N T I
SEQ. ID. NO. 35   I E E V R C S T A A H A F K V A A R A T L R R S N
SEQ. ID. NO. 31   Y V T S S D Y R V Q T T T M C V S V S L S G S V V
SEQ. ID. NO. 27

SEQ. ID. NO. 39   E E V R C S T A A H A F K V A A R A T L R R S N V
SEQ. ID. NO. 35   V S R K R S S S L G G S T G S T P S S S I S S K S
SEQ. ID. NO. 31   L G C L F A P K L H I I L F Q P Q K N V V S H R A
SEQ. ID. NO. 27

SEQ. ID. NO. 39   S R K R S S S L G G S T G S T P S S S I S S K S N
SEQ. ID. NO. 35   N S E D P F P Q P E R Q K Q Q Q P L A L T Q Q E Q
SEQ. ID. NO. 31   P T S R F G S A A A R A S S S L G Q G S G S Q F V
SEQ. ID. NO. 27

SEQ. ID. NO. 39   S E D P F P Q P E R Q K Q Q Q P L A L T Q Q E Q Q
SEQ. ID. NO. 35   Q Q Q P L T L P Q Q Q R S Q Q Q P R C K Q K V I F
SEQ. ID. NO. 31   P T V C N G R E V V D S T T S S L
SEQ. ID. NO. 27

SEQ. ID. NO. 39   Q Q P L T L P Q Q Q R S Q Q Q P R C K Q K V I F G
SEQ. ID. NO. 35   G S G T V T F S L S F D E P Q K N A M A H G N S T
SEQ. ID. NO. 31
SEQ. ID. NO. 27

SEQ. ID. NO. 39   S G T V T F S L S F D E P Q K N A M A H G N S T H
SEQ. ID. NO. 35   H Q N S L E A Q K S S D T L T R H Q P L L P L Q C
SEQ. ID. NO. 31
SEQ. ID. NO. 27

SEQ. ID. NO. 39   Q N S L E A Q K S S D T L T R H Q P L L P L Q C G
SEQ. ID. NO. 35   G E T D L D L T V Q E T G L Q G P V G G D Q R P E
SEQ. ID. NO. 31
SEQ. ID. NO. 27

Figure 10e

SEQ. ID. NO. 39  E T D L D L T V Q E T G L Q G P V G G D Q R P E V
SEQ. ID. NO. 35  V E D P E E L S P A L V V S S S Q S F V I S G G G
SEQ. ID. NO. 31
SEQ. ID. NO. 27

SEQ. ID. NO. 39  E D P E E L S P A L V V S S S Q S F V I S G G G S
SEQ. ID. NO. 35  S T V T E N V V N S
SEQ. ID. NO. 31
SEQ. ID. NO. 27

SEQ. ID. NO. 39  T V T E N V V N S
SEQ. ID. NO. 35
SEQ. ID. NO. 31
SEQ. ID. NO. 27

Figure 10f

ClustalW Formatted Alignments

```
SEQ. ID. NO. 40  A T G G T A T G C G A G G G A A A G C G A T C A G
SEQ. ID. NO. 46  A T G G G A T C G C T G C T T G C G C T C C C G G
SEQ. ID. NO. 36  A T G G G A T C G C T G C T T G C G C T C C C G G
SEQ. ID. NO. 32  A T G G C A T T T T A T A G C T G C T G C T G G G

SEQ. ID. NO. 40  C C T C T T G C C C T T G T T T C T T C C T C T T
SEQ. ID. NO. 46  C A C T G C T G C T G C T G T G G G G T G C T G T
SEQ. ID. NO. 36  C A C T G C T G C T G C T G T G G G G T G C T G T
SEQ. ID. NO. 32  T C C T C T T G G C A C T C A C C T G G C A C A C

SEQ. ID. NO. 40  G A C C G C C A A G T T C T A C T G G A T C C T C
SEQ. ID. NO. 46  G G C T G A G G G C C C A G C C A A G A A G G T G
SEQ. ID. NO. 36  G G C T G A G G G C C C A G C C A A G A A G G T G
SEQ. ID. NO. 32  C T C T G C C T A C G G G C C A G A C C A G C G A

SEQ. ID. NO. 40  A C A A T G A T G C A A A G A A C T C A C A G C C
SEQ. ID. NO. 46  C T G A C C C T G G A G G G A G A C T T G G T G C
SEQ. ID. NO. 36  C T G A C C C T G G A G G G A G A C T T G G T G C
SEQ. ID. NO. 32  G C C C A A A A G A A G G G G A C A T T A T C C

SEQ. ID. NO. 40  A G G A G T A T G C C C A T T C C A T A C G G G T
SEQ. ID. NO. 46  T G G G T G G G C T G T T C C C A G T G C A C C A
SEQ. ID. NO. 36  T G G G T G G G C T G T T C C C A G T G C A C C A
SEQ. ID. NO. 32  T T G G G C G G C T C T T T C C T A T T C A T T T

SEQ. ID. NO. 40  G G A T G G G G A C A T T A T T T T G G G G G G T
SEQ. ID. NO. 46  G A A G G G C G G C C C A G C A G A G G A C T G T
SEQ. ID. NO. 36  G A A G G G C G G C C C A G C A G A G G A C T G T
SEQ. ID. NO. 32  T G G A G T A G C A G C T A A A G A T C A A G A T

SEQ. ID. NO. 40  C T C T T C C C T G T C C A C G C A A A G G G A G
SEQ. ID. NO. 46  G G T C C T G T C A A T G A G C A C C G T G G C A
SEQ. ID. NO. 36  G G T C C T G T C A A T G A G C A C C G T G G C A
SEQ. ID. NO. 32  C T C A A A T C A A G G C C G G A G T C T G T G G

SEQ. ID. NO. 40  A G A G A G G G G T G C C T T G T G G G A G C T
SEQ. ID. NO. 46  T C C A G C G C C T G G A G G C C A T G C T T T T
SEQ. ID. NO. 36  T C C A G C G C C T G G A G G C C A T G C T T T T
SEQ. ID. NO. 32  A A T G T A T C A G G T A T A A T T T C C G T G G
```

Figure 11a

SEQ. ID. NO. 40  G A A G A A G G A A A A G G G G A T T C A C A G A
SEQ. ID. NO. 46  T G C A C T G G A C C G C A T C A A C C G T G A C
SEQ. ID. NO. 36  T G C A C T G G A C C G C A T C A A C C G T G A C
SEQ. ID. NO. 32  G T T T C G C T G G T T A C A G G C T A T G A T A

SEQ. ID. NO. 40  C T G G A G G C C A T G C T T T A T G C A A T T G
SEQ. ID. NO. 46  C C G C A C C T G C T G C C T G G C G T G C G C C
SEQ. ID. NO. 36  C C G C A C C T G C T G C C T G G C G T G C G C C
SEQ. ID. NO. 32  T T T G C C A T A G A G G A G A T A A A C A G C A

SEQ. ID. NO. 40  A C C A G A T T A A C A A G G A C C C T G A T C T
SEQ. ID. NO. 46  T G G G T G C A C A C A T C C T C G A C A G T T G
SEQ. ID. NO. 36  T G G G T G C A C A C A T C C T C G A C A G T T G
SEQ. ID. NO. 32  G C C C A G C C C T T C T T C C C A A C T T G A C

SEQ. ID. NO. 40  C C T T T C C A A C A T C A C T C T G G G T G T C
SEQ. ID. NO. 46  C T C C A A G G A C A C A C A T G C G C T G G A G
SEQ. ID. NO. 36  C T C C A A G G A C A C A C A T G C G C T G G A G
SEQ. ID. NO. 32  G C T G G A T A C A G G A T A T T T G A C A C T

SEQ. ID. NO. 40  C G C A T C C T C G A C A C G T G C T C T A G G G
SEQ. ID. NO. 46  C A G G C A C T G G A C T T T G T G C G T G C C T
SEQ. ID. NO. 36  C A G G C A C T G G A C T T T G T G C G T G C C T
SEQ. ID. NO. 32  T G C A A C A C C G T T T C T A A G G C C T T G G

SEQ. ID. NO. 40  A C A C C T A T G C T T T G G A G C A G T C T C T
SEQ. ID. NO. 46  C A C T C A G C C G T G G T G C T G A T G G C T C
SEQ. ID. NO. 36  C A C T C A G C C G T G G T G C T G A T G G C T C
SEQ. ID. NO. 32  A A G C C A C C C T G A G T T T T G T T G C T C A

SEQ. ID. NO. 40  A A C A T T C G T G C A G G C A T T A A T A G A G
SEQ. ID. NO. 46  A C G C C A C A T C T G C C C C G A C G G C T C T
SEQ. ID. NO. 36  A C G C C A C A T C T G C C C C G A C G G C T C T
SEQ. ID. NO. 32  A A A C A A A A T T G A T T C T T T G A A C C T T

SEQ. ID. NO. 40  A A A G A T G C T T C G G A T G T G A A G T G T G
SEQ. ID. NO. 46  T A T G C G A C C C A T G G T G A T G C T C C C A
SEQ. ID. NO. 36  T A T G C G A C C C A T G G T G A T G C T C C C A
SEQ. ID. NO. 32  G A T G A G T T C T G C A A C T G C T C A G A G C

Figure 11b

```
SEQ. ID. NO. 40   C T A A T G G A G A T C C A C C C A T T T T C A C
SEQ. ID. NO. 46   C T G C C A T C A C T G G T G T T A T T G G C G G
SEQ. ID. NO. 36   C T G C C A T C A C T G G T G T T A T T G G C G G
SEQ. ID. NO. 32   A C A T T C C C T C T A C G A T T G C T G T G G T

SEQ. ID. NO. 40   C A A G C C C G A C A A G A T T T C T G G C G T C
SEQ. ID. NO. 46   T T C C T A C A G T G A T G T C T C C A T C C A G
SEQ. ID. NO. 36   T T C C T A C A G T G A T G T C T C C A T C C A G
SEQ. ID. NO. 32   G G G A G C A A C T G G C T C A G G C G T C T C C

SEQ. ID. NO. 40   A T A G G T G C T G C A G C A A G C T C C G T G T
SEQ. ID. NO. 46   G T G G C C A A C C T C T T G A G G C T A T T T C
SEQ. ID. NO. 36   G T G G C C A A C C T C T T G A G G C T A T T T C
SEQ. ID. NO. 32   A C G G C A G T G G C A A A T C T G C T G G G G C

SEQ. ID. NO. 40   C C A T C A T G G T T G C T A A C A T T T T A A G
SEQ. ID. NO. 46   A G A T C C C A C A G A T T A G C T A C G C C T C
SEQ. ID. NO. 36   A G A T C C C A C A G A T T A G C T A C G C C T C
SEQ. ID. NO. 32   T C T T C T A C A T T C C C C A G G T C A G T T A

SEQ. ID. NO. 40   A C T T T T T A A G A T A C C T C A A A T C A G C
SEQ. ID. NO. 46   T A C C A G T G C C A A G C T G A G T G A C A A G
SEQ. ID. NO. 36   T A C C A G T G C C A A G C T G A G T G A C A A G
SEQ. ID. NO. 32   T G C C T C C T C C A G C A G A C T C C T C A G C

SEQ. ID. NO. 40   T A T G C A T C C A C A G C C C C A G A G C T A A
SEQ. ID. NO. 46   T C C C G C T A T G A C T A C T T T G C C C G C A
SEQ. ID. NO. 36   T C C C G C T A T G A C T A C T T T G C C C G C A
SEQ. ID. NO. 32   A A C A A G A A T C A A T T C A A G T C T T T C C

SEQ. ID. NO. 40   G T G A T A A C A C C A G G T A T G A C T T T T T
SEQ. ID. NO. 46   C A G T G C C T C C T G A C T T C T T C C A A G C
SEQ. ID. NO. 36   C A G T G C C T C C T G A C T T C T T C C A A G C
SEQ. ID. NO. 32   T C C G A A C C A T C C C C A A T G A T G A G C A

SEQ. ID. NO. 40   C T C T C G A G T G G T T C C G C C T G A C T C C
SEQ. ID. NO. 46   C A A G G C C A T G G C T G A G A T T C T C C G C
SEQ. ID. NO. 36   C A A G G C C A T G G C T G A G A T T C T C C G C
SEQ. ID. NO. 32   C C A G G C C A C T G C C A T G G C A G A C A T C
```

Figure 11c

```
SEQ. ID. NO. 40    T A C C A A G C C C A A G C C A T G G T G G A C A
SEQ. ID. NO. 46    T T C T T C A A C T G G A C C T A T G T G T C C A
SEQ. ID. NO. 36    T T C T T C A A C T G G A C C T A T G T G T C C A
SEQ. ID. NO. 32    A T C G A G T A T T T C C G C T G G A A C T G G

SEQ. ID. NO. 40    T C G T G A C A G C A C T G G G A T G G A A T T A
SEQ. ID. NO. 46    C T G T G G C G T C T G A G G G C G A C T A T G G
SEQ. ID. NO. 36    C T G T G G C G T C T G A G G G C G A C T A T G G
SEQ. ID. NO. 32    T G G G C A C A A T T G C A G C T G A T G A C G A

SEQ. ID. NO. 40    T G T T T C G A C A C T G G C T T C T G A G G G G
SEQ. ID. NO. 46    C G A G A C A G G C A T T G A G G C C T T T G A G
SEQ. ID. NO. 36    C G A G A C A G G C A T T G A G G C C T T T G A G
SEQ. ID. NO. 32    C T A T G G C G G C C G G G A T T G A G A A A

SEQ. ID. NO. 40    A A C T A T G G T G A G A G C G G T G T G G A G G
SEQ. ID. NO. 46    C T A G A G G C T C G T G C C C G C A A C A T C T
SEQ. ID. NO. 36    C T A G A G G C T C G T G C C C G C A A C A T C T
SEQ. ID. NO. 32    T T C G A G A G G A A G C T G A G G A A A G G G

SEQ. ID. NO. 40    C C T T C A C C C A G A T C T C G A G G G A G A T
SEQ. ID. NO. 46    G T G T G G C C A C C T C G G A G A A A G T G G G
SEQ. ID. NO. 36    G T G T G G C C A C C T C G G A G A A A G T G G G
SEQ. ID. NO. 32    A T A T C T G C A T C G A C T T C A G T G A A C T

SEQ. ID. NO. 40    T G G T G G T G T T T G C A T T G C T C A G T C A
SEQ. ID. NO. 46    C C G T G C C A T G A G C C G C G C G G C C T T T
SEQ. ID. NO. 36    C C G T G C C A T G A G C C G C G C G G C C T T T
SEQ. ID. NO. 32    C A T C T C C C A G T A C T C T G A T G A G G A A

SEQ. ID. NO. 40    C A G A A A A T C C A C G T G A A C C A A G A C
SEQ. ID. NO. 46    G A G G G T G T G G T G C G A G C C C T G C T G C
SEQ. ID. NO. 36    G A G G G T G T G G T G C G A G C C C T G C T G C
SEQ. ID. NO. 32    G A G A T C C A G C A T G T G G T A G A G G T G A

SEQ. ID. NO. 40    C T G G A G A A T T T G A A A A A A T T A T C A A
SEQ. ID. NO. 46    A G A A G C C C A G T G C C C G C G T G G C T G T
SEQ. ID. NO. 36    A G A A G C C C A G T G C C C G C G T G G C T G T
SEQ. ID. NO. 32    T T C A A A A T T C C A C G G C C A A A G T C A T
```

Figure 11d

```
SEQ. ID. NO. 40  A C G C C T G C T A G A A A C A C C T A A T G C T
SEQ. ID. NO. 46  C C T G T T C A C C C G T T C T G A G G A T G C C
SEQ. ID. NO. 36  C C T G T T C A C C C G T T C T G A G G A T G C C
SEQ. ID. NO. 32  C G T G G T T T T C T C C A G T G G C C C A G A T

SEQ. ID. NO. 40  C G A G C A G T G A T T A T G T T T G C C A A T G
SEQ. ID. NO. 46  C G G G A G C T G C T T G C T G C C A G C C A G C
SEQ. ID. NO. 36  C G G G A G C T G C T T G C T G C C A G C C A G C
SEQ. ID. NO. 32  C T T G A G C C C C T C A T C A A G G A G A T T G

SEQ. ID. NO. 40  A G G A T G A C A T C A G G A G G A T A T T G G A
SEQ. ID. NO. 46  G C C T C A A T G C C A G C T T C A C C T G G G T
SEQ. ID. NO. 36  G C C T C A A T G C C A G C T T C A C C T G G G T
SEQ. ID. NO. 32  T C C G G C G C A A T A T C A C G G G C A A G A T

SEQ. ID. NO. 40  A G C A G C A A A A A A A C T A A A C C A A A G T
SEQ. ID. NO. 46  G G C C A G T G A T G G T T G G G G G G C C C T G
SEQ. ID. NO. 36  G G C C A G T G A T G G T T G G G G G G C C C T G
SEQ. ID. NO. 32  C T G G C T G G C C A G C G A G G C C T G G G C C

SEQ. ID. NO. 40  G G G C A T T T T C T C T G G A T T G G C T C A G
SEQ. ID. NO. 46  G A G A G T G T G G T G G C A G G C A G T G A G G
SEQ. ID. NO. 36  G A G A G T G T G G T G G C A G G C A G T G A G G
SEQ. ID. NO. 32  A G C T C C T C C C T G A T C G C C A T G C C T C

SEQ. ID. NO. 40  A T A G T T G G G G A T C C A A A A T A G C A C C
SEQ. ID. NO. 46  G G G C T G C T G A G G G T G C T A T C A C C A T
SEQ. ID. NO. 36  G G G C T G C T G A G G G T G C T A T C A C C A T
SEQ. ID. NO. 32  A G T A C T T C C A C G T G G T T G G C G G C A C

SEQ. ID. NO. 40  T G T C T A T C A G C A A G A G G A G A T T G C A
SEQ. ID. NO. 46  C G A G C T G G C C T C C T A C C C C A T C A G T
SEQ. ID. NO. 36  C G A G C T G G C C T C C T A C C C C A T C A G T
SEQ. ID. NO. 32  C A T T G G A T T C G C T C T G A A G G C T G G G

SEQ. ID. NO. 40  G A A G G G G C T G T G A C A A T T T T G C C C A
SEQ. ID. NO. 46  G A C T T T G C C T C C T A C T T C C A G A G C C
SEQ. ID. NO. 36  G A C T T T G C C T C C T A C T T C C A G A G C C
SEQ. ID. NO. 32  C A G A T C C C A G G C T T C C G G G A A T T C C
```

Figure 11e

```
SEQ. ID. NO. 40   A A C G A G C A T C A A T T G A T G G A T T T G A
SEQ. ID. NO. 46   T G G A C C C T T G G A A C A A C A G C C G G A A
SEQ. ID. NO. 36   T G G A C C C T T G G A A C A A C A G C C G G A A
SEQ. ID. NO. 32   T G A A G A A G G T C C A T C C C A G G A A G T C

SEQ. ID. NO. 40   T C G A T A C T T T A G A A G C C G A A C T C T T
SEQ. ID. NO. 46   C C C C T G G T T C C G T G A A T T C T G G G A G
SEQ. ID. NO. 36   C C C C T G G T T C C G T G A A T T C T G G G A G
SEQ. ID. NO. 32   T G T C C A C A A T G G T T T T G C C A A G G A G

SEQ. ID. NO. 40   G C C A A T A A T C G A A G A A A T G T G T G G T
SEQ. ID. NO. 46   C A G A G G T T C C G C T G C A G C T T C C G G C
SEQ. ID. NO. 36   C A G A G G T T C C G C T G C A G C T T C C G G C
SEQ. ID. NO. 32   T T T T G G G A A G A A A C A T T T A A C T G C C

SEQ. ID. NO. 40   T T G C A G A A T T C T G G G A G G A G A A T T T
SEQ. ID. NO. 46   A G C G A G A C T G C G C A G C C C A C T C T C T
SEQ. ID. NO. 36   A G C G A G A C T G C G C A G C C C A C T C T C T
SEQ. ID. NO. 32   A C C T C C A A G A A G G T G C A A A A G G A C C

SEQ. ID. NO. 40   T G G C T G C A A G T T A G G A T C A C A T G G G
SEQ. ID. NO. 46   C C G G G C T G T G C C C T T T G A G C A G G A G
SEQ. ID. NO. 36   C C G G G C T G T G C C C T T T G A G C A G G A G
SEQ. ID. NO. 32   T T T A C C T G T G G A C A C C T T T C T G A G A

SEQ. ID. NO. 40   A A A A G G A A C A G T C A T A T A A A G A A A T
SEQ. ID. NO. 46   T C C A A G A T C A T G T T T G T G G T C A A T G
SEQ. ID. NO. 36   T C C A A G A T C A T G T T T G T G G T C A A T G
SEQ. ID. NO. 32   G G T C A C G A A G A A A G T G G C G A C A G G T

SEQ. ID. NO. 40   G C A C A G G G C T G G A G C G A A T T G C T C G
SEQ. ID. NO. 46   C A G T G T A C G C C A T G G C C C A T G C G C T
SEQ. ID. NO. 36   C A G T G T A C G C C A T G G C C C A T G C G C T
SEQ. ID. NO. 32   T T A G C A A C A G C T C G A C A G C C T T C C G

SEQ. ID. NO. 40   G G A T T C A T C T T A T G A A C A G G A A G G A
SEQ. ID. NO. 46   C C A C A A C A T G C A C C G T G C C C T C T G C
SEQ. ID. NO. 36   C C A C A A C A T G C A C C G T G C C C T C T G C
SEQ. ID. NO. 32   A C C C C T C T G T A C A G G G G A T G A G A A C
```

Figure 11f

```
SEQ. ID. NO. 40   A A G G T C C A A T T T G T A A T T G A T G C T G
SEQ. ID. NO. 46   C C C A A C A C C A C C C G G C T C T G T G A C G
SEQ. ID. NO. 36   C C C A A C A C C A C C C G G C T C T G T G A C G
SEQ. ID. NO. 32   A T C A G C A G T G T C G A G A C C C C T T A C A

SEQ. ID. NO. 40   T A T A T T C C A T G G C T T A C G C C C T G C A
SEQ. ID. NO. 46   C G A T G C G G C C A G T T A A C G G G C G C C G
SEQ. ID. NO. 36   C G A T G C G G C C A G T T A A C G G G C G C C G
SEQ. ID. NO. 32   T A G A T T A C A C G C A T T T A C G G A T A T C

SEQ. ID. NO. 40   C A A T A T G C A C A A A G A T C T C T G C C C T
SEQ. ID. NO. 46   C C T C T A C A A G G A C T T T G T G C T C A A C
SEQ. ID. NO. 36   C C T C T A C A A G G A C T T T G T G C T C A A C
SEQ. ID. NO. 32   C T A C A A T G T G T A C T T A G C A G T C T A C

SEQ. ID. NO. 40   G G A T A C A T T G G C C T T T G T C C A C G A A
SEQ. ID. NO. 46   G T C A A G T T T G A T G C C C C T T T C G C C
SEQ. ID. NO. 36   G T C A A G T T T G A T G C C C C T T T C G C C
SEQ. ID. NO. 32   T C C A T T G C C C A C G C C T T G C A A G A T A

SEQ. ID. NO. 40   T G A G T A C C A T T G A T G G G A A A G A G C T
SEQ. ID. NO. 46   C A G C T G A C A C C C A C A A T G A G G T C C G
SEQ. ID. NO. 36   C A G C T G A C A C C C A C A A T G A G G T C C G
SEQ. ID. NO. 32   T A T A T A C C T G C T T A C C T G G G A G A G G

SEQ. ID. NO. 40   A C T T G G T T A T A T T C G G G C T G T A A A T
SEQ. ID. NO. 46   C T T T G A C C G C T T T G G T G A T G G T A T T
SEQ. ID. NO. 36   C T T T G A C C G C T T T G G T G A T G G T A T T
SEQ. ID. NO. 32   G C T C T T C A C C A A T G G C T C C T G T G C A

SEQ. ID. NO. 40   T T T A A T G G C A G T G C T G G C A C T C C T G
SEQ. ID. NO. 46   G G C C G C T A C A A C A T C T T C A C C T A T C
SEQ. ID. NO. 36   G G C C G C T A C A A C A T C T T C A C C T A T C
SEQ. ID. NO. 32   G A C A T C A A G A A A G T T G A G G C G T G G C

SEQ. ID. NO. 40   T C A C T T T T A A T G A A A A C G G A G A T G C
SEQ. ID. NO. 46   T G C G T G C A G G C A G T G G G C G C T A T C G
SEQ. ID. NO. 36   T G C G T G C A G G C A G T G G G C G C T A T C G
SEQ. ID. NO. 32   A G G T C C T G A A G C A C C T A C G G C A T C T
```

Figure 11g

SEQ. ID. NO. 40  T C C T G G A C G T T A T G A T A T C T T C C A G
SEQ. ID. NO. 46  C T A C C A G A A G G T G G G C T A C T G G G C A
SEQ. ID. NO. 36  C T A C C A G A A G G T G G G C T A C T G G G C A
SEQ. ID. NO. 32  A A A C T T T A C A A A C A A T A T G G G G A G

SEQ. ID. NO. 40  T A T C A A A T A A C C A A C A A A A G C A C A G
SEQ. ID. NO. 46  G A A G G C T T G A C T C T G G A C A C C A G C C
SEQ. ID. NO. 36  G A A G G C T T G A C T C T G G A C A C C A G C C
SEQ. ID. NO. 32  C A G G T G A C C T T T G A T G A G T G T G G T G

SEQ. ID. NO. 40  A G T A C A A A G T C A T C G G C C A C T G G A C
SEQ. ID. NO. 46  T C A T C C C A T G G G C C T C A C C C T C A G C
SEQ. ID. NO. 36  T C A T C C C A T G G G C C T C A C C C T C A G C
SEQ. ID. NO. 32  A C C T G G T G G G G A A C T A T T C C A T C A T

SEQ. ID. NO. 40  C A A T C A G C T T C A T C T A A A A G T G G A A
SEQ. ID. NO. 46  C G G C C C C C T G C C C G C C T C T C G C T G C
SEQ. ID. NO. 36  C G G C C C C C T G C C C G C C T C T C G C T G C
SEQ. ID. NO. 32  C A A C T G G C A C C T C T C C C C A G A G G A T

SEQ. ID. NO. 40  G A C A T G C A G T G G G C T C A T A G A G A A C
SEQ. ID. NO. 46  A G T G A G C C C T G C C T C C A G A A T G A G G
SEQ. ID. NO. 36  A G T G A G C C C T G C C T C C A G A A T G A G G
SEQ. ID. NO. 32  G G C T C C A T C G T G T T T A A G G A A G T C G

SEQ. ID. NO. 40  A T A C T C A C C C G G C G T C T G T C T G C A G
SEQ. ID. NO. 46  T G A A G A G T G T G C A G C C G G G C G A A G T
SEQ. ID. NO. 36  T G A A G A G T G T G C A G C C G G G C G A A G T
SEQ. ID. NO. 32  G G T A T T A C A A C G T C T A T G C C A A G A A

SEQ. ID. NO. 40  C C T G C C G T G T A A G C C A G G G G A G A G G
SEQ. ID. NO. 46  C T G C T G C T G G C T C T G C A T T C C G T G C
SEQ. ID. NO. 36  C T G C T G C T G G C T C T G C A T T C C G T G C
SEQ. ID. NO. 32  G G G A G A A A G A C T C T T C A T C A A C G A G

SEQ. ID. NO. 40  A A G A A A A C G G T G A A A G G G G T C C C T T
SEQ. ID. NO. 46  C A G C C C T A T G A G T A C C G A T T G G A C G
SEQ. ID. NO. 36  C A G C C C T A T G A G T A C C G A T T G G A C G
SEQ. ID. NO. 32  G A G A A A A T C C T G T G G A G T G G G T T C T

Figure 11h

SEQ. ID. NO. 40  G C T G C T G G C A C T G T G A A C G C T G T G A
SEQ. ID. NO. 46  A A T T C A C T T G C G C T G A T T G T G G C C T
SEQ. ID. NO. 36  A A T T C A C T T G C G C T G A T T G T G G C C T
SEQ. ID. NO. 32  C C A G G G A G G T G C C C T T C T C C A A C T G

SEQ. ID. NO. 40  A G G T T A C A A C T A C C A C G T G G A T G A G
SEQ. ID. NO. 46  G G G C T A C T G G C C C A A T G C C A G C C T G
SEQ. ID. NO. 36  G G G C T A C T G G C C C A A T G C C A G C C T G
SEQ. ID. NO. 32  C A G C C G A G A C T G C C T G G C A G G G A C C

SEQ. ID. NO. 40  C T G T C C T G T G A A C T T T G C C C T C T G G
SEQ. ID. NO. 46  A C T G G C T G C T T C G A A C T G C C C C A G G
SEQ. ID. NO. 36  A C T G G C T G C T T C G A A C T G C C C C A G G
SEQ. ID. NO. 32  A G G A A A G G G A T C A T T G A G G G G A G C

SEQ. ID. NO. 40  A T C A G A G A C C C A A C A T G A A C C G C A C
SEQ. ID. NO. 46  A G T A C A T C C G C T G G G G C G A T G C C T G
SEQ. ID. NO. 36  A G T A C A T C C G C T G G G G C G A T G C C T G
SEQ. ID. NO. 32  C C A C C T G C T G C T T T G A G T G T G T G G A

SEQ. ID. NO. 40  A G G C T G C C A G C T T A T C C C C A T C A T C
SEQ. ID. NO. 46  G G C T G T G G G A C C T G T C A C C A T C G C C
SEQ. ID. NO. 36  G G C T G T G G G A C C T G T C A C C A T C G C C
SEQ. ID. NO. 32  G T G T C C T G A T G G G G A G T A T A G T G A T

SEQ. ID. NO. 40  A A A T T G G A G T G G C A T T C T C C C T G G G
SEQ. ID. NO. 46  T G C C T C G G T G C C C T G G C C A C C C T C T
SEQ. ID. NO. 36  T G C C T C G G T G C C C T G G C C A C C C T C T
SEQ. ID. NO. 32  G A G A C A G A T G C C A G T G C C T G T A A C A

SEQ. ID. NO. 40  C T G T G G T G C C T G T G T T T G T T G C A A T
SEQ. ID. NO. 46  T T G T G C T G G G T G T C T T T G T G C G G C A
SEQ. ID. NO. 36  T T G T G C T G G G T G T C T T T G T G C G G C A
SEQ. ID. NO. 32  A G T G C C C A G A T G A C T T C T G G T C C A A

SEQ. ID. NO. 40  A T T G G G A A T C A T C G C C A C C A C C T T T
SEQ. ID. NO. 46  C A A T G C C A C A C C A G T G G T C A A G G C C
SEQ. ID. NO. 36  C A A T G C C A C A C C A G T G G T C A A G G C C
SEQ. ID. NO. 32  T G A G A A C C A C A C C T C C T G C T T C G A A

Figure 11i

SEQ. ID. NO. 40   G T G A T C G T G A C C T T T G T C C G C T A T A
SEQ. ID. NO. 46   T C A G G T C G G G A G C T C T G C T A C A T C C
SEQ. ID. NO. 36   T C A G G T C G G G A G C T C T G C T A C A T C C
SEQ. ID. NO. 32   C T G C C C C A G G A G T A C A T C C G C T G G G

SEQ. ID. NO. 40   A T G A C A C A C C T A T C G T G A G G G C T T C
SEQ. ID. NO. 46   T G C T G G C T G G T G T C T T C C T C T G C T A
SEQ. ID. NO. 36   T G C T G G G T G G T G T C T T C C T C T G C T A
SEQ. ID. NO. 32   G C G A T G C C T G G C T G T G G G A C C T G T

SEQ. ID. NO. 40   A G G A C G C G A A C T T A G T T A C G T G C T C
SEQ. ID. NO. 46   C T G C A T G A C C T T C A T C T T C A T T G C C
SEQ. ID. NO. 36   C T G C A T G A C C T T C A T C T T C A T T G C C
SEQ. ID. NO. 32   C A C C A T C G C C T G C C T C G G T G C C C T G

SEQ. ID. NO. 40   C T A A C G G G G A T T T T T C T C T G T T A T T
SEQ. ID. NO. 46   A A G C C A T C C A C G G C A G T G T G T A C C T
SEQ. ID. NO. 36   A A G C C A T C C A C G G C A G T G T G T A C C T
SEQ. ID. NO. 32   G C C A C C C T G T T T G T G C T G G G T G T C T

SEQ. ID. NO. 40   C A A T C A C G T T T T T A A T G A T T G C A G C
SEQ. ID. NO. 46   T A C G G C G T C T T G G T T T G G G C A C T G C
SEQ. ID. NO. 36   T A C G G C G T C T T G G T T T G G G C A C T G C
SEQ. ID. NO. 32   T T G T G C G G C A C A A T G C C A C A C C A G T

SEQ. ID. NO. 40   A C C A G A T A C A A T C A T A T G C T C C T T C
SEQ. ID. NO. 46   C T T C T C T G T C T G C T A C T C A G C C C T G
SEQ. ID. NO. 36   C T T C T C T G T C T G C T A C T C A G C C C T G
SEQ. ID. NO. 32   G G T C A A G G C C T C A G G T C G G G A G C T C

SEQ. ID. NO. 40   C G A C G G G T C T T C C T A G G A C T T G G C A
SEQ. ID. NO. 46   C T C A C C A A G A C C A A C C G C A T T G C A C
SEQ. ID. NO. 36   C T C A C C A A G A C C A A C C G C A T T G C A C
SEQ. ID. NO. 32   T G C T A C A T C C T G C T G G G T G G T G T C T

SEQ. ID. NO. 40   T G T G T T T C A G C T A T G C A G C C C T T C T
SEQ. ID. NO. 46   G C A T C T T C G G T G G G G C C C G G G A G G G
SEQ. ID. NO. 36   G C A T C T T C G G T G G G G C C C G G G A G G G
SEQ. ID. NO. 32   T C C T C T G C T A C T G C A T G A C C T T C A T

Figure 11j

SEQ. ID. NO. 40  G A C C A A A A C A A A C C G T A T C C A C C G A
SEQ. ID. NO. 46  T G C C C A G C G G C C A C G C T T C A T C A G T
SEQ. ID. NO. 36  T G C C C A G C G G C C A C G C T T C A T C A G T
SEQ. ID. NO. 32  C T T C A T T G C C A A G C C A T C C A C G G C A

SEQ. ID. NO. 40  A T A T T T G A G C A G G G G A A G A A A T C T G
SEQ. ID. NO. 46  C C T G C C T C A C A G G T G G C C A T C T G C C
SEQ. ID. NO. 36  C C T G C C T C A C A G G T G G C C A T C T G C C
SEQ. ID. NO. 32  G T G T G T A C C T T A C G G C G T C T T G G T T

SEQ. ID. NO. 40  T C A C A G C G C C C A A G T T C A T T A G T C C
SEQ. ID. NO. 46  T G G C A C T T A T C T C G G C C A G C T G C T
SEQ. ID. NO. 36  T G G C A C T T A T C T C G G C C A G C T G C T
SEQ. ID. NO. 32  T G G G C A C T G C C T T C T C T G T C T G C T A

SEQ. ID. NO. 40  A G C A T C T C A G C T G G T G A T C A C C T T C
SEQ. ID. NO. 46  C A T C G T G G T C G C C T G G C T G G T G G T G
SEQ. ID. NO. 36  C A T C G T G G T C G C C T G G C T G G T G G T G
SEQ. ID. NO. 32  C T C A G C C C T G C T C A C C A A G A C C A A C

SEQ. ID. NO. 40  A G C C T C A T C T C C G T C C A G C T C C T T G
SEQ. ID. NO. 46  G A G G C A C C G G G C A C A G G C A A G G A G A
SEQ. ID. NO. 36  G A G G C A C C G G G C A C A G G C A A G G A G A
SEQ. ID. NO. 32  C G C A T T G C A C G C A T C T T C G G T G G G G

SEQ. ID. NO. 40  G A G T G T T T G T C T G G T T T G T T G T G G A
SEQ. ID. NO. 46  C A G C C C C C G A A C G G C G G G A G G T G G T
SEQ. ID. NO. 36  C A G C C C C C G A A C G G C G G G A G G T G G T
SEQ. ID. NO. 32  C C C G C G A G G G T G C C C A G C G G C C A C G

SEQ. ID. NO. 40  T C C C C C C C A C A T C A T C A T T G A C T A T
SEQ. ID. NO. 46  G A C A C T G C G C T G C A A C C A C C G C G A T
SEQ. ID. NO. 36  G A C A C T G C G C T G C A A C C A C C G C G A T
SEQ. ID. NO. 32  C T T C A T C A G T C C T G C C T C A C A G G T G

SEQ. ID. NO. 40  G G A G A G C A G C G G A C A C T A G A T C C A G
SEQ. ID. NO. 46  G C A A G T A T G T T G G G C T C G C T G G C C T
SEQ. ID. NO. 36  G C A A G T A T G T T G G G C T C G C T G G C C T
SEQ. ID. NO. 32  G C C A T C T G C C T G G C A C T T A T C T C G G

Figure 11k

SEQ. ID. NO. 40  A G A A G G C C A G G G G A G T G C T C A A G T G
SEQ. ID. NO. 46  A C A A T G T G C T C C T C A T C G C G C T C T G
SEQ. ID. NO. 36  A C A A T G T G C T C C T C A T C G C G C T C T G
SEQ. ID. NO. 32  G C C A G C T G C T C A T C G T G G T C G C C T G

SEQ. ID. NO. 40  T G A C A T T T C T G A T C T C T C A C T C A T T
SEQ. ID. NO. 46  C A C G C T T T A T G C C T T C A A G A C T C G C
SEQ. ID. NO. 36  C A C G C T T T A T G C C T T C A A G A C T C G C
SEQ. ID. NO. 32  G C T G G T G G T G G A G G C A C C G G G C A C A

SEQ. ID. NO. 40  T G T T C A C T T G G A T A C A G T A T C C T C T
SEQ. ID. NO. 46  A A G T G C C C C G A A A A C T T C A A C G A G G
SEQ. ID. NO. 36  A A G T G C C C C G A A A A C T T C A A C G A G G
SEQ. ID. NO. 32  G G C A A G G A G A C A G C C C C C G A A C G G C

SEQ. ID. NO. 40  T G A T G G T C A C T T G T A C T G T T T A T G C
SEQ. ID. NO. 46  C C A A G T T C A T T G G C T T C A C C A T G T A
SEQ. ID. NO. 36  C C A A G T T C A T T G G C T T C A C C A T G T A
SEQ. ID. NO. 32  G G G A G G T G G T G A C A C T G C G C T G C A A

SEQ. ID. NO. 40  C A T T A A A A C G A G A G G T G T C C C A G A G
SEQ. ID. NO. 46  C A C C A C C T G C A T C A T C T G G C T G G C A
SEQ. ID. NO. 36  C A C C A C C T G C A T C A T C T G G C T G G C A
SEQ. ID. NO. 32  C C A C C G C G A T G C A A G T A T G T T G G G C

SEQ. ID. NO. 40  A C T T T C A A T G A A G C C A A A C C T A T T G
SEQ. ID. NO. 46  T T C C T G C C C A T C T T C T A T G T C A C C T
SEQ. ID. NO. 36  T T C C T G C C C A T C T T C T A T G T C A C C T
SEQ. ID. NO. 32  T C G C T G G C C T A C A A T G T G C T C C T C A

SEQ. ID. NO. 40  G A T T T A C C A T G T A T A C C A C C T G C A T
SEQ. ID. NO. 46  C C A G T G A C T A C C G G G T A C A G A C C A C
SEQ. ID. NO. 36  C C A G T G A C T A C C G G G T A C A G A C C A C
SEQ. ID. NO. 32  T C G C G C T C T G C A C G C T T T A T G C C T T

SEQ. ID. NO. 40  C A T T T G G T T A G C T T T C A T C C C C A T C
SEQ. ID. NO. 46  C A C C A T G T G C G T G T C A G T C A G C C T C
SEQ. ID. NO. 36  C A C C A T G T G C G T G T C A G T C A G C C T C
SEQ. ID. NO. 32  C A A T A C T C G C A A G T G C C C C G A A A A C

Figure 111

SEQ. ID. NO. 40  T T T T T T G G T A C A G C C C A G T C A G C A G
SEQ. ID. NO. 46  A G C G G C T C C G T G G T G C T T G G C T G C C
SEQ. ID. NO. 36  A G C G G C T C C G T G G T G C T T G G C T G C C
SEQ. ID. NO. 32  T T C A A C G A G G C C A A G T T C A T T G G C T

SEQ. ID. NO. 40  A A A A G A T G T A C A T C C A G A C A A C A A C
SEQ. ID. NO. 46  T C T T T G C G C C C A A G C T G C A C A T C A T
SEQ. ID. NO. 36  T C T T T G C G C C C A A G C T G C A C A T C A T
SEQ. ID. NO. 32  T C A C C A T G T A C A C C A C C T G C A T C A T

SEQ. ID. NO. 40  A C T T A C T G T C T C C A T G A G T T T A A G T
SEQ. ID. NO. 46  C C T C T T C C A G C C G C A G A A G A A C A C C
SEQ. ID. NO. 36  C C T C T T C C A G C C G C A G A A G A A C A C C
SEQ. ID. NO. 32  C T G G C T G G C A T T G T T G C C C A T C T T C

SEQ. ID. NO. 40  G C T T C A G T A T C T C T G G G C A T G C T C T
SEQ. ID. NO. 46  A T C G A G G A G G T G C G T T G C A G C A C C G
SEQ. ID. NO. 36  A T C G A G G A G G T G C G T T G C A G C A C C G
SEQ. ID. NO. 32  T A T G T C A C C T C C A G T G A C T A C C G G G

SEQ. ID. NO. 40  A T A T G C C C A A G G T T T A T A T T A T A A T
SEQ. ID. NO. 46  C A G C T C A C G C T T T C A A G G T G G C T G C
SEQ. ID. NO. 36  C A G C T C A C G C T T T C A A G G T G G C T G C
SEQ. ID. NO. 32  T A C A G A C C A C C A C C A T G T G C G T G T C

SEQ. ID. NO. 40  T T T T C A T C C A G A A C A G A A T A C C A T C
SEQ. ID. NO. 46  C C G G G C C A C G C T G C G C C G C A G C A A C
SEQ. ID. NO. 36  C C G G G C C A C G C T G C G C C G C A G C A A C
SEQ. ID. NO. 32  A G T C A G C C T C A G C G G C T C C G T G G T G

SEQ. ID. NO. 40  G A G G A G G T G C G T T G C A G C A C C G C A G
SEQ. ID. NO. 46  G T C T C C C G C A A G C G G T C C A G C A G C C
SEQ. ID. NO. 36  G T C T C C C G C A A G C G G T C C A G C A G C C
SEQ. ID. NO. 32  C T T G G C T G C C T C T T T G C G C C C A A G C

SEQ. ID. NO. 40  C T C A C G C T T T C A A G G T G G C T G C C C G
SEQ. ID. NO. 46  T T G G A G G C T C C A C G G G A T C C A C C C C
SEQ. ID. NO. 36  T T G G A G G C T C C A C G G G A T C C A C C C C
SEQ. ID. NO. 32  T G C A C A T C A T C C T C T T C C A G C C G C A

Figure 11m

```
SEQ. ID. NO. 40  G G C C A C G C T G C G C C G C A G C A A C G T C
SEQ. ID. NO. 46  C T C C T C C T C C A T C A G C A G C A A G A G C
SEQ. ID. NO. 36  C T C C T C C T C C A T C A G C A G C A A G A G C
SEQ. ID. NO. 32  G A A G A A C G T G G T T A G C C A C C G G G C A

SEQ. ID. NO. 40  T C C C G C A A G C G G T C C A G C A G C C T T G
SEQ. ID. NO. 46  A A C A G C G A A G A C C C A T T C C C A C A G C
SEQ. ID. NO. 36  A A C A G C G A A G A C C C A T T C C C A C A G C
SEQ. ID. NO. 32  C C C A C C A G C C G C T T T G G C A G T G C T G

SEQ. ID. NO. 40  G A G G C T C C A C G G G A T C C A C C C C C T C
SEQ. ID. NO. 46  C C G A G A G G C A G A A G C A G C A G C A G C C
SEQ. ID. NO. 36  C C G A G A G G C A G A A G C A G C A G C A G C C
SEQ. ID. NO. 32  C T G C C A G G G C C A G C T C C A G C C T T G G

SEQ. ID. NO. 40  C T C C T C C A T C A G C A G C A A G A G C A A C
SEQ. ID. NO. 46  G C T G G C C C T A A C C C A G C A A G A G C A G
SEQ. ID. NO. 36  G C T G G C C C T A A C C A G C A A G A G C A G
SEQ. ID. NO. 32  C C A A G G G T C T G G C T C C A G T T T G T C

SEQ. ID. NO. 40  A G C G A A G A C C C A T T C C C A C A G C C C G
SEQ. ID. NO. 46  C A G C A G C A G C C C C T G A C C C T C C C A C
SEQ. ID. NO. 36  C A G C A G C A G C C C C T G A C C C T C C C A C
SEQ. ID. NO. 32  C C C A C T G T T T G C A A T G G C C G T G A G G

SEQ. ID. NO. 40  A G A G G C A G A A G C A G C A G C A G C C G C T
SEQ. ID. NO. 46  A G C A G C A A C G A T C T C A G C A G C A G C C
SEQ. ID. NO. 36  A G C A G C A A C G A T C T C A G C A G C A G C C
SEQ. ID. NO. 32  T G G T G G A C T C G A C A A C G T C A T C G C T

SEQ. ID. NO. 40  G G C C C T A A C C C A G C A A G A G C A G C A G
SEQ. ID. NO. 46  C A G A T G C A A G C A G A A G G T C A T C T T T
SEQ. ID. NO. 36  C A G A T G C A A G C A G A A G G T C A T C T T T
SEQ. ID. NO. 32  T A T G A C T C T G G A G T C C A T C A T G G C G

SEQ. ID. NO. 40  C A G C A G C C C C T G A C C C T C C C A C A G C
SEQ. ID. NO. 46  G G C A G C G G C A C G G T C A C C T T C T C A C
SEQ. ID. NO. 36  G G C A G C G G C A C G G T C A C C T T C T C A C
SEQ. ID. NO. 32  T G C T G C C T G A G C G A G G A G G C C A A G G
```

Figure 11n

SEQ. ID. NO. 40   A G C A A C G A T C T C A G C A G C A G C C C A G
SEQ. ID. NO. 46   T G A G C T T T G A T G A G C C T C A G A A G A A
SEQ. ID. NO. 36   T G A G C T T T G A T G A G C C T C A G A A G A A
SEQ. ID. NO. 32   A A G C C C G G C G G A T C A A C G A C G A G A T

SEQ. ID. NO. 40   A T G C A A G C A G A A G G T C A T C T T T G G C
SEQ. ID. NO. 46   C G C C A T G G C C C A C G G G A A T T C T A C G
SEQ. ID. NO. 36   C G C C A T G G C C C A C G G G A A T T C T A C G
SEQ. ID. NO. 32   C G A G C G G C A G C T C C G C A G G G A C A A G

SEQ. ID. NO. 40   A G C G G C A C G G T C A C C T T C T C A C T G A
SEQ. ID. NO. 46   C A C C A G A A C T C C C T G G A G G C C C A G A
SEQ. ID. NO. 36   C A C C A G A A C T C C C T G G A G G C C C A G A
SEQ. ID. NO. 32   C G G G A C G C C C G C C G G G A G C T C A A G C

SEQ. ID. NO. 40   G C T T T G A T G A G C C T C A G A A G A A C G C
SEQ. ID. NO. 46   A A A G C A G C G A T A C G C T G A C C C G A C A
SEQ. ID. NO. 36   A A A G C A G C G A T A C G C T G A C C C G A C A
SEQ. ID. NO. 32   T G C T G C T G C T C G G G A C A G G A G A G A G

SEQ. ID. NO. 40   C A T G G C C C A C G G G A A T T C T A C G C A C
SEQ. ID. NO. 46   C C A G C C A T T A C T C C C G C T G C A G T G C
SEQ. ID. NO. 36   C C A G C C A T T A C T C C C G C T G C A G T G C
SEQ. ID. NO. 32   T G G C A A G A G T A C G T T T A T C A A G C A G

SEQ. ID. NO. 40   C A G A A C T C C C T G G A G G C C C A G A A A A
SEQ. ID. NO. 46   G G G G A A A C G G A C T T A G A T C T G A C C G
SEQ. ID. NO. 36   G G G G A A A C G G A C T T A G A T C T G A C C G
SEQ. ID. NO. 32   A T G A G A A T C A T C C A T G G G T C A G G A T

SEQ. ID. NO. 40   G C A G C G A T A C G C T G A C C C G A C A C C A
SEQ. ID. NO. 46   T C C A G G A A A C A G G T C T G C A A G G A C C
SEQ. ID. NO. 36   T C C A G G A A A C A G G T C T G C A A G G A C C
SEQ. ID. NO. 32   A C T C T G A T G A A G A T A A A A G G G G C T T

SEQ. ID. NO. 40   G C C A T T A C T C C C G C T G C A G T G C G G G
SEQ. ID. NO. 46   T G T G G G T G G A G A C C A G C G G C C A G A G
SEQ. ID. NO. 36   T G T G G G T G G A G A C C A G C G G C C A G A G
SEQ. ID. NO. 32   C A C C A A G C T G G T G T A T C A G A A C A T C

Figure 11o

```
SEQ. ID. NO. 40   G A A A C G G A C T T A G A T C T G A C C G T C C
SEQ. ID. NO. 46   G T G G A G G A C C C T G A A G A G T T G T C C C
SEQ. ID. NO. 36   G T G G A G G A C C C T G A A G A G T T G T C C C
SEQ. ID. NO. 32   T T C A C G G C C A T G C A G G C C A T G A T C A

SEQ. ID. NO. 40   A G G A A A C A G G T C T G C A A G G A C C T G T
SEQ. ID. NO. 46   C A G C A C T T G T A G T G T C C A G T T C A C A
SEQ. ID. NO. 36   C A G C A C T T G T A G T G T C C A G T T C A C A
SEQ. ID. NO. 32   G A G C C A T G G A C A C T C A A G A T C C C

SEQ. ID. NO. 40   G G G T G G A G A C C A G C G G C C A G A G G T G
SEQ. ID. NO. 46   G A G C T T T G T C A T C A G T G G T G G A G G C
SEQ. ID. NO. 36   G A G C T T T G T C A T C A G T G G T G G A G G C
SEQ. ID. NO. 32   A T A C A A G T A T G A G C A C A A T A A G G C T

SEQ. ID. NO. 40   G A G G A C C C T G A A G A G T T G T C C C A G
SEQ. ID. NO. 46   A G C A C T G T T A C A G A A A A C G T A G T G A
SEQ. ID. NO. 36   A G C A C T G T T A C A G A A A A C G T A G T G A
SEQ. ID. NO. 32   C A T G C A C A A T T A G T T C G A G A A G T T G

SEQ. ID. NO. 40   C A C T T G T A G T G T C C A G T T C A C A G A G
SEQ. ID. NO. 46   A T T C A G C G G C C G C C A T G A C T C T G G A
SEQ. ID. NO. 36   A T T C A A T G A C T C T G G A G T C C A T C A T
SEQ. ID. NO. 32   A T G T G G A G A A G G T G T C T G C T T T T G A

SEQ. ID. NO. 40   C T T T G T C A T C A G T G G T G G A G G C A G C
SEQ. ID. NO. 46   G T C C A T C A T G G C G T G C T G C C T G A G C
SEQ. ID. NO. 36   G G C G T G C T G C C T G A G C G A G G A G G C C
SEQ. ID. NO. 32   G A A T C C A T A T G T A G A T G C A A T A A A G

SEQ. ID. NO. 40   A C T G T T A C A G A A A C G T A G T G A A T T
SEQ. ID. NO. 46   G A G G A G G C C A A G G A A G C C C G G C G G A
SEQ. ID. NO. 36   A A G G A A G C C C G G C G G A T C A A C G A C G
SEQ. ID. NO. 32   A G T T T A T G G A A T G A T C C T G G A A T C C

SEQ. ID. NO. 40   C A - - - - - - - - - - - - - - - - - - - - - - -
SEQ. ID. NO. 46   T C A A C G A C G A G A T C G A G C G G C A G C T
SEQ. ID. NO. 36   A G A T C G A G C G G C A G C T C C G C A G G G A
SEQ. ID. NO. 32   A G G A A T G C T A T G A T A G A C G A C G A G A
```

Figure 11p

```
SEQ. ID. NO. 40  - - - - - , - - - - - - - - - - - - - - - - - - -
SEQ. ID. NO. 46  C C G C A G G G A C A A G C G G G A C G C C C G C
SEQ. ID. NO. 36  C A A G C G G G A C G C C C G C C G G G A G C T C
SEQ. ID. NO. 32  A T A T C A A T T A T C T G A C T C T A C C A A A

SEQ. ID. NO. 40  - - - - - - - - - - - - - - - - A T G A C T C T G G
SEQ. ID. NO. 46  C G G G A G C T C A A G C T G C T G C T G C T C G
SEQ. ID. NO. 36  A A G C T G C T G C T G C T C G G G A C A G G A G
SEQ. ID. NO. 32  T A C T A T C T T A A T G A C T T G G A C C G C G

SEQ. ID. NO. 40  A G T C C A T C A T G G C G T G C T G C C T G A G
SEQ. ID. NO. 46  G G A C A G G A G A G A G T G G C A A G A G T A C
SEQ. ID. NO. 36  A G A G T G G C A A G A G T A C G T T T A T C A A
SEQ. ID. NO. 32  T A G C T G A C C C T G C C T A C C T G C C T A C

SEQ. ID. NO. 40  C G A G G A G G C C A A G G A A G C C C G G C G G
SEQ. ID. NO. 46  G T T T A T C A A G C A G A T G A G A A T C A T C
SEQ. ID. NO. 36  G C A G A T G A G A A T C A T C C A T G G G T C A
SEQ. ID. NO. 32  G C A A C A A G A T G T G C T T A G A G T T C G A

SEQ. ID. NO. 40  A T C A A C G A C G A G A T C G A G C G G C A G C
SEQ. ID. NO. 46  C A T G G G T C A G G A T A C T C T G A T G A A G
SEQ. ID. NO. 36  G G A T A C T C T G A T G A A G A T A A A A G G G
SEQ. ID. NO. 32  G T C C C C A C C A C A G G G A T C A T C G A A T

SEQ. ID. NO. 40  T C C G C A G G G A C A A G C G G G A C G C C C G
SEQ. ID. NO. 46  A T A A A A G G G G C T T C A C C A A G C T G G T
SEQ. ID. NO. 36  G C T T C A C C A A G C T G G T G T A T C A G A A
SEQ. ID. NO. 32  A C C C C T T T G A C T T A C A A A G T G T C A T

SEQ. ID. NO. 40  C C G G G A G C T C A A G C T G C T G C T G C T C
SEQ. ID. NO. 46  G T A T C A G A A C A T C T T C A C G G C C A T G
SEQ. ID. NO. 36  C A T C T T C A C G G C C A T G C A G G C C A T G
SEQ. ID. NO. 32  T T T C A G A A T G G T C G A T G T A G G G G C C

SEQ. ID. NO. 40  G G G A C A G G A G A G A G T G G C A A G A G T A
SEQ. ID. NO. 46  C A G G C C A T G A T C A G A G C C A T G G A C A
SEQ. ID. NO. 36  A T C A G A G C C A T G G A C A C A C T C A A G A
SEQ. ID. NO. 32  C A A A G G T C A G A G A G A A G A A A A T G G A
```

Figure 11q

```
SEQ. ID. NO. 40   C G T T T A T C A A G C A G A T G A G A A T C A T
SEQ. ID. NO. 46   C A C T C A A G A T C C C A T A C A A G T A T G A
SEQ. ID. NO. 36   T C C C A T A C A A G T A T G A G C A C A A T A A
SEQ. ID. NO. 32   T A C A C T G C T T T G A A A A T G T C A C C T C

SEQ. ID. NO. 40   C C A T G G G T C A G G A T A C T C T G A T G A A
SEQ. ID. NO. 46   G C A C A A T A A G G C T C A T G C A C A A T T A
SEQ. ID. NO. 36   G G C T C A T G C A C A A T T A G T T C G A G A A
SEQ. ID. NO. 32   T A T C A T G T T T C T A G T A G C G C T T A G T

SEQ. ID. NO. 40   G A T A A A G G G G C T T C A C C A A G C T G G
SEQ. ID. NO. 46   G T T C G A G A A G T T G A T G T G G A G A A G G
SEQ. ID. NO. 36   G T T G A T G T G G A G A A G G T G T C T G C T T
SEQ. ID. NO. 32   G A A T A T G A T C A A G T T C T C G T G G A G T

SEQ. ID. NO. 40   T G T A T C A G A A C A T C T T C A C G G C C A T
SEQ. ID. NO. 46   T G T C T G C T T T T G A G A A T C C A T A T G T
SEQ. ID. NO. 36   T T G A G A A T C C A T A T G T A G A T G C A A T
SEQ. ID. NO. 32   C A G A C A A T G A G A A C C G A A T G G A G G A

SEQ. ID. NO. 40   G C A G G C C A T G A T C A G A G C C A T G G A C
SEQ. ID. NO. 46   A G A T G C A A T A A A G A G T T T A T G G A A T
SEQ. ID. NO. 36   A A A G A G T T T A T G G A A T G A T C C T G G A
SEQ. ID. NO. 32   A A G C A A G G C T C T C T T T A G A A C A A T T

SEQ. ID. NO. 40   A C A C T C A A G A T C C C A T A C A A G T A T G
SEQ. ID. NO. 46   G A T C C T G G A A T C C A G G A A T G C T A T G
SEQ. ID. NO. 36   A T C C A G G A A T G C T A T G A T A G A C G A C
SEQ. ID. NO. 32   A T C A C A T A C C C C T G G T T C C A G A A C T

SEQ. ID. NO. 40   A G C A C A A T A A G G C T C A T G C A C A A T T
SEQ. ID. NO. 46   A T A G A C G A C G A G A A T A T C A A T T A T C
SEQ. ID. NO. 36   G A G A A T A T C A A T T A T C T G A C T C T A C
SEQ. ID. NO. 32   C C T C G G T T A T T C T G T T C T T A A A C A A

SEQ. ID. NO. 40   A G T T C G A G A A G T T G A T G T G G A G A A G
SEQ. ID. NO. 46   T G A C T C T A C C A A A T A C T A T C T T A A T
SEQ. ID. NO. 36   C A A A T A C T A T C T T A A T G A C T T G G A C
SEQ. ID. NO. 32   G A A A G A T C T T C T A G A G G A G A A A A T C

Figure 11r
```

```
SEQ. ID. NO. 40  G T G T C T G C T T T T G A G A A T C C A T A T G
SEQ. ID. NO. 46  G A C T T G G A C C G C G T A G C T G A C C C T G
SEQ. ID. NO. 36  C G C G T A G C T G A C C C T G C C T A C C T G C
SEQ. ID. NO. 32  A T G T A T T C C C A T C T A G T C G A C T A C T

SEQ. ID. NO. 40  T A G A T G C A A T A A A G A G T T T A T G G A A
SEQ. ID. NO. 46  C C T A C C T G C C T A C G C A A C A A G A T G T
SEQ. ID. NO. 36  C T A C G C A A C A A G A T G T G C T T A G A G T
SEQ. ID. NO. 32  T C C A G A A T A T G A T G G A C C C A G A G

SEQ. ID. NO. 40  T G A T C C T G G A A T C C A G G A A T G C T A T
SEQ. ID. NO. 46  G C T T A G A G T T C G A G T C C C A C C A C A
SEQ. ID. NO. 36  T C G A G T C C C A C C A C A G G G A T C A T C
SEQ. ID. NO. 32  A G A T G C C C A G G C A G C C C G A G A A T T C

SEQ. ID. NO. 40  G A T A G A C G A C G A G A A T A T C A A T T A T
SEQ. ID. NO. 46  G G G A T C A T C G A A T A C C C C T T T G A C T
SEQ. ID. NO. 36  G A A T A C C C C T T T G A C T T A C A A A G T G
SEQ. ID. NO. 32  A T T C T G A A G A T G T T C G T G G A C C T G A

SEQ. ID. NO. 40  C T G A C T C T A C C A A A T A C T A T C T T A A
SEQ. ID. NO. 46  T A C A A A G T G T C A T T T T C A G A A T G G T
SEQ. ID. NO. 36  T C A T T T T C A G A A T G G T C G A T G T A G G
SEQ. ID. NO. 32  A C C A G A C A G T G A C A A A A T T A T C T A

SEQ. ID. NO. 40  T G A C T T G G A C C G C G T A G C T G A C C C T
SEQ. ID. NO. 46  C G A T G T A G G G G G C C A A A G G T C A G A G
SEQ. ID. NO. 36  G G G C C A A A G G T C A G A G A G A A G A A A A
SEQ. ID. NO. 32  C T C C C A C T T C A C G T G C G C C A C A G A C

SEQ. ID. NO. 40  G C C T A C C T G C C T A C G C A A C A A G A T G
SEQ. ID. NO. 46  A G A A G A A A A T G G A T A C A C T G C T T T G
SEQ. ID. NO. 36  T G G A T A C A C T G C T T T G A A A A T G T C A
SEQ. ID. NO. 32  A C C G A G A A T A T C C G C T T T G T C T T T G

SEQ. ID. NO. 40  T G C T T A G A G T T C G A G T C C C A C C A C
SEQ. ID. NO. 46  A A A A T G T C A C C T C T A T C A T G T T T C T
SEQ. ID. NO. 36  C C T C T A T C A T G T T T C T A G T A G C G C T
SEQ. ID. NO. 32  C T G C C G T C A A G G A C A C C A T C C T C C A
```

Figure 11s

SEQ. ID. NO. 40  A G G G A T C A T C G A A T A C C C C T T T G A C
SEQ. ID. NO. 46  A G T A G C G C T T A G T G A A T A T G A T C A A
SEQ. ID. NO. 36  T A G T G A A T A T G A T C A A G T T C T C G T G
SEQ. ID. NO. 32  G T T G A A C C T G A A G G A C T G C G G T C T G

SEQ. ID. NO. 40  T T A C A A A G T G T C A T T T T C A G A A T G G
SEQ. ID. NO. 46  G T T C T C G T G G A G T C A G A C A A T G A G A
SEQ. ID. NO. 36  G A G T C A G A C A A T G A G A A C C G A A T G G
SEQ. ID. NO. 32  T T C T A A

SEQ. ID. NO. 40  T C G A T G T A G G G G C C A A A G G T C A G A
SEQ. ID. NO. 46  A C C G A A T G G A G G A A A G C A A G G C T C T
SEQ. ID. NO. 36  A G G A A A G C A A G G C T C T C T T T A G A A C
SEQ. ID. NO. 32

SEQ. ID. NO. 40  G A G A A G A A A A T G G A T A C A C T G C T T T
SEQ. ID. NO. 46  C T T T A G A A C A A T T A T C A C A T A C C C C
SEQ. ID. NO. 36  A A T T A T C A C A T A C C C C T G G T T C C A G
SEQ. ID. NO. 32

SEQ. ID. NO. 40  G A A A A T G T C A C C T C T A T C A T G T T T C
SEQ. ID. NO. 46  T G G T T C C A G A A C T C C T C G G T T A T T C
SEQ. ID. NO. 36  A A C T C C T C G G T T A T T C T G T T C T T A A
SEQ. ID. NO. 32

SEQ. ID. NO. 40  T A G T A G C G C T T A G T G A A T A T G A T C A
SEQ. ID. NO. 46  T G T T C T T A A A C A A G A A A G A T C T T C T
SEQ. ID. NO. 36  A C A A G A A A G A T C T T C T A G A G G A G A A
SEQ. ID. NO. 32

SEQ. ID. NO. 40  A G T T C T C G T G G A G T C A G A C A A T G A G
SEQ. ID. NO. 46  A G A G G A G A A A A T C A T G T A T T C C C A T
SEQ. ID. NO. 36  A A T C A T G T A T T C C C A T C T A G T C G A C
SEQ. ID. NO. 32

SEQ. ID. NO. 40  A A C C G A A T G G A G G A A A G C A A G G C T C
SEQ. ID. NO. 46  C T A G T C G A C T A C T T C C C A G A A T A T G
SEQ. ID. NO. 36  T A C T T C C C A G A A T A T G A T G G A C C C C
SEQ. ID. NO. 32

Figure 11t

SEQ. ID. NO. 40  TCTTTAGAACAATTATCACATACCC
SEQ. ID. NO. 46  ATGGACCCCAGAGAGATGCCCAGGC
SEQ. ID. NO. 36  AGAGAGATGCCCAGGCAGCCCGAGA
SEQ. ID. NO. 32

SEQ. ID. NO. 40  CTGGTTCCAGAACTCCTCGGTTATT
SEQ. ID. NO. 46  AGCCCGAGAATTCATTCTGAAGATG
SEQ. ID. NO. 36  ATTCATTCTGAAGATGTTCGTGGAC
SEQ. ID. NO. 32

SEQ. ID. NO. 40  CTGTTCTTAAACAAGAAAGATCTTC
SEQ. ID. NO. 46  TTCGTGGACCTGAACCCAGACAGTG
SEQ. ID. NO. 36  CTGAACCCAGACAGTGACAAAATTA
SEQ. ID. NO. 32

SEQ. ID. NO. 40  TAGAGGAGAAAATCATGTATTCCCA
SEQ. ID. NO. 46  ACAAAATTATCTACTCCCACTTCAC
SEQ. ID. NO. 36  TCTACTCCCACTTCACGTGCGCCAC
SEQ. ID. NO. 32

SEQ. ID. NO. 40  TCTAGTCGACTACTTCCCAGAATAT
SEQ. ID. NO. 46  GTGCGCCACAGACACCGAGAATATC
SEQ. ID. NO. 36  AGACACCGAGAATATCCGCTTTGTC
SEQ. ID. NO. 32

SEQ. ID. NO. 40  GATGGACCCCAGAGAGATGCCCAGG
SEQ. ID. NO. 46  CGCTTTGTCTTTGCTGCCGTCAAGG
SEQ. ID. NO. 36  TTTGCTGCCGTCAAGGACACCATCC
SEQ. ID. NO. 32

SEQ. ID. NO. 40  CAGCCCGAGAATTCATTCTGAAGAT
SEQ. ID. NO. 46  ACACCATCCTCCAGTTGAACCTGAA
SEQ. ID. NO. 36  TCCAGTTGAACCTGAAGGACTGCGG
SEQ. ID. NO. 32

SEQ. ID. NO. 40  GTTCGTGGACCTGAACCCAGACAGT
SEQ. ID. NO. 46  GGACTGCGGTCTGTTCTAATTGTGC
SEQ. ID. NO. 36  TCTGTTCTAA
SEQ. ID. NO. 32

Figure 11u

SEQ. ID. NO. 40  G A C A A A A T T A T C T A C T C C C A C T T C A
SEQ. ID. NO. 46  C T C C T A G A C A C C C G C C C T G C C C T T C
SEQ. ID. NO. 36
SEQ. ID. NO. 32

SEQ. ID. NO. 40  C G T G C G C C A C A G A C A C C G A G A A T A T
SEQ. ID. NO. 46  C C T G G T
SEQ. ID. NO. 36
SEQ. ID. NO. 32

SEQ. ID. NO. 40  C C G C T T T G T C T T T G C T G C C G T C A A G
SEQ. ID. NO. 46
SEQ. ID. NO. 36
SEQ. ID. NO. 32

SEQ. ID. NO. 40  G A C A C C A T C C T C C A G T T G A A C C T G A
SEQ. ID. NO. 46
SEQ. ID. NO. 36
SEQ. ID. NO. 32

SEQ. ID. NO. 40  A G G A C T G C G G T C T G T T C T A A
SEQ. ID. NO. 46
SEQ. ID. NO. 36
SEQ. ID. NO. 32

Figure 11v

ClustalW Formatted Alignments

```
SEQ. ID. NO. 41   M V C E G K R S A S C P C F F L L T A K F Y W I L
SEQ. ID. NO. 47   M G S L L A L P A L L L L W G A V A E G P A K K V
SEQ. ID. NO. 37   M G S L L A L P A L L L L W G A V A E G P A K K V
SEQ. ID. NO. 33   M A F Y S C C W V L L A L T W H T S A Y G P D Q R

SEQ. ID. NO. 41   T M M Q R T H S Q E Y A H S I R V D G D I I L G G
SEQ. ID. NO. 47   L T L E G D L V L G G L F P V H Q K G G P A E D C
SEQ. ID. NO. 37   L T L E G D L V L G G L F P V H Q K G G P A E D C
SEQ. ID. NO. 33   A Q K K G D I I L G G L F P I H F G V A A K D Q D

SEQ. ID. NO. 41   L F P V H A K G E R G V P C G E L K K E K G I H R
SEQ. ID. NO. 47   G P V N E H R G I Q R L E A M L F A L D R I N R D
SEQ. ID. NO. 37   G P V N E H R G I Q R L E A M L F A L D R I N R D
SEQ. ID. NO. 33   L K S R P E S V E C I R Y N F R G F R W L Q A M I

SEQ. ID. NO. 41   L E A M L Y A I D Q I N K D P D L L S N I T L G V
SEQ. ID. NO. 47   P H L L P G V R L G A H I L D S C S K D T H A L E
SEQ. ID. NO. 37   P H L L P G V R L G A H I L D S C S K D T H A L E
SEQ. ID. NO. 33   F A I E E I N S S P A L L P N L T L G Y R I F D T

SEQ. ID. NO. 41   R I L D T C S R D T Y A L E Q S L T F V Q A L I E
SEQ. ID. NO. 47   Q A L D F V R A S L S R G A D G S R H I C P D G S
SEQ. ID. NO. 37   Q A L D F V R A S L S R G A D G S R H I C P D G S
SEQ. ID. NO. 33   C N T V S K A L E A T L S F V A Q N K I D S L N L

SEQ. ID. NO. 41   K D A S D V K C A N G D P P I F T K P D K I S G V
SEQ. ID. NO. 47   Y A T H G D A P T A I T G V I G G S Y S D V S I Q
SEQ. ID. NO. 37   Y A T H G D A P T A I T G V I G G S Y S D V S I Q
SEQ. ID. NO. 33   D E F C N C S E H I P S T I A V V G A T G S G V S

SEQ. ID. NO. 41   I G A A A S S V S I M V A N I L R L F K I P Q I S
SEQ. ID. NO. 47   V A N L L R L F Q I P Q I S Y A S T S A K L S D K
SEQ. ID. NO. 37   V A N L L R L F Q I P Q I S Y A S T S A K L S D K
SEQ. ID. NO. 33   T A V A N L L G L F Y I P Q V S Y A S S S R L L S

SEQ. ID. NO. 41   Y A S T A P E L S D N T R Y D F F S R V V P P D S
SEQ. ID. NO. 47   S R Y D Y F A R T V P P D F F Q A K A M A E I L R
SEQ. ID. NO. 37   S R Y D Y F A R T V P P D F F Q A K A M A E I L R
SEQ. ID. NO. 33   N K N Q F K S F L R T I P N D E H Q A T A M A D I
```

Figure 12a

SEQ. ID. NO. 41  Y Q A Q A M V D I V T A L G W N Y V S T L A S E G
SEQ. ID. NO. 47  F F N W T Y V S T V A S E G D Y G E T G I E A F E
SEQ. ID. NO. 37  F F N W T Y V S T V A S E G D Y G E T G I E A F E
SEQ. ID. NO. 33  I E Y F R W N W V G T I A A D D D Y G R P G I E K

SEQ. ID. NO. 41  N Y G E S G V E A F T Q I S R E I G G V C I A Q S
SEQ. ID. NO. 47  L E A R A R N I C V A T S E K V G R A M S R A A F
SEQ. ID. NO. 37  L E A R A R N I C V A T S E K V G R A M S R A A F
SEQ. ID. NO. 33  F R E E A E E R D I C I D F S E L I S Q Y S D E E

SEQ. ID. NO. 41  Q K I P R E P R P G E F E K I I K R L L E T P N A
SEQ. ID. NO. 47  E G V V R A L L Q K P S A R V A V L F T R S E D A
SEQ. ID. NO. 37  E G V V R A L L Q K P S A R V A V L F T R S E D A
SEQ. ID. NO. 33  E I Q H V V E V I Q N S T A K V I V V F S S G P D

SEQ. ID. NO. 41  R A V I M F A N E D D I R R I L E A A K K L N Q S
SEQ. ID. NO. 47  R E L L A A S Q R L N A S F T W V A S D G W G A L
SEQ. ID. NO. 37  R E L L A A S Q R L N A S F T W V A S D G W G A L
SEQ. ID. NO. 33  L E P L I K E I V R R N I T G K I W L A S E A W A

SEQ. ID. NO. 41  G H F L W I G S D S W G S K I A P V Y Q Q E E I A
SEQ. ID. NO. 47  E S V V A G S E G A A E G A I T I E L A S Y P I S
SEQ. ID. NO. 37  E S V V A G S E G A A E G A I T I E L A S Y P I S
SEQ. ID. NO. 33  S S S L I A M P Q Y F H V V G G T I G F A L K A G

SEQ. ID. NO. 41  E G A V T I L P K R A S I D G F D R Y F R S R T L
SEQ. ID. NO. 47  D F A S Y F Q S L D P W N N S R N P W F R E F W E
SEQ. ID. NO. 37  D F A S Y F Q S L D P W N N S R N P W F R E F W E
SEQ. ID. NO. 33  Q I P G F R E F L K K V H P R K S V H N G F A K E

SEQ. ID. NO. 41  A N N R R N V W F A E F W E E N F G C K L G S H G
SEQ. ID. NO. 47  Q R F R C S F R Q R D C A A H S L R A V P F E Q E
SEQ. ID. NO. 37  Q R F R C S F R Q R D C A A H S L R A V P F E Q E
SEQ. ID. NO. 33  F W E E T F N C H L Q E G A K G P L P V D T F L R

SEQ. ID. NO. 41  K R N S H I K K C T G L E R I A R D S S Y E Q E G
SEQ. ID. NO. 47  S K I M F V V N A V Y A M A H A L H N M H R A L C
SEQ. ID. NO. 37  S K I M F V V N A V Y A M A H A L H N M H R A L C
SEQ. ID. NO. 33  G H E E S G D R F S N S S T A F R P L C T G D E N

Figure 12b

SEQ. ID. NO. 41   K V Q F V I D A V Y S M A Y A L H N M H K D L C P
SEQ. ID. NO. 47   P N T T R L C D A M R P V N G R R L Y K D F V L N
SEQ. ID. NO. 37   P N T T R L C D A M R P V N G R R L Y K D F V L N
SEQ. ID. NO. 33   I S S V E T P Y I D Y T H L R I S Y N V Y L A V Y

SEQ. ID. NO. 41   G Y I G L C P R M S T I D G K E L L G Y I R A V N
SEQ. ID. NO. 47   V K F D A P F R P A D T H N E V R F D R F G D G I
SEQ. ID. NO. 37   V K F D A P F R P A D T H N E V R F D R F G D G I
SEQ. ID. NO. 33   S I A H A L Q D I Y T C L P G R G L F T N G S C A

SEQ. ID. NO. 41   F N G S A G T P V T F N E N G D A P G R Y D I F Q
SEQ. ID. NO. 47   G R Y N I F T Y L R A G S G R Y R Y Q K V G Y W A
SEQ. ID. NO. 37   G R Y N I F T Y L R A G S G R Y R Y Q K V G Y W A
SEQ. ID. NO. 33   D I K K V E A W Q V L K H L R H L N F T N N M G E

SEQ. ID. NO. 41   Y Q I T N K S T E Y K V I G H W T N Q L H L K V E
SEQ. ID. NO. 47   E G L T L D T S L I P W A S P S A G P L P A S R C
SEQ. ID. NO. 37   E G L T L D T S L I P W A S P S A G P L P A S R C
SEQ. ID. NO. 33   Q V T F D E C G D L V G N Y S I I N W H L S P E D

SEQ. ID. NO. 41   D M Q W A H R E H T H P A S V C S L P C K P G E R
SEQ. ID. NO. 47   S E P C L Q N E V K S V Q P G E V C C W L C I P C
SEQ. ID. NO. 37   S E P C L Q N E V K S V Q P G E V C C W L C I P C
SEQ. ID. NO. 33   G S I V F K E V G Y Y N V Y A K K G E R L F I N E

SEQ. ID. NO. 41   K K T V K G V P C C W H C E R C E G Y N Y Q V D E
SEQ. ID. NO. 47   Q P Y E Y R L D E F T C A D C G L G Y W P N A S L
SEQ. ID. NO. 37   Q P Y E Y R L D E F T C A D C G L G Y W P N A S L
SEQ. ID. NO. 33   E K I L W S G F S R E V P F S N C S R D C L A G T

SEQ. ID. NO. 41   L S C E L C P L D Q R P N M N R T G C Q L I P I I
SEQ. ID. NO. 47   T G C F E L P Q E Y I R W G D A W A V G P V T I A
SEQ. ID. NO. 37   T G C F E L P Q E Y I R W G D A W A V G P V T I A
SEQ. ID. NO. 33   R K G I I E G E P T C C F E C V E C P D G E Y S D

SEQ. ID. NO. 41   K L E W H S P W A V V P V F V A I L G I I A T T F
SEQ. ID. NO. 47   C L G A L A T L F V L G V F V R H N A T P V V K A
SEQ. ID. NO. 37   C L G A L A T L F V L G V F V R H N A T P V V K A
SEQ. ID. NO. 33   E T D A S A C N K C P D D F W S N E N H T S C F E

Figure 12c

```
SEQ. ID. NO. 41   V I V T F V R Y N D T P I V R A S G R E L S Y V L
SEQ. ID. NO. 47   S G R E L C Y I L L G G V F L C Y C M T F I F I A
SEQ. ID. NO. 37   S G R E L C Y I L L G G V F L C Y C M T F I F I A
SEQ. ID. NO. 33   L P Q E Y I R W G D A W A Y G P V T I A C L G A L

SEQ. ID. NO. 41   L T G I F L C Y S I T F L M I A A P D T I I C S F
SEQ. ID. NO. 47   K P S T A V C T L R R L G L G T A F S V C Y S A L
SEQ. ID. NO. 37   K P S T A V C T L R R L G L G T A F S V C Y S A L
SEQ. ID. NO. 33   A T L F V L G V F V R H N A T P V V K A S G R E L

SEQ. ID. NO. 41   R R V F L G L G M C F S Y A A L L T K T N R I H R
SEQ. ID. NO. 47   L T K T N R I A R I F G G A R E G A Q R P R F I S
SEQ. ID. NO. 37   L T K T N R I A R I F G G A R E G A Q R P R F I S
SEQ. ID. NO. 33   C Y I L L G G V F L C Y C M T F I F I A K P S T A

SEQ. ID. NO. 41   I F E Q G K K S V T A P K F I S P A S Q L V I T F
SEQ. ID. NO. 47   P A S Q V A I C L A L I S G Q L L I V V A W L V V
SEQ. ID. NO. 37   P A S Q V A I C L A L I S G Q L L I V V A W L V V
SEQ. ID. NO. 33   V C T L R R L G L G T A F S V C Y S A L L T K T N

SEQ. ID. NO. 41   S L I S V Q L L G V F V W F V V D P P H I I I D Y
SEQ. ID. NO. 47   E A P G T G K E T A P E R R E V V T L R C N H R D
SEQ. ID. NO. 37   E A P G T G K E T A P E R R E V V T L R C N H R D
SEQ. ID. NO. 33   R I A R I F G G A R E G A Q R P R F I S P A S Q V

SEQ. ID. NO. 41   G E Q R T L D P E K A R G V L K C D I S D L S L I
SEQ. ID. NO. 47   A S M L G S L A Y N V L L I A L C T L Y A F K T R
SEQ. ID. NO. 37   A S M L G S L A Y N V L L I A L C T L Y A F K T R
SEQ. ID. NO. 33   A I C L A L I S G Q L L I V V A W L V V E A P G T

SEQ. ID. NO. 41   C S L G Y S I L L M V T C T V Y A I K T R G V P E
SEQ. ID. NO. 47   K C P E N F N E A K F I G F T M Y T T C I I W L A
SEQ. ID. NO. 37   K C P E N F N E A K F I G F T M Y T T C I I W L A
SEQ. ID. NO. 33   G K E T A P E R R E V V T L R C N H R D A S M L G

SEQ. ID. NO. 41   T F N E A K P I G F T M Y T T C I I W L A F I P I
SEQ. ID. NO. 47   F L P I F Y V T S S D Y R V Q T T T M C V S V S L
SEQ. ID. NO. 37   F L P I F Y V T S S D Y R V Q T T T M C V S V S L
SEQ. ID. NO. 33   S L A Y N V L L I A L C T L Y A F N T R K C P E N
```

Figure 12d

```
SEQ. ID. NO. 41  F F G T A Q S A E K M Y I Q T T T L T V S M S L S
SEQ. ID. NO. 47  S G S V V L G C L F A P K L H I I L F Q P Q K N T
SEQ. ID. NO. 37  S G S V V L G C L F A P K L H I I L F Q P Q K N T
SEQ. ID. NO. 33  F N E A K F I G F T M Y T T C I I W L A L L P I F

SEQ. ID. NO. 41  A S V S L G M L Y M P K V Y I I I F H P E Q N T I
SEQ. ID. NO. 47  I E E V R C S T A A H A F K V A A R A T L R R S N
SEQ. ID. NO. 37  I E E V R C S T A A H A F K V A A R A T L R R S N
SEQ. ID. NO. 33  Y V T S S D Y R V Q T T T M C V S V S L S G S V V

SEQ. ID. NO. 41  E E V R C S T A A H A F K V A A R A T L R R S N V
SEQ. ID. NO. 47  V S R K R S S S L G G S T G S T P S S S I S S K S
SEQ. ID. NO. 37  V S R K R S S S L G G S T G S T P S S S I S S K S
SEQ. ID. NO. 33  L G C L F A P K L H I I L F Q P Q K N V V S H R A

SEQ. ID. NO. 41  S R K R S S S L G G S T G S T P S S S I S S K S N
SEQ. ID. NO. 47  N S E D P F P Q P E R Q K Q Q Q P L A L T Q Q E Q
SEQ. ID. NO. 37  N S E D P F P Q P E R Q K Q Q Q P L A L T Q Q E Q
SEQ. ID. NO. 33  P T S R F G S A A A R A S S S L G Q G S G S Q F V

SEQ. ID. NO. 41  S E D P F P Q P E R Q K Q Q Q P L A L T Q Q E Q Q
SEQ. ID. NO. 47  Q Q Q P L T L P Q Q Q R S Q Q Q P R C K Q K V I F
SEQ. ID. NO. 37  Q Q Q P L T L P Q Q Q R S Q Q Q P R C K Q K V I F
SEQ. ID. NO. 33  P T V C N G R E V V D S T T S S L M T L E S I M A

SEQ. ID. NO. 41  Q Q P L T L P Q Q Q R S Q Q Q P R C K Q K V I F G
SEQ. ID. NO. 47  G S G T V T F S L S F D E P Q K N A M A H G N S T
SEQ. ID. NO. 37  G S G T V T F S L S F D E P Q K N A M A H G N S T
SEQ. ID. NO. 33  C C L S E E A K E A R R I N D E I E R Q L R R D K

SEQ. ID. NO. 41  S G T V T F S L S F D E P Q K N A M A H G N S T H
SEQ. ID. NO. 47  H Q N S L E A Q K S S D T L T R H Q P L L P L Q C
SEQ. ID. NO. 37  H Q N S L E A Q K S S D T L T R H Q P L L P L Q C
SEQ. ID. NO. 33  R D A R R E L K L L L L G T G E S G K S T F I K Q

SEQ. ID. NO. 41  Q N S L E A Q K S S D T L T R H Q P L L P L Q C G
SEQ. ID. NO. 47  G E T D L D L T V Q E T G L Q G P V G G D Q R P E
SEQ. ID. NO. 37  G E T D L D L T V Q E T G L Q G P V G G D Q R P E
SEQ. ID. NO. 33  M R I I H G S G Y S D E D K R G F T K L V Y Q N I
```

Figure 12e

```
SEQ. ID. NO. 41   E T D L D L T V Q E T G L Q G P V G G D Q R P E V
SEQ. ID. NO. 47   V E D P E E L S P A L V V S S S Q S F V I S G G G
SEQ. ID. NO. 37   V E D P E E L S P A L V V S S S Q S F V I S G G G
SEQ. ID. NO. 33   F T A M Q A M I R A M D T L K I P Y K Y E H N K A

SEQ. ID. NO. 41   E D P E E L S P A L V V S S S Q S F V I S G G G S
SEQ. ID. NO. 47   S T V T E N V V N S A A A M T L E S I M A C C L S
SEQ. ID. NO. 37   S T V T E N V V N S M T L E S I M A C C L S E E A
SEQ. ID. NO. 33   H A Q L V R E V D V E K V S A F E N P Y V D A I K

SEQ. ID. NO. 41   T V T E N V V N S M T L E S I M A C C L S E E A K
SEQ. ID. NO. 47   E E A K E A R R I N D E I E R Q L R R D K R D A R
SEQ. ID. NO. 37   K E A R R I N D E I E R Q L R R D K R D A R R E L
SEQ. ID. NO. 33   S L W N D P G I Q E C Y D R R R E Y Q L S D S T K

SEQ. ID. NO. 41   E A R R I N D E I E R Q L R R D K R D A R R E L K
SEQ. ID. NO. 47   R E L K L L L L G T G E S G K S T F I K Q M R I I
SEQ. ID. NO. 37   K L L L L G T G E S G K S T F I K Q M R I I H G S
SEQ. ID. NO. 33   Y Y L N D L D R V A D P A Y L P T Q Q D V L R V R

SEQ. ID. NO. 41   L L L L G T G E S G K S T F I K Q M R I I H G S G
SEQ. ID. NO. 47   H G S G Y S D E D K R G F T K L V Y Q N I F T A M
SEQ. ID. NO. 37   G Y S D E D K R G F T K L V Y Q N I F T A M Q A M
SEQ. ID. NO. 33   V P T T G I I E Y P F D L Q S V I F R M V D V G G

SEQ. ID. NO. 41   Y S D E D K R G F T K L V Y Q N I F T A M Q A M I
SEQ. ID. NO. 47   Q A M I R A M D T L K I P Y K Y E H N K A H A Q L
SEQ. ID. NO. 37   I R A M D T L K I P Y K Y E H N K A H A Q L V R E
SEQ. ID. NO. 33   Q R S E R R K W I H C F E N V T S I M F L V A L S

SEQ. ID. NO. 41   R A M D T L K I P Y K Y E H N K A H A Q L V R E V
SEQ. ID. NO. 47   V R E V D V E K V S A F E N P Y V D A I K S L W N
SEQ. ID. NO. 37   V D V E K V S A F E N P Y V D A I K S L W N D P G
SEQ. ID. NO. 33   E Y D Q V L V E S D N E N R M E E S K A L F R T I

SEQ. ID. NO. 41   D V E K V S A F E N P Y V D A I K S L W N D P G I
SEQ. ID. NO. 47   D P G I Q E C Y D R R R E Y Q L S D S T K Y Y L N
SEQ. ID. NO. 37   I Q E C Y D R R R E Y Q L S D S T K Y Y L N D L D
SEQ. ID. NO. 33   I T Y P W F Q N S S V I L F L N K K D L L E E K I
```

Figure 12f

```
SEQ. ID. NO. 41   Q E C Y D R R R E Y Q L S D S T K Y Y L N D L D R
SEQ. ID. NO. 47   D L D R V A D P A Y L P T Q Q D V L R V R V P T T
SEQ. ID. NO. 37   R V A D P A Y L P T Q Q D V L R V R V P T T G I I
SEQ. ID. NO. 33   M Y S H L V D Y F P E Y D G P Q R D A Q A A R E F

SEQ. ID. NO. 41   V A D P A Y L P T Q Q D V L R V R V P T T G I I E
SEQ. ID. NO. 47   G I I E Y P F D L Q S V I F R M V D V G G Q R S E
SEQ. ID. NO. 37   E Y P F D L Q S V I F R M V D V G G Q R S E R R K
SEQ. ID. NO. 33   I L K M F V D L N P D S D K I I Y S H F T C A T D

SEQ. ID. NO. 41   Y P F D L Q S V I F R M V D V G G Q R S E R R K W
SEQ. ID. NO. 47   R R K W I H C F E N V T S I M F L V A L S E Y D Q
SEQ. ID. NO. 37   W I H C F E N V T S I M F L V A L S E Y D Q V L V
SEQ. ID. NO. 33   T E N I R F V F A A V K D T I L Q L N L K D C G L

SEQ. ID. NO. 41   I H C F E N V T S I M F L V A L S E Y D Q V L V E
SEQ. ID. NO. 47   V L V E S D N E N R M E E S K A L F R T I I T Y P
SEQ. ID. NO. 37   E S D N E N R M E E S K A L F R T I I T Y P W F Q
SEQ. ID. NO. 33   F

SEQ. ID. NO. 41   S D N E N R M E E S K A L F R T I I T Y P W F Q N
SEQ. ID. NO. 47   W F Q N S S V I L F L N K K D L L E E K I M Y S H
SEQ. ID. NO. 37   N S S V I L F L N K K D L L E E K I M Y S H L V D
SEQ. ID. NO. 33

SEQ. ID. NO. 41   S S V I L F L N K K D L L E E K I M Y S H L V D Y
SEQ. ID. NO. 47   L V D Y F P E Y D G P Q R D A Q A A R E F I L K M
SEQ. ID. NO. 37   Y F P E Y D G P Q R D A Q A A R E F I L K M F V D
SEQ. ID. NO. 33

SEQ. ID. NO. 41   F P E Y D G P Q R D A Q A A R E F I L K M F V D L
SEQ. ID. NO. 47   F V D L N P D S D K I I Y S H F T C A T D T E N I
SEQ. ID. NO. 37   L N P D S D K I I Y S H F T C A T D T E N I R F V
SEQ. ID. NO. 33

SEQ. ID. NO. 41   N P D S D K I I Y S H F T C A T D T E N I R F V F
SEQ. ID. NO. 47   R F V F A A V K D T I L Q L N L K D C G L F
SEQ. ID. NO. 37   F A A V K D T I L Q L N L K D C G L F
SEQ. ID. NO. 33
```

Figure 12g

SEQ. ID. NO. 41  A A V K D T I L Q L N L K D C G L F
SEQ. ID. NO. 47
SEQ. ID. NO. 37
SEQ. ID. NO. 33

Figure 12h

ClustalW Formatted Alignments

SEQ. ID. NO. 44  A T G T T G C T G C T G C T G C T A C T G G C G C
SEQ. ID. NO. 42  A T G G C T T C C C C G C G G A G C T C C G G G C

SEQ. ID. NO. 44  C A C T C T T C C T C C G C C C C C G G G C G C
SEQ. ID. NO. 42  A G C C C G G G C C G C C G C C G C C G C C G C C

SEQ. ID. NO. 44  G G G C G G G G C G C A G A C C C C A A C G C C
SEQ. ID. NO. 42  A C C G C C G C C C G C G C G C C T G C T A C T G

SEQ. ID. NO. 44  A C C T C A G A A G G T T G C C A G A T C A T A C
SEQ. ID. NO. 42  C T A C T G C T G C T G C C G C T G C T G C T G C

SEQ. ID. NO. 44  A C C C G C C C T G G G A A G G G G G C A T C A G
SEQ. ID. NO. 42  C T C T G G C G C C C G G G G C C T G G G G C T G

SEQ. ID. NO. 44  G T A C C G G G G C C T G A C T C G G G A C C A G
SEQ. ID. NO. 42  G G C G C G G G G C G C C C C C G G C C G C C G

SEQ. ID. NO. 44  G T G A A G G C T A T C A A C T T C C T G C C A G
SEQ. ID. NO. 42  C C C A G C A G C C C G C C G C T C T C C A T C A

SEQ. ID. NO. 44  T G G A C T A T G A G A T T G A G T A T G T G T G
SEQ. ID. NO. 42  T G G G C C T C A T G C C G C T C A C C A A G G A

SEQ. ID. NO. 44  C C G G G G G G A G C G C G A G G T G G T G G G G
SEQ. ID. NO. 42  G G T G G C C A A G G G C A G C A T C G G G C G C

SEQ. ID. NO. 44  C C C A A G G T C C G C A A G T G C C T G G C C A
SEQ. ID. NO. 42  G G T G T G C T C C C C G C C G T G G A A C T G G

SEQ. ID. NO. 44  A C G G C T C C T G G A C A G A T A T G G A C A C
SEQ. ID. NO. 42  C C A T C G A G C A G A T C C G C A A C G A G T C

SEQ. ID. NO. 44  A C C C A G C C G C T G T G T C C G A A T C T G C
SEQ. ID. NO. 42  A C T C C T G C G C C C T T A C T T C C T C G A C

Figure 13a

SEQ. ID. NO. 44  T C C A A G T C T T A T T T G A C C C T G G A A A
SEQ. ID. NO. 42  C T G C G G C T C T A T G A C A C G G A G T G C G

SEQ. ID. NO. 44  A T G G G A A G G T T T T C C T G A C G G G T G G
SEQ. ID. NO. 42  A C A A C G C A A A A G G G T T G A A A G C C T T

SEQ. ID. NO. 44  G G A C C T C C C A G C T C T G G A C G G A G C C
SEQ. ID. NO. 42  C T A C G A T G C A A T A A A T A C G G G C C G

SEQ. ID. NO. 44  C G G G T G G A T T T C C G G T G T G A C C C C G
SEQ. ID. NO. 42  A A C C A C T T G A T G G T G T T T G G A G G C G

SEQ. ID. NO. 44  A C T T C C A T C T G G T G G G C A G C T C C C G
SEQ. ID. NO. 42  T C T G T C C A T C C G T C A C A T C C A T C A T

SEQ. ID. NO. 44  G A G C A T C T G T A G T C A G G G C C A G T G G
SEQ. ID. NO. 42  T G C A G A G T C C C T C C A A G G C T G G A A T

SEQ. ID. NO. 44  A G C A C C C C C A A G C C C C A C T G C C A G G
SEQ. ID. NO. 42  C T G G T G C A G C T T T C T T T T G C T G C A A

SEQ. ID. NO. 44  T G A A T C G A A C G C C A C A C T C A G A A C G
SEQ. ID. NO. 42  C C A C G C C T G T T C T A G C C G A T A A G A A

SEQ. ID. NO. 44  G C G C G C A G T G T A C A T C G G G G C A C T G
SEQ. ID. NO. 42  A A A A T A C C C T T A T T T C T T T C G G A C C

SEQ. ID. NO. 44  T T T C C C A T G A G C G G G G G C T G G C C A G
SEQ. ID. NO. 42  G T C C C A T C A G A C A A T G C G G T G A A T C

SEQ. ID. NO. 44  G G G G C C A G G C C T G C C A G C C C G C G G T
SEQ. ID. NO. 42  C A G C C A T T C T G A A G T T G C T C A A G C A

SEQ. ID. NO. 44  G G A G A T G G C G C T G G A G G A C G T G A A T
SEQ. ID. NO. 42  C T A C C A G T G G A A G C G C G T G G G C A C G

SEQ. ID. NO. 44  A G C C G C A G G G A C A T C C T G C C G G A C T
SEQ. ID. NO. 42  C T G A C G C A A G A C G T T C A G A G G T T C T

Figure 13b

SEQ. ID. NO. 44  A T G A G C T C A A G C T C A T C C A C C A C G A
SEQ. ID. NO. 42  C T G A G G T G C G G A A T G A C C T G A C T G G

SEQ. ID. NO. 44  C A G C A A G T G T G A T C C A G G C C A A G C C
SEQ. ID. NO. 42  A G T T C T G T A T G G C G A G G A C A T T G A G

SEQ. ID. NO. 44  A C C A A G T A C C T A T A T G A G C T G C T C T
SEQ. ID. NO. 42  A T T T C A G A C A C C G A G A G C T T C T C C A

SEQ. ID. NO. 44  A C A A C G A C C C T A T C A A G A T C A T C C T
SEQ. ID. NO. 42  A C G A T C C C T G T A C C A G T G T C A A A A A

SEQ. ID. NO. 44  T A T G C C T G G C T G C A G C T C T G T C T C C
SEQ. ID. NO. 42  G C T G A A G G G G A A T G A T G T G C G G A T C

SEQ. ID. NO. 44  A C G C T G G T G G C T G A G G C T G C T A G G A
SEQ. ID. NO. 42  A T C C T T G G C C A G T T T G A C C A G A A T A

SEQ. ID. NO. 44  T G T G G A A C C T C A T T G T G C T T T C C T A
SEQ. ID. NO. 42  T G G C A G C A A A A G T G T T C T G T T G T G C

SEQ. ID. NO. 44  T G G C T C C A G C T C A C C A G C C C T G T C A
SEQ. ID. NO. 42  A T A C G A G G A G A A C A T G T A T G G T A G T

SEQ. ID. NO. 44  A A C C G G C A G C G T T T C C C C A C T T T C T
SEQ. ID. NO. 42  A A A T A T C A G T G G A T C A T T C C G G G C T

SEQ. ID. NO. 44  T C C G A A C G C A C C C A T C A G C C A C A C T
SEQ. ID. NO. 42  G G T A C G A G C C T T C T T G G T G G G A G C A

SEQ. ID. NO. 44  C C A C A A C C C T A C C C G C G T G A A A C T C
SEQ. ID. NO. 42  G G T G C A C A C G G A A G C C A A C T C A T C C

SEQ. ID. NO. 44  T T T G A A A A G T G G G G C T G G A A G A A G A
SEQ. ID. NO. 42  C G C T G C C T C C G G A A G A A T C T G C T T G

SEQ. ID. NO. 44  T T G C T A C C A T C C A G C A G A C C A C T G A
SEQ. ID. NO. 42  C T G C C A T G G A G G G C T A C A T T G G C G T

Figure 13c

SEQ. ID. NO. 44  G G T C T T C A C T T C G A C T C T G G A C G A C
SEQ. ID. NO. 42  G G A T T T C G A G C C C C T G A G C T C C A A G

SEQ. ID. NO. 44  C T G G A G G A A C G A G T G A A G G A G G C T G
SEQ. ID. NO. 42  C A G A T C A A G A C C A T C T C A G G A A A G A

SEQ. ID. NO. 44  G A A T T G A G A T T A C T T T C C G C C A G A G
SEQ. ID. NO. 42  C T C C A C A G C A G T A T G A G A G A G T A

SEQ. ID. NO. 44  T T T C T T C T C A G A T C C A G C T G T G C C C
SEQ. ID. NO. 42  C A A C A A C A A G C G G T C A G G C G T G G G G

SEQ. ID. NO. 44  G T C A A A A A C C T G A A G C G C C A G G A T G
SEQ. ID. NO. 42  C C C A G C A A G T T C C A C G G G T A C G C C T

SEQ. ID. NO. 44  C C C G A A T C A T C G T G G G A C T T T T C T A
SEQ. ID. NO. 42  A C G A T G G C A T C T G G G T C A T C G C C A A

SEQ. ID. NO. 44  T G A G A C T G A A G C C C G G A A A G T T T T T
SEQ. ID. NO. 42  G A C A C T G C A G A G G G C C A T G G A G A C A

SEQ. ID. NO. 44  T G T G A G G T G T A C A A G G A G C G T C T C T
SEQ. ID. NO. 42  C T G C A T G C C A G C A G C C G G C A C C A G C

SEQ. ID. NO. 44  T T G G G A A G A A G T A C G T C T G G T T C C T
SEQ. ID. NO. 42  G G A T C C A G G A C T T C A A C T A C A C G G A

SEQ. ID. NO. 44  C A T T G G G T G G T A T G C T G A C A A T T G G
SEQ. ID. NO. 42  C C A C A C G C T G G G C A G G A T C A T C C T C

SEQ. ID. NO. 44  T T C A A G A T C T A C G A C C C T T C T A T C A
SEQ. ID. NO. 42  A A T G C C A T G A A C G A G A C C A A C T T C T

SEQ. ID. NO. 44  A C T G C A C A G T G G A T G A G A T G A C T G A
SEQ. ID. NO. 42  T C G G G G T C A C G G G T C A A G T T G T A T T

SEQ. ID. NO. 44  G G C G G T G G A G G G C C A C A T C A C A A C T
SEQ. ID. NO. 42  C C G G A A T G G G G A G A G A A T G G G C A C C

Figure 13d

```
SEQ. ID. NO. 44   G A G A T T G T C A T G C T G A A T C C T G C C A
SEQ. ID. NO. 42   A T T A A A T T T A C T C A A T T T C A A G A C A

SEQ. ID. NO. 44   A T A C C C G C A G C A T T T C C A A C A T G A C
SEQ. ID. NO. 42   G C A G G G A G G T G A A G G T G G G A G A G T A

SEQ. ID. NO. 44   A T C C C A G G A A T T T G T G G A G A A A C T A
SEQ. ID. NO. 42   C A A C G C T G T G G C C G A C A C A C T G G A G

SEQ. ID. NO. 44   A C C A A G C G A C T G A A A A G A C A C C C T G
SEQ. ID. NO. 42   A T C A T C A A T G A C A C C A T C A G G T T C C

SEQ. ID. NO. 44   A G G A G A C A G G A G G C T T C C A G G A G G C
SEQ. ID. NO. 42   A A G G A T C C G A A C C A C C A A A A G A C A A

SEQ. ID. NO. 44   A C C G C T G G C C T A T G A T G C C A T C T G G
SEQ. ID. NO. 42   G A C C A T C A T C C T G G A G C A G C T G C G G

SEQ. ID. NO. 44   G C C T T G G C A C T G G C C C T G A A C A A G A
SEQ. ID. NO. 42   A A G A T C T C C C T A C C T C T C T A C A G C A

SEQ. ID. NO. 44   C A T C T G G A G G A G G C G G C C G T T C T G G
SEQ. ID. NO. 42   T C C T C T C T G C C C T C A C C A T C C T C G G

SEQ. ID. NO. 44   T G T G C G C C T G G A G G A C T T C A A C T A C
SEQ. ID. NO. 42   G A T G A T C A T G G C C A G T G C T T T T C T C

SEQ. ID. NO. 44   A A C A A C C A G A C C A T T A C C G A C C A A A
SEQ. ID. NO. 42   T T C T T C A A C A T C A A G A A C C G G A A T C

SEQ. ID. NO. 44   T C T A C C G G G C A A T G A A C T C T T C G T C
SEQ. ID. NO. 42   A G A A G C T C A T A A A G A T G T C G A G T C C

SEQ. ID. NO. 44   C T T T G A G G G T G T C T C T G G C C A T G T G
SEQ. ID. NO. 42   A T A C A T G A A C A A C C T T A T C A T C C T T

SEQ. ID. NO. 44   G T G T T T G A T G C C A G C G G C T C T C G G A
SEQ. ID. NO. 42   G G A G G G A T G C T C T C C T A T G C T T C C A
```

Figure 13e

SEQ. ID. NO. 44  T G G C A T G G A C G C T T A T C G A G C A G C T
SEQ. ID. NO. 42  T A T T T C T C T T T G G C C T T G A T G G A T C

SEQ. ID. NO. 44  T C A G G G T G G C A G C T A C A A G A A G A T T
SEQ. ID. NO. 42  C T T T G T C T C T G A A A A G A C C T T T G A A

SEQ. ID. NO. 44  G G C T A C T A T G A C A G C A C C A A G G A T G
SEQ. ID. NO. 42  A C A C T T T G C A C C G T C A G G A C C T G G A

SEQ. ID. NO. 44  A T C T T T C C T G G T C C A A A A C A G A T A A
SEQ. ID. NO. 42  T T C T C A C C G T G G G C T A C A C G A C C G C

SEQ. ID. NO. 44  A T G G A T T G G A G G G T C C C C C C A G C T
SEQ. ID. NO. 42  T T T T G G G G C C A T G T T T G C A A A G A C C

SEQ. ID. NO. 44  G A C C A G A C C C T G G T C A T C A A G A C A T
SEQ. ID. NO. 42  T G G A G A G T C C A C G C C A T C T T C A A A A

SEQ. ID. NO. 44  T C C G C T T C C T G T C A C A G A A A C T C T T
SEQ. ID. NO. 42  A T G T G A A A A T G A A G A A G A A G A T C A T

SEQ. ID. NO. 44  T A T C T C C G T C T C A G T T C T C T C C A G C
SEQ. ID. NO. 42  C A A G G A C C A G A A A C T G C T T G T G A T C

SEQ. ID. NO. 44  C T G G G C A T T G T C C T A G C T G T T G T C T
SEQ. ID. NO. 42  G T G G G G G G C A T G C T G C T G A T C G A C C

SEQ. ID. NO. 44  G T C T G T C C T T T A A C A T C T A C A A C T C
SEQ. ID. NO. 42  T G T G T A T C C T G A T C T G C T G G C A G G C

SEQ. ID. NO. 44  A C A T G T C C G T T A T A T C C A G A A C T C A
SEQ. ID. NO. 42  T G T G G A C C C C C T G C G A A G G A C A G T G

SEQ. ID. NO. 44  C A G C C C A A C C T G A A C A A C C T G A C T G
SEQ. ID. NO. 42  G A G A A G T A C A G C A T G G A G C C G G A C C

SEQ. ID. NO. 44  C T G T G G G C T G C T C A C T G G C T T T A G C
SEQ. ID. NO. 42  C A G C A G G A C G G G A T A T C T C C A T C C G

Figure 13f

SEQ. ID. NO. 44  T G C T G T C T T C C C C C T G G G G C T C G A T
SEQ. ID. NO. 42  C C C T C T C C T G G A G C A C T G T G A G A A C

SEQ. ID. NO. 44  G G T T A C C A C A T T G G G A G G A A C C A G T
SEQ. ID. NO. 42  A C C C A T A T G A C C A T C T G G C T T G G C A

SEQ. ID. NO. 44  T T C C T T T C G T C T G C C A G G C C C G C C T
SEQ. ID. NO. 42  T C G T C T A T G C C T A C A A G G G A C T T C T

SEQ. ID. NO. 44  C T G G C T C C T G G G C C T G G G C T T T A G T
SEQ. ID. NO. 42  C A T G T T G T T C G G T T G T T T C T T A G C T

SEQ. ID. NO. 44  C T G G G C T A C G G T T C C A T G T T C A C C A
SEQ. ID. NO. 42  T G G G A G A C C C G C A A C G T C A G C A T C C

SEQ. ID. NO. 44  A G A T T T G G T G G G T C C A C A C G G T C T T
SEQ. ID. NO. 42  C C G C A C T C A A C G A C A G C A A G T A C A T

SEQ. ID. NO. 44  C A C A A A G A A G G A A G A A A A G A A G G A G
SEQ. ID. NO. 42  C G G G A T G A G T G T C T A C A A C G T G G G G

SEQ. ID. NO. 44  T G G A G G A A G A C T C T G G A A C C C T G G A
SEQ. ID. NO. 42  A T C A T G T G C A T C A T C G G G G C C G C T G

SEQ. ID. NO. 44  A G C T G T A T G C C A C A G T G G G C C T G C T
SEQ. ID. NO. 42  T C T C C T T C C T G A C C C G G G A C C A G C C

SEQ. ID. NO. 44  G G T G G G C A T G G A T G T C C T C A C T C T C
SEQ. ID. NO. 42  C A A T G T G C A G T T C T G C A T C G T G G C T

SEQ. ID. NO. 44  G C C A T C T G G C A G A T C G T G G A C C C T C
SEQ. ID. NO. 42  C T G G T C A T C A T C T T C T G C A G C A C C A

SEQ. ID. NO. 44  T G C A C C G G A C C A T T G A G A C A T T T G C
SEQ. ID. NO. 42  T C A C C C T C T G C C T G G T A T T C G T G C C

SEQ. ID. NO. 44  C A A G G A G G A A C C T A A G G A A G A T A T T
SEQ. ID. NO. 42  G A A G C T C A T C A C C C T G A G A A C A A A C

Figure 13g

SEQ. ID. NO. 44  G A C G T C T C T A T T C T G C C C C A G C T G G
SEQ. ID. NO. 42  C C A G A T G C A G C A A C G C A G A A C A G G C

SEQ. ID. NO. 44  A G C A T T G C A G C T C C A G G A A G A T G A A
SEQ. ID. NO. 42  G A T T C C A G T T C A C T C A G A A T C A G A A

SEQ. ID. NO. 44  T A C A T G G C T T G G C A T T T T C T A T G G T
SEQ. ID. NO. 42  G A A A G A A G A T T C T A A A A C G T C C A C C

SEQ. ID. NO. 44  T A C A A G G G G C T G C T G C T G C T G C T G G
SEQ. ID. NO. 42  T C G G T C A C C A G T G T G A A C C A A G C C A

SEQ. ID. NO. 44  G A A T C T T C C T T G C T T A T G A G A C C A A
SEQ. ID. NO. 42  G C A C A T C C C G C C T G G A G G G C C T A C A

SEQ. ID. NO. 44  G A G T G T G T C C A C T G A G A A G A T C A A T
SEQ. ID. NO. 42  G T C A G A A A A C C A T C G C C T G C G A A T G

SEQ. ID. NO. 44  G A T C A C C G G G C T G T G G G C A T G G C T A
SEQ. ID. NO. 42  A A G A T C A C A G A G C T G G A T A A A G A C T

SEQ. ID. NO. 44  T C T A C A A T G T G G C A G T C C T G T G C C T
SEQ. ID. NO. 42  T G G A A G A G G T C A C C A T G C A G C T G C A

SEQ. ID. NO. 44  C A T C A C T G C T C C T G T C A C C A T G A T T
SEQ. ID. NO. 42  G G A C A C C A G A A A A G A C C A C C T A C

SEQ. ID. NO. 44  C T G T C C A G C C A G C A G G A T G C A G C C T
SEQ. ID. NO. 42  A T T A A A C A G A A C C A C T A C C A A G A G C

SEQ. ID. NO. 44  T T G C C T T T G C C T C T C T T G C C A T A G T
SEQ. ID. NO. 42  T C A A T G A C A T C C T C A A C C T G G G A A A

SEQ. ID. NO. 44  T T T C T C C T C C T A T A T C A C T C T T G T T
SEQ. ID. NO. 42  C T T C A C T G A G A G C A C A G A T G G A G G A

SEQ. ID. NO. 44  G T G C T C T T T G T G C C C A A G A T G C G C A
SEQ. ID. NO. 42  A A G G C C A T T T T A A A A A A T C A C C T C G

Figure 13h

SEQ. ID. NO. 44 GGCTGATCACCCGAGCGGAATGGCA
SEQ. ID. NO. 42 ATCAAAATCCCCAGCTACAGTGGAA

SEQ. ID. NO. 44 GTCGGAGGCGCAGGACACCATGAAG
SEQ. ID. NO. 42 CACAACAGAGCCCTCTCGAACATGC

SEQ. ID. NO. 44 ACAGGGTCATCGACCAACAACAACG
SEQ. ID. NO. 42 AAAGATCCTATAGAAGATATAAACT

SEQ. ID. NO. 44 AGGAGGAGAAGTCCCGGCTGTTGGA
SEQ. ID. NO. 42 CTCCAGAACACATCCAGCGTCGGCT

SEQ. ID. NO. 44 GAAGGAGAACCGTGAACTGGAAAAG
SEQ. ID. NO. 42 GTCCCTCCAGCTCCCCATCCTCCAC

SEQ. ID. NO. 44 ATCATTGCTGAGAAAGAGGAGCGTG
SEQ. ID. NO. 42 CACGCCTACCTCCCATCCATCGGAG

SEQ. ID. NO. 44 TCTCTGAACTGCGCCATCAACTCCA
SEQ. ID. NO. 42 GCGTGGACGCCAGCTGTGTCAGCCC

SEQ. ID. NO. 44 GTCTCGGCAGCAGCTCCGCTCCCGG
SEQ. ID. NO. 42 CTGCGTCAGCCCCACCGCCAGCCCC

SEQ. ID. NO. 44 CGCCACCCACCGACACCCCAGAAC
SEQ. ID. NO. 42 CGCCACAGACATGTGCCACCCTCCT

SEQ. ID. NO. 44 CCTCTGGGGGCCTGCCCAGGGGACC
SEQ. ID. NO. 42 TCCGAGTCATGGTCTCGGGCCTGGC

SEQ. ID. NO. 44 CCCTGAGCCCCCCGACCGGCTTAGC
SEQ. ID. NO. 42 GGCCGCCATGACTCTGGAGTCCATC

SEQ. ID. NO. 44 TGTGATGGGAGTCGAGTGCATTTGC
SEQ. ID. NO. 42 ATGGCGTGCTGCCTGAGCGAGGAGG

SEQ. ID. NO. 44 TTTATAAGGCGGCCGCCATGACTCT
SEQ. ID. NO. 42 CCAAGGAAGCCCGGCGGATCAACGA

Figure 13i

SEQ. ID. NO. 44  G G A G T C C A T C A T G G C G T G C T G C C T G
SEQ. ID. NO. 42  C G A G A T C G A G C G G C A G C T C C G C A G G

SEQ. ID. NO. 44  A G C G A G G A G G C C A A G G A A G C C C G G C
SEQ. ID. NO. 42  G A C A A G C G G G A C G C C C G C C G G G A G C

SEQ. ID. NO. 44  G G A T C A A C G A C G A G A T C G A G C G G C A
SEQ. ID. NO. 42  T C A A G C T G C T G C T G C T C G G G A C A G G

SEQ. ID. NO. 44  G C T C C G C A G G G A C A A G C G G G A C G C C
SEQ. ID. NO. 42  A G A G A G T G G C A A G A G T A C G T T T A T C

SEQ. ID. NO. 44  C G C C G G G A G C T C A A G C T G C T G C T G C
SEQ. ID. NO. 42  A A G C A G A T G A G A A T C A T C C A T G G T

SEQ. ID. NO. 44  T C G G G A C A G G A G A G A G T G G C A A G A G
SEQ. ID. NO. 42  C A G G A T A C T C T G A T G A A G A T A A A A G

SEQ. ID. NO. 44  T A C G T T T A T C A A G C A G A T G A G A A T C
SEQ. ID. NO. 42  G G G C T T C A C C A A G C T G G T G T A T C A G

SEQ. ID. NO. 44  A T C C A T G G G T C A G G A T A C T C T G A T G
SEQ. ID. NO. 42  A A C A T C T T C A C G G C C A T G C A G G C C A

SEQ. ID. NO. 44  A A G A T A A A A G G G G C T T C A C C A A G C T
SEQ. ID. NO. 42  T G A T C A G A G C C A T G G A C A C A C T C A A

SEQ. ID. NO. 44  G G T G T A T C A G A A C A T C T T C A C G G C C
SEQ. ID. NO. 42  G A T C C C A T A C A A G T A T G A G C A C A A T

SEQ. ID. NO. 44  A T G C A G G C C A T G A T C A G A G C C A T G G
SEQ. ID. NO. 42  A A G G C T C A T G C A C A A T T A G T T C G A G

SEQ. ID. NO. 44  A C A C A C T C A A G A T C C C A T A C A A G T A
SEQ. ID. NO. 42  A A G T T G A T G T G G A G A A G G T G T C T G C

SEQ. ID. NO. 44  T G A G C A C A A T A A G G C T C A T G C A C A A
SEQ. ID. NO. 42  T T T T G A G A A T C C A T A T G T A G A T G C A

Figure 13j

SEQ. ID. NO. 44  T T A G T T C G A G A A G T T G A T G T G G A G A
SEQ. ID. NO. 42  A T A A A G A G T T T A T G G A A T G A T C C T G

SEQ. ID. NO. 44  A G G T G T C T G C T T T T G A G A A T C C A T A
SEQ. ID. NO. 42  G A A T C C A G G A A T G C T A T G A T A G A C G

SEQ. ID. NO. 44  T G T A G A T G C A A T A A A G A G T T T A T G G
SEQ. ID. NO. 42  A C G A G A A T A T C A A T T A T C T G A C T C T

SEQ. ID. NO. 44  A A T G A T C C T G G A A T C C A G G A A T G C T
SEQ. ID. NO. 42  A C C A A A T A C T A T C T T A A T G A C T T G G

SEQ. ID. NO. 44  A T G A T A G A C G A C G A G A A T A T C A A T T
SEQ. ID. NO. 42  A C C G C G T A G C T G A C C C T G C C T A C C T

SEQ. ID. NO. 44  A T C T G A C T C T A C C A A A T A C T A T C T T
SEQ. ID. NO. 42  G C C T A C G C A A C A A G A T G T G C T T A G A

SEQ. ID. NO. 44  A A T G A C T T G G A C C G C G T A G C T G A C C
SEQ. ID. NO. 42  G T T C G A G T C C C C A C C A C A G G G A T C A

SEQ. ID. NO. 44  C T G C C T A C C T G C C T A C G C A A C A A G A
SEQ. ID. NO. 42  T C G A A T A C C C C T T T G A C T T A C A A A G

SEQ. ID. NO. 44  T G T G C T T A G A G T T C G A G T C C C C A C C
SEQ. ID. NO. 42  T G T C A T T T T C A G A A T G G T C G A T G T A

SEQ. ID. NO. 44  A C A G G G A T C A T C G A A T A C C C C T T T G
SEQ. ID. NO. 42  G G G G G C C A A A G G T C A G A G A G A A G A A

SEQ. ID. NO. 44  A C T T A C A A A G T G T C A T T T T C A G A A T
SEQ. ID. NO. 42  A A T G G A T A C A C T G C T T T G A A A A T G T

SEQ. ID. NO. 44  G G T C G A T G T A G G G G G C C A A A G G T C A
SEQ. ID. NO. 42  C A C C T C T A T C A T G T T T C T A G T A G C G

SEQ. ID. NO. 44  G A G A G A A G A A A A T G G A T A C A C T G C T
SEQ. ID. NO. 42  C T T A G T G A A T A T G A T C A A G T T C T G G

Figure 13k

SEQ. ID. NO. 44   T T G A A A A T G T C A C C T C T A T C A T G T T
SEQ. ID. NO. 42   T G G A G T C A G A C A A T G A G A A C C G A A T

SEQ. ID. NO. 44   T C T A G T A G C G C T T A G T G A A T A T G A T
SEQ. ID. NO. 42   G G A G G A A A G C A A G G C T C T C T T T A G A

SEQ. ID. NO. 44   C A A G T T C T C G T G G A G T C A G A C A A T G
SEQ. ID. NO. 42   A C A A T T A T C A C A T A C C C T G G T T C C

SEQ. ID. NO. 44   A G A A C C G A A T G G A G G A A A G C A A G G C
SEQ. ID. NO. 42   A G A A C T C C T C G G T T A T T C T G T T C T T

SEQ. ID. NO. 44   T C T C T T T A G A A C A A T T A T C A C A T A C
SEQ. ID. NO. 42   A A A C A A G A A A G A T C T T C T A G A G G A G

SEQ. ID. NO. 44   C C C T G G T T C C A G A A C T C C T C G G T T A
SEQ. ID. NO. 42   A A A A T C A T G T A T T C C C A T C T A G T C G

SEQ. ID. NO. 44   T T C T G T T C T T A A A C A A G A A A G A T C T
SEQ. ID. NO. 42   A C T A C T T C C C A G A A T A T G A T G G A C C

SEQ. ID. NO. 44   T C T A G A G G A G A A A A T C A T G T A T T C C
SEQ. ID. NO. 42   C C A G A G A G A T G C C C A G G C A G C C C G A

SEQ. ID. NO. 44   C A T C T A G T C G A C T A C T T C C C A G A A T
SEQ. ID. NO. 42   G A A T T C A T T C T G A A G A T G T T C G T G G

SEQ. ID. NO. 44   A T G A T G G A C C C C A G A G A G A T G C C C A
SEQ. ID. NO. 42   A C C T G A A C C C A G A C A G T G A C A A A A T

SEQ. ID. NO. 44   G G C A G C C C G A G A A T T C A T T C T G A A G
SEQ. ID. NO. 42   T A A C T A C T C C C A C T T C A C G T G C G C C

SEQ. ID. NO. 44   A T G T T C G T G G A C C T G A A C C C A G A C A
SEQ. ID. NO. 42   A C A G A C A C C G A G A A T A T C C G C T T T G

SEQ. ID. NO. 44   G T G A C A A A A T T A T C T A C T C C C A C T T
SEQ. ID. NO. 42   T C T T T G C T G C C G T C A A G G A C A C C A T

Figure 131

SEQ. ID. NO. 44  C A C G T G C G C C A C A G A C A C C G A G A A T
SEQ. ID. NO. 42  C C T C C A G T T G A A C C T G A A G G G C T G C

SEQ. ID. NO. 44  A T C C G C T T T G T C T T T G C T G C C G T C A
SEQ. ID. NO. 42  G G T C T G T A C

SEQ. ID. NO. 44  A G G A C A C C A T C C T C C A G T T G A A C C T
SEQ. ID. NO. 42

SEQ. ID. NO. 44  G A A G G G C T G C G G T C T G T A C
SEQ. ID. NO. 42

Figure 13m

ClustalW Formatted Alignments

SEQ. ID. NO. 45 M L L L L L L A P L F L R P P G A G G A Q T P N A
SEQ. ID. NO. 43 M A S P R S S G Q P G P P P P P P P P A R L L L

SEQ. ID. NO. 45 T S E G C Q I I H P P W E G G I R Y R G L T R D Q
SEQ. ID. NO. 43 L L L L P L L L P L A P G A W G W A R G A P R P P

SEQ. ID. NO. 45 V K A I N F L P V D Y E I E Y V C R G E R E V V G
SEQ. ID. NO. 43 P S S P P L S I M G L M P L T K E V A K G S I G R

SEQ. ID. NO. 45 P K V R K C L A N G S W T D M D T P S R C V R I C
SEQ. ID. NO. 43 G V L P A V E L A I E Q I R N E S L L R P Y F L D

SEQ. ID. NO. 45 S K S Y L T L E N G K V F L T G G D L P A L D G A
SEQ. ID. NO. 43 L R L Y D T E C D N A K G L K A F Y D A I K Y G P

SEQ. ID. NO. 45 R V D F R C D P D F H L V G S S R S I C S Q G Q W
SEQ. ID. NO. 43 N H L M V F G G V C P S V T S I I A E S L Q G W N

SEQ. ID. NO. 45 S T P K P H C Q V N R T P H S E R R A V Y I G A L
SEQ. ID. NO. 43 L V Q L S F A A T T P V L A D K K K Y P Y F F R T

SEQ. ID. NO. 45 F P M S G G W P G G Q A C Q P A V E M A L E D V N
SEQ. ID. NO. 43 V P S D N A V N P A I L K L L K H Y Q W K R V G T

SEQ. ID. NO. 45 S R R D I L P D Y E L K L I H H D S K C D P G Q A
SEQ. ID. NO. 43 L T Q D V Q R F S E V R N D L T G V L Y G E D I E

SEQ. ID. NO. 45 T K Y L Y E L L Y N D P I K I I L M P G C S S V S
SEQ. ID. NO. 43 I S D T E S F S N D P C T S V K K L K G N D V R I

SEQ. ID. NO. 45 T L V A E A A R M W N L I V L S Y G S S S P A L S
SEQ. ID. NO. 43 I L G Q F D Q N M A A K V F C C A Y E E N M Y G S

SEQ. ID. NO. 45 N R Q R F P T F F R T H P S A T L H N P T R V K L
SEQ. ID. NO. 43 K Y Q W I I P G W Y E P S W W E Q V H T E A N S S

Figure 14a

SEQ. ID. NO. 45    F E K W G W K K I A T I Q Q T T E V F T S T L D D
SEQ. ID. NO. 43    R C L R K N L L A A M E G Y I G V D F E P L S S K

SEQ. ID. NO. 45    L E E R V K E A G I E I T F R Q S F F S D P A V P
SEQ. ID. NO. 43    Q I K T I S G K T P Q Q Y E R E Y N N K R S G V G

SEQ. ID. NO. 45    V K N L K R Q D A R I I V G L F Y E T E A R K V F
SEQ. ID. NO. 43    P S K F H G Y A Y D G I W V I A K T L Q R A M E T

SEQ. ID. NO. 45    C E V Y K E R L F G K K Y V W F L I G W Y A D N W
SEQ. ID. NO. 43    L H A S S R H Q R I Q D F N Y T D H T L G R I I L

SEQ. ID. NO. 45    F K I Y D P S I N C T V D E M T E A V E G H I T T
SEQ. ID. NO. 43    N A M N E T N P F G V T G Q V V F R N G E R M G T

SEQ. ID. NO. 45    E I V M L N P A N T R S I S N M T S Q E F V E K L
SEQ. ID. NO. 43    I K F T Q F Q D S R E V K V G E Y N A V A D T L E

SEQ. ID. NO. 45    T K R L K R H P E E T G G - F Q E A P L A Y D A I
SEQ. ID. NO. 43    I I N D T I R F Q G S E P P K D K T I I L E Q L R

SEQ. ID. NO. 45    W A L A L A L N K T S G G G G R S G V R L E D F N
SEQ. ID. NO. 43    K I S L P L Y S I L S A L T I L G M I M A S A F L

SEQ. ID. NO. 45    Y N N Q T I T D Q I Y R A M N S S S F E G V S G H
SEQ. ID. NO. 43    F F N I K N R N Q K L I K M S S P Y M N N L I I L

SEQ. ID. NO. 45    V V F D A S G S R M A W T L I E Q L Q G G S Y K K
SEQ. ID. NO. 43    G G M L S Y A S I F L F G L D G S F V S E K T F E

SEQ. ID. NO. 45    I G Y Y D S T K D D L S W S K T D K W I G G S P P
SEQ. ID. NO. 43    T L C T V R T W I L T V G Y T T A F G A M F A K T

SEQ. ID. NO. 45    A D Q T L V I K T F R F L S Q K L F I S V S V L S
SEQ. ID. NO. 43    W R V H A I F K N V K M K K K I I K D Q K L L V I

SEQ. ID. NO. 45    S L G I V L A V V C L S F N I Y N S H V R Y I Q N
SEQ. ID. NO. 43    V G G M L L I D L C I L I C W Q A V D P L R R T V

Figure 14b

SEQ. ID. NO. 45  S Q P N L N N L T A V G C S L A L A A V F P L G L
SEQ. ID. NO. 43  E K Y S M E P D P A G R D I S I R P L L E H C E N

SEQ. ID. NO. 45  D G Y H I G R N Q F P F V C Q A R L W L L G L G F
SEQ. ID. NO. 43  T H M T I W L G I V Y A Y K G L L M L F G C F L A

SEQ. ID. NO. 45  S L G Y G S M F T K I W W V H T V F T K K E E K K
SEQ. ID. NO. 43  W E T R N V S I P A L N D S K Y I G M S V Y N V G

SEQ. ID. NO. 45  E W R K T L E P W K L Y A T V G L L V G M D V L T
SEQ. ID. NO. 43  I M C I I G A A V S F L T R D Q P N V Q F C I V A

SEQ. ID. NO. 45  L A I W Q I V D P L H R T I E T F A K E E P K E D
SEQ. ID. NO. 43  L V I I F C S T I T L C L V F V P K L I T L R T N

SEQ. ID. NO. 45  I D V S I L P Q L E H C S S R K M N T W L G I F Y
SEQ. ID. NO. 43  P D A A T Q N R R F Q F T Q N Q K K E D S K T S T

SEQ. ID. NO. 45  G Y K G L L L L L G I F L A Y E T K S V S T E K I
SEQ. ID. NO. 43  S V T S V N Q A S T S R L E G L Q S E N H R L R M

SEQ. ID. NO. 45  N D H R A V G M A I Y N V A V L C L I T A P V T M
SEQ. ID. NO. 43  K I T E L D K D L E E V T M Q L Q D T P E K T T Y

SEQ. ID. NO. 45  I L S S Q Q D A A F A F A S L A I V F S S Y I T L
SEQ. ID. NO. 43  I K Q N H Y Q E L N D I L N L G N F T E S T D G G

SEQ. ID. NO. 45  V V L F V P K M R R L I T R G E W Q S E A Q D T M
SEQ. ID. NO. 43  K A I L K N H L D Q N P Q L Q W N T T E P S R T C

SEQ. ID. NO. 45  K T G S S T N N N E E E K S R L L E K E N R E L E
SEQ. ID. NO. 43  K D P I E D I N S P E H I Q R R L S L Q L P I L H

SEQ. ID. NO. 45  K I I A E K E E R V S E L R H Q L Q S R Q Q L R S
SEQ. ID. NO. 43  H A Y L P S I G G V D A S C V S P C V S P T A S P

SEQ. ID. NO. 45  R R H P P T P P E P S G G L P R G P P E P P D R L
SEQ. ID. NO. 43  R H R H V P P S F R V M V S G L A A A M T L E S I

Figure 14c

SEQ. ID. NO. 45  S C D G S R V H L L Y K A A A M T L E S I M A C C
SEQ. ID. NO. 43  M A C C L S E E A K E A R R I N D E I E R Q L R R

SEQ. ID. NO. 45  L S E E A K E A R R I N D E I E R Q L R R D K R D
SEQ. ID. NO. 43  D K R D A R R E L K L L L L G T G E S G K S T F I

SEQ. ID. NO. 45  A R R E L K L L L L G T G E S G K S T F I K Q M R
SEQ. ID. NO. 43  K Q M R I I H G S G Y S D E D K R G F T K L V Y Q

SEQ. ID. NO. 45  I I H G S G Y S D E D K R G F T K L V Y Q N I F T
SEQ. ID. NO. 43  N I F T A M Q A M I R A M D T L K I P Y K Y E H N

SEQ. ID. NO. 45  A M Q A M I R A M D T L K I P Y K Y E H N K A H A
SEQ. ID. NO. 43  K A H A Q L V R E V D V E K V S A F E N P Y V D A

SEQ. ID. NO. 45  Q L V R E V D V E K V S A F E N P Y V D A I K S L
SEQ. ID. NO. 43  I K S L W N D P G I Q E C Y D R R R E Y Q L S D S

SEQ. ID. NO. 45  W N D P G I Q E C Y D R R R E Y Q L S D S T K Y Y
SEQ. ID. NO. 43  T K Y Y L N D L D R V A D P A Y L P T Q Q D V L R

SEQ. ID. NO. 45  L N D L D R V A D P A Y L P T Q Q D V L R V R V P
SEQ. ID. NO. 43  V R V P T T G I I E Y P F D L Q S V I F R M V D V

SEQ. ID. NO. 45  T T G I I E Y P F D L Q S V I F R M V D V G G Q R
SEQ. ID. NO. 43  G G Q R S E R R K W I H C F E N V T S I M F L V A

SEQ. ID. NO. 45  S E R R K W I H C F E N V T S I M F L V A L S E Y
SEQ. ID. NO. 43  L S E Y D Q V L V E S D N E N R M E E S K A L F R

SEQ. ID. NO. 45  D Q V L V E S D N E N R M E E S K A L F R T I I T
SEQ. ID. NO. 43  T I I T Y P W F Q N S S V I L F L N K K D L L E E

SEQ. ID. NO. 45  Y P W F Q N S S V I L F L N K K D L L E E K I M Y
SEQ. ID. NO. 43  K I M Y S H L V D Y F P E Y D G P Q R D A Q A A R

SEQ. ID. NO. 45  S H L V D Y F P E Y D G P Q R D A Q A A R E F I L
SEQ. ID. NO. 43  E F I L K M F V D L N P D S D K I N Y S H F T C A

Figure 14d

SEQ. ID. NO. 45  K M F V D L N P D S D K I I Y S H F T C A T D T E
SEQ. ID. NO. 43  T D T E N I R F V F A A V K D T I L Q L N L K G C

SEQ. ID. NO. 45  N I R F V F A A V K D T I L Q L N L K G C G L Y
SEQ. ID. NO. 43  G L Y

Figure 14e

SEQ. ID. NO. 48  M V C E G K R S A S C P C F F L L T A K F Y W I L T M M Q R
SEQ. ID. NO. 49  M V C E G K R S A S C P C F F L L T A K F Y W I L T M M Q R
SEQ. ID. NO. 50  M V C E G K R S A S C P C F F L L T A K F Y W I L T M M Q R

SEQ. ID. NO. 48  T H S Q E Y A H S I R I D G D I T L G G L F P V H G R G S E
SEQ. ID. NO. 49  T H S Q E Y A H S I R I D G D I T L G G L F P V H G R G S E
SEQ. ID. NO. 50  T H S Q E Y A H S I R V D G D I I L G G L F P V H A K G E R

SEQ. ID. NO. 48  G K P C G E L K K E K G I H R L E A M L F A L D R I N N D P
SEQ. ID. NO. 49  G K P C G E L K K E K G I H R L E A M L F A L D R I N N D P
SEQ. ID. NO. 50  G V P C G E L K K E K G I H R L E A M L Y A I D Q I N K D P

SEQ. ID. NO. 48  D L L P N I T L G A R I L D T C S R D T H A L E Q S L T F V
SEQ. ID. NO. 49  D L L P N I T L G A R I L D T C S R D T H A L E Q S L T F V
SEQ. ID. NO. 50  D L L S N I T L G V R I L D T C S R D T Y A L E Q S L T F V

SEQ. ID. NO. 48  Q A L I E K D G T E V R C G S G G P P I I T K P E R V V G V
SEQ. ID. NO. 49  Q A L I E K D G T E V R C G S G G P P I I T K P E R V V G V
SEQ. ID. NO. 50  Q A L I E K D A S D V K C A N G D P P I F T K P D K I S G V

SEQ. ID. NO. 48  I G A S G S S V S I M V A N I L R L F K I P Q I S Y A S T A
SEQ. ID. NO. 49  I G A S G S S V S I M V A N I L R L F K I P Q I S Y A S T A
SEQ. ID. NO. 50  I G A A A S S V S I M V A N I L R L F K I P Q I S Y A S T A

SEQ. ID. NO. 48  P D L S D N S R Y D F F S R V V P S D T Y Q A Q A M V D I V
SEQ. ID. NO. 49  P D L S D N S R Y D F F S R V V P S D T Y Q A Q A M V D I V
SEQ. ID. NO. 50  P E L S D N T R Y D F F S R V V P P D S Y Q A Q A M V D I V

SEQ. ID. NO. 48  R A L K W N Y V S T V A S E G S Y G E S G V E A F I Q K S R
SEQ. ID. NO. 49  R A L K W N Y V S T V A S E G S Y G E S G V E A F I Q K S R
SEQ. ID. NO. 50  T A L G W N Y V S T L A S E G N Y G E S G V E A F T Q I S R

SEQ. ID. NO. 48  E D G G V C I A Q S V K I P R E P K A G E F D K I I R R L L
SEQ. ID. NO. 49  E D G G V C I A Q S V K I P R E P K A G E F D K I I R R L L
SEQ. ID. NO. 50  E I G G V C I A Q S Q K I P R E P R P G E F E K I I K R L L

Figure 16a

SEQ. ID. NO. 48  E T S N A R A V I I F A N E D D I R R V L E A A R R A N Q T
SEQ. ID. NO. 49  E T S N A R A V I I F A N E D D I R R V L E A A R R A N Q T
SEQ. ID. NO. 50  E T P N A R A V I M F A N E D D I R R I L E A A K K L N Q S

SEQ. ID. NO. 48  G H F F W M G S D S W G S K I A P V L H L E E V A E G A V T
SEQ. ID. NO. 49  G H F F W M G S D S W G S K I A P V L H L E E V A E G A V T
SEQ. ID. NO. 50  G H F L W I G S D S W G S K I A P V Y Q Q E E I A E G A V T

SEQ. ID. NO. 48  I L P K R M S V R G F D R Y F S S R T L D N N R R N I W F A
SEQ. ID. NO. 49  I L P K R M S V R G F D R Y F S S R T L D N N R R N I W F A
SEQ. ID. NO. 50  I L P K R A S I D G F D R Y F R S R T L A N N R R N V W F A

SEQ. ID. NO. 48  E F W E D N F H C K L S R H A L K K G S H V K K C T N R E R
SEQ. ID. NO. 49  E F W E D N F H C K L S R H A L K K G S H V K K C T N R E R
SEQ. ID. NO. 50  E F W E E N F G C K L G S H G K R N - S H I K K C T G L E R

SEQ. ID. NO. 48  I G Q D S A Y E Q E G K V Q F V I D A V Y A M G H A L H A M
SEQ. ID. NO. 49  I G Q D S A Y E Q E G K V Q F V I D A V Y A M G H A L H A M
SEQ. ID. NO. 50  I A R D S S Y E Q E G K V Q F V I D A V Y S M A Y A L H N M

SEQ. ID. NO. 48  H R D L C P G R V G L C P R M D P V D G T Q L L K Y I R N V
SEQ. ID. NO. 49  H R D L C P G R V G L C P R M D P V D G T Q L L K Y I R N V
SEQ. ID. NO. 50  H K D L C P G Y I G L C P R M S T I D G K E L L G Y I R A V

SEQ. ID. NO. 48  N F S G I A G N P V T F N E N G D A P G R Y D I Y Q Y Q L R
SEQ. ID. NO. 49  N F S G I A G N P V T F N E N G D A P G R Y D I Y Q F Q L R
SEQ. ID. NO. 50  N F N G S A G T P V T F N E N G D A P G R Y D I F Q Y Q I T

SEQ. ID. NO. 48  N D S A E Y K V I G S W T D H L H L R I E R M H W P G S G Q
SEQ. ID. NO. 49  N D S A E Y K V I G S W T D H L H L R I E R M H W P G S G Q
SEQ. ID. NO. 50  N K S T E Y K V I G H W T N Q L H L K V E D M Q W A H R E H

SEQ. ID. NO. 48  Q L P R S I C S L P C Q P G E R K K T V K G M P C C W H C E
SEQ. ID. NO. 49  Q L P R S I C S L P C Q P G E R K K T V K G M P C C W H C E
SEQ. ID. NO. 50  T H P A S V C S L P C K P G E R K K T V K G V P C C W H C E

SEQ. ID. NO. 48  P C T G Y Q Y Q V D R Y T C K T C P Y D M R P T E N R T G C
SEQ. ID. NO. 49  P C T G Y Q Y Q V D R Y T C K T C P Y D M R P T E N R T G C
SEQ. ID. NO. 50  R C E G Y N Y Q V D E L S C E L C P L D Q R P N M N R T G C

Figure 16b

```
SEQ. ID. NO. 48   R P I P I I K L E W G S P W A V L P L F L A V V G I A A T L
SEQ. ID. NO. 49   R P I P I I K L E W G S P W A V L P L F L A V V G I A A T L
SEQ. ID. NO. 50   Q L I P I I K L E W H S P W A V V P V F V A I L G I I A T T

SEQ. ID. NO. 48   F V V I T F V R Y N D T P I V K A S G R E L S Y V L L A G I
SEQ. ID. NO. 49   F V V I T F V R Y N D T P I V K A S G R E L S Y V L L A G I
SEQ. ID. NO. 50   F V I V T F V R Y N D T P I V R A S G R E L S Y V L L T G I

SEQ. ID. NO. 48   F L C Y A T T F L M I A E P D L G T C S L R R I F L G L G M
SEQ. ID. NO. 49   F L C Y A T T F L M I A E P D L G T C S L R R I F L G L G M
SEQ. ID. NO. 50   F L C Y S I T F L M I A A P D T I I C S F R R V F L G L G M

SEQ. ID. NO. 48   S I S Y A A L L T K T N R I Y R I F E Q G K R S V S A P R F
SEQ. ID. NO. 49   S I S Y A A L L T K T N R I Y R I F E Q G K R S V S A P R F
SEQ. ID. NO. 50   C F S Y A A L L T K T N R I H R I F E Q G K K S V T A P K F

SEQ. ID. NO. 48   I S P A S Q L A I T F S L I S L Q L L G I C V W F V V D P S
SEQ. ID. NO. 49   I S P A S Q L A I T F S L I S L Q L L G I C V W F V V D P S
SEQ. ID. NO. 50   I S P A S Q L V I T F S L I S V Q L L G V F V W F V V D P P

SEQ. ID. NO. 48   H S V V D F Q D Q R T L D P R F A R G V L K C D I S D L S L
SEQ. ID. NO. 49   H S V V D F Q D Q R T L D P R F A R G V L K C D I S D L S L
SEQ. ID. NO. 50   H I I I D Y G E Q R T L D P E K A R G V L K C D I S D L S L

SEQ. ID. NO. 48   I C L L G Y S M L L M V T C T V Y A I K T R G V P E T F N E
SEQ. ID. NO. 49   I C L L G Y S M L L M V T C T V Y A I K T R G V P E T F N E
SEQ. ID. NO. 50   I C S L G Y S I L L M V T C T V Y A I K T R G V P E T F N E

SEQ. ID. NO. 48   A K P I G F T M Y T T C I V W L A F I P I F F G T S Q S A D
SEQ. ID. NO. 49   A K P I G F T M Y T T C I V W L A F I P I F F G T S Q S A D
SEQ. ID. NO. 50   A K P I G F T M Y T T C I I W L A F I P I F F G T A Q S A E

SEQ. ID. NO. 48   K L Y I Q T T T L T V S V S L S A S V S L G M L Y M P K V Y
SEQ. ID. NO. 49   K L Y I Q T T T L T V S V S L S A S V S L G M L Y M P K V Y
SEQ. ID. NO. 50   K M Y I Q T T T L T V S M S L S A S V S L G M L Y M P K V Y

SEQ. ID. NO. 48   I I L F H P E Q N V P K R K R S L K A V V T A A T M S N K F
SEQ. ID. NO. 49   I I L F H P E Q N T I E E V R C S T A A H A F K V A A R A T
SEQ. ID. NO. 50   I I I F H P E Q N T I E E V R C S T A A H A F K V A A R A T
```

Figure 16c

SEQ. ID. NO. 48
SEQ. ID. NO. 49  A H A Q L V R E V D V E K V S A F E N P Y V D A I K S L W N
SEQ. ID. NO. 50  A H A Q L V R E V D V E K V S A F E N P Y V D A I K S L W N

SEQ. ID. NO. 48
SEQ. ID. NO. 49  D P G I Q E C Y D R R R E Y Q L S D S T K Y Y L N D L D R V
SEQ. ID. NO. 50  D P G I Q E C Y D R R R E Y Q L S D S T K Y Y L N D L D R V

SEQ. ID. NO. 48
SEQ. ID. NO. 49  A D P A Y L P T Q Q D V L R V R V P T T G I I E Y P F D L Q
SEQ. ID. NO. 50  A D P A Y L P T Q Q D V L R V R V P T T G I I E Y P F D L Q

SEQ. ID. NO. 48
SEQ. ID. NO. 49  S V I F R M V D V G G Q R S E R R K W I H C F E N V T S I M
SEQ. ID. NO. 50  S V I F R M V D V G G Q R S E R R K W I H C F E N V T S I M

SEQ. ID. NO. 48
SEQ. ID. NO. 49  F L V A L S E Y D Q V L V E S D N E N R M E E S K A L F R T
SEQ. ID. NO. 50  F L V A L S E Y D Q V L V E S D N E N R M E E S K A L F R T

SEQ. ID. NO. 48
SEQ. ID. NO. 49  I I T Y P W F Q N S S V I L F L N K K D L L E E K I M Y S H
SEQ. ID. NO. 50  I I T Y P W F Q N S S V I L F L N K K D L L E E K I M Y S H

SEQ. ID. NO. 48
SEQ. ID. NO. 49  L V D Y F P E Y D G P Q R D A Q A A R E F I L K M F V D L N
SEQ. ID. NO. 50  L V D Y F P E Y D G P Q R D A Q A A R E F I L K M F V D L N

SEQ. ID. NO. 48
SEQ. ID. NO. 49  P D S D K I I Y S H F T C A T D T E N I R F V F A A V K D T
SEQ. ID. NO. 50  P D S D K I I Y S H F T C A T D T E N I R F V F A A V K D T

SEQ. ID. NO. 48
SEQ. ID. NO. 49  I L Q L N L K D C G L F
SEQ. ID. NO. 50  I L Q L N L K D C G L F

Figure 16d

SEQ. ID. NO. 48  T Q K G N F R P N G E A K S E L C E N L E A P A L A T K Q T
SEQ. ID. NO. 49  L R R S N V S R K R S S S L G G S T G S T P S S S I S S K S
SEQ. ID. NO. 50  L R R S N V S R K R S S S L G G S T G S T P S S S I S S K S

SEQ. ID. NO. 48  Y V T Y T N H A I
SEQ. ID. NO. 49  N S E D P F P Q P E R Q K Q Q Q P L A L T Q Q E Q Q Q Q P L
SEQ. ID. NO. 50  N S E D P F P Q P E R Q K Q Q Q P L A L T Q Q E Q Q Q Q P L

SEQ. ID. NO. 48
SEQ. ID. NO. 49  T L P Q Q Q R S Q Q Q P R C K Q K V I F G S G T V T F S L S
SEQ. ID. NO. 50  T L P Q Q Q R S Q Q Q P R C K Q K V I F G S G T V T F S L S

SEQ. ID. NO. 48
SEQ. ID. NO. 49  F D E P Q K N A M A H G N S T H Q N S L E A Q K S S D T L T
SEQ. ID. NO. 50  F D E P Q K N A M A H G N S T H Q N S L E A Q K S S D T L T

SEQ. ID. NO. 48
SEQ. ID. NO. 49  R H Q P L L P L Q C G E T D L D L T V Q E T G L Q G P V G G
SEQ. ID. NO. 50  R H Q P L L P L Q C G E T D L D L T V Q E T G L Q G P V G G

SEQ. ID. NO. 48
SEQ. ID. NO. 49  D Q R P E V E D P E E L S P A L V V S S S Q S F V I S G G G
SEQ. ID. NO. 50  D Q R P E V E D P E E L S P A L V V S S S Q S F V I S G G G

SEQ. ID. NO. 48
SEQ. ID. NO. 49  S T V T E N V V N S A A A M T L E S I M A C C L S E E A K E
SEQ. ID. NO. 50  S T V T E N V V N S A A A M T L E S I M A C C L S E E A K E

SEQ. ID. NO. 48
SEQ. ID. NO. 49  A R R I N D E I E R Q L R R D K R D A R R E L K L L L L G T
SEQ. ID. NO. 50  A R R I N D E I E R Q L R R D K R D A R R E L K L L L L G T

SEQ. ID. NO. 48
SEQ. ID. NO. 49  G E S G K S T F I K Q M R I I H G S G Y S D E D K R G F T K
SEQ. ID. NO. 50  G E S G K S T F I K Q M R I I H G S G Y S D E D K R G F T K

SEQ. ID. NO. 48
SEQ. ID. NO. 49  L V Y Q N I F T A M Q A M I R A M D T L K I P Y K Y E H N K
SEQ. ID. NO. 50  L V Y Q N I F T A M Q A M I R A M D T L K I P Y K Y E H N K

Figure 16e

G-PROTEIN FUSION RECEPTORS AND CONSTRUCTS ENCODING SAME

CROSS-REFERENCE TO RELATED APPLICATIONS

The present application is a continuation-in-part of PCT/US99/07333 filed on Apr. 2, 1999, which claims priority to Garrett et al. U.S. Ser. No. 60/080,671, filed Apr. 3, 1998, which is hereby incorporated by reference herein in its entirety including the drawings.

FIELD OF THE INVENTION

The present invention relates to G-protein fusion receptors, chimeric $GABA_B$ (γ-aminobutyric acid) receptors, nucleic acid encoding such receptors, and uses of such receptors, and nucleic acid encoding such receptors.

BACKGROUND

The references cited herein are not admitted to be prior art to the claimed invention.

Chimeric receptors made up of peptide segments from different receptors have different uses, such as being used to assess the functions of different sequence regions and to assess the activity of different compounds at a particular receptor. Examples of using chimeric receptors to assess the activity of different compounds are provided by Dull et al., U.S. Pat. No. 4,859,609; Dull et al., U.S. Pat. No. 5,030,576; Fuller et al., U.S. Pat. No. 5,981,195; and International Application No. PCT/US96/12336, International Publication No. WO 97/05252.

Dull et al. U.S. Pat. No. 4,859,609, and Dull et al. U.S. Pat. No. 5,030,576, indicate the production and use of chimeric receptors comprising a ligand-binding domain of a predetermined receptor and a heterologous reporter polypeptide. The Dull et al. patents provide as examples of chimerics: (1) a chimeric receptor made up of the insulin receptor extracellular a chain, and the EGF receptor transmembrane and cytoplasmic domains without any HIR B-chain sequence; and (2) a hybrid receptor made up of the v-erB oncogene product intracellular domain fused to the EGF receptor extracellular and transmembrane domains.

Fuller et al. International Publication No. WO 97/05252 feature chimeric receptors made up of metabotropic glutamate receptor (mGluR) domains and calcium receptor (CaR) domains. The chimeric receptors allow the coupling of functional aspects of a mGluR with a CaR.

An example of the use of chimeric receptors to assess the functions of different sequence region receptors are found in studies identifying regions of different guanine nucleotide-binding protein-coupled receptors important for guanine nucleotide-binding protein coupling. (See, Kobilka et al., *Science* 240:1310-1316, 1988; Wess et al., *FEBS Lett.* 258:133-136, 1989; Cotecchia et al., *Proc. Natl. Acad. Sci. USA* 87:2896-2900, 1990; Lechleiter et al., *EMBO J.* 9:4381-4390, 1990; Wess et al., *Mol. Pharmacol.* 38:517-523, 1990; and Pin et al, *EMBO J.* 13:342-348, 1994.)

SUMMARY OF THE INVENTION

The present invention features G-protein fusion receptors and chimeric $GABA_B$ receptors ($GABA_B$Rs), nucleic acid encoding such receptors, and the use of such receptors and nucleic acid. G-protein fusion receptors comprise at least one domain from a CaR, an mGluR, and/or a $GABA_B$ receptor fused directly or through a linker to a guanine nucleotide-binding protein (G-protein). Chimeric $GABA_B$Rs comprise at least one of a $GABA_B$R extracellular domain, a $GABA_B$R transmembrane domain, or a $GABA_B$R intracellular domain and one or more domains from a mGluR subtype 8 (mGluR8) and/or a CaR.

G-proteins are peripheral membrane proteins made up of an α subunit, a β subunit, and a γ subunit. G-proteins interconvert between a GDP-bound and a GTP-bound form. Different types of G-proteins can affect different enzymes, such as adenylate cyclase and phospholipase-C.

Thus, a first aspect of the present invention describes a G-protein fusion receptor comprising:

an extracellular domain comprising an extracellular domain amino acid sequence substantially similar to either an extracellular CaR amino acid sequence, an extracellular mGluR amino acid sequence, or an extracellular $GABA_B$ receptor amino acid sequence;

a transmembrane domain joined to the carboxy terminus of the extracellular domain, the transmembrane domain comprising a transmembrane domain amino acid sequence substantially similar to either a transmembrane CaR amino acid sequence, a transmembrane mGluR amino acid sequence, or a transmembrane $GABA_B$ receptor amino acid sequence;

an intracellular domain joined to the carboxy terminus of the transmembrane domain comprising all or a portion of an intracellular amino acid sequence substantially similar to either an intracellular CaR amino acid sequence, an intracellular mGluR amino acid sequence, or an intracellular $GABA_B$ receptor amino acid sequence, provided that the portion is at least about ten amino acids;

an optionally present linker joined to the carboxy terminus of the intracellular domain, where the optionally present linker is a polypeptide 3 to 30 amino acids in length, wherein the amino acids of the optionally present linker are selected from the group consisting of alanine, proline, serine, and glycine; and a G-protein joined either to the intracellular domain or to the optionally present linker, provided that the G-protein is joined to the optionally present linker when the optionally present linker is present.

"Substantially similar" refers to at least 40% sequence similarity between respective polypeptide regions making up a domain. In preferred embodiments, "substantially similar" refers to at least 50%, at least 75%, at least 90%, at least 95% sequence similarity, or 100% (the same sequence), between polypeptide domains. The degree to which two polypeptide domains are substantially similar is determined by comparing the amino acid sequences located in corresponding domains. Sequence similarity is preferably determined using BLASTN (Altschul et al., *J. Mol. Biol.* 215: 403-410, 1990).

The different receptor components of the G-protein receptor can come from the same receptor protein or from a chimeric receptor made up of different receptor domains. By swapping different domains, compounds able to affect different domains of a particular receptor can be identified and the activity of different compounds at different domains can be measured.

Different embodiments the CaR region(s) present in the G-protein fusion are substantially similar to, comprise, or consist of portion(s) of a mammalian CaR, preferably, the human CaR; mGluR region(s) present in the G-protein fusion are substantially similar to, comprise, or consist of portion(s) of a mammalian mGluR, preferably a human mGluR; and $GABA_B$R region(s) present in the G-protein fusion are substantially similar to, comprise, or consist of portion(s) of a mammalian $GABA_BR$, preferably a human $GABA_BR$ receptor.

In preferred embodiments concerning $GABA_BR$ regions that are present: the $GABA_BR$ extracellular domain is substantially similar to a $GABA_BR$ extracellular domain provided in SEQ. ID. NOs. 2-4; the $GABA_BR$ transmembrane domain is substantially similar to the $GABA_BR$ transmembrane domain provided in SEQ. ID. NOs. 7-9; and the $GABA_BR$ intracellular domain is substantially similar to a $GABA_BR$ intracellular domain provided in SEQ. ID. NOs. 12-14.

In preferred embodiments concerning CaR regions that are present: the CaR extracellular domain is substantially similar to the CaR extracellular domain provided in SEQ. ID. NO. 1; the CaR transmembrane domain is substantially similar to the CaR transmembrane domain provided in SEQ. ID. NO. 6; and the CaR intracellular domain is substantially similar to the CaR intracellular domain such as that provided in SEQ. ID. NO. 11.

Various different mGluR subtypes present in different organisms, including humans, are described in different patent publications as follows: $mGluR_1$—WO 94/29449, EP 569 240 A1, WO 92/10583 and U.S. Pat. No. 5,385,831; $mGluR_2$—WO 94/29449, WO 96/06167, and EP 711 832 A2; $mGluR_3$—WO 94/29449, and WO 95/22609; $mGluR_4$—WO 95/08627, WO 95/22609, and WO 96/29404; $mGluR_5$—WO 94/29449; $mGluR_6$—WO 95/08627; $mGluR_7$— U.S. Pat. No. 5,831,047, WO 95/08627 and WO 96/29404; and $mGluR_8$—U.S. Pat. Nos. 6,051,688, 6,077,675, 6,084,084, WO 97/48724 and EP 816 498 A2. (Each of these references is hereby incorporated by reference herein.)

In preferred embodiments concerning mGluR regions that are present: the mGluR extracellular domain is substantially similar to either human mGluR 1, human mGluR 2, human mGluR 3, human mGluR 4, human mGluR 5, human mGluR 6, human mGluR 7, or human mGluR 8; the mGluR transmembrane domain is substantially similar to either human mGluR 1, human mGluR 2, human mGluR 3, human mGluR 4, human mGluR 5, human mGluR 6, human mGluR 7, or human mGluR 8; and the mGluR intracellular domain is substantially similar to either human mGluR 1, human mGluR 2, human mGluR 3, human mGluR 4, human mGluR 5, human mGluR 6, human mGluR 7, or human mGluR 8. Preferred embodiments also include any mGluR splice variant.

In preferred embodiments concerning the optionally present linker, the optionally present linker is a polypeptide 3 to 30 amino acids in length, wherein the amino acids of the optionally present linker are selected from the group consisting of alanine, proline, serine, and glycine; and more preferably, the optionally present linker is comprised of alanine amino acids.

Another aspect of the present invention describes a recombinant cell comprising an expression vector encoding for a G-protein fusion receptor, and a cell where the G-protein fusion receptor is expressed. Preferably, the G-protein fusion receptor is functional in the cell.

Another aspect of the present invention describes a recombinant cell produced by combining (a) a cell where a G-protein fusion receptor is expressed, and (b) a vector comprising nucleic acid encoding a G-protein fusion receptor and elements for introducing heterologous nucleic acid into the cell. Preferably, the G-protein fusion receptor is functional in the cell.

Another aspect of the present invention describes a process for the production of a G-protein fusion receptor. The process is performed by growing host cells comprising a G-protein fusion receptor.

Another aspect of the present invention describes a method of measuring the ability of a compound to affect G-protein fusion receptor activity.

Another aspect of the present invention describes a chimeric $GABA_BR$ comprising an extracellular domain, a transmembrane domain and an intracellular domain, wherein at least one domain is from a $GABA_BR$ and at least one domain is from CaR or mGluR8. The extracellular domain comprises an amino acid sequence substantially similar to a CaR extracellular domain (SEQ. ID. NO. 1), a $GABA_BR1a$ extracellular domain (SEQ. ID. NO. 2), a $GABA_BR1b$ extracellular domain (SEQ. ID. NO. 3), a $GABA_BR2$ extracellular domain (SEQ. ID. NO. 4), or a mGluR8 extracellular domain (SEQ. ID. NO. 5).

The transmembrane domain comprises an amino acid sequence substantially similar to a CaR transmembrane domain (SEQ. ID. NO. 6), a $GABA_BR1a$ transmembrane domain (SEQ. ID. NO. 7), a $GABA_BR1b$ transmembrane domain (SEQ. ID. NO. 8), a $GABA_BR2$ transmembrane domain (SEQ. ID. NO. 9), or a mGluR8 transmembrane domain (SEQ. ID. NO. 10).

The intracellular domain comprises an amino acid sequence substantially similar to a CaR intracellular domain (SEQ. ID. NO. 11), a $GABA_BR1a$ intracellular domain (SEQ. ID. NO. 12), a $GABA_BR1b$ intracellular domain (SEQ. ID. NO. 13), a $GABA_BR2$ intracellular domain (SEQ. ID. NO. 14), or a mGluR8 intracellular domain (SEQ. ID. NO. 15).

Preferred chimeric $GABA_BRs$ contain at least one mGluR8 intracellular, transmembrane or extracellular domain, or at least one CaR intracellular, transmembrane or extracellular domain. More preferably, the chimeric $GABA_BR$ contains at least one CaR domain.

In preferred embodiments concerning mGluR8 regions that are present: the mGluR8 extracellular domain is substantially similar to the mGluR8 extracellular domain provided in SEQ. ID. NO. 5; the mGluR8 transmembrane domain is substantially similar to the mGluR8 transmembrane domain provided in SEQ. ID. NO. 10; and the mGluR8 intracellular domain is substantially similar to the mGluR8 receptor intracellular domain provided in SEQ. ID. NO. 15.

Preferably, the domains are functionally coupled such that a signal from the binding of an extracellular ligand is transduced to the intracellular domain when the chimeric receptor is present in a suitable host cell. A suitable host cell contains the elements for functional signal transduction for receptors coupled to a G-protein.

Another aspect of the present invention describes a nucleic acid comprising a nucleotide sequence encoding for a chimeric $GABA_BR$.

Another aspect of the present invention describes a recombinant cell comprising an expression vector encoding for a chimeric $GABA_BR$, and a cell where the chimeric $GABA_BR$ is expressed. Preferably, the chimeric $GABA_BR$ is functional in the cell.

Another aspect of the present invention describes a recombinant cell produced by combining (a) a cell where a chimeric $GABA_BR$ is expressed, and (b) a vector comprising nucleic acid encoding the chimeric $GABA_BR$ and elements for introducing heterologous nucleic acid into the cell. Preferably, the chimeric $GABA_BR$ is functional in the cell.

Another aspect of the present invention describes a process for the production of a chimeric receptor. The process is performed by growing host cells comprising a chimeric GABA$_B$R.

Another aspect of the present invention describes a method of measuring the ability of a compound to affect GABA$_B$R or mGluR activity. The method is performed by measuring the ability of a compound to affect chimeric GABA$_B$R or mGluR activity.

Another aspect of the present invention describes a fusion receptor polypeptide comprising a receptor and a G-protein α subunit, wherein the G-protein α subunit is fused to the intracellular domain of the receptor, provided that the receptor is not an adrenoreceptor.

Various examples are described herein. These examples are not intended in any way to limit the claimed invention.

Other features and advantages of the invention will be apparent from the following drawings, the description of the invention, the examples, and the claims.

BRIEF DESCRIPTION OF THE DRAWINGS

FIGS. 1a-1d illustrate the amino acid sequences of a human CaR extracellular domain (SEQ. ID. NO. 1), a human GABA$_B$R1a extracellular domain (SEQ. ID. NO. 2), a human GABA$_B$R1b extracellular domain (SEQ. ID. NO. 3), a human GABA$_B$R2 extracellular domain (SEQ. ID. NO. 4), and a human mGluR8 extracellular domain (SEQ. ID. NO. 5).

FIGS. 2a-2b illustrate the amino acid sequences of a human CaR transmembrane domain (SEQ. ID. NO. 6), a human GABA$_B$R1a transmembrane domain (SEQ. ID. NO. 7), a human GABA$_B$R1b transmembrane domain (SEQ. ID. NO. 8), a human GABA$_B$R2 transmembrane domain (SEQ. ID. NO. 9), and a human mGluR8 transmembrane domain (SEQ. ID. NO. 10).

FIGS. 3a-3b illustrate the amino acid sequences of a human CaR intracellular domain (SEQ. ID. NO. 11), a human GABA$_B$R1a intracellular domain (SEQ. ID. NO. 12), a human GABA$_B$R1b intracellular domain (SEQ. ID. NO. 13), a human GABA$_B$R2 intracellular domain (SEQ. ID. NO. 14), and a human mGluR8 intracellular domain (SEQ. ID. NO. 15).

FIGS. 4a-4b illustrate the amino acid sequence of G$_{\alpha 15}$ (SEQ. ID. NO. 16) and G$_{\alpha 16}$ (SEQ. ID. NO. 17).

FIGS. 5a-5r illustrate the cDNA sequences encoding for human CaR (SEQ. ID. NO. 18), human GABA$_B$R1a (SEQ. ID. NO. 19), human GABA$_B$R1b (SEQ. ID. NO. 20), and human GABA$_B$R2 (SEQ. ID. NO. 21).

FIGS. 6a-6h illustrate the cDNA sequence for rat GABA$_B$R1a (SEQ. ID. NO. 22) and rat GABA$_B$R1b (SEQ. ID. NO. 23).

FIGS. 7a-7c illustrate the amino sequence for rat GABA$_B$R1a (SEQ. ID. NO. 24) and rat GABA$_B$R1b (SEQ. ID. NO. 25).

FIGS. 9a-9p illustrate the cDNA sequence for human mGluR2 (SEQ. ID. NO. 26), chimeric hCaR/hmGluR2 (SEQ. ID. NO. 30), chimeric hmGluR2/hCaR (SEQ. ID. NO. 34), and chimeric hmGluR8/hCaR (SEQ. ID. NO. 38).

FIGS. 10a-10f illustrate the amino acid sequence for human mGluR2 (SEQ. ID. NO. 27), chimeric hCaR/hm-GluR2 (SEQ. ID. NO. 31), chimeric hmGluR2/hCaR (SEQ. ID. NO. 35), chimeric hmGluR8/hCaR (SEQ. ID. NO. 39).

FIGS. 11a-11v illustrate the cDNA sequence for the phCaR/hmGluR2*Gqi5 fusion construct (SEQ. ID. NO. 32), pmGluR2//CaR*Gαqi5 fusion construct (SEQ. ID. NO. 36), pmGluR2/CaR*Gαqi5+3Ala linker fusion construct (SEQ. ID. NO. 46), and the mGluR8//CaR*Gαqi5 fusion construct (SEQ. ID. NO. 40).

FIGS. 12a-12h illustrate the amino acid sequence for the phCaR/hmGluR2*Gqi5 fusion construct (SEQ. ID. NO. 33), pmGluR2//CaR*Gαqi5 fusion construct (SEQ. ID. NO. 37), pmGluR2/CaR*Gαqi5+3Ala linker fusion construct (SEQ. ID. NO. 47), and the mGluR8//CaR*Gαqi5 fusion construct (SEQ. ID. NO. 41).

FIGS. 13a-13m illustrate the cDNA sequence for the GABA$_B$R2*Gqo5 fusion construct (SEQ. ID. NO. 42) and the GABA$_B$R1a*Gqo5 fusion construct (SEQ. ID. NO. 44).

FIGS. 14a-14e illustrates the amino acid sequence for the GABA$_B$R2*Gqo5 fusion construct (SEQ. ID. NO. 43) and the GABA$_B$R1a*Gqo5 fusion construct (SEQ. ID. NO. 45).

FIGS. 16a-16e illustrate the amino acid sequence for the ph8SpmGluR4 chimeric construct (SEQ. ID. No. 48), the amino sequence for the phmGluR4/CaR*AAA*Gαqi5 fusion construct (SEQ. ID. No. 49), and the phmGluR8//CaR*AAA*Gαqi5 fusion construct (SEQ. ID. NO. 50).

DETAILED DESCRIPTION OF THE INVENTION

Figure 8:
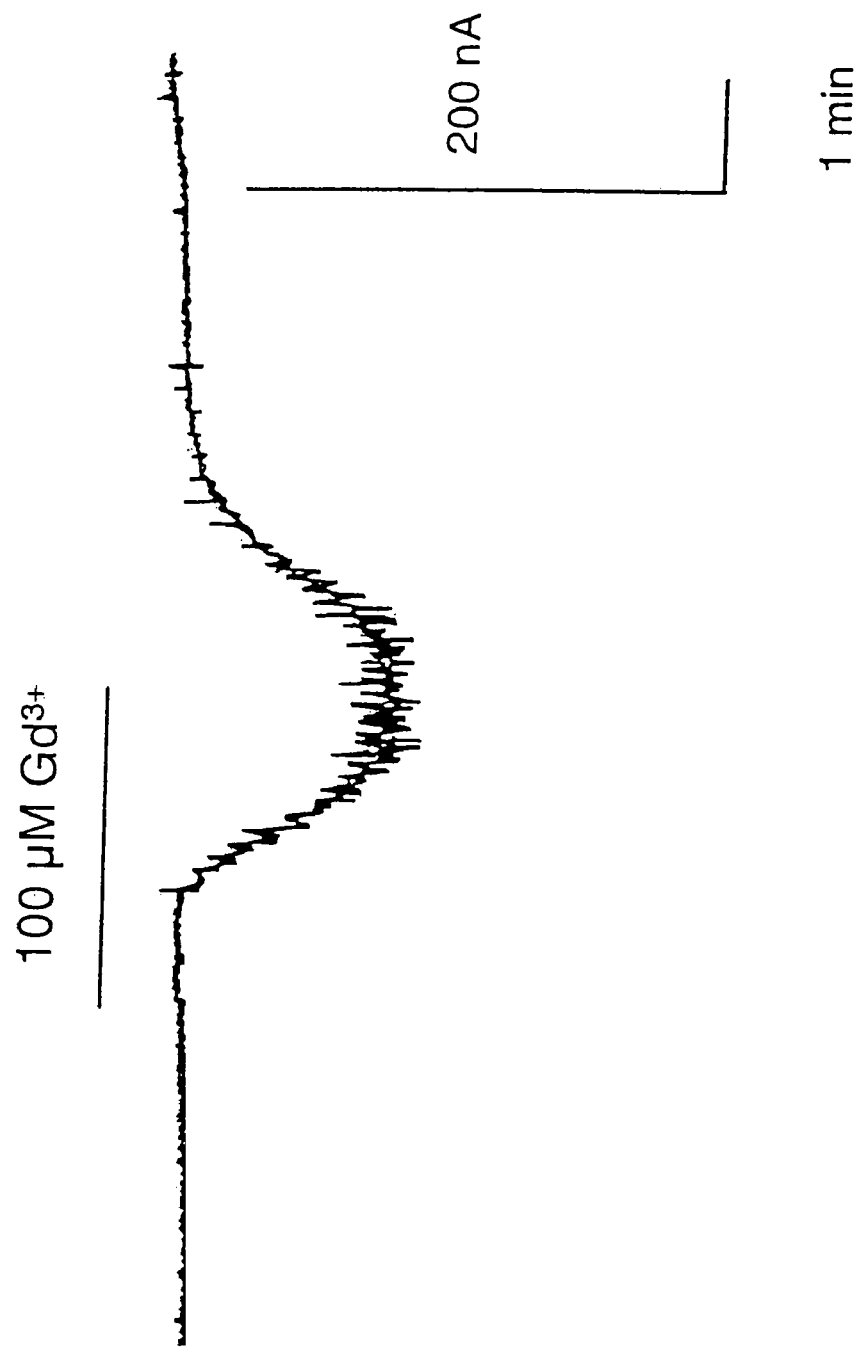
FIG. 8 illustrates the ability of a chimeric CaR/GABA$_B$R2 (CaR extracellular and transmembrane domains, and intracellular GABA$_B$R2 domain) to transduce a signal. Signal production was measured by detecting an increase in the calcium-activated chloride current. The line in the middle of the increase signifies a wash step.

The CaR, mGluR, and the GABA$_B$R are structurally similar in that they are each a single subunit membrane protein possessing an extracellular domain, a transmembrane domain comprising seven putative membrane spanning helices connected by three intracellular and three extracellular loops, and an intracellular carboxy-terminal domain. Signal transduction is activated by the extracellular binding of an agonist. The signal is transduced to the intracellular components of the receptor causing an intracellular effect.

Signal transduction from agonist binding to an extracellular region can be modulated by compounds acting at a downstream transmembrane domain or the intracellular domain. Downstream effects include antagonist actions of compounds and allosteric actions of compounds.

The transmembrane domain provides different types of target sites for compounds modulating receptor activity in different environments. As noted above, the transmembrane domain contains extracellular, transmembrane, and intracellular components.

Compounds modulating GABA$_B$R, CaR, or mGluR activity can be obtained, for example, by screening a group or library of compounds to identify those compounds having the desired activity and then synthesizing such compound. Thus, included in the present invention is a method of making a GABA$_B$R, CaR, or mGluR active compound by first screening for a compound having desired properties and then chemically synthesizing that compound.

Metabotropic Glutamate Receptors (mGluRs)

mGluRs are G protein-coupled receptors capable of activating a variety of intracellular secondary messenger systems following the binding of glutamate (Schoepp et al., *Trends Pharmacol. Sci.* 11:508, 1990; Schoepp and Conn, *Trends Pharmacol. Sci.* 14:13, 1993, hereby incorporated by reference herein).

Activation of different mGluR subtypes in situ elicits one or more of the following responses: activation of phospholipase C, increases in phosphoinositide (PI) hydrolysis, intracellular calcium release, activation of phospholipase D, activation or inhibition of adenylyl cyclase, increases and decreases in the formation of cyclic adenosine monophosphate (cAMP), activation of guanylyl cyclase, increases in the formation of cyclic guanosine monophosphate (cGMP), activation of phospholipase $A_2$, increases in arachidonic acid release, and increases or decreases in the activity of voltage- and ligand-gated ion channels (Schoepp and Conn, *Trends Pharmacol. Sci.* 14:13, 1993; Schoepp, *Neurochem. Int.* 24:439, 1994; Pin and Duvoisin, *Neuropharmacology* 34:1, 1995, hereby incorporated by reference herein).

Eight distinct mGluR subtypes have been isolated. (Nakanishi, *Neuron* 13:1031, 1994; Pin and Duvoisin, *Neuropharmacology* 34:1, 1995; Knopfel et al., *J. Med. Chem.* 38:1417; *Eur. J. Neuroscience* 7:622-629, 1995, each of these references is hereby incorporated by reference herein.) The different mGluRs possess a large amino-terminal extracellular domain (ECD) followed by seven putative transmembrane domains (7TMD) comprising seven putative membrane-spanning helices connected by three intracellular and three extracellular loops, and an intracellular carboxy-terminal domain of variable length (cytoplasmic tail).

Human mGluR8 is described by Stormann et al., U.S. Pat. Nos. 6,051,688, 6,077,675, and 6,084,084, International Application No. PCT/US97/09025, International Publication No. WO 97/48724, and mouse mGluR8 is described by Duvoisin et al., *J. Neurosci.* 15:3075-3083, 1995 (both of these references are hereby incorporated by reference herein). mGluR8 couples to $G_i$. Agonists of mGluR8 include L-glutamate and L-2-amino-4-phosphonobutyrate.

mGluR8 activity can be measured using standard techniques. For example, $G_i$ negatively couples to adenylate cyclase to inhibit intracellular cAMP accumulation in a pertussis toxin-sensitive fashion. Thus, mGluR8 activity can be measured, for example, by measuring inhibition of forskolin-stimulated cAMP production as described by Duvoisin et al., *J. Neurosci.* 15:3075-3083, 1995.

mGluRs have been implicated in a variety of neurological pathologies. Examples of such pathologies include stroke, head trauma, spinal cord injury, epilepsy, ischemia, hypoglycemia, anoxia, and neurodegenerative diseases such as Alzheimer's disease (Schoepp and Conn, *Trends Pharmacol. Sci.* 14:13, 1993; Cunningham et al., *Life Sci.* 54:135, 1994; Pin et al., *Neuropharmacology* 34:1, 1995; Knopfel et al., *J. Med. Chem.* 38:1417, 1995, each of which is hereby incorporated by reference herein).

Calcium Receptor

The CaR responds to changes of extracellular calcium concentration and also responds to other divalent and trivalent cations. The CaR is a G-protein-coupled receptor containing an extracellular $Ca^{2+}$ binding domain. Activation of the CaR, descriptions of CaRs isolated from different sources, and examples of CaR active compound are provided in Nemeth *NIPS* 10:1-5, 1995; Brown et al. U.S. Pat. No. 5,688,938; Van Wagenen et al., International Application No. PCT/US97/05558 International Publication No. WO 97/37967; Brown E. M. et al., *Nature* 366:575, 1993; Riccardi D., et al., *Proc. Nat'l. Acad. Sci. USA* 92:131-135, 1995; and Garrett J. E., et al., *J. Biol. Chem.* 31:12919-12925, 1995. (Each of these references is hereby incorporated by reference herein.) Brown et al. U.S. Pat. No. 5,688,938, and Van Wagenen et al., International Application No. PCT/US97/05558 International Publication No. WO 97/37967, describe different types of compounds active at the CaR including compounds that appear to be allosteric modulators and CaR antagonists.

The CaR can be targeted to achieve therapeutic effects. Examples of target diseases are provided in Brown et al. U.S. Pat. No. 5,688,938, and Van Wagenen et al., International Application No. PCT/US97/05558 International Publication No. WO 97/37967, and include hyperparathyroidism and osteoporosis.

γ-Aminobutyric Acid Receptors ($GABA_BRs$)

$GABA_BRs$ are G-protein-coupled metabotropic receptors. $GABA_BRs$ modulate synaptic transmission by inhibiting presynaptic transmitter release and by increasing $K^+$ conductance responsible for long-lasting inhibitory postsynaptic potentials. (See, Kaupmann et al., *Nature* 386:239-246, 1997, hereby incorporated by reference herein.)

$GABA_BRs$ are found in the mammalian brain, in locations outside of the brain, and in lower species. Outside of the brain, $GABA_BRs$ have been identified on axon terminals and ganglion cell bodies of the autonomic nervous system, on fallopian tube and uterine intestinal smooth muscle cells, in the kidney cortex, urinary bladder muscle and on testicular interstitial cells. (See, Bowery, *Annu. Rev. Pharmacol. Toxicol.* 33:109-147, 1993, hereby incorporated by reference herein.)

Different $GABA_BR$ subtypes exist. Kaupmann et al., *Nature* 386:239-246, 1997, indicate that they cloned $GABA_BRs$. Nucleic acid encoding two $GABA_BR$ proteins were indicated to be cloned from rat brain: $GABA_BR1a$ and $GABA_BR1b$. $GABA_BR1a$ differs from $GABA_BR1b$ in that the N-terminal 147 residues are replaced by 18 amino acids. $GABA_BR1a$ and $GABA_BR1b$ appear to be splice variants. The cloned $GABA_BRs$ were indicated to negatively couple adenylyl cyclases and show sequence similarity to the metabotropic receptors for L-glutamate (mGluR). Northern blot analysis indicated that $GABA_BR1a$ and $GABA_BR1b$ are present in brain and testes, but not in kidney, skeletal muscle, liver, lung, spleen, or heart.

Kaupmann et al., International Application No. PCT/EP97/01370, International Publication No. WO 97/46675, indicate that they have obtained rat $GABA_BR$ clones, $GABA_BR1a$ and $GABA_BR1b$; and human $GABA_BR$ clones, $GABA_BR1a/b$ (representing a partial receptor clone) and $GABA_BR1b$ (representing a full-length receptor clone). Amino acid sequence information and encoding cDNA sequence information are provided for the different $GABA_BR$ clones.

Another $GABA_BR$ subtype is $GABA_BR2$. Northern blot analysis reveals that an approximate 6.3-Kb human $GABA_BR2$ transcript is abundantly expressed in the human brain. Expression is not detected in the heart, placenta, lung, liver, skeletal muscle, kidney and pancreas under conditions where $GABA_BR2$ transcript was identified in the human brain. Within the human brain, $GABA_BR2$ is broadly expressed at variable levels.

$GABA_BR$ functions as a heterodimer of the subunits $GABA_BR1$ or $GABA_BR2$. (Jones et al., *Nature* 396:674-679, 1998, hereby incorporated by reference herein.)

$GABA_BRs$ have been targeted to achieve therapeutic effects. Kerr and Ong, *DDT* 1:371-380, 1996, describe different compounds indicated to be GABA$_B$R agonists and GABA$_B$R antagonists. Kerr and Ong also review therapeutic implications of affecting GABA$_B$R activity including, spasticity and motor control, analgesia, epilepsy, cognitive effects, psychiatric disorders, alcohol dependence and withdrawal, feeding behavior, cardiovascular and respiratory functions, and peripheral functions.

Bittiger et al., *TIPS* 4:391-394, 1993, review therapeutic applications of GABA$_B$R antagonists. Potential therapeutic applications noted by Bittiger et al. include cognitive processes, epilepsy, and depression.

G-Protein Fusion Receptors

Examples of some different types of G-protein fusion receptors, and advantages of some receptors, are provided below. Using the present application as a guide, additional G-protein fusion receptors can be constructed.

G-protein fusion receptors contain an intracellular domain of a receptor fused to a G-protein α subunit ($G_\alpha$). $G_\alpha$ fusions to adrenoreceptors have been reported by Bertin et al., *Receptors and Channels* 5:41-51, 1997; Wise and Milligan, *Journal of Biological Chemistry* 39:24673-24678, 1997; and Bertin et al., *Proc. Natl. Acad. Sci. USA* 91:8827-8831, 1994 (each of which are hereby incorporated by reference herein). These studies were indicated to produce a functional chimeric by fusing the $\alpha_{2A}$-adrenoreceptor to the $G_{i1\alpha}$, or the $\beta_2$-adrenoreceptor to the $G_{s\alpha}$.

The G-protein fusion receptors described by the present invention include a G-protein fused to an intracellular domain, where the intracellular domain, when present in a wild-type receptor, does not interact with that type of G-protein. Thus, the present invention also describes swapping of signals by fusing an intracellular domain to a $G_\alpha$ normally not coupled to that intracellular domain. The use of such fusion proteins, while applicable to chimeric GABA$_B$Rs, is not limited to chimeric GABA$_B$Rs. Indeed, such technology can be applied to receptors containing an extracellular domain, transmembrane domain and intracellular domain of a wild-type receptor.

Preferred G-protein fusion receptors contain an intracellular domain fused to a promiscuous $G_\alpha$ that couples to phospholipase C, resulting in the mobilization of intracellular calcium. Increases in intracellular calcium can be conveniently measured through the use of dyes. Such techniques are well known in the art and are described, for example, by Brown et al. U.S. Pat. No. 5,688,938.

In an embodiment, G-protein fusions can also be used to decrease receptor desensitization.

Examples of promiscuous $G_\alpha$s coupling to phospholipase C include naturally occurring G-proteins such as $G_{\alpha15}$ and $G_{\alpha16}$, and chimeric G-protein such as Gqo5 and Gqi5. Gqo5 and Gqi5 are made of a Gq portion where the five amino acids at the C-terminal are from either $G_o$ or $G_i$, respectively (Conklin et al., *Nature* 363:274-277, 1993, hereby incorporated by reference herein). The Gq portion of such chimeric receptors provides for phospholipase C coupling while the terminal $G_o$ or $G_i$ portion allows the chimeric G-protein to couple to different receptor proteins that are normally involved in inhibitor effects on adenylate cyclase.

In an embodiment of the present invention, the employed G-protein is from a human source or is made up of different G-protein components, each from a human source.

G-protein fusions can be created, for example, by fusing directly or indirectly the intracellular domain of a receptor protein to a polypeptide having an amino acid sequence substantially similar to $G_{\alpha15}$, $G_{\alpha16}$, Gqo5 or Gqi5. In different embodiments, the receptor is fused directly or indirectly to a G-protein consisting of the amino acid sequence of $G_{\alpha15}$, $G_{\alpha16}$, Gqo5 or Gqi5.

The intracellular domain portion of a receptor protein fused directly or indirectly to a G-protein should be at least about 10 amino acids in length. In different embodiments, the portion is at least about 10 amino acids, is at least about 50 amino acids, at least about 100 amino acids, or the full length of an intracellular domain.

The intracellular domain can be directly linked to a G-protein or can be indirectly linked through an optionally present linker. Optionally present linkers are preferably about 3 to about 30 amino acids in length. Preferred linkers are made up of alanine, glycine, or a combination thereof.

Chimeric Receptors

Examples of some different types of chimeric receptors, and advantages of some receptors, are provided below. Using the present application as a guide, additional chimeric receptors can be constructed.

Chimeric GABA$_B$R Extracellular Domain

Chimeric GABA$_B$Rs containing a GABA$_B$R extracellular domain are particularly useful for studying the importance of the GABA$_B$R extracellular domain and assaying for compounds active at the extracellular domain. Preferably, chimeric GABA$_B$Rs containing a GABA$_B$R extracellular domain also contain a CaR intracellular domain.

A variety of different activities have been generally attributed to GABA$_B$R subtypes. (E.g., Kerr and Ong, *DDT* 1:371-380, 1996.) Kaupmann et al., *Nature* 386:239-246, 1997, report that in preliminary experiments involving GABA$_B$R1a, they did not detect positive coupling to the adenylyl cyclase or coupling to the phospholipase effector system.

An intracellular CaR domain can be used to couple with G-proteins that activate phospholipase C and mobilize intracellular calcium. Mobilization of intracellular calcium is readily detected, for example, by fluorescent indicators of intracellular $Ca^{2+}$.

An additional advantage of using the intracellular CaR domain is that CaR G-protein activation is not rapidly desensitized. Thus, the intracellular CaR domain can be used to produce a stronger intracellular signal than a signal produced from a receptor that is desensitized rapidly.

More preferably, the chimeric GABA$_B$R contains an intracellular CaR domain, and also contains either a CaR or a GABA$_B$R transmembrane domain. Advantages of using a CaR transmembrane domain include separating the effects occurring at a GABA$_B$R extracellular domain from effects occurring at a transmembrane domain and providing additional intracellular elements, present on transmembrane intracellular loops, useful for coupling to G-protein.

A GABA$_B$R transmembrane domain is useful for examining whether the transmembrane GABA$_B$R can be targeted to affect GABA$_B$R activity and obtaining compounds active at the GABA$_B$R transmembrane domain. For example, a transmembrane GABA$_B$R can be used to screen for transmembrane allosteric modulators and antagonists.

Chimeric GABA$_B$R Transmembrane Domain

Chimeric GABA$_B$Rs containing a GABA$_B$R transmembrane are particularly useful for studying the importance of the GABA$_B$R transmembrane domain and assaying for compounds active at the transmembrane domain. Preferably, chimeric GABA$_B$Rs containing a GABA$_B$R transmembrane domain contain an extracellular domain that is either mGluR8 or CaR, and an intracellular CaR domain.

More preferably, the chimeric $GABA_BR$ contains an extracellular domain from either mGluR8 or CaR, a $GABA_BR$ transmembrane, and an intracellular CaR domain. A chimeric $GABA_BR$ containing extracellular mGluR8 or CaR domains can readily be stimulated using mGluR8 or CaR ligands.

Chimeric $GABA_BR$ Intracellular Domain

Chimeric $GABA_BRs$ containing a $GABA_BR$ intracellular domain are particularly useful for studying the importance of the $GABA_BR$ intracellular domain and assaying for compounds active at the intracellular domain. Preferably, the chimeric receptors contain an extracellular domain from either mGluR8 or CaR. The extracellular mGluR8 or CaR domains can readily be activated using mGluR8 or CaR ligands.

Receptor Domains

Domains of a G-protein fusion receptor, a chimeric receptor, and $G_\alpha$, substantially similar to a particular sequence can be readily produced using the disclosure provided herein in conjunction with information well known in the art. Substantially similar sequences can be obtained taking into account sequence information for a particular type of receptor obtained from different sources, different types of amino acids that are to some extent interchangeable, and the ease of experimentation with which functional receptor activity can be assayed.

Substantially similar sequences include amino acid alterations such as deletions, substitutions, additions, and amino acid modifications. A "deletion" refers to the absence of one or more amino acid residue(s) in the related polypeptide. An "addition" refers to the presence of one or more amino acid residue(s) in the related polypeptide. Additions and deletions to a polypeptide may be at the amino terminus, the carboxy terminus, and/or internal terminus. Amino acid "modification" refers to the alteration of a naturally occurring amino acid to produce a non-naturally occurring amino acid. A "substitution" refers to the replacement of one or more amino acid residue(s) by another amino acid residue(s) in the polypeptide. Derivatives can contain different combinations of alterations including more than one alteration and different types of alterations.

The sequences of polypeptides can be compared from different sources to help identify variable amino acids not essential for receptor activity. For example, FIG. 7 provides the rat $GABA_BR1a$ and $GABA_BR1b$ amino acid sequences. The rat $GABA_BR1a$ and $GABA_BR1b$ amino acid sequences can be compared with the human $GABA_BR1a$ and $GABA_BR1b$ sequences to identify conserved and variable amino acids. Derivatives can then be produced where a variable amino acid is changed, and receptor activity can be readily tested.

Similarly, the amino acid sequences for CaR, mGluR8, and G-proteins from different sources are either known in the art or can readily be obtained. Examples of such references are provided above.

While the effect of an amino acid change varies depending upon factors, such as phosphorylation, glycosylation, intrachain linkages, tertiary structure, and the role of the amino acid in the active site or a possible allosteric site, it is generally preferred that a substituted amino acid is from the same group as the amino acid being replaced. To some extent, the following groups contain amino acids that are interchangeable: the basic amino acids lysine, arginine, and histidine; the acidic amino acids aspartic and glutamic acids; the neutral polar amino acids serine, threonine, cysteine, glutamine, asparagine and, to a lesser extent, methionine; the nonpolar aliphatic amino acids glycine, alanine, valine, isoleucine, and leucine (however, because of size, glycine and alanine are more closely related and valine, isoleucine and leucine are more closely related); and the aromatic amino acids phenylalanine, tryptophan, and tyrosine. In addition, although classified in different categories, alanine, glycine, and serine seem to be interchangeable to some extent, and cysteine additionally fits into this group, or may be classified with the polar neutral amino acids.

While proline is a nonpolar neutral amino acid, its replacement represents difficulties because of its effects on conformation. Thus, substitutions by or for proline are not preferred, except when the same or similar conformational results can be obtained. The conformation conferring properties of proline residues may be obtained if one or more of these is substituted by hydroxyproline (Hyp).

Examples of modified amino acids include the following: altered neutral nonpolar amino acids such as ω-amino acids of the formula $H_2N(CH_2)_nCOOH$ where n is 2-6, sarcosine (Sar), t-butylalanine (t-BuAla), t-butylglycine (t-BuGly), N-methyl isoleucine (N-MeIle), and norleucine (Nleu); altered neutral aromatic amino acids such as phenylglycine; altered polar, but neutral amino acids such as citrulline (Cit) and methionine sulfoxide (MSO); altered neutral and nonpolar amino acids such as cyclohexyl alanine (Cha); altered acidic amino acids such as cysteic acid (Cya); and altered basic amino acids such as ornithine (Orn).

Preferred derivatives have one or more amino acid alteration(s) that do not significantly affect the receptor activity of the related receptor protein. In regions of receptor domains not necessary for receptor activity, amino acids may be deleted, added or substituted with less risk of affecting activity. In regions required for receptor activity, amino acid alterations are less preferred as there is a greater risk of affecting receptor activity.

Derivatives can be produced using standard chemical techniques and recombinant nucleic acid techniques. Modifications to a specific polypeptide may be deliberate, as through site-directed mutagenesis and amino acid substitution during solid-phase synthesis, or may be accidental such as through mutations in hosts that produce the polypeptide. Polypeptides including derivatives can be obtained using standard techniques such as those described by Sambrook et al., *Molecular Cloning*, Cold Spring Harbor Laboratory Press (1989). For example, Chapter 15 of Sambrook describes procedures for site-directed mutagenesis of cloned DNA.

Receptor Nucleic Acid

G-protein fusion and chimeric receptor nucleic acid can be produced based on the information provided herein along with standard recombinant nucleic acid techniques. Examples of references describing recombinant nucleic acid techniques include *Molecular Cloning*, Sambrook et al., Cold Spring Harbor Laboratory Press (1989); and *Current Protocols in Molecular Biology*, Frederick et al., John Wiley & Sons, Inc. (1995).

Due to the degeneracy of the genetic code, different nucleic acid sequences can encode for a particular polypeptide. Thus, a large number of nucleic acids encoding for a receptor having the same amino acid sequence can be produced.

An embodiment of the present invention uses human nucleic acid encoding for the domains from CaR, $GABA_BR1A$, $GABA_BR1B$, $GABA_BR2$ and/or mGluR8. The amino acid sequences of different domains is provided in FIGS. 1-3.

Recombinant Cells

Nucleic acid expressing a functional G-Protein fusion or a chimeric receptor can be used to create transfected cell lines expressing such receptors. Such cell lines have a variety of uses such as being used for high-throughput screening for compounds modulating receptor activity, being used to assay binding to the receptor, and as factories to produce large amounts of a receptor.

A variety of cell lines can couple exogenously expressed receptors to endogenous functional responses. Cell lines such as NIH-3T3, HeLa, NG115, CHO, HEK 293 and COS7, which are expected to lack CaR, mGluR8, and $GABA_BR$, can be tested to confirm that they lack these receptors.

Production of stable transfectants can be accomplished by transfection of an appropriate cell line with, for example, an expression vector such as pMSG vector, in which the coding sequence for the G-protein fusion or chimeric $GABA_BR$ cDNA has been cloned. Expression vectors containing a promoter region, such as the mouse mammary tumor virus promoter (MMTV), drive high-level transcription of cDNAs in a variety of mammalian cells. In addition, these vectors contain genes for selecting cells stably expressing cDNA of interest. The selectable marker in the pMSG vectors encode an enzyme, xanthine-guanine phosphoribosyl transferase (XGPRT), conferring resistance to a metabolic inhibitor that is added to the culture to kill nontransfected cells.

The most effective method for transfection of eukaryotic cell lines with plasmid DNA varies with the given cell type. The expression construct will be introduced into cultured cells by the appropriate technique, such as $Ca^{2+}$ phosphate precipitation, DEAE-dextran transfection, lipofection or electroporation. Expression of the receptor cDNA in cell lines can be assessed by solution hybridization and Northern blot analysis.

Binding Assays

The present invention also includes using G-protein fusion receptors or chimeric $GABA_BR$ in a binding assay. G-protein fusion receptors or chimeric $GABA_BRs$ having a particular $GABA_BR$ domain can be used, for example, to facilitate obtaining compounds able to bind to that particular receptor domain and to determine whether a compound binds to a particular domain. For example, in a complete chimeric $GABA_BR$ containing extracellular, transmembrane, and intracellular domains, the presence of one or more domains from CaR or mGluR are useful to present $GABA_BR$ domain(s) to a binding agent in a form more like the $GABA_BR$ domain(s) in the wild-type receptor, compared to an incomplete $GABA_BR$ receptor fragment lacking one or more domains.

Binding assays can be carried out using techniques well known in the art. Binding assays preferably employ radiolabeled binding agents.

An example of a binding procedure is carried out by first attaching chimeric $GABA_BR$ to a solid-phase support to create an affinity matrix. The affinity matrix is then contacted with potential $GABA_BR$ binding agents. A large library of compounds may be used to determine those compounds binding to the affinity matrix. Bound compounds can be eluted from the column.

Therapeutic Modulation

As pointed out above, different types of diseases and disorders can be treated using compounds modulating CaR, mGluR, or $GABA_BR$ activity. Additionally, such compounds can be used prophylactically. Compounds modulating $GABA_BR2$ activity can be administered to patients who would benefit from such treatment. Patients are mammals, preferably humans.

Modulators of CaR, mGluR, or $GABA_BR$ activity can be administered to a patient using standard techniques. Techniques and formulations generally may be found in *Remington's Pharmaceutical Sciences* $18^{th}$ ed., Mack Publishing Co., Easton, Pa., 1990 (hereby incorporated by reference herein).

Suitable dosage forms, in part, depend upon the use or the route of entry, for example, oral, transdermal, transmucosal, or by injection (parenteral). Such dosage forms should allow the therapeutic agent to reach a target cell whether the target cell is present in a multicellular host or in culture. For example, pharmacological compounds or compositions injected into the blood stream should be soluble. Other factors are well known in the art, and include considerations such as toxicity and dosage forms that retard the therapeutic agent from exerting its effect.

Therapeutic compounds can be formulated as pharmaceutically acceptable salts and complexes thereof. Pharmaceutically acceptable salts are non-toxic salts in the amounts and concentrations at which they are administered. The preparation of such salts can facilitate the pharmacological use by altering the physical characteristics of the compound without preventing it from exerting its physiological effect. Useful alterations in physical properties include lowering the melting point to facilitate transmucosal administration and increasing the solubility to facilitate administering higher concentrations of the drug.

The pharmaceutically acceptable salt of a compound may be present as a complex. Examples of complexes include an 8-chlorotheophylline complex (analogous to, e.g., dimenhydrinate:diphenhydramine 8-chlorotheophylline (1:1) complex; Dramamine) and various cyclodextrin inclusion complexes.

Pharmaceutically acceptable salts include acid addition salts, such as those containing sulfate, hydrochloride, fumarate, maleate, phosphate, sulfamate, acetate, citrate, lactate, tartrate, methanesulfonate, ethanesulfonate, benzenesulfonate, p-toluene-sulfonate, cyclohexylsulfamate and quinate.

Pharmaceutically acceptable salts can be obtained from acids, such as hydrochloric acid, maleic acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, fumaric acid, and quinic acid.

Pharmaceutically acceptable salts also include basic addition salts, such as those containing benzathine, chloroprocaine, choline, diethanolamine, ethylenediamine, meglumine, procaine, aluminum, calcium, lithium, magnesium, potassium, sodium, ammonium, alkylamine, and zinc, when acidic functional groups, such as carboxylic acid or phenol are present. For example, see *Remington's Pharmaceutical*

Sciences 18th ed., Mack Publishing Co., Easton, Pa., p. 1445, 1990. Such salts can be prepared using the appropriate corresponding bases.

Carriers or excipients can also be used to facilitate administration of therapeutic agents. Examples of carriers include calcium carbonate, calcium phosphate, various sugars such as lactose, glucose, or sucrose, or types of starch, cellulose derivatives, gelatin, vegetable oils, polyethylene glycols and physiologically compatible solvents. Examples of physiologically compatible solvents include sterile solutions of water for injection (WFI), saline solution and dextrose.

$GABA_B$R-modulating compounds can be administered by different routes including intravenous, intraperitoneal, subcutaneous, intramuscular, oral, topical (transdermal), or transmucosal administration. For systemic administration, oral administration is preferred. For oral administration, for example, the compounds can be formulated into conventional oral dosage forms such as capsules, tablets, and liquid preparations such as syrups, elixirs, and concentrated drops.

Alternatively, injection (parenteral administration) may be used, e.g., intramuscular, intravenous, intraperitoneal, and subcutaneous. For injection, compounds are formulated in liquid solutions, preferably, in physiologically compatible buffers or solutions, such as saline solution, Hank's solution, or Ringer's solution. In addition, the compounds may be formulated in solid form and redissolved or suspended immediately prior to use. Lyophilized forms can also be produced.

Systemic administration can be by transmucosal or transdermal means. For transmucosal or transdermal administration, penetrants appropriate to the barrier to be permeated are used in the formulation. Such penetrants are well known in the art, and include, for example, for transmucosal administration, bile salts and fusidic acid derivatives. In addition, detergents may be used to facilitate permeation. Transmucosal administration, for example, may be through nasal sprays, rectal suppositories, or vaginal suppositories.

For topical administration, compounds can be formulated into ointments, salves, gels, or creams, as is well known in the art.

The amounts of various $GABA_B$R-modulating compounds to be administered can be determined by standard procedures taking into account factors such as the compound $IC_{50}$, $EC_{50}$, the biological half-life of the compound, the age, size and weight of the patient, and the disease or disorder associated with the patient. The importance of these and other factors to be considered are well known to those of ordinary skill in the art. Generally, the amount is expected to preferably be between about 0.01 and 50 mg/kg of the animal to be treated.

EXAMPLES

Examples are provided below illustrating different aspects and embodiments of the present invention. The examples include techniques that can be used to produce and use G-protein fusion receptors and chimeric receptors. These examples are not intended to limit the claimed invention.

Example 1

Construction of G-Protein Fusions

This example illustrates different G-protein fusion receptor constructs and techniques used to produce different G-protein fusion receptor constructs. Numbering of nucleotide position for all the following constructs is such that nucleotide number 1 corresponds to the A of the ATG start codon of the nucleotide sequence encoding the designated protein.

I. Full-Length Constructs

A. phCaR

The cDNA encoding the human CaR (Garrett et al., (1995) *J. Biol. Chem.* 270:12919) is harbored in the Bluescript SK(-) plasmid (Stratagene). This construct is referred to as phCaR.

B. phmGluR2

A full-length human mGluR2 cDNA was amplified from human cerebellum MarathonReady cDNA (Clontech) using PCR primers based on the human mGluR2 cDNA sequence (Genbank Accession #4504136). The obtained PCR fragment was subcloned into the pT7Blue TA vector (Novagen). A Hind III-Not I fragment containing the human mGluR2 cDNA was then subcloned into the Bluescript SKII(-) plasmid (Stratagene). This construct is referred to as phmGluR2.

C. $phG\alpha_q$

A full-length human $G\alpha_q$ cDNA was amplified from human cerebral cortex Quick-Clone cDNA (Clontech) using PCR primers based on the human $G\alpha_q$ cDNA sequence (Genbank Accession #4504044). The obtained PCR fragment was subcloned into the Bluescript SKII(-) plasmid (Stratagene). This construct is referred to as $phG\alpha_q$.

D. phmGluR8

The cDNA encoding the full-length human mGluR8 cDNA (Stormann et al., U.S. Pat. Nos. 6,051,688, 6,077,675, and 6,084,084, and International Publication No. WO97/48724) is harbored in the Bluescript SKII(-) plasmid (Stratagene). This construct is referred to as phmGluR8.

E. ph8SpmGluR4

A full-length human mGluR4 cDNA was amplified from human cerebellum MarathonReady cDNA (Clontech) using PCR primers based on the human mGluR4 cDNA sequence (Genbank Accession #X80818). The obtained PCR fragment was cloned into the pT7Blue TA vector (Novagen). A 2977 bp BamHI fragment containing the human mGluR4 cDNA was then subcloned into the vector pcDNA3.1/Hygro+ (Invitrogen). This construct is referred to as phmGluR4.

Next, the predicted signal peptide of mGluR4 was replaced with the predicted signal peptide and 87 bp of 5' UTR from phmGluR8 using a recombinant PCR strategy similar to those described above. The first reaction used a phmGluR8 construct with two primers, 3.1-535F (sense 21-mer, complementary to vector sequence upstream of the hmGluR8 insert; sequence 5'-ggcattatgcccagtacatga-3') (SEQ ID NO:51), and the hybrid primer 8/4RP (antisense 42-mer, containing 21 nucleotides complementary to human mGluR8 and 21 nucleotides complementary human mGLuR4; sequence 5'-caagcctctcttcccaggcattttctc-cacaggtggtattgc-3') (SEQ ID NO:52). These primers were used to amplify a 469 bp PCR fragment of human mGluR8.

In a separate PCR reaction using phmGluR4 as template, a 472 bp fragment of human mGluR4 was amplified using a hybrid primer 4/8RP (sense 42-mer, exactly complementary to primer 8/4RP) and oligo mG4-472R (antisense 18-mer, complementary to the human mGluR4 cDNA; sequence 5'-ctgaagcaccgatgacae-3') (SEQ ID NO:53). The two PCR products generated from the above two reactions were annealed together in equimolar ratios in the presence of the external primers mG4-472R and 3.1-535F, and Turbo Pfu DNA polymerase (Strategene).

The resulting chimeric PCR product was digested with NarI and NheI (New England Biolabs) and subcloned into phmGluR4 digested with the same two restriction enzymes. The sequence of the resultant chimeric construct, ph8SPmGluR4, was verified by ABI automated DNA sequence analysis.

The replacement of the predicted signal peptide of mGluR4 with that of mGluR8 greatly increased the activity of this receptor in in vitro assays.

II. $G\alpha_q i5$

The cDNA encoding the human $G\alpha_q i5$ cDNA (Conklin et al. (1993) *Nature* 363:274-77) is harbored in the Bluescript SKII(−) plasmid (Stratagene). This construct is referred to as $G\alpha_q i5$. The nucleic acid and amino acid sequences for $G\alpha_q i5$ are provided by SEQ. ID. NOs. 28 and 29, respectively.

III. phCaR/hmGluR2

This chimera contains the extracellular domain of the human CaR and transmembrane domain and intracellular cytoplasmic tail of human mGluR2. The chimeric junction between the CaR and hmGluR2 was created using a recombinant PCR strategy similar to those described above.

The first reaction used two primers, CA1156 (sense 19-mer, corresponding to nucleotides 1156-1174 of human CaR), and the hybrid primer CA/2 (antisense 42-mer, containing 21 nucleotides complementary to nucleotides 1774-1794 of human CaR and 21 nucleotides complementary to nucleotides 1660-1680 of the human mGluR2). These primers were used to amplify a 659 bp PCR fragment of human CaR.

In a separate PCR reaction using phmGluR2 as template, a 692 bp fragment of the human mGluR2 was amplified using a hybrid primer 2/CA (sense 42-mer, exactly complementary to primer CA/2) and oligo 2-2330m, (antisense 23-mer, complementary to nucleotides 2309-2331 of the human mGluR2 cDNA). The two PCR products generated from the above two reactions were annealed together in equimolar ratios in the presence of the external primers CA1156 and 2-2330m, and the Pfu DNA polymerase (Stratagene).

The resulting chimeric PCR product was digested with SexA1 (Boehringer Mannheim) and BamHI (New England Biolabs) and subcloned into phCaR digested with the same two restriction enzymes. In the final cloning step, the 3' end of human mGluR2 was subcloned into this construct using the restriction enzymes BsrGI and BamHI (both New England Biolabs). The sequence of the resultant chimeric construct, phCaR/hmGluR2, was verified by ABI automated DNA sequence analysis.

IV. phCaR/hmGluR2*Gqi5

This construct contains the phCaR/hmGluR2 chimeric receptor fused to human $G\alpha_q i5$. A HindIII-BamHI fragment containing the phCaR/hmGluR2 construct was subcloned into pcDNA3.1/Hygro(+) (Invitrogen) to aid in constructing this fusion protein. The chimeric junction between the C-terminus of phCaR/hmGluR2 and the N-terminus of $G\alpha_q i5$ was created using a recombinant PCR strategy similar to those described above.

The first reaction used two primers, 2-1713 (sense 21-mer, corresponding to nucleotides 1710-1730 of human mGluR2) and the hybrid primer 2/Q (antisense 42-mer, containing 21 nucleotides complementary to nucleotides 2596-2616 of human mGluR2, and 21 nucleotides complementary to nucleotides 1-21 of $pG\alpha_q i5$). These primers were used to amplify a 927 bp PCR fragment of phCaR/hmGluR2. In a separate PCR reaction, all of $G\alpha_q i5$ was amplified using a hybrid primer Q/2 (sense 42-mer, exactly complementary to primer 2/Q) and the T3 primer commercially available from Stratagene.

These two PCR products generated from the above two reactions were annealed together in equimolar ratios in the presence of the external primers 2-1713 and T3, and the Pfu DNA polymerase (Stratagene). The resulting chimeric PCR product was digested with Bsu361 and BamHI (New England Biolabs) and subcloned into phCaR/hmGluR2 digested with the same two restriction enzymes. The sequence of the resultant chimeric fusion construct, phCaR/hmGluR2*$G\alpha_q i5$, was verified by DNA sequence analysis.

V. phmGluR2//CaR Construct

This chimera contains the extracellular and transmembrane domains of human mGluR2 linked to the intracellular cytoplasmic tail domain of the human CaR. The chimeric junction was created using three separate PCR reactions.

The first reaction used two primers, 2-1713 (sense 21-mer, corresponding to nucleotides 1710-1730 of human mGluR2, Genbank Accession #4504136) and the hybrid primer 2/CT (antisense 42-mer, containing 21 nucleotides complementary to nucleotides 2452-2472 of human mGluR2 and 21 nucleotides complementary to nucleotides 2602-2622 of the human CaR). These primers were used to amplify a 783 bp PCR fragment of human mGluR2. In a separate PCR reaction using phCaR in the BlueScript SK⁻ plasmid as a template, a 750 bp fragment of the human CaR was amplified using a hybrid primer CT/2 (sense 42-mer, exactly complementary to primer 2/CT) and the T3 primer commercially available from Stratagene.

The two PCR products generated from the above two reactions were annealed together in equimolar ratios in the presence of the external primers 2-1713 and T3, and the Pfu DNA polymerase (Stratagene). The resulting chimeric PCR product was digested with BsrGI and NotI (New England Biolabs) and subcloned into pmGluR2 digested with the same two restriction enzymes. The sequence of the resultant chimeric construct, pmGluR2//CaR, was verified by ABI automated DNA sequence analysis.

VI. pmGluR2/CaR*$G\alpha_q i5$ Construct

This construct contains the hmGluR2//CaR chimeric receptor fused to human $G\alpha_q i5$. The chimeric junction between the C-terminus of hmGluR2//CaR and the N-terminus of $G\alpha qi5$ was created using a recombinant PCR strategy similar to that described above for the construction of phmGluR2//CaR.

The first reaction used two primers, CRP10A (sense 18-mer, corresponding to nucleotides 2812-2829 of phCaR) and the hybrid primer CaRQ (antisense 42-mer, containing 21 nucleotides complementary to nucleotides 3214-3234 phCaR, and 21 nucleotides complementary to nucleotides 1-21 of $pG\alpha_q i5$). These primers were used to amplify a 443 bp PCR fragment of hmGluR2//CaR. In a separate PCR reaction, all of $G\alpha_q i5$ was amplified using a hybrid primer QCaR (sense 42-mer, exactly complementary to primer CaRQ) and the T3 primer commercially available from Stratagene.

The two PCR products generated from the above two reactions were annealed together in equimolar ratios in the presence of the external primers CRP10A and T3, and the Pfu DNA polymerase (Stratagene). The resulting chimeric PCR product was digested with BstEII and NotI (New England Biolabs) and subcloned into pmGluR2//CaR digested with the same two restriction enzymes. The sequence of the resultant chimeric fusion construct, pmGluR2//CaR*Gα$_q$i5, was verified by ABI automated DNA sequence analysis.

VII. Fusion Receptor Protein Linker Addition Constructs

A. phmGluR2//CaR*AAA*Gα$_q$i5

A linker encoding three alanine residues was incorporated into the phmGluR2//CaR*Gα$_q$i5 construct by mutagenesis (Stratagene QuickChange Mutagenesis Kit). A sense 40-mer, 2CQ+LP, contained 16 nucleotides corresponding to 3219-3234 of human CaR, followed by the nine nucleotide sequence (GCGGCCGC) encoding three alanine residues and a NotI restriction enzyme site, and then 15 nucleotides corresponding to nucleotides 1-15 of Gα$_q$i5. 2CQ+LP was annealed to an antisense 40-mer, 2CQ+LM, the exact complement of 2CQ+LP. These oligos were used in the mutagenesis reaction according to the manufacturer's protocol. Restriction enzyme analysis and DNA sequence analysis confirmed the insertion of the nine nucleotide linker (GCGGCCGC) between the C-terminus of phmGluR2//CaR and the N-terminus of Gα$_q$i5. This construct was designated phmGluR2//CaR*AAA*Gα$_q$i5.

B. Human GABA$_B$R2*AAA*Gα$_q$o5 and Human GABA$_B$R1a*AAA*Gα$_q$o5

These constructs contain the human GABA$_B$R2 (hGABA$_B$R2: Genbank Accession #AJ 012188) and human GABA$_B$R1a (hGABA$_B$R1a: Genbank Accession #AJ 012185) fused at their C-terminus to the N-terminus of human Gα$_q$o5 (hGα$_q$o5: Nature 363:274-276, 1993). Human GABA$_B$R2, hGABA$_B$R1a, and hGα$_q$o5 were cloned into the plasmid pcDNA3.1/Hygro+ (Invitrogen) and are designated phGABA$_B$R2, phGABA$_B$R1a, and phGα$_q$o5. The first reaction used two primers, XcmI-R2 (sense 20-mer, corresponding to nucleotides 2650-2669 of phGABA$_B$R2) and the hybrid primer R2/Go5(–) (antisense 45-mer, containing 18 nucleotides complementary to nucleotides 2806-2823 of phGABA$_B$R2 and 18 nucleotides complementary to nucleotides 1-18 of hGα$_q$o5). These two complementary areas flank a nine nucleotide sequence coding for three alanine sequences with a unique NotI restriction site. These primers were used to amplify a 200 base-pair PCR fragment.

In a separate PCR reaction, part of hGα$_q$o5 was amplified using a hybrid primer R2/Gα$_q$o5(+) (sense 45-mer), exactly complementary to R$^2$/Go5(–) and XbaI-Go5 primer (22-mer containing 22 nucleotides complementary to nucleotides 873-895 of hGα$_q$o5). These primers were used to amplify a 914 base-pair PCR product. The two PCR products generated from the above two reactions were annealed together in equimolar ratios in the presence of the external primers, XcmI-R2 and XbaI-Go5, and Pfu polymerase (Stratagene).

The resulting chimeric PCR product was digested with the restriction endonucleases XcmI and XbaI (New England Biolabs) and subcloned into phGABA$_B$R2 digested with the same two restriction enzymes. The resulting clone was then digested with HindIII and XbaI and subcloned into phGα$_q$o5 cut with HindIII and XbaI resulting in the chimeric hGABA$_B$R*AAA*Gα$_q$o5. The chimeric junction between the C-terminus hGABA$_B$R1a, the Ala linker, and the N-terminus of hGα$_q$o5 was created using a recombinant PCR strategy similar to those described above.

To construct hGABA$_B$R1a*AAA*Gqo5, the first reaction used a commercially available T7 primer (Novagen) and the NtI hGBR1 primer (CAGAGTCATGGCGGCCGCCT-TATAAAGCAAATGCACTCG) (SEQ ID NO:54) corresponding to nucleotide numbers 1-9 of hGα$_q$o5 and nucleotide numbers 2863-2883 of hGABA$_B$R1a.

C. phmGluR8//CaR*AAA*Gα$_q$i5

A linker encoding three alanine residues was incorporated into the phmGluR8//CaR*Gα$_q$i5 construct by mutagenesis (Stratagene QuickChange Mutagenesis Kit), exactly as described in Section A above, to create phmGluR2//CaR*AAA*Gα$_q$i5. The same primers, 2CQ+LP and 2CQ+LM, were used for this mutagenesis. Restriction enzyme analysis and DNA sequence analysis confirmed the insertion of the nine-nucleotide linker (GCGGCCGC) between the C-terminus of phmGluR8//CaR and the N-terminus of Gα$_q$i5. This construct was designated phmGluR8//CaR*AAA*Gα$_q$i5.

D. ph8SPmGluR4//CaR*AAA*Gα$_q$i5

This chimera contains the extracellular and transmembrane domains of the human 8SPmGluR4 construct and intracellular cytoplasmic tail of human CaR fused to Gα$_q$i5 through the three-alanine residue linker.

The chimeric junction between the human 8SPmGluR4 and hCaR was created using a recombinant PCR strategy similar to those previously described. The first reaction used two primers, mG4-2028R (sense 19-mer, corresponding to nucleotides of human 8SPmGluR4; sequence 5'-catctaccg-catcttcgag-3') (SEQ ID NO:55), and the hybrid primer 4CT (antisense 42-mer, containing 21 nucleotides complementary to human 8SPmGluR4 and 21 nucleotides complementary to human CaR; sequence 5'-acgcacctcctcgatggtgttct-gctccgggtggaagaggat-3') (SEQ ID NO:56). These primers were used to amplify a 549 bp PCR fragment from human 8SPmGluR4.

In a separate PCR reaction, using phmGluR2//CaR*AAA*Gαqi5 as a template, a 743 bp fragment of the human CaR*AAA*Gα$_q$i5 was amplified using the hybrid primer CT4 (sense 42-mer, exactly complementary to primer 4CT) and oligo Gαqi58R (antisense 21-mer, complementary to Gα$_q$i5 cDNA; sequence 5'-ctcgatctcgtcgttgatccg-3') (SEQ ID NO:57). The two PCR products generated from the above two reactions were annealed together in equimolar ratios in the presence of the external primers mG4-2028R and Gαqi58R, and Pfu DNA polymerase (Stratagene).

The resulting chimeric PCR product was digested sequentially with KpnI and NotI (New England Biolabs) and subcloned into ph8SPmGluR4 prepared with the same two restriction enzymes. This intermediate construct was known as ph8SPmGluR4//CaR(no stop). In the final cloning step, a fragment containing the Gα$_q$i5 cDNA was released from phmGluR8H/CaR*AAA*Gα$_q$i5 using the restriction enzymes ApaI and NotI (both New England Biolabs) and subcloned into the ph8SPmGluR4//CaR(no stop) construct, which was prepared with the same restriction enzymes. The sequences of the resultant chimeric construct, ph8SPmGluR4H/CaR*AAA*Gα$_q$i5, was verified by ABI automated DNA sequence analysis.

VIII. phmGluR8//CaR Construct

This chimera contains the extracellular and transmembrane domains of human mGluR8 linked to the intracellular cytoplasmic tail domain of the human CaR. The chimeric junction between hmGluR8 and the CaR was created using a recombinant PCR strategy similar to those described above.

The first reaction used two primers, CH5A (sense 19-mer, corresponding to nucleotides 2187-2205 of human mGluR8, Stormann et al., U.S. Pat. Nos. 6,051,688, 6,077,675, and 6,084,084, and International Publication No. WO97/48724) and the hybrid primer CH5B (antisense 40-mer, containing 22 nucleotides complementary to nucleotides 2523-2544 of human mGluR8, and 18 nucleotides complementary to nucleotides 2602-2619 of the human CaR). These primers were used to amplify a 375 bp PCR fragment of human mGluR8. In a separate PCR reaction using phCaR in the BlueScript SK(-) plasmid as a template, a 750 bp fragment of the human CaR was amplified using a hybrid primer CH5C (sense 40-mer, exactly complementary to primer CH5B) and the T3 primer commercially available from Stratagene.

The two PCR products generated from the above two reactions were annealed together in equimolar ratios in the presence of the external primers CH5A and T3, and the Pfu DNA polymerase (Stratagene). The resulting chimeric PCR product was digested with BsrGI and XbaI (New England Biolabs) and subcloned into pmGluR8 digested with the same two restriction enzymes. The sequence of the resultant chimeric construct, pmGluR8//CaR, was verified by DNA sequence analysis.

IX. mGluR8//CaR*G$\alpha_q$i5 Construct

This construct contains the hmGluR8//CaR chimeric receptor fused to human G$\alpha_q$i5. The chimeric junction between the C-terminus of hmGluR8//CaR and the N-terminus of G$\alpha_q$i5 was created using a recombinant PCR strategy similar to that described above for the construction of phmGluR2//CaR*G$\alpha_q$i5.

The first reaction used two primers, CRP10A (sense 18-mer, corresponding to nucleotides 2812-2829 of phCaR) and the hybrid primer Gqi5/CaR (antisense 40-mer, containing 21 nucleotides complementary to nucleotides 3214-3234 phCaR, and 19 nucleotides complementary to nucleotides 1-19 of pG$\alpha_q$i5). These primers were used to amplify a 441 bp PCR fragment of hmGluR8//CaR.

In a separate PCR reaction, all of G$\alpha_q$i5 was amplified using a hybrid primer CaR/Gqi5 (sense 40-mer, exactly complementary to primer Gqi5/CaR) and the ApaI-mut primer (20-mer). The two PCR products generated from the above two reactions were annealed together in equimolar ratios in the presence of the external primers CRP10A and ApaI-mut, and the Pfu DNA polymerase (Stratagene). The resulting chimeric PCR product was digested with BstEII and ApaI (New England Biolabs) and subcloned into pmGluR8//CaR digested with the same two restriction enzymes. The sequence of the resultant chimeric fusion construct, pmGluR8//CaR*G$\alpha_q$i5, was verified by DNA sequence analysis.

Example 2

Functional Expression of CaR/GABA$_B$R2

In vitro-transcribed RNA (7 ng) encoding a chimeric CaR/GABA$_B$R2 (CaR extracellular and transmembrane domains, and intracellular GABA$_B$R2 domain) was co-injected with in vitro-transcribed RNA (2 ng) encoding G$_\alpha$15 into Xenopus oocytes. Following a 72-hour incubation, the oocytes were voltage-clamped using standard electrophysiological techniques (B. Hille, *Ionic Channels of Exictable Membranes*, pp. 30-33, Sinauer Associates, Inc., Sunderland, Ma., 1992). Activation of the chimeric receptor was detected by increases in the calcium-activated chloride current.

Application of the CaR activator 100 µM Gd$^{3+}$, resulted in reversible, oscillatory increases in the calcium-activated chloride current as shown in FIG. 8. These data demonstrate the functional response of the chimeric CaR/GABA$_B$R2 receptor upon activation via a site within the CaR extracellular domain. In this assay, the G$_\alpha$15 subunit acts to promote signal transduction through intracellular pathways that mobilize intracellular Ca$^{++}$.

Example 3

Expression of Different G-Protein Fusion Receptors

Figure 15:
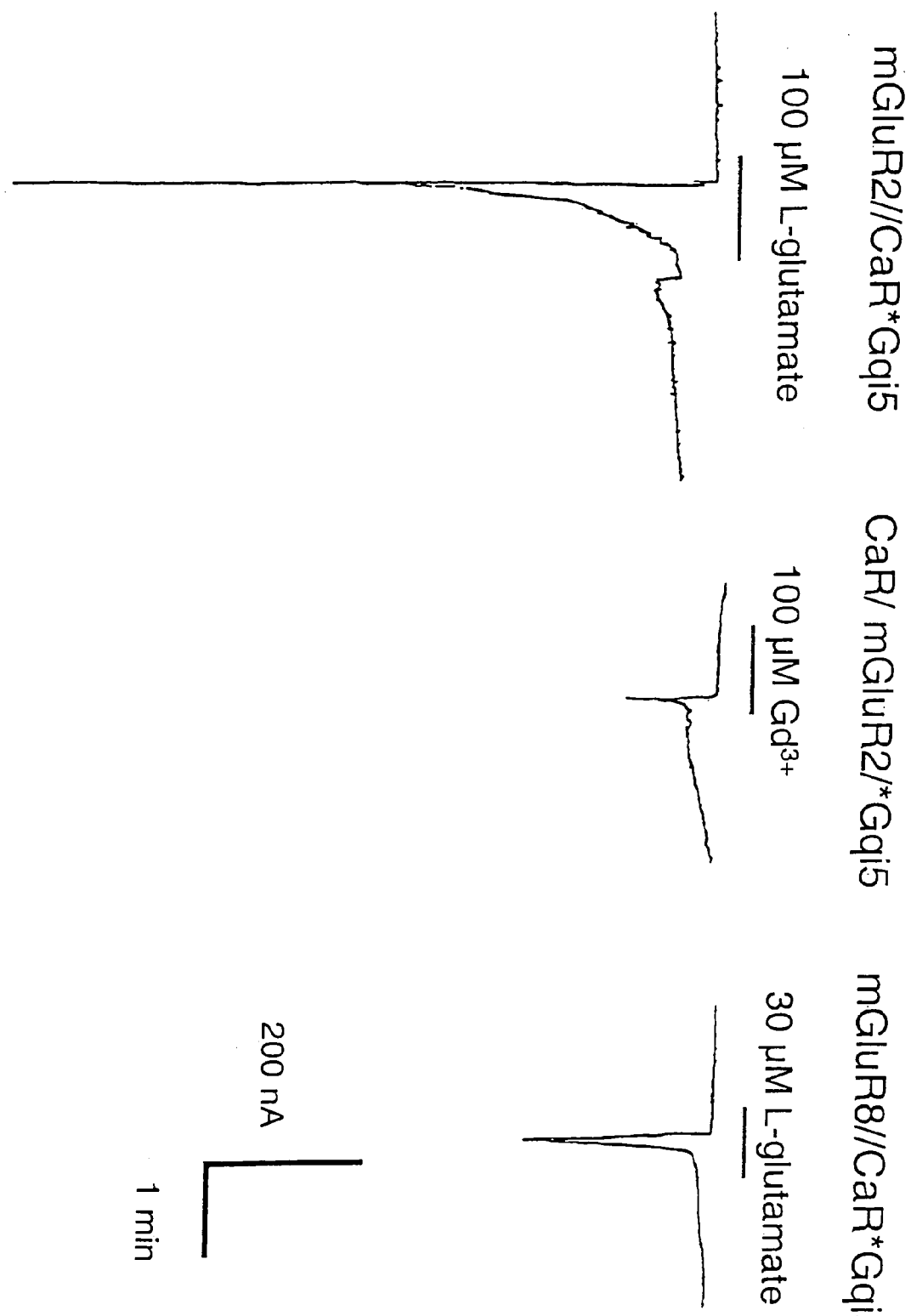
FIG. 15 illustrates the ability of different G-protein fusions to transduce signals resulting from ligand binding. mGluR2//CaR*Gqi5 is shown by SEQ. ID. NO. 37, CaR/mGluR2*Gqi5 is shown by SEQ. ID. NO. 33, mGluR8//CaR*Gqi5 is shown by SEQ. ID. NO. 41.

The ability of different G-protein fusions to transduce signals resulting from ligand binding is shown in FIG. 15. The different G-protein fusion receptors used in this example were as follows: mGluR2//CaR*Gqi5 (SEQ. ID. NO. 37), CaR/mGluR2*Gqi5 (SEQ. ID. NO. 33), and mGluR8//CaR*Gqi5 SEQ. ID. NO. 41.

Oocytes suitable for injection were obtained from adult female *Xenopus laevis* toads using procedures described in C. J. Marcus-Sekura and M. J. M. Hitchcock, *Methods in Enzymology*, Vol. 152 (1987).

Receptor fusion cRNAs were dissolved in water and 50 nl (12.5 ng/oocyte) were injected into individual oocytes. Following injection, oocytes were incubated at 16° C. in MBS containing 1 mM CaCl$_2$ for two to seven days prior to electrophysiological recording.

Test substances were applied by superfusion at a flow rate of about 5 ml/minute. Receptor fusion activation was determined by measuring the increase in calcium-activated chloride current (I$_{Cl}$). Increases in I$_{Cl}$ were quantified by measuring the peak inward current stimulated by activating agent, relative to the holding current at −60 mV. Application of 100 µM L-glutamate elicited a response from the mGluR2//CaR*G$\alpha$qi5 and mGluR8//CaR*G$\alpha$qi5. Application of 100 µM Gd$^{3+}$ activated the CaR/mGluR2*Gqi5.

Example 4

Expression of Different G-Protein Fusion Receptors in Mammalian Cells

HEK293 cells were transiently transfected with the p8SPhmGluR4//CaR*AAA*G$\alpha$qi5 or phmGluR8//CaR*G$\alpha$qi5 plasmid DNAs using the following protocol. Initially, 150 cm$^2$ tissue culture flasks containing HEK293 cells at 75% confluence were transfected with 24 µg of plasmid DNA using Gibco BRL Life Technologies' Lipofectamine reagent. Following liposomal gene delivery, the cells were allowed to recover for 24 hours. They were then plated overnight at 100,000 cells per well in black, clear bottom, Collagen I-coated 96-well plates (Becton Dickinson, Biocoat) using DMEM supplemented with 10% fetal bovine serum (Hyclone Laboratories). The cells were assayed for function 48 hours after transient transfection.

On the day of the assay, tissue culture medium was aspirated from the wells of a 96-well plate and 80 µL of Assay Buffer (Assay Buffer is: 20 mM HEPES, 146 mM NaCl, 5 mM KCl, 1 mM MgCl$_2$, 1 mM CaCl$_2$, 1 mg/ml BSA, 1 mg/ml glucose, pH 7.4) supplemented with 6 µM of the $Ca^{2+}$-sensitive dye, Fluo-3 AM (Molecular Probes) and 0.025% Pluronic (Molecular Probes) was added to each well.

The plate was then incubated in the dark for one hour at room temperature to efficiently load the cells with Fluo-3. At the end of the incubation, extracellular Fluo-3 was removed by washing the plate with Assay Buffer. Assay Buffer was added back to each well (final volume=160 µL) prior to beginning the assay. The plate was loaded into a fluorescence imaging plate reader (FLIPR) robotic device (Molecular Devices) with the laser setting at 0.8 Watts. At a time of 15 seconds after initiation of the assay, 40 µL of Assay Buffer containing 150 µM L-AP4 was added to the 160 µL of Assay Buffer in each well of the plate to yield a final concentration of 30 µM L-AP4.

Relative fluorescence intensity (excitation $\lambda$=488 nm/emission $\lambda$=510 nm) was monitored at relevant time intervals throughout the assay period to measure L-AP4-induced receptor activation.

Other embodiments are within the following claims. Thus, while several embodiments have been shown and described, various modifications may be made, without departing from the spirit and scope of the present invention.

The invention claimed is:

1. A G-protein fusion receptor comprising:
   a) an extracellular domain comprising an extracellular domain amino acid sequence selected from the group consisting of SEQ ID NO: 1, SEQ ID NO: 2, SEQ ID NO: 3, SEQ ID NO: 4, and SEQ ID NO: 5, wherein said extracellular domain is capable of binding a native CaR, mGluR, or GABA$_B$R ligand;
   b) a transmembrane domain joined to the carboxy terminus of said extracellular domain, said transmembrane domain comprising a transmembrane domain amino acid sequence selected from the group consisting of SEQ ID NO: 6, SEQ ID NO: 7, SEQ ID NO: 8, SEQ ID NO: 9, and SEQ ID NO: 10;
   c) an intracellular domain joined to the carboxy terminus of said transmembrane domain, said intracellular domain comprising all or a portion of an intracellular amino acid sequence selected from the group consisting of SEQ ID NO: 11, SEQ ID NO: 12, SEQ ID NO: 13, SEQ ID NO: 14, and SEQ ID NO: 15, provided that said portion is at least 10 amino acids in length;
   d) an optionally present linker joined to the carboxy terminus of said intracellular domain; and
   e) a G-protein joined either to said intracellular domain or to said optionally present linker, provided that said G-protein is joined to said optionally present linker when said optionally present linker is present, wherein said G-protein interconverts between a GDP-bound and a GTP-bound form,
   wherein said domains are functionally coupled such that a signal from the binding of a ligand is transduced to the intracellular domain when said G-protein fusion receptor is present in a suitable host cell, and wherein said intracellular domain when present in a wild type receptor does not interact with said G-protein.

2. The G-protein fusion receptor of claim 1, wherein said optionally present linker is present and is a polypeptide 3 amino acids to 30 amino acids in length.

3. The G-protein fusion receptor of claim 1, wherein said optionally present linker is not present.

4. The G-protein fusion receptor of claim 2, wherein said G-protein is selected from the group consisting of: G$\alpha_{15}$, G$\alpha_{16}$, Gqo5, and Gqi5.

5. The G-protein fusion receptor of claim 3, wherein said G-protein is selected from the group consisting of G$\alpha_{15}$, G$\alpha_{16}$, Gqo5, and Gqi5.

6. A nucleic acid comprising a nucleotide sequence encoding for the G-protein fusion receptor of any one of claims 1, 2-4, or 5.

7. An expression vector comprising a nucleotide sequence encoding for the G-protein fusion receptor of any one of claims 1, 2-4, or 5 transcriptionally coupled to a promoter.

8. An isolated recombinant cell comprising the expression vector of claim 7 and a cell wherein the G-protein fusion receptor is expressed and is functional.

9. An isolated recombinant cell produced by combining an expression vector of claim 7, wherein said expression vector comprises the nucleic acid of claim 6 and elements for introducing heterologous nucleic acid into a cell wherein the G-protein fusion receptor is expressed.

10. A process for the production of a G-protein fusion receptor comprising:
   growing procaryotic or eukaryotic host cells comprising a nucleic acid sequence expressing the G-protein fusion receptor of any one of claims 1, 2-4, or 5, under suitable nutrient conditions allowing for cell growth.

11. The G-protein fusion receptor of claim 1, wherein said extracellular domain and said transmembrane domain are from a Type 2 mGluR.

12. The G-protein fusion receptor of claim 1, wherein said extracellular domain and said transmembrane domain are from a Type 3 mGluR.

13. The G-protein fusion receptor of claim 1, wherein said extracellular domain and said transmembrane domain are from a Type 4 mGluR.

14. The G-protein fusion receptor of claim 1, wherein said extracellular domain and said transmembrane domain are from a Type 6 mGluR.

15. The G-protein fusion receptor of claim 1, wherein said extracellular domain and said transmembrane domain are from a Type 7 mGluR.

16. The G-protein fusion receptor of claim 1, wherein said extracellular domain and said transmembrane domain are from a Type 8 mGluR.

17. The G-protein fusion receptor of claim 1, wherein said extracellular domain and said transmembrane domain are from a $GABA_BR$.

18. The G-protein fusion receptor of claim 1, wherein said G-protein is a chimeric G-protein.

19. The G-protein fusion receptor of claim 1, wherein said extracellular domain comprises SEQ ID NO: 1, said transmembrane domain comprises SEQ ID NO: 6, and said intracellular domain comprises SEQ ID NO: 11.

20. The G-protein fusion receptor of claim 1, wherein said extracellular domain comprises SEQ ID NO: 5, said transmembrane domain comprises SEQ ID NO: 10, and said intracellular domain comprises SEQ ID NO: 15.

21. The G-protein fusion receptor of claim 1, wherein the G-protein fusion receptor comprises phCaR/hmGluR2*Gqi5.

22. The G-protein fusion receptor of claim 1, wherein the G-protein fusion receptor comprises pmGluR2//CaR*$G\alpha_q$i5.

23. The G-protein fusion receptor of claim 1, wherein the G-protein fusion receptor comprises phmGluR2//CaR*AAA*$G\alpha_q$i5.

24. The G-protein fusion receptor of claim 1, wherein the G-protein fusion receptor comprises $hGABA_BR2$*AAA*$G\alpha_q$o5.

25. The G-protein fusion receptor of claim 1, wherein the G-protein fusion receptor comprises $hGABA_BR1a$*AAA*$G\alpha_q$o5.

26. The G-protein fusion receptor of claim 1, wherein the G-protein fusion receptor comprises phmGluR8//CaR*AAA*$G\alpha_q$i5.

27. The G-protein fusion receptor of claim 1, wherein the G-protein fusion receptor comprises pmGluR8//CaR*$G\alpha_q$i5.

28. The G-protein fusion receptor of claim 1, wherein the G-protein fusion receptor comprises ph8SPmGluR4//CaR*AAA*$G\alpha_q$i5.

* * * * *

SEQUENCE LISTING

```
<160> NUMBER OF SEQ ID NOS: 57

<210> SEQ ID NO 1
<211> LENGTH: 612
<212> TYPE: PRT
<213> ORGANISM: Human
<220> FEATURE:
<221> NAME/KEY: misc_feature
<223> OTHER INFORMATION: CaR extracellular domain

<400> SEQUENCE: 1

Met Ala Phe Tyr Ser Cys Cys Trp Val Leu Leu Ala Leu Thr Trp His
1               5                   10                  15

Thr Ser Ala Tyr Gly Pro Asp Gln Arg Ala Gln Lys Lys Gly Asp Ile
            20                  25                  30

Ile Leu Gly Gly Leu Phe Pro Ile His Phe Gly Val Ala Ala Lys Asp
        35                  40                  45

Gln Asp Leu Lys Ser Arg Pro Glu Ser Val Glu Cys Ile Arg Tyr Asn
    50                  55                  60

Phe Arg Gly Phe Arg Trp Leu Gln Ala Met Ile Phe Ala Ile Glu Glu
65                  70                  75                  80

Ile Asn Ser Ser Pro Ala Leu Leu Pro Asn Leu Thr Leu Gly Tyr Arg
                85                  90                  95

Ile Phe Asp Thr Cys Asn Thr Val Ser Lys Ala Leu Glu Ala Thr Leu
            100                 105                 110

Ser Phe Val Ala Gln Asn Lys Ile Asp Ser Leu Asn Leu Asp Glu Phe
        115                 120                 125

Cys Asn Cys Ser Glu His Ile Pro Ser Thr Ile Ala Val Val Gly Ala
    130                 135                 140

Thr Gly Ser Gly Val Ser Thr Ala Val Ala Asn Leu Leu Gly Leu Phe
145                 150                 155                 160

Tyr Ile Pro Gln Val Ser Tyr Ala Ser Ser Ser Arg Leu Leu Ser Asn
                165                 170                 175

Lys Asn Gln Phe Lys Ser Phe Leu Arg Thr Ile Pro Asn Asp Glu His
            180                 185                 190

Gln Ala Thr Ala Met Ala Asp Ile Ile Glu Tyr Phe Arg Trp Asn Trp
        195                 200                 205

Val Gly Thr Ile Ala Ala Asp Asp Tyr Gly Arg Pro Gly Ile Glu
    210                 215                 220

Lys Phe Arg Glu Glu Ala Glu Glu Arg Asp Ile Cys Ile Asp Phe Ser
225                 230                 235                 240

Glu Leu Ile Ser Gln Tyr Ser Asp Glu Glu Ile Gln His Val Val
                245                 250                 255
```

```
Glu Val Ile Gln Asn Ser Thr Ala Lys Val Ile Val Phe Ser Ser
            260                 265                 270

Gly Pro Asp Leu Glu Pro Leu Ile Lys Glu Ile Val Arg Arg Asn Ile
        275                 280                 285

Thr Gly Lys Ile Trp Leu Ala Ser Glu Ala Trp Ala Ser Ser Ser Leu
    290                 295                 300

Ile Ala Met Pro Gln Tyr Phe His Val Gly Gly Thr Ile Gly Phe
305                 310                 315                 320

Ala Leu Lys Ala Gly Gln Ile Pro Gly Phe Arg Glu Phe Leu Lys Lys
                325                 330                 335

Val His Pro Arg Lys Ser Val His Asn Gly Phe Ala Lys Glu Phe Trp
            340                 345                 350

Glu Glu Thr Phe Asn Cys His Leu Gln Glu Gly Ala Lys Gly Pro Leu
        355                 360                 365

Pro Val Asp Thr Phe Leu Arg Gly His Glu Glu Ser Gly Asp Arg Phe
    370                 375                 380

Ser Asn Ser Ser Thr Ala Phe Arg Pro Leu Cys Thr Gly Asp Glu Asn
385                 390                 395                 400

Ile Ser Ser Val Glu Thr Pro Tyr Ile Asp Tyr Thr His Leu Arg Ile
                405                 410                 415

Ser Tyr Asn Val Tyr Leu Ala Val Tyr Ser Ile Ala His Ala Leu Gln
            420                 425                 430

Asp Ile Tyr Thr Cys Leu Pro Gly Arg Gly Leu Phe Thr Asn Gly Ser
        435                 440                 445

Cys Ala Asp Ile Lys Lys Val Glu Ala Trp Gln Val Leu Lys His Leu
    450                 455                 460

Arg His Leu Asn Phe Thr Asn Asn Met Gly Glu Gln Val Thr Phe Asp
465                 470                 475                 480

Glu Cys Gly Asp Leu Val Gly Asn Tyr Ser Ile Ile Asn Trp His Leu
                485                 490                 495

Ser Pro Glu Asp Gly Ser Ile Val Phe Lys Glu Val Gly Tyr Tyr Asn
            500                 505                 510

Val Tyr Ala Lys Lys Gly Glu Arg Leu Phe Ile Asn Glu Glu Lys Ile
        515                 520                 525

Leu Trp Ser Gly Phe Ser Arg Glu Val Pro Phe Ser Asn Cys Ser Arg
    530                 535                 540

Asp Cys Leu Ala Gly Thr Arg Lys Gly Ile Ile Glu Gly Pro Thr
545                 550                 555                 560

Cys Cys Phe Glu Cys Val Glu Cys Pro Asp Gly Glu Tyr Ser Asp Glu
                565                 570                 575

Thr Asp Ala Ser Ala Cys Asn Lys Cys Pro Asp Asp Phe Trp Ser Asn
            580                 585                 590

Glu Asn His Thr Ser Cys Ile Ala Lys Glu Ile Glu Phe Leu Ser Trp
        595                 600                 605

Thr Glu Pro Phe
    610

<210> SEQ ID NO 2
<211> LENGTH: 590
<212> TYPE: PRT
<213> ORGANISM: Human
<220> FEATURE:
<221> NAME/KEY: misc_feature
<223> OTHER INFORMATION: GABA-betaR1a extracellular domain

<400> SEQUENCE: 2
```

```
Met Leu Leu Leu Leu Leu Ala Pro Leu Phe Leu Arg Pro Pro Gly
1               5                   10                  15

Ala Gly Gly Ala Gln Thr Pro Asn Ala Thr Ser Glu Gly Cys Gln Ile
            20                  25                  30

Ile His Pro Pro Trp Glu Gly Gly Ile Arg Tyr Arg Gly Leu Thr Arg
        35                  40                  45

Asp Gln Val Lys Ala Ile Asn Phe Leu Pro Val Asp Tyr Glu Ile Glu
    50                  55                  60

Tyr Val Cys Arg Gly Glu Arg Glu Val Val Gly Pro Lys Val Arg Lys
65              70                  75                      80

Cys Leu Ala Asn Gly Ser Trp Thr Asp Met Asp Thr Pro Ser Arg Cys
                85                  90                  95

Val Arg Ile Cys Ser Lys Ser Tyr Leu Thr Leu Glu Asn Gly Lys Val
            100                 105                 110

Phe Leu Thr Gly Gly Asp Leu Pro Ala Leu Asp Gly Ala Arg Val Asp
        115                 120                 125

Phe Arg Cys Asp Pro Asp Phe His Leu Val Gly Ser Ser Arg Ser Ile
    130                 135                 140

Cys Ser Gln Gly Gln Trp Ser Thr Pro Lys Pro His Cys Gln Val Asn
145             150                 155                     160

Arg Thr Pro His Ser Glu Arg Arg Ala Val Tyr Ile Gly Ala Leu Phe
                165                 170                 175

Pro Met Ser Gly Gly Trp Pro Gly Gly Gln Ala Cys Gln Pro Ala Val
            180                 185                 190

Glu Met Ala Leu Glu Asp Val Asn Ser Arg Arg Asp Ile Leu Pro Asp
        195                 200                 205

Tyr Glu Leu Lys Leu Ile His His Asp Ser Lys Cys Asp Pro Gly Gln
    210                 215                 220

Ala Thr Lys Tyr Leu Tyr Glu Leu Leu Tyr Asn Asp Pro Ile Lys Ile
225             230                 235                     240

Ile Leu Met Pro Gly Cys Ser Ser Val Ser Thr Leu Val Ala Glu Ala
                245                 250                 255

Ala Arg Met Trp Asn Leu Ile Val Leu Ser Tyr Gly Ser Ser Ser Pro
            260                 265                 270

Ala Leu Ser Asn Arg Gln Arg Phe Pro Thr Phe Phe Arg Thr His Pro
        275                 280                 285

Ser Ala Thr Leu His Asn Pro Thr Arg Val Lys Leu Phe Glu Lys Trp
    290                 295                 300

Gly Trp Lys Lys Ile Ala Thr Ile Gln Gln Thr Thr Glu Val Phe Thr
305             310                 315                     320

Ser Thr Leu Asp Asp Leu Glu Glu Arg Val Lys Glu Ala Gly Ile Glu
                325                 330                 335

Ile Thr Phe Arg Gln Ser Phe Phe Ser Asp Pro Ala Val Pro Val Lys
            340                 345                 350

Asn Leu Lys Arg Gln Asp Ala Arg Ile Ile Val Gly Leu Phe Tyr Glu
        355                 360                 365

Thr Glu Ala Arg Lys Val Phe Cys Glu Val Tyr Lys Glu Arg Leu Phe
    370                 375                 380

Gly Lys Lys Tyr Val Trp Phe Leu Ile Gly Trp Ile Ala Asp Asn Trp
385             390                 395                     400

Phe Lys Ile Tyr Asp Pro Ser Ile Asn Cys Thr Val Asp Glu Met Thr
                405                 410                 415
```

```
Glu Ala Val Glu Gly His Ile Thr Thr Glu Ile Val Met Leu Asn Pro
            420                 425                 430

Ala Asn Thr Arg Ser Ile Ser Asn Met Thr Ser Gln Glu Phe Val Glu
        435                 440                 445

Lys Leu Thr Lys Arg Leu Lys Arg His Pro Glu Glu Thr Gly Gly Phe
    450                 455                 460

Gln Glu Ala Pro Leu Ala Tyr Asp Ala Ile Trp Ala Leu Ala Leu Ala
465                 470                 475                 480

Leu Asn Lys Thr Ser Gly Gly Gly Arg Ser Gly Val Arg Leu Glu
                485                 490                 495

Asp Phe Asn Tyr Asn Asn Gln Thr Ile Thr Asp Gln Ile Tyr Arg Ala
                500                 505                 510

Met Asn Ser Ser Ser Phe Glu Gly Val Ser Gly His Val Val Phe Asp
            515                 520                 525

Ala Ser Gly Ser Arg Met Ala Trp Thr Leu Ile Glu Gln Leu Gln Gly
530                 535                 540

Gly Ser Tyr Lys Lys Ile Gly Tyr Tyr Asp Ser Thr Lys Asp Asp Leu
545                 550                 555                 560

Ser Trp Ser Lys Thr Asp Lys Trp Ile Gly Ser Pro Pro Ala Asp
                565                 570                 575

Gln Thr Leu Val Ile Lys Thr Phe Arg Phe Leu Ser Gln Lys
            580                 585                 590

<210> SEQ ID NO 3
<211> LENGTH: 473
<212> TYPE: PRT
<213> ORGANISM: Human
<220> FEATURE:
<221> NAME/KEY: misc_feature
<223> OTHER INFORMATION: GABA-betaR1b extracellular domain

<400> SEQUENCE: 3

Met Gly Pro Gly Ala Pro Phe Ala Arg Val Gly Trp Pro Leu Pro Leu
1               5                   10                  15

Leu Val Val Met Ala Ala Gly Val Ala Pro Val Trp Ala Ser His Ser
                20                  25                  30

Pro His Leu Pro Arg Pro His Ser Arg Val Pro Pro His Pro Ser Ser
            35                  40                  45

Glu Arg Arg Ala Val Tyr Ile Gly Ala Leu Phe Pro Met Ser Gly Gly
        50                  55                  60

Trp Pro Gly Gly Gln Ala Cys Gln Pro Ala Val Glu Met Ala Leu Glu
65                  70                  75                  80

Asp Val Asn Ser Arg Arg Asp Ile Leu Pro Asp Tyr Glu Leu Lys Leu
                85                  90                  95

Ile His His Asp Ser Lys Cys Asp Pro Gly Gln Ala Thr Lys Tyr Leu
            100                 105                 110

Tyr Glu Leu Leu Asn Tyr Asp Pro Ile Lys Ile Ile Leu Met Pro Gly
        115                 120                 125

Cys Ser Ser Val Ser Thr Leu Val Ala Glu Ala Ala Arg Met Trp Asn
130                 135                 140

Leu Ile Val Leu Ser Tyr Gly Ser Ser Pro Ala Leu Ser Asn Arg
145                 150                 155                 160

Gln Arg Phe Pro Thr Phe Phe Arg Thr His Pro Ser Ala Thr Leu His
                165                 170                 175

Asn Pro Thr Arg Val Lys Leu Phe Glu Lys Trp Gly Trp Lys Lys Ile
            180                 185                 190
```

```
Ala Thr Ile Gln Gln Thr Thr Glu Val Phe Thr Ser Thr Leu Asp Asp
            195                 200                 205

Leu Glu Glu Arg Val Lys Glu Ala Gly Ile Glu Ile Thr Phe Arg Gln
            210                 215                 220

Ser Phe Phe Ser Asp Pro Ala Val Pro Val Lys Asn Leu Lys Arg Gln
225                 230                 235                 240

Asp Ala Arg Ile Ile Val Gly Leu Phe Tyr Glu Thr Glu Ala Arg Lys
            245                 250                 255

Val Phe Cys Glu Val Tyr Lys Glu Arg Leu Phe Gly Lys Lys Tyr Val
            260                 265                 270

Trp Phe Leu Ile Gly Trp Tyr Ala Asp Asn Trp Phe Lys Ile Tyr Asp
            275                 280                 285

Pro Ser Ile Asn Cys Thr Val Asp Glu Met Thr Glu Ala Val Glu Gly
            290                 295                 300

His Ile Thr Thr Glu Ile Val Met Leu Asn Pro Ala Asn Thr Arg Ser
305                 310                 315                 320

Ile Ser Asn Met Thr Ser Gln Glu Phe Val Glu Lys Leu Thr Lys Arg
            325                 330                 335

Leu Lys Arg His Pro Glu Glu Thr Gly Gly Phe Gln Glu Ala Pro Leu
            340                 345                 350

Ala Tyr Asp Ala Ile Trp Ala Leu Ala Leu Ala Leu Asn Lys Thr Ser
            355                 360                 365

Gly Gly Gly Gly Arg Ser Gly Val Arg Leu Glu Asp Phe Asn Tyr Asn
370                 375                 380

Asn Gln Thr Ile Thr Asp Gln Ile Tyr Arg Ala Met Asn Ser Ser Ser
385                 390                 395                 400

Phe Glu Gly Val Ser Gly His Val Val Phe Asp Ala Ser Gly Ser Arg
            405                 410                 415

Met Ala Trp Thr Leu Ile Glu Gln Leu Gln Gly Gly Ser Tyr Lys Lys
            420                 425                 430

Ile Gly Tyr Tyr Asp Ser Thr Lys Asp Asp Leu Ser Trp Ser Lys Thr
            435                 440                 445

Asp Lys Trp Ile Gly Gly Ser Pro Pro Ala Asp Gln Thr Leu Val Ile
450                 455                 460

Lys Thr Phe Arg Phe Leu Ser Gln Lys
465                 470

<210> SEQ ID NO 4
<211> LENGTH: 480
<212> TYPE: PRT
<213> ORGANISM: Human
<220> FEATURE:
<221> NAME/KEY: misc_feature
<223> OTHER INFORMATION: Xaa is any amino acid
<221> NAME/KEY: misc_feature
<223> OTHER INFORMATION: GABA-betaR2 extracellular domain

<400> SEQUENCE: 4

Met Ala Ser Pro Arg Ser Ser Gly Gln Pro Gly Pro Xaa Pro Pro Pro
1               5                   10                  15

Pro Pro Pro Pro Ala Arg Leu Leu Leu Leu Leu Leu Pro Leu Leu
            20                  25                  30

Leu Pro Leu Ala Pro Gly Ala Trp Gly Trp Ala Arg Gly Ala Pro Arg
            35                  40                  45

Pro Pro Pro Ser Ser Pro Pro Leu Ser Ile Met Gly Leu Met Pro Leu
50                  55                  60
```

-continued

```
Thr Lys Glu Val Ala Lys Gly Ser Ile Gly Arg Gly Val Leu Pro Ala
 65                  70                  75                  80

Val Glu Leu Ala Ile Glu Gln Ile Arg Asn Glu Ser Leu Leu Arg Pro
                 85                  90                  95

Tyr Phe Leu Asp Leu Arg Leu Tyr Asp Thr Glu Cys Asp Asn Ala Lys
            100                 105                 110

Gly Leu Lys Ala Phe Tyr Asp Ala Ile Lys Tyr Gly Pro Asn His Leu
        115                 120                 125

Met Val Phe Gly Gly Val Cys Pro Ser Val Thr Ser Ile Ile Ala Glu
    130                 135                 140

Ser Leu Gln Gly Trp Asn Leu Val Gln Leu Ser Phe Ala Ala Thr Thr
145                 150                 155                 160

Pro Val Leu Ala Asp Lys Lys Tyr Pro Tyr Phe Phe Arg Thr Val
                165                 170                 175

Pro Ser Asp Asn Ala Val Asn Pro Ala Ile Leu Lys Leu Leu Lys His
            180                 185                 190

Tyr Gln Trp Lys Arg Val Gly Thr Leu Thr Gln Asp Val Gln Arg Phe
        195                 200                 205

Ser Glu Val Arg Asn Asp Leu Thr Gly Val Leu Tyr Gly Glu Asp Ile
    210                 215                 220

Glu Ile Ser Asp Thr Glu Ser Phe Ser Asn Asp Pro Cys Thr Ser Val
225                 230                 235                 240

Lys Lys Leu Lys Gly Asn Asp Val Arg Ile Ile Leu Gly Gln Phe Asp
                245                 250                 255

Gln Asn Met Ala Ala Lys Val Phe Cys Cys Ala Tyr Glu Glu Asn Met
            260                 265                 270

Tyr Gly Ser Lys Tyr Gln Trp Ile Ile Pro Gly Trp Tyr Glu Pro Ser
        275                 280                 285

Trp Trp Glu Gln Val His Thr Glu Ala Asn Ser Ser Arg Cys Leu Arg
    290                 295                 300

Lys Asn Leu Leu Ala Ala Met Glu Gly Tyr Ile Gly Val Asp Phe Glu
305                 310                 315                 320

Pro Leu Ser Ser Lys Gln Ile Lys Thr Ile Ser Gly Lys Thr Pro Gln
                325                 330                 335

Gln Tyr Glu Arg Glu Tyr Asn Asn Lys Arg Ser Gly Val Gly Pro Ser
            340                 345                 350

Lys Phe His Gly Tyr Ala Tyr Asp Gly Ile Trp Val Ile Ala Lys Thr
        355                 360                 365

Leu Gln Arg Ala Met Glu Thr Leu His Ala Ser Ser Arg His Gln Arg
    370                 375                 380

Ile Gln Asp Phe Asn Tyr Thr Asp His Thr Leu Gly Arg Ile Ile Leu
385                 390                 395                 400

Asn Ala Met Asn Glu Thr Asn Phe Phe Gly Val Thr Gly Gln Val Val
                405                 410                 415

Phe Arg Asn Gly Glu Arg Met Gly Thr Ile Lys Phe Thr Gln Phe Gln
            420                 425                 430

Asp Ser Arg Glu Val Lys Val Gly Glu Tyr Asn Ala Val Ala Asp Thr
        435                 440                 445

Leu Glu Ile Ile Asn Asp Thr Ile Arg Phe Gln Gly Ser Glu Pro Pro
    450                 455                 460

Lys Asp Lys Thr Ile Ile Leu Glu Gln Leu Arg Lys Ile Ser Leu Pro
465                 470                 475                 480
```

<210> SEQ ID NO 5
<211> LENGTH: 583
<212> TYPE: PRT
<213> ORGANISM: Human
<220> FEATURE:
<221> NAME/KEY: misc_feature
<223> OTHER INFORMATION: mGluR8 extracellular domain

<400> SEQUENCE: 5

```
Met Val Cys Glu Gly Lys Arg Ser Ala Ser Cys Pro Cys Phe Phe Leu
1               5                   10                  15

Leu Thr Ala Lys Phe Tyr Trp Ile Leu Thr Met Met Gln Arg Thr His
            20                  25                  30

Ser Gln Glu Tyr Ala His Ser Ile Arg Val Asp Gly Asp Ile Ile Leu
        35                  40                  45

Gly Gly Leu Phe Pro Val His Ala Lys Gly Glu Arg Gly Val Pro Cys
    50                  55                  60

Gly Glu Leu Lys Lys Glu Lys Gly Ile His Arg Leu Glu Ala Met Leu
65                  70                  75                  80

Tyr Ala Ile Asp Gln Ile Asn Lys Asp Pro Asp Leu Leu Ser Asn Ile
                85                  90                  95

Thr Leu Gly Val Arg Ile Leu Asp Thr Cys Ser Arg Asp Thr Tyr Ala
            100                 105                 110

Leu Glu Gln Ser Leu Thr Phe Val Gln Ala Leu Ile Glu Lys Asp Ala
        115                 120                 125

Ser Asp Val Lys Cys Ala Asn Gly Asp Pro Pro Ile Phe Thr Lys Pro
    130                 135                 140

Asp Lys Ile Ser Gly Val Ile Gly Ala Ala Ser Ser Val Ser Ile
145                 150                 155                 160

Met Val Ala Asn Ile Leu Arg Leu Phe Lys Ile Pro Gln Ile Ser Tyr
                165                 170                 175

Ala Ser Thr Ala Pro Glu Leu Ser Asp Asn Thr Arg Tyr Asp Phe Phe
            180                 185                 190

Ser Arg Val Val Pro Pro Asp Ser Tyr Gln Ala Gln Ala Met Val Asp
        195                 200                 205

Ile Val Thr Ala Leu Gly Trp Asn Thr Val Ser Thr Leu Ala Ser Glu
    210                 215                 220

Gly Asn Tyr Gly Glu Ser Gly Val Glu Ala Phe Thr Gln Ile Ser Arg
225                 230                 235                 240

Glu Ile Gly Gly Val Cys Ile Ala Gln Ser Gln Lys Ile Pro Arg Glu
                245                 250                 255

Pro Arg Pro Gly Glu Phe Glu Lys Ile Ile Lys Arg Leu Leu Glu Thr
            260                 265                 270

Pro Asn Ala Arg Ala Val Ile Met Phe Ala Asn Glu Asp Asp Ile Arg
        275                 280                 285

Arg Ile Leu Glu Ala Ala Lys Lys Leu Asn Gln Ser Gly His Phe Leu
    290                 295                 300

Trp Ile Gly Ser Asp Ser Trp Gly Ser Lys Ile Ala Pro Val Tyr Gln
305                 310                 315                 320

Gln Glu Glu Ile Ala Glu Gly Ala Val Thr Ile Leu Pro Lys Arg Ala
                325                 330                 335

Ser Ile Asp Gly Phe Asp Arg Tyr Phe Arg Ser Arg Thr Leu Ala Asn
            340                 345                 350

Asn Arg Arg Asn Val Trp Phe Ala Glu Phe Trp Glu Glu Asn Phe Gly
        355                 360                 365
```

-continued

Cys Lys Leu Gly Ser His Gly Lys Arg Asn Ser His Ile Lys Lys Cys
    370                 375                 380

Thr Gly Leu Glu Arg Ile Ala Arg Asp Ser Ser Tyr Glu Gln Glu Gly
385                 390                 395                 400

Lys Val Gln Phe Val Ile Asp Ala Val Tyr Ser Met Ala Tyr Ala Leu
                405                 410                 415

His Asn Met His Lys Asp Leu Cys Pro Gly Tyr Ile Gly Leu Cys Pro
            420                 425                 430

Arg Met Ser Thr Ile Asp Gly Lys Glu Leu Leu Gly Tyr Ile Arg Ala
            435                 440                 445

Val Asn Phe Asn Gly Ser Ala Gly Thr Pro Val Thr Phe Asn Glu Asn
    450                 455                 460

Gly Asp Ala Pro Gly Arg Tyr Asp Ile Phe Gln Tyr Gln Ile Thr Asn
465                 470                 475                 480

Lys Ser Thr Glu Tyr Lys Val Ile Gly His Trp Thr Asn Gln Leu His
                485                 490                 495

Leu Lys Val Glu Asp Met Gln Trp Ala His Arg Glu His Thr His Pro
            500                 505                 510

Ala Ser Val Cys Ser Leu Pro Cys Lys Pro Gly Glu Arg Lys Lys Thr
            515                 520                 525

Val Lys Gly Val Pro Cys Cys Trp His Cys Glu Arg Cys Glu Gly Tyr
    530                 535                 540

Asn Tyr Gln Val Asp Glu Leu Ser Cys Glu Leu Cys Pro Leu Asp Gln
545                 550                 555                 560

Arg Pro Asn Met Asn Arg Thr Gly Cys Gln Leu Ile Pro Ile Ile Lys
                565                 570                 575

Leu Glu Trp His Ser Pro Trp
            580

<210> SEQ ID NO 6
<211> LENGTH: 250
<212> TYPE: PRT
<213> ORGANISM: Human
<220> FEATURE:
<221> NAME/KEY: misc_feature
<223> OTHER INFORMATION: CaR transmembrane domain

<400> SEQUENCE: 6

Gly Ile Ala Leu Thr Leu Phe Ala Val Leu Gly Ile Phe Leu Thr Ala
1               5                   10                  15

Phe Val Leu Gly Val Phe Ile Lys Phe Arg Asn Thr Pro Ile Val Lys
                20                  25                  30

Ala Thr Asn Arg Glu Leu Ser Tyr Leu Leu Leu Phe Ser Leu Leu Cys
            35                  40                  45

Cys Phe Ser Ser Ser Leu Phe Phe Ile Gly Glu Pro Gln Asp Trp Thr
        50                  55                  60

Cys Arg Leu Arg Gln Pro Ala Phe Gly Ile Ser Phe Val Leu Cys Ile
65                  70                  75                  80

Ser Cys Ile Leu Val Lys Thr Asn Arg Val Leu Leu Val Phe Glu Ala
                85                  90                  95

Lys Ile Pro Thr Ser Phe His Arg Lys Trp Trp Gly Leu Asn Leu Gln
            100                 105                 110

Phe Leu Leu Val Phe Leu Cys Thr Phe Met Gln Ile Val Ile Cys Val
        115                 120                 125

Ile Trp Leu Tyr Thr Ala Pro Pro Ser Ser Tyr Arg Asn Gln Glu Leu

```
                130                 135                 140
Glu Asp Glu Ile Ile Phe Ile Thr Cys His Gly Ser Leu Met Ala
145                 150                 155                 160

Leu Gly Phe Leu Ile Gly Tyr Thr Cys Leu Leu Ala Ala Ile Cys Phe
                165                 170                 175

Phe Phe Ala Phe Lys Ser Arg Lys Leu Pro Glu Asn Phe Asn Glu Ala
                180                 185                 190

Lys Phe Ile Thr Phe Ser Met Leu Ile Phe Phe Ile Val Trp Ile Ser
                195                 200                 205

Phe Ile Pro Ala Tyr Ala Ser Thr Tyr Gly Lys Phe Val Ser Ala Val
                210                 215                 220

Glu Val Ile Ala Ile Leu Ala Ala Ser Phe Gly Leu Leu Ala Cys Ile
225                 230                 235                 240

Phe Phe Asn Lys Ile Tyr Ile Ile Leu Phe
                245                 250

<210> SEQ ID NO 7
<211> LENGTH: 267
<212> TYPE: PRT
<213> ORGANISM: Human
<220> FEATURE:
<221> NAME/KEY: misc_feature
<223> OTHER INFORMATION: GABA-betaR1a transmembrane domain

<400> SEQUENCE: 7

Leu Phe Ile Ser Val Ser Val Leu Ser Ser Leu Gly Ile Val Leu Ala
1               5                   10                  15

Val Val Cys Leu Ser Phe Asn Ile Tyr Asn Ser His Val Arg Tyr Ile
                20                  25                  30

Gln Asn Ser Gln Pro Asn Leu Asn Asn Leu Thr Ala Val Gly Cys Ser
                35                  40                  45

Leu Ala Leu Ala Ala Val Phe Pro Leu Gly Leu Asp Gly Tyr His Ile
    50                  55                  60

Gly Arg Asn Gln Phe Pro Phe Val Cys Gln Ala Arg Leu Trp Leu Leu
65                  70                  75                  80

Gly Leu Gly Phe Ser Leu Gly Tyr Gly Ser Met Phe Thr Lys Ile Trp
                85                  90                  95

Trp Val His Thr Val Phe Thr Lys Lys Glu Glu Lys Lys Glu Trp Arg
                100                 105                 110

Lys Thr Leu Glu Pro Trp Lys Leu Tyr Ala Thr Val Gly Leu Leu Val
                115                 120                 125

Gly Met Asp Val Leu Thr Leu Ala Ile Trp Gln Ile Val Asp Pro Leu
130                 135                 140

His Arg Thr Ile Glu Thr Phe Ala Lys Glu Glu Pro Lys Glu Asp Ile
145                 150                 155                 160

Asp Val Ser Ile Leu Pro Gln Leu Glu His Cys Ser Ser Arg Lys Met
                165                 170                 175

Asn Thr Trp Leu Gly Ile Phe Tyr Gly Tyr Lys Gly Leu Leu Leu Leu
                180                 185                 190

Leu Gly Ile Phe Leu Ala Tyr Glu Thr Lys Ser Val Ser Thr Glu Lys
                195                 200                 205

Ile Asn Asp His Arg Ala Val Gly Met Ala Ile Tyr Asn Val Ala Val
                210                 215                 220

Leu Cys Leu Ile Thr Ala Pro Val Thr Met Ile Leu Ser Ser Gln Gln
225                 230                 235                 240
```

```
Asp Ala Ala Phe Ala Phe Ala Ser Leu Ala Ile Val Phe Ser Ser Tyr
                245                 250                 255

Ile Thr Leu Val Val Leu Phe Val Pro Lys Met
            260                 265

<210> SEQ ID NO 8
<211> LENGTH: 267
<212> TYPE: PRT
<213> ORGANISM: Human
<220> FEATURE:
<221> NAME/KEY: misc_feature
<223> OTHER INFORMATION: GABA-betaR1b transmembrane domain

<400> SEQUENCE: 8

Leu Phe Ile Ser Val Ser Val Leu Ser Ser Leu Gly Ile Val Leu Ala
1               5                   10                  15

Val Val Cys Leu Ser Phe Asn Ile Tyr Asn Ser His Val Arg Tyr Ile
            20                  25                  30

Gln Asn Ser Gln Pro Asn Leu Asn Leu Thr Ala Val Gly Cys Ser
        35                  40                  45

Leu Ala Leu Ala Ala Val Phe Pro Leu Gly Leu Asp Gly Tyr His Ile
    50                  55                  60

Gly Arg Asn Gln Phe Pro Phe Val Cys Gln Ala Arg Leu Trp Leu Leu
65                  70                  75                  80

Gly Leu Gly Phe Ser Leu Gly Tyr Gly Ser Met Phe Thr Lys Ile Trp
                85                  90                  95

Trp Val His Thr Val Phe Thr Lys Lys Glu Glu Lys Lys Glu Trp Arg
            100                 105                 110

Lys Thr Leu Glu Pro Trp Lys Leu Tyr Ala Thr Val Gly Leu Leu Val
        115                 120                 125

Gly Met Asp Val Leu Thr Leu Ala Ile Trp Gln Ile Val Asp Pro Leu
130                 135                 140

His Arg Thr Ile Glu Thr Phe Ala Lys Glu Glu Pro Lys Glu Asp Ile
145                 150                 155                 160

Asp Val Ser Ile Leu Pro Gln Leu Glu His Cys Ser Ser Arg Lys Met
                165                 170                 175

Asn Thr Trp Leu Gly Ile Phe Tyr Gly Tyr Lys Gly Leu Leu Leu Leu
            180                 185                 190

Leu Gly Ile Phe Leu Ala Tyr Glu Thr Lys Ser Val Ser Thr Glu Lys
        195                 200                 205

Ile Asn Asp His Arg Ala Val Gly Met Ala Ile Tyr Asn Val Ala Val
    210                 215                 220

Leu Cys Leu Ile Thr Ala Pro Val Thr Met Ile Leu Ser Ser Gln Gln
225                 230                 235                 240

Asp Ala Ala Phe Ala Phe Ala Ser Leu Ala Ile Val Phe Ser Ser Tyr
                245                 250                 255

Ile Thr Leu Val Val Leu Phe Val Pro Lys Met
            260                 265

<210> SEQ ID NO 9
<211> LENGTH: 264
<212> TYPE: PRT
<213> ORGANISM: Human
<220> FEATURE:
<221> NAME/KEY: misc_feature
<223> OTHER INFORMATION: GABA-betaR2 transmembrane domain

<400> SEQUENCE: 9
```

-continued

```
Leu Tyr Ser Ile Leu Ser Ala Leu Thr Ile Leu Gly Met Ile Met Ala
1               5                   10                  15

Ser Ala Phe Leu Phe Asn Ile Lys Asn Arg Asn Gln Lys Leu Ile
            20                  25                  30

Lys Met Ser Ser Pro Tyr Met Asn Asn Leu Ile Ile Leu Gly Gly Met
        35                  40                  45

Leu Ser Tyr Ala Ser Ile Phe Leu Phe Gly Leu Asp Gly Ser Phe Val
    50                  55                  60

Ser Glu Lys Thr Phe Glu Thr Leu Cys Thr Val Arg Thr Trp Ile Leu
65                  70                  75                  80

Thr Val Gly Tyr Thr Thr Ala Phe Gly Ala Met Phe Ala Lys Thr Trp
                85                  90                  95

Arg Val His Ala Ile Phe Lys Asn Val Lys Met Lys Lys Ile Ile
            100                 105                 110

Lys Asp Gln Lys Leu Leu Val Ile Val Gly Gly Met Leu Leu Ile Asp
        115                 120                 125

Leu Cys Ile Leu Ile Cys Trp Gln Ala Val Asp Pro Leu Arg Arg Thr
    130                 135                 140

Val Glu Lys Tyr Ser Met Glu Pro Asp Pro Ala Gly Arg Asp Ile Ser
145                 150                 155                 160

Ile Arg Pro Leu Leu Glu His Cys Glu Asn Thr His Met Thr Ile Trp
                165                 170                 175

Leu Gly Ile Val Tyr Ala Tyr Lys Gly Leu Leu Met Leu Phe Gly Cys
            180                 185                 190

Phe Leu Ala Trp Glu Thr Arg Asn Val Ser Ile Pro Ala Leu Asn Asp
        195                 200                 205

Ser Lys Tyr Ile Gly Met Ser Val Tyr Asn Val Gly Ile Met Cys Ile
    210                 215                 220

Ile Gly Ala Ala Val Ser Phe Leu Thr Arg Asp Gln Pro Asn Val Gln
225                 230                 235                 240

Phe Cys Ile Val Ala Leu Val Ile Ile Phe Cys Ser Thr Ile Thr Leu
                245                 250                 255

Cys Leu Val Phe Val Pro Lys Leu
            260

<210> SEQ ID NO 10
<211> LENGTH: 260
<212> TYPE: PRT
<213> ORGANISM: Human
<220> FEATURE:
<221> NAME/KEY: misc_feature
<223> OTHER INFORMATION: mGluR8 transmembrane domain

<400> SEQUENCE: 10

Ala Val Val Pro Val Phe Val Ala Ile Leu Gly Ile Ile Ala Thr Thr
1               5                   10                  15

Phe Val Ile Val Thr Phe Val Arg Tyr Asn Asp Thr Pro Ile Val Arg
            20                  25                  30

Ala Ser Gly Arg Glu Leu Ser Tyr Val Leu Leu Thr Gly Ile Phe Leu
        35                  40                  45

Cys Tyr Ser Ile Thr Phe Leu Met Ile Ala Ala Pro Asp Thr Ile Ile
    50                  55                  60

Cys Ser Phe Arg Arg Val Phe Leu Gly Leu Gly Met Cys Phe Ser Tyr
65                  70                  75                  80

Ala Ala Leu Leu Thr Lys Thr Asn Arg Ile His Arg Ile Phe Glu Gln
                85                  90                  95
```

-continued

```
Gly Lys Lys Ser Val Thr Ala Pro Lys Phe Ile Ser Pro Ala Ser Gln
             100                 105                 110

Leu Val Ile Thr Phe Ser Leu Ile Ser Val Gln Leu Leu Gly Val Phe
            115                 120                 125

Val Trp Phe Val Val Asp Pro Pro His Ile Ile Ile Asp Tyr Gly Glu
        130                 135                 140

Gln Arg Thr Leu Asp Pro Glu Lys Ala Arg Gly Val Leu Lys Cys Asp
145                 150                 155                 160

Ile Ser Asp Leu Ser Leu Ile Cys Ser Leu Gly Tyr Ser Ile Leu Leu
                165                 170                 175

Met Val Thr Cys Thr Val Tyr Ala Ile Lys Thr Arg Gly Val Pro Glu
            180                 185                 190

Thr Phe Asn Glu Ala Lys Pro Ile Gly Phe Thr Met Tyr Thr Thr Cys
        195                 200                 205

Ile Ile Trp Leu Ala Phe Ile Pro Ile Phe Phe Gly Thr Ala Gln Ser
    210                 215                 220

Ala Glu Lys Met Tyr Ile Gln Thr Thr Thr Leu Thr Val Ser Met Ser
225                 230                 235                 240

Leu Ser Ala Ser Val Ser Leu Gly Met Leu Tyr Met Pro Lys Val Tyr
                245                 250                 255

Ile Ile Ile Phe
            260

<210> SEQ ID NO 11
<211> LENGTH: 216
<212> TYPE: PRT
<213> ORGANISM: Human
<220> FEATURE:
<221> NAME/KEY: misc_feature
<223> OTHER INFORMATION: CaR intracellular domain

<400> SEQUENCE: 11

Lys Pro Ser Arg Asn Thr Ile Glu Glu Val Arg Cys Ser Thr Ala Ala
1               5                   10                  15

His Ala Phe Lys Val Ala Ala Arg Ala Thr Leu Arg Arg Ser Asn Val
            20                  25                  30

Ser Arg Lys Arg Ser Ser Ser Leu Gly Gly Ser Thr Gly Ser Thr Pro
        35                  40                  45

Ser Ser Ser Ile Ser Ser Lys Ser Asn Ser Glu Asp Pro Phe Pro Gln
    50                  55                  60

Pro Glu Arg Gln Lys Gln Gln Gln Pro Leu Ala Leu Thr Gln Gln Glu
65                  70                  75                  80

Gln Gln Gln Gln Pro Leu Thr Leu Pro Gln Gln Arg Ser Gln Gln
                85                  90                  95

Gln Pro Arg Cys Lys Gln Lys Val Ile Phe Gly Ser Gly Thr Val Thr
            100                 105                 110

Phe Ser Leu Ser Phe Asp Glu Pro Gln Lys Asn Ala Met Ala His Gly
        115                 120                 125

Asn Ser Thr His Gln Asn Ser Leu Glu Ala Gln Lys Ser Ser Asp Thr
    130                 135                 140

Leu Thr Arg His Gln Pro Leu Leu Pro Leu Gln Cys Gly Glu Thr Asp
145                 150                 155                 160

Leu Asp Leu Thr Val Gln Glu Thr Gly Leu Gln Gly Pro Val Gly Gly
                165                 170                 175

Asp Gln Arg Pro Glu Val Glu Asp Pro Glu Glu Leu Ser Pro Ala Leu
```

```
                    180                 185                 190
Val Val Ser Ser Gln Ser Phe Val Ile Ser Gly Gly Ser Thr
            195                 200                 205

Val Thr Glu Asn Val Val Asn Ser
    210                 215

<210> SEQ ID NO 12
<211> LENGTH: 104
<212> TYPE: PRT
<213> ORGANISM: Human
<220> FEATURE:
<221> NAME/KEY: misc_feature
<223> OTHER INFORMATION: GABA-betaR1a intracellular domain

<400> SEQUENCE: 12

Arg Arg Leu Ile Thr Arg Gly Glu Trp Gln Ser Glu Ala Gln Asp Thr
1               5                   10                  15

Met Lys Thr Gly Ser Ser Thr Asn Asn Asn Glu Glu Glu Lys Ser Arg
            20                  25                  30

Leu Leu Glu Lys Glu Asn Arg Glu Leu Glu Lys Ile Ile Ala Glu Lys
        35                  40                  45

Glu Glu Arg Val Ser Glu Leu Arg His Gln Leu Gln Ser Arg Gln Gln
    50                  55                  60

Leu Arg Ser Arg Arg His Pro Pro Thr Pro Pro Glu Pro Ser Gly Gly
65                  70                  75                  80

Leu Pro Arg Gly Pro Pro Glu Pro Pro Asp Arg Leu Ser Cys Asp Gly
                85                  90                  95

Ser Arg Val His Leu Leu Tyr Lys
            100

<210> SEQ ID NO 13
<211> LENGTH: 104
<212> TYPE: PRT
<213> ORGANISM: Human
<220> FEATURE:
<221> NAME/KEY: misc_feature
<223> OTHER INFORMATION: GABA-betaR1b intracellular domain

<400> SEQUENCE: 13

Arg Arg Leu Ile Thr Arg Gly Glu Trp Gln Ser Glu Ala Gln Asp Thr
1               5                   10                  15

Met Lys Thr Gly Ser Ser Thr Asn Asn Asn Glu Glu Glu Lys Ser Arg
            20                  25                  30

Leu Leu Glu Lys Glu Asn Arg Glu Leu Glu Lys Ile Ile Ala Glu Lys
        35                  40                  45

Glu Glu Arg Val Ser Glu Leu Arg His Gln Leu Gln Ser Arg Gln Gln
    50                  55                  60

Leu Arg Ser Arg Arg His Pro Pro Thr Pro Pro Glu Pro Ser Gly Gly
65                  70                  75                  80

Leu Pro Arg Gly Pro Pro Glu Pro Pro Asp Arg Leu Ser Cys Asp Gly
                85                  90                  95

Ser Arg Val His Leu Leu Tyr Lys
            100

<210> SEQ ID NO 14
<211> LENGTH: 197
<212> TYPE: PRT
<213> ORGANISM: Human
<220> FEATURE:
<221> NAME/KEY: misc_feature
```

```
<223> OTHER INFORMATION: GABA-betaR2 intracellular domain

<400> SEQUENCE: 14

Ile Thr Leu Arg Thr Asn Pro Asp Ala Ala Thr Gln Asn Arg Arg Phe
1               5                   10                  15

Gln Phe Thr Gln Asn Gln Lys Lys Glu Asp Ser Lys Thr Ser Thr Ser
                20                  25                  30

Val Thr Ser Val Asn Gln Ala Ser Thr Ser Arg Leu Glu Gly Leu Gln
            35                  40                  45

Ser Glu Asn His Arg Leu Arg Met Lys Ile Thr Glu Leu Asp Lys Asp
        50                  55                  60

Leu Glu Glu Val Thr Met Gln Leu Gln Asp Thr Pro Glu Lys Thr Thr
65                  70                  75                  80

Tyr Ile Lys Gln Asn His Tyr Gln Glu Leu Asn Asp Ile Leu Asn Leu
                85                  90                  95

Gly Asn Phe Thr Glu Ser Thr Asp Gly Gly Lys Ala Ile Leu Lys Asn
                100                 105                 110

His Leu Asp Gln Asn Pro Gln Leu Gln Trp Asn Thr Thr Glu Pro Ser
            115                 120                 125

Arg Thr Cys Lys Asp Pro Ile Glu Asp Ile Asn Ser Pro Glu His Ile
        130                 135                 140

Gln Arg Arg Leu Ser Leu Gln Leu Pro Ile Leu His His Ala Tyr Leu
145                 150                 155                 160

Pro Ser Ile Gly Gly Val Asp Ala Ser Cys Val Ser Pro Cys Val Ser
                165                 170                 175

Pro Thr Ala Ser Pro Arg His Arg His Val Pro Pro Ser Phe Arg Val
                180                 185                 190

Met Val Ser Gly Leu
        195

<210> SEQ ID NO 15
<211> LENGTH: 65
<212> TYPE: PRT
<213> ORGANISM: Human
<220> FEATURE:
<221> NAME/KEY: misc_feature
<223> OTHER INFORMATION: mGluR8 intracellular domain

<400> SEQUENCE: 15

His Pro Glu Gln Asn Val Gln Lys Arg Lys Arg Ser Phe Lys Ala Val
1               5                   10                  15

Val Thr Ala Ala Thr Met Gln Ser Lys Leu Ile Gln Lys Gly Asn Asp
                20                  25                  30

Arg Pro Asn Gly Glu Val Lys Ser Glu Leu Cys Glu Ser Leu Glu Thr
            35                  40                  45

Asn Ser Lys Ser Ser Val Glu Phe Pro Met Val Lys Ser Gly Ser Thr
        50                  55                  60

Ser
65

<210> SEQ ID NO 16
<211> LENGTH: 374
<212> TYPE: PRT
<213> ORGANISM: Human
<220> FEATURE:
<221> NAME/KEY: misc_feature
<223> OTHER INFORMATION: G15 protein

<400> SEQUENCE: 16
```

```
Met Ala Arg Ser Leu Thr Trp Gly Cys Cys Pro Trp Cys Leu Thr Glu
 1               5                  10                  15

Glu Glu Lys Thr Ala Ala Arg Ile Asp Gln Glu Ile Asn Arg Ile Leu
            20                  25                  30

Leu Glu Gln Lys Lys Gln Arg Glu Glu Leu Lys Leu Leu Leu Leu Leu
        35                  40                  45

Gly Pro Gly Glu Ser Gly Lys Ser Thr Phe Ile Lys Gln Met Arg Ile
    50                  55                  60

Ile His Gly Val Gly Tyr Ser Glu Glu Asp Arg Arg Ala Phe Arg Leu
65                  70                  75                  80

Leu Ile Tyr Gln Asn Ile Phe Val Ser Met Gln Ala Met Ile Asp Ala
                85                  90                  95

Met Asp Arg Leu Gln Ile Pro Phe Ser Arg Pro Asp Ser Lys Gln His
            100                 105                 110

Ala Ser Leu Val Met Thr Gln Asp Pro Tyr Lys Val Ser Thr Phe Glu
        115                 120                 125

Lys Pro Tyr Ala Val Ala Met Gln Tyr Leu Trp Arg Asp Ala Gly Ile
    130                 135                 140

Arg Ala Cys Tyr Glu Arg Arg Arg Glu Phe His Leu Leu Asp Ser Ala
145                 150                 155                 160

Val Tyr Tyr Leu Ser His Leu Glu Arg Ile Ser Glu Asp Ser Tyr Ile
                165                 170                 175

Pro Thr Ala Gln Asp Val Leu Arg Ser Arg Met Pro Thr Thr Gly Ile
            180                 185                 190

Asn Glu Tyr Cys Phe Ser Val Lys Lys Thr Lys Leu Arg Ile Val Asp
        195                 200                 205

Val Gly Gly Gln Arg Ser Glu Arg Arg Lys Trp Ile His Cys Phe Glu
    210                 215                 220

Asn Val Ile Ala Leu Ile Tyr Leu Ala Ser Leu Ser Glu Tyr Asp Gln
225                 230                 235                 240

Cys Leu Glu Glu Asn Asp Gln Glu Asn Arg Met Glu Glu Ser Leu Ala
                245                 250                 255

Leu Phe Ser Thr Ile Leu Glu Leu Pro Trp Phe Lys Ser Thr Ser Val
            260                 265                 270

Ile Leu Phe Leu Asn Lys Thr Asp Ile Leu Glu Asp Lys Ile His Thr
        275                 280                 285

Ser His Leu Ala Thr Tyr Phe Pro Ser Phe Gln Gly Pro Arg Arg Asp
    290                 295                 300

Ala Glu Ala Ala Lys Ser Phe Ile Leu Asp Met Tyr Ala Arg Val Tyr
305                 310                 315                 320

Ala Ser Cys Ala Glu Pro Gln Asp Gly Gly Arg Lys Gly Ser Arg Ala
                325                 330                 335

Arg Arg Phe Phe Ala His Phe Thr Cys Ala Thr Asp Thr Gln Ser Val
            340                 345                 350

Arg Ser Val Phe Lys Asp Val Arg Asp Ser Val Leu Ala Arg Tyr Leu
        355                 360                 365

Asp Glu Ile Asn Leu Leu
    370

<210> SEQ ID NO 17
<211> LENGTH: 374
<212> TYPE: PRT
<213> ORGANISM: Human
<220> FEATURE:
```

-continued

```
<221> NAME/KEY: misc_feature
<223> OTHER INFORMATION: G16 protein

<400> SEQUENCE: 17

Met Ala Arg Ser Leu Thr Trp Arg Cys Cys Pro Trp Cys Leu Thr Glu
1               5                   10                  15

Asp Glu Lys Ala Ala Ala Arg Val Asp Gln Glu Ile Asn Arg Ile Leu
            20                  25                  30

Leu Glu Gln Lys Lys Gln Asp Arg Gly Glu Leu Lys Leu Leu Leu Leu
        35                  40                  45

Gly Pro Gly Glu Ser Gly Lys Ser Thr Phe Ile Lys Gln Met Arg Ile
50                  55                  60

Ile His Gly Ala Gly Tyr Ser Glu Glu Arg Lys Gly Phe Arg Pro
65                  70                  75                  80

Leu Val Tyr Gln Asn Ile Phe Val Ser Met Arg Ala Met Ile Glu Ala
                85                  90                  95

Met Glu Arg Leu Gln Ile Pro Phe Ser Arg Pro Glu Ser Lys His His
            100                 105                 110

Ala Ser Leu Val Met Ser Gln Asp Pro Tyr Lys Val Thr Thr Phe Glu
        115                 120                 125

Lys Arg Tyr Ala Ala Ala Met Gln Trp Leu Trp Arg Asp Ala Gly Ile
    130                 135                 140

Arg Ala Cys Tyr Glu Arg Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
        195                 200                 205

Val Gly Gly Gln Lys Ser Glu Arg Lys Lys Trp Ile His Cys Phe Glu
210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                245                 250                 255

Leu Phe Gly Thr Ile Leu Glu Leu Pro Trp Phe Lys Ser Thr Ser Val
            260                 265                 270

Ile Leu Phe Leu Asn Lys Thr Asp Ile Leu Glu Glu Lys Ile Pro Thr
        275                 280                 285

Ser His Leu Ala Thr Tyr Phe Pro Ser Phe Gln Gly Pro Lys Gln Asp
    290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Lys Lys Gly Ala Arg Ser
                325                 330                 335

Arg Arg Leu Phe Ser His Tyr Thr Cys Ala Thr Asp Thr Gln Asn Ile
            340                 345                 350

Arg Lys Val Phe Lys Asp Val Arg Asp Ser Val Leu Ala Arg Tyr Leu
        355                 360                 365

Asp Glu Ile Asn Leu Leu
    370

<210> SEQ ID NO 18
```

<211> LENGTH: 3234
<212> TYPE: DNA
<213> ORGANISM: Human
<220> FEATURE:
<221> NAME/KEY: misc_feature
<223> OTHER INFORMATION: human CaR

<400> SEQUENCE: 18

| | | | | | |
|---|---|---|---|---|---|
| atggcatttt | atagctgctg | ctgggtcctc | ttggcactca | cctggcacac | ctctgcctac | 60 |
| gggccagacc | agcgagccca | aaagaagggg | gacattatcc | ttgggggct | ctttcctatt | 120 |
| cattttggag | tagcagctaa | agatcaagat | ctcaaatcaa | ggccgagtc | tgtggaatgt | 180 |
| atcaggtata | atttccgtgg | gtttcgctgg | ttacaggcta | tgatatttgc | catagaggag | 240 |
| ataaacagca | gcccagccct | tcttcccaac | ttgacgctgg | gatacaggat | atttgacact | 300 |
| tgcaacaccg | tttctaaggc | cttggaagcc | accctgagtt | ttgttgctca | aaacaaaatt | 360 |
| gattctttga | accttgatga | gttctgcaac | tgctcagagc | acattccctc | tacgattgct | 420 |
| gtggtgggag | caactggctc | aggcgtctcc | acggcagtgg | caaatctgct | ggggctcttc | 480 |
| tacattcccc | aggtcagtta | tgcctcctcc | agcagactcc | tcagcaacaa | gaatcaattc | 540 |
| aagtctttcc | tccgaaccat | ccccaatgat | gagcaccagg | ccactgccat | ggcagacatc | 600 |
| atcgagtatt | tccgctggaa | ctgggtgggc | acaattgcag | ctgatgacga | ctatgggcgg | 660 |
| ccggggattg | agaaattccg | agaggaagct | gaggaaaggg | atatctgcat | cgacttcagt | 720 |
| gaactcatct | cccagtactc | tgatgaggaa | gagatccagc | atgtggtaga | ggtgattcaa | 780 |
| aattccacgg | ccaaagtcat | cgtggttttc | tccagtggcc | cagatcttga | gcccctcatc | 840 |
| aaggagattg | tccggcgcaa | tatcacgggc | aagatctggc | tggccagcga | ggcctgggcc | 900 |
| agctcctccc | tgatcgccat | gcctcagtac | ttccacgtgg | ttggcggcac | cattggattc | 960 |
| gctctgaagg | ctgggcagat | cccaggcttc | cgggaattcc | tgaagaaggt | ccatcccagg | 1020 |
| aagtctgtcc | acaatggttt | tgccaaggag | ttttgggaag | aaacatttaa | ctgccacctc | 1080 |
| caagaaggtg | caaaaggacc | tttacctgtg | acacctttc | tgagaggtca | cgaagaaagt | 1140 |
| ggcgacaggt | ttagcaacag | ctcgacagcc | ttccgacccc | tctgtacagg | ggatgagaac | 1200 |
| atcagcagtg | tcgagacccc | ttacatagat | tacacgcatt | tacggatatc | ctacaatgtg | 1260 |
| tacttagcag | tctactccat | tgcccacgcc | ttgcaagata | tatatacctg | cttacctggg | 1320 |
| agagggctct | tcaccaatgg | ctcctgtgca | gacatcaaga | agttgaggc | gtggcaggtc | 1380 |
| ctgaagcacc | tacggcatct | aaactttaca | aacaatatgg | gggagcaggt | gaccttttga t | 1440 |
| gagtgtggtg | acctggtggg | gaactattcc | atcatcaact | ggcacctctc | cccagaggat | 1500 |
| ggctccatcg | tgtttaagga | agtcgggtat | tacaacgtct | atgccaagaa | gggagaaaga | 1560 |
| ctcttcatca | acgaggagaa | aatcctgtgg | agtgggttct | ccagggaggt | gccttctcc | 1620 |
| aactgcagcc | gagactgcct | ggcagggacc | aggaaaggga | tcattgaggg | ggagcccacc | 1680 |
| tgctgctttg | agtgtgtgga | gtgtcctgat | ggggagtata | gtgatgagac | agatgccagt | 1740 |
| gcctgtaaca | agtgcccaga | tgacttctgg | tccaatgaga | accacaccct | ctgcattgcc | 1800 |
| aaggagatcg | agtttctgtc | gtggacggag | cccttggga | tcgcactcac | cctcttgcc | 1860 |
| gtgctgggca | ttttcctgac | agcctttgtg | ctgggtgtgt | ttatcaagtt | ccgcaacaca | 1920 |
| cccattgtca | aggccaccaa | ccgagagctc | tcctacctcc | tcctcttctc | cctgctctgc | 1980 |
| tgcttctcca | gctccctgtt | cttcatcggg | gagcccagg | actggacgtg | ccgcctgcgc | 2040 |
| cagccggcct | ttggcatcag | cttcgtgctc | tgcatctcat | gcatcctggt | gaaaaccaac | 2100 |

-continued

| | |
|---|---|
| cgtgtcctcc tggtgtttga ggccaagatc cccaccagct tccaccgcaa gtggtggggg | 2160 |
| ctcaacctgc agttcctgct ggttttcctc tgcaccttca tgcagattgt catctgtgtg | 2220 |
| atctggctct acaccgcgcc ccctcaagc taccgcaacc aggagctgga ggatgagatc | 2280 |
| atcttcatca cgtgccacga gggctccctc atggccctgg gcttcctgat cggctacacc | 2340 |
| tgcctgctgg ctgccatctg cttcttcttt gccttcaagt cccggaagct gccggagaac | 2400 |
| ttcaatgaag ccaagttcat caccttcagc atgctcatct tcttcatcgt ctggatctcc | 2460 |
| ttcattccag cctatgccag cacctatggc aagtttgtct ctgccgtaga ggtgattgcc | 2520 |
| atcctggcag ccagctttgg cttgctggcg tgcatcttct tcaacaagat ctacatcatt | 2580 |
| ctcttcaagc catcccgcaa caccatcgag gaggtgcgtt gcagcaccgc agctcacgct | 2640 |
| ttcaaggtgg ctgcccgggc cacgctgcgc cgcagcaacg tctcccgcaa gcggtccagc | 2700 |
| agccttggag gctccacggg atccaccccc tcctcctcca tcagcagcaa gagcaacagc | 2760 |
| gaagacccat tcccacagcc cgagaggcag aagcagcagc agccgctggc cctaaccccag | 2820 |
| caagagcagc agcagcagcc cctgaccctc ccacagcagc aacgatctca gcagcagccc | 2880 |
| agatgcaagc agaaggtcat ctttggcagc ggcacggtca ccttctcact gagctttgat | 2940 |
| gagcctcaga gaacgccat ggcccacggg aattctacgc accagaactc cctggaggcc | 3000 |
| cagaaaagca gcgatacgct gacccgcaca cagccattac tcccgctgca gtgcggggaa | 3060 |
| acggacttag atctgaccgt ccaggaaaca ggtctgcaag gacctgtggg tggagaccag | 3120 |
| cggccagagg tggaggaccc tgaagagttg tccccagcac ttgtcgtgtc cagttcacag | 3180 |
| agctttgtca tcagtggtgg aggcagcact gttacagaaa acgtagtgaa ttca | 3234 |

<210> SEQ ID NO 19
<211> LENGTH: 3462
<212> TYPE: DNA
<213> ORGANISM: Human
<220> FEATURE:
<221> NAME/KEY: misc_feature
<223> OTHER INFORMATION: human GABA-betaR1a

<400> SEQUENCE: 19

| | |
|---|---|
| atgttgctgc tgctgctact ggcgccactc ttcctccgcc cccgggcgc gggcggggcg | 60 |
| cagaccccca cgccacctc agaaggttgc cagatcatac cccgccctg ggaaggggc | 120 |
| atcaggtacc ggggcctgac tcgggaccag gtgaaggcta tcaacttcct gccagtggac | 180 |
| tatgagattg agtatgtgtg ccgggggggag cgcgaggtgg tggggcccaa ggtccgcaag | 240 |
| tgcctggcca acggctcctg gacagatatg gacacaccca gccgctgtgt ccgaatctgc | 300 |
| tccaagtctt atttgaccct ggaaaatggg aaggttttcc tgacgggtgg ggaccctccca | 360 |
| gctctggacg gagcccgggt ggatttccgg tgtgaccccg acttccatct ggtgggcagc | 420 |
| tcccggagca tctgtagtca gggccagtgg agcacccccca agcccactg ccaggtgaat | 480 |
| cgaacgccac actcagaacg cgcgcagtg tacatcgggg cactgtttcc catgagcggg | 540 |
| ggctggccag ggggccaggc ctgccagccc gcggtggaga tggcgctgga ggacgtgaat | 600 |
| agccgcaggg acatcctgcc ggactatgag ctcaagctca tccaccacga cagcaagtgt | 660 |
| gatccaggcc aagccaccaa gtacctatat gagctgctct acaacgaccc tatcaagatc | 720 |
| atccttatgc ctggctgcag ctctgtctcc acgctggtgg ctgaggctgc taggatgtgg | 780 |
| aacctcattg tgctttccta tggctccagc tcaccagccc tgtcaaaccg gcagcgtttc | 840 |
| cccacttcct tccgaacgca cccatcagcc acactccaca ccctacccg cgtgaaactc | 900 |

-continued

```
tttgaaaagt ggggctggaa gaagattgct accatccagc agaccactga ggtcttcact      960
tcgactctgg acgacctgga ggaacgagtg aaggaggctg gaattgagat tactttccgc     1020
cagagtttct tctcagatcc agctgtgccc gtcaaaaacc tgaagcgcca ggatgcccga     1080
atcatcgtgg gacttttcta tgagactgaa gcccggaaag ttttttgtga ggtgtacaag     1140
gagcgtctct tgggaagaa gtacgtctgg ttcctcattg ggtggtatgc tgacaattgg     1200
ttcaagatct acgacccttc tatcaactgc acagtggatg agatgactga ggcggtggag     1260
ggccacatca caactgagat tgtcatgctg aatcctgcca ataccgcag catttccaac     1320
atgacatccc aggaatttgt ggagaaacta accaagcgac tgaaaagaca ccctgaggag     1380
acaggaggct ccaggaggc accgctggcc tatgatgcca tctgggcctt ggcactggcc      1440
ctgaacaaga catctggagg aggcggccgt tctggtgtgc gcctggagga cttcaactac     1500
aacaaccaga ccattaccga ccaaatctac cgggcaatga actcttcgtc ctttgagggt     1560
gtctctggcc atgtggtgtt tgatgccagc ggctctcgga tggcatggac gcttatcgag     1620
cagcttcagg gtggcagcta caagaagatt ggctactatg acagcaccaa ggatgatctt     1680
tcctggtcca aaacagataa atggattgga ggtcccccc cagctgacca gaccctggtc      1740
atcaagacat tccgcttcct gtcacagaaa ctctttatct ccgtctcagt tctctccagc     1800
ctgggcattg tcctagctgt tgtctgtctg tcctttaaca tctacaactc acatgtccgt     1860
tatatccaga actcacagcc caacctgaac aacctgactg ctgtgggctg ctcactggct     1920
ttagctgctg tcttcccct ggggctcgat ggttaccaca ttgggaggaa ccagtttcct      1980
ttcgtctgcc aggcccgcct ctggctcctg gcctgggct ttagtctggg ctacggttcc      2040
atgttcacca agatttggtg ggtccacacg gtcttcacaa agaaggaaga aaagaaggag    2100
tggaggaaga ctctggaacc ctggaagctg tatgccacag tgggcctgct ggtgggcatg     2160
gatgtcctca ctctcgccat ctggcagatc gtggaccctc tgcaccggac cattgagaca     2220
tttgccaagg aggaacctaa ggaagatatt gacgtctcta ttctgcccca gctggagcat    2280
tgcagctcca ggaagatgaa tacatggctt ggcattttct atggttacaa ggggctgctg     2340
ctgctgctgg gaatcttcct tgcttatgag accaagagtg tgtccactga aagatcaat     2400
gatcaccggg ctgtgggcat ggctatctac aatgtggcag tcctgtgcct catcactgct     2460
cctgtcacca tgattctgtc cagccagcag gatgcagcct ttgcctttgc ctctcttgcc     2520
atagttttct cctcctatat cactcttgtt gtgctctttg tgcccaagat gcgcaggctg     2580
atcacccgag gggaatggca gtcggaggcg caggacacca tgaagacagg gtcatcgacc     2640
aacaacaacg aggaggagaa gtcccggctg ttggagaagg agaaccgtga actggaaaag     2700
atcattgctg agaaaggaga gcgtgtctct gaactgcgcc atcagctcca gtctcggcag     2760
cagctccgct cccggcgcca cccaccgaca cccccagaac cctctggggg cctgcccagg     2820
ggaccccctg agccccccga ccggcttagc tgtgatggga gtcgagtgca tttgcttat     2880
aagtgagggt agggtgaggg aggacaggcc agtaggggga gggaaaggga gaggggaagg     2940
gcagggact caggaagcag ggggtcccca tccccagctg gaagaacat gctatccaat     3000
ctcatctctt gtaaatacat gtcccctgt gagttctggg ctgatttggg tctctcatac     3060
ctctgggaaa cagaccttt tctctcttac tgcttcatgt aattttgtat cacctcttca     3120
caatttagtt cgtacctggc ttgaagctgc tcactgctca cacgctgcct cctcagcagc     3180
ctcactgcat ctttctcttc ccatgcaaca ccctcttcta gttaccacgg caaccctgc     3240
agctcctctg cctttgtgct ctgttcctgt ccagcagggg tctcccaaca agtgctcttt     3300
```

-continued

| | |
|---|---|
| ccaccccaaa gggcctctc cttttctcca ctgtcataat ctctttccat cttacttgcc | 3360 |
| cttctatact ttctcacatg tggctccccc tgaattttgc ttcctttggg gagctcattc | 3420 |
| tttcgccaag gtcacatgct cccttgcctc tggctccgtg ca | 3462 |

<210> SEQ ID NO 20
<211> LENGTH: 2887
<212> TYPE: DNA
<213> ORGANISM: Human
<220> FEATURE:
<221> NAME/KEY: misc_feature
<223> OTHER INFORMATION: human GABA-betaR1b

<400> SEQUENCE: 20

| | |
|---|---|
| atggggcccg ggcccccttt tgcccgggtg gggtggccac tgccgcttct ggttgtgatg | 60 |
| gcggcagggg tggctccggt gtgggcctcc cactcccccc atctcccgcg gcctcactcg | 120 |
| cgggtccccc cgcaccccctc ctcagaacgg cgcgcagtgt acatcgggc actgtttccc | 180 |
| atgagcgggg gctggccagg gggccaggcc tgccagcccg cggtggagat ggcgctggag | 240 |
| gacgtgaata gccgcaggga catcctgccg gactatgagc tcaagctcat ccaccacgac | 300 |
| agcaagtgtg atccaggcca agccaccaag tacctatatg agctgctcta caacgaccct | 360 |
| atcaagatca tccttatgcc tggctgcagc tctgtctcca cgctggtggc tgaggctgct | 420 |
| aggatgtgga acctcattgt gctttcctat ggctccagct caccagccct gtcaaaccgg | 480 |
| cagcgttttc ccactttctt ccgaacgcac ccatcagcca cactccacaa ccctacccgc | 540 |
| gtgaaactct ttgaaaagtg gggctggaag aagattgcta ccatccagca gaccactgag | 600 |
| gtcttcactt cgactctgga cgacctggag gaacgagtga aggaggctgg aattgagatt | 660 |
| actttccgcc agagtttctt ctcagatcca gctgtgcccg tcaaaaacct gaagcgccag | 720 |
| gatgcccgaa tcatcgtggg actttttctat gagactgaag cccggaaagt ttttttgtgag | 780 |
| gtgtacaagg agcgtctctt tgggaagaag tacgtctggt tcctcattgg gtggtatgct | 840 |
| gacaattggt tcaagatcta cgacccttct atcaactgca cagtggatga gatgactgag | 900 |
| gcggtggagg gccacatcac aactgagatt gtcatgctga atcctgccaa tacccgcagc | 960 |
| atttccaaca tgacatccca ggaatttgtg agaaaactaa ccaagcgact gaaaagacac | 1020 |
| cctgaggaga caggaggctt ccaggaggca ccgctggcct atgatgccat ctgggccttg | 1080 |
| gcactggccc tgaacaagac atctggagga ggcggccgtt ctggtctgcg cctggaggac | 1140 |
| ttcaactaca acaaccagac cattaccgac caaatctacc gggcaatgaa ctcttcgtcc | 1200 |
| tttgagggtg tctctggcca tgtggtgttt gatgccagcg gctctcggat ggcatggacg | 1260 |
| cttatcgagc agcttcaggg tggcagctac aagaagattg ctactatga cagccaccaag | 1320 |
| gatgatcttt cctggtccaa aacagataaa tggattggag gtccccccc agctgaccag | 1380 |
| accctggtca tcaagacatt ccgcttcctg tcacagaaac tctttatctc cgtctcagtt | 1440 |
| ctctccagcc tgggcattgt cctagctgtt gtctgtctgt cctttaacat ctacaactca | 1500 |
| catgtccgtt atatccagaa ctcacagccc aacctgaaca acctgactgc tgtgggctgc | 1560 |
| tcactggctt tagctgctgt cttcccctg gggctcgatg ttaccacat tgggaggaac | 1620 |
| cagtttcctt tcgtctgcca ggcccgcctc tggctcctgg gctgggctt tagtctgggc | 1680 |
| tacggttcca tgttcaccaa gatttggtgg gtccacacgg tcttcacaaa gaaggaagaa | 1740 |
| aagaaggagt ggaggaagac tctggaaccc tggaagctgt atgccacagt gggcctgctg | 1800 |
| gtgggcatgg atgtcctcac tctcgccatc tggcagatcg tggaccctct gcaccggacc | 1860 |

-continued

```
attgagacat tgccaagga ggaacctaag gaagatattg acgtctctat tctgccccag    1920
ctggagcatt gcagctccag gaagatgaat acatggcttg gcatttttcta tggttacaag   1980 gggctgctgc tgctgctggg aatcttcctt gcttatgaga ccaagagtgt gtccactgag   2040
aagatcaatg atcaccgggc tgtgggcatg gctatctaca atgtggcagt cctgtgcctc   2100
atcactgctc ctgtcaccat gattctgtcc agccagcagg atgcagcctt tgcctttgcc   2160
tctcttgcca tagttttctc ctcctatatc actcttgttg tgctctttgt gcccaagatg   2220
cgcaggctga tcacccgagg ggaatggcag tcggaggcgc aggacaccat gaagacaggg   2280
tcatcgacca acaacaacga ggaggagaag tcccggctgt tggagaagga gaaccgtgaa   2340
ctggaaaaga tcattgctga gaagaggag cgtgtctctg aactgcgcca tcaactccag    2400
tctcggcagc agctccgctc ccggcgccac ccaccgacac ccccagaacc ctctggggc    2460 ctgcccaggg gacccctga gccccccgac cggcttagct gtgatgggag tcgagtgcat   2520
ttgctttata agtgagggta gggtgaggga ggacaggcca gtaggggag ggaaagggag    2580 aggggaaggg cagggactc aggaagcagg gggtccccat cccagctgg gaagaacatg    2640 ctatccaatc tcatctcttg taaatacatg tcccctgtg agttctgggc tgatttgggt    2700
ctctcatacc tctgggaaac agaccttttt ctctcttact gcttcatgta attttgtatc   2760
acctcttcac aatttagttc gtacctggct tgaagctgct cactgctcac acgctgcctc   2820
ctcagcagcc tcactgcatc tttctcttcc catgcaacac cctcttctag ttaccacggc   2880
aacccct                                                             2887
```

<210> SEQ ID NO 21
<211> LENGTH: 3137
<212> TYPE: DNA
<213> ORGANISM: Human
<220> FEATURE:
<221> NAME/KEY: misc_feature
<223> OTHER INFORMATION: human GABA-betaR1b
<221> NAME/KEY: MOD_RES
<222> LOCATION: (38)..(38)
<223> OTHER INFORMATION: n is a or g or c or t/u, unknown, or other

<400> SEQUENCE: 21

```
atggcttccc cgcggagctc cgggcagccc gggccgcngc cgccgccgcc accgccgccc    60
gcgcgcctgc tactgctact gctgctgccg ctgctgctgc ctctggcgcc cgggggcctgg   120 ggctgggcg gggcgcccc ccggccgccg cccagcagcc cgccgctctc catcatgggc     180
ctcatgccgc tcaccaagga ggtggccaag gcagcatcg ggcgcggtgt gctccccgcc    240
gtggaactgg ccatcgagca gatccgcaac gagtcactcc tgcgcccta cttcctcgac   300 ctgcggctct atgacacgga gtgcgacaac gcaaaaggt tgaaagcctt ctacgatgca   360
ataaaatacg gccgaaccca cttgatggtg ttggaggcg tctgtccatc cgtcacatcc    420
atcattgcag agtccctcca aggctggaat ctggtgcagc tttcttttgc tgcaaccacg   480
cctgttctag ccgataagaa aaaatacct tatttctttc ggaccgtccc atcagacaat    540
gcggtgaatc cagccattct gaagttgctc aagcactacc agtggaagcg cgtgggcacg   600
ctgacgcaag acgttcagag gttctctgag gtgcggaatg acctgactgg agttctgtat   660
ggcgaggaca ttgagatttc agacaccgag agcttctcca cgatccctg taccagtgtc   720 aaaaagctga agggaatga tgtgcggatc atccttggcc agtttgacca gaatatggca   780
gcaaaagtgt tctgttgtgc atacgaggag aacatgtatg gtagtaaata tcagtggatc   840
```

```
attccgggct ggtacgagcc ttcttggtgg gagcaggtgc acacggaagc caactcatcc      900
cgctgcctcc ggaagaatct gcttgctgcc atggagggct acattggcgt ggatttcgag      960
cccctgagct ccaagcagat caagaccatc tcaggaaaga ctccacagca gtatgagaga     1020
gagtacaaca acaagcggtc aggcgtgggg cccagcaagt tccacgggta cgcctacgat     1080
ggcatctggg tcatcgccaa gacactgcag agggccatgg agacactgca tgccagcagc     1140
cggcaccagc ggatccagga cttcaactac acggaccaca cgctgggcag gatcatcctc     1200
aatgccatga cgagaccaa cttcttcggg gtcacgggtc aagttgtatt ccggaatggg      1260
gagagaatgg ggaccattaa atttactcaa tttcaagaca gcagggaggt gaaggtggga     1320
gagtacaacg ctgtggccga cacactggag atcatcaatg acaccatcag gttccaagga     1380
tccgaaccac caaaagacaa gaccatcatc ctggagcagc tgcggaagat ctccctacct     1440
ctctacagca tcctctctgc cctcaccatc tcgggatga tcatggccag tgcttttctc      1500
ttcttcaaca tcaagaaccg gaatcagaag ctcataaaga tgtcgagtcc atacatgaac     1560
aaccttatca tccttggagg gatgctctcc tatgcttcca tatttctctt tggccttgat     1620
ggatcctttg tctctgaaaa gacctttgaa acactttgca ccgtcaggac ctggattctc     1680
accgtgggct acacgaccgc ttttggggcc atgtttgcaa agacctggag agtccacgcc     1740
atcttcaaaa atgtgaaaat gaagaagaag atcatcaagg accagaaact gcttgtgatc     1800
gtgggggca tgctgctgat cgacctgtgt atcctgatct gctggcaggc tgtggacccc     1860
ctgcgaagga cagtggagaa gtacagcatg gagccggacc cagcaggacg ggatatctcc     1920
atccgccctc tcctggagca ctgtgagaac acccatatga ccatctggct tggcatcgtc     1980
tatgcctaca agggacttct catgttgttc ggttgtttct tagcttggga gacccgcaac     2040
gtcagcatcc ccgcactcaa cgacagcaag tacatcggga tgagtgtcta caacgtgggg     2100
atcatgtgca tcatcggggc cgctgtctcc ttcctgaccc gggaccagcc caatgtgcag     2160
ttctgcatcg tggctctggt catcatcttc tgcagcacca tcaccctctg cctggtattc     2220
gtgccgaagc tcatcaccct gagaacaaac ccagatgcag caacgcagaa caggcgattc     2280
cagttcactc agaatcagaa gaaagaagat tctaaaacgt ccacctcggt caccagtgtg     2340
aaccaagcca gcacatcccg cctggagggc ctacagtcag aaaaccatcg cctgcgaatg     2400
aagatcacag agctggataa agacttggaa gaggtcacca tgcagctgca ggacacacca     2460
gaaaagacca cctacattaa acagaaccac taccaagagc tcaatgacat cctcaacctg     2520
ggaaacttca ctgagagcac agatggagga aaggccattt taaaaaatca cctcgatcaa     2580
aatccccagc tacagtggaa cacaacagag ccctctcgaa catgcaaaga tcctatagaa     2640
gatataaact ctccagaaca catccagcgt cggctgtccc tccagctccc catcctccac     2700
cacgcctacc tcccatccat cggaggcgtg gacgccagct gtgtcagccc ctgcgtcagc     2760
cccaccgcca gccccgcca cagacatgtg ccacctcct tccgagtcat ggtctcgggc     2820
ctgtaagggt gggaggcctg ggcccggggc ctcccccgtg acagaaccac actgggcaga     2880
ggggtctgct gcagaaacac tgtcggctct ggctgcggag aagctgggca ccatggctgg     2940
cctctcagga ccactcggat ggcactcagg tggacaggac ggggcagggg gagacttggc     3000
acctgacctc gagccttatt tgtgaagtcc ttatttcttc acaaagaaga ggaacgaaa      3060
tgggacgtct tccttaacat ctgcaaacaa ggaggcgctg ggatatcaaa cttgcaaaaa     3120
aaaaaaaaaa aaaaaaa                                                    3137
```

<210> SEQ ID NO 22
<211> LENGTH: 2880
<212> TYPE: DNA
<213> ORGANISM: Rat
<220> FEATURE:
<221> NAME/KEY: misc_feature
<223> OTHER INFORMATION: rat GABA-betaR1a

<400> SEQUENCE: 22

| | | | | | |
|---|---|---|---|---|---|
| atgctgctgc | tgctgctggt | gcctctcttc | ctccgccccc | tgggcgctgg | cggggcgcag | 60 |
| accccccaacg | ccacctcgga | aggttgccag | attatacatc | cgccctggga | aggtggcatc | 120 |
| aggtaccgtg | gcttgactcg | cgaccaggtg | aaggccatca | cttcctgcc | tgtggactat | 180 |
| gagatcgaat | atgtgtgccg | aggggagcgc | gaggtggtgg | ggcccaaggt | gcgcaaatgc | 240 |
| ctggccaacg | gctcctggac | ggatatggac | acacccagcc | gctgtgtccg | aatctgctcc | 300 |
| aagtcttatt | tgaccctgga | aaatgggaag | ttttcctga | cgggtgggga | cctcccagct | 360 |
| ctggatggag | cccgggtgga | gttccgatgt | gacccccgact | tccatctggt | gggcagctcc | 420 |
| cggagcgtct | gtagtcaggg | ccagtggagc | accccccaagc | cccactgcca | ggtgaatcga | 480 |
| acgccacact | cagaacggcg | tgcagtatac | atcggggcgc | tgtttcccat | gagcgggggc | 540 |
| tggccgggg | gccaggcctg | ccagcccgcg | gtggagatgg | cgctggagga | cgttaacagc | 600 |
| cgcagagaca | tcctgccgga | ctacgagctc | aagcttatcc | accacgacag | caagtgtgac | 660 |
| ccagggcaag | ccaccaagta | cttgtacgaa | ctactctaca | atgaccccat | caagatcatt | 720 |
| ctcatgcctg | gctgtagttc | tgtctccaca | cttgtagctg | aggctgcccg | gatgtggaac | 780 |
| cttattgtgc | tctcatatgg | ctccagttca | ccagccttgt | caaaccgaca | gcggtttccc | 840 |
| acgttcttcc | ggacgcatcc | atcgccaca | ctccacaatc | ccacccgggt | gaaactcttc | 900 |
| gaaaagtggg | gctggaagaa | gatcgctacc | atccaacaga | ccaccgaggt | cttcacctca | 960 |
| acgctggatg | acctggagga | gcgagtgaaa | gaggctggga | tcgagatcac | tttccgacag | 1020 |
| agtttcttct | cggatccagc | tgtgcctgtt | aaaaacctga | agcgtcaaga | tgctcgaatc | 1080 |
| atcgtgggac | ttttctatga | gacggaagcc | cggaaagttt | tttgtgaggt | ctataaggaa | 1140 |
| aggctctttg | ggaagaagta | cgtctggttc | ctcatcgggt | ggtatgctga | caactggttc | 1200 |
| aagacctatg | acccgtcaat | caattgtaca | gtggaagaaa | tgaccgaggc | ggtgagggc | 1260 |
| cacatcacca | cggagattgt | catgctgaac | cctgccaaca | cccgaagcat | tccaacatg | 1320 |
| acgtcacagg | aatttgtgga | gaaactaacc | aagcggctga | aaagacaccc | cgaggagact | 1380 |
| ggaggcttcc | aggaggcacc | actggcctat | gatgctatct | gggccttggc | tttggccttg | 1440 |
| aacaagacgt | ctggaggagg | tggtcgttcc | ggcgtgcgcc | tggaggactt | taactacaac | 1500 |
| aaccagacca | ttacagacca | gatctaccgg | gccatgaact | cctcctcctt | tgagggcgtt | 1560 |
| tctggccatg | tggtctttga | tgccagcggc | tcccggatgg | catggacact | tatcgagcag | 1620 |
| ctacagggcg | gcagctacaa | gaagatcggc | tactacgaca | gcaccaagga | tgatcttttcc | 1680 |
| tggtccaaaa | cggacaagtg | gattggaggg | tctcccccag | ctgaccagac | cttggtcatc | 1740 |
| aagacattcc | gtttcctgtc | tcagaaactc | tttatctccg | tctcagttct | ctccagcctg | 1800 |
| ggcattgttc | ttgctgttgt | ctgtctgtcc | tttaacatct | acaactccca | cgttcgttat | 1860 |
| atccagaact | cccagcccaa | cctgaacaat | ctgactgctg | tgggctgctc | actggcactg | 1920 |
| gctgctgtct | ccctctcgg | gctggatggt | taccacatag | ggagaagcca | gttcccgttt | 1980 |
| gtctgccagg | cccgcctttg | gctcttgggc | ttgggcttta | gtctgggcta | tggctctatg | 2040 |
| ttcaccaaga | tctggtgggt | ccacacagtc | ttcacgaaga | aggaggagaa | gaaggagtgg | 2100 |

```
aggaagaccc tagagccctg gaaactctat gccactgtgg gcctgctggt gggcatggat     2160
gtcctgactc ttgccatctg cagattgtg accccttgc accgaaccat tgagactttt      2220
gccaaggagg aaccaaagga agacatcgat gtctccattc tgccccagtt ggagcactgc    2280
agctccaaga agatgaatac gtggcttggc attttctatg gttacaaggg gctgctgctg    2340
ctgctgggaa tctttcttgc ttacgaaacc aagagcgtgt ccactgaaaa gatcaatgac    2400
cacagggccg tgggcatggc tatctacaat gtcgcggtcc tgtgtctcat cactgctcct    2460
gtgaccatga tcctttccag tcagcaggac gcagcctttg cctttgcctc tctggccatc    2520
gtgttctctt cctacatcac tctggttgtg ctctttgtgc caagatgcg caggctgatc     2580 acccgagggg aatggcagtc tgaaacgcag gacaccatga aaacaggatc atccaccaac    2640
aacaacgagg aagagaagtc ccgactgttg gagaaggaaa accgagaact ggaaaagatc    2700
atcgctgaga agaggagcg cgtctctgaa ctgcgccatc agctccagtc tcggcagcaa     2760
ctccgctcac ggcgccaccc cccaacaccc ccagatccct ctgggggcct tcccagggga    2820
ccctctgagc cccctgaccg gcttagctgt gatgggagtc gagtacattt gctttacaag    2880
```

<210> SEQ ID NO 23
<211> LENGTH: 2532
<212> TYPE: DNA
<213> ORGANISM: Rat
<220> FEATURE:
<221> NAME/KEY: misc_feature
<223> OTHER INFORMATION: rat GABA-betaR1b

<400> SEQUENCE: 23

```
atgggcccgg gggaccctg taccccagtg gggtggccgc tgcctcttct gctggtgatg     60
gcggctgggg tggctccggt gtgggcctct cactcccctc atctcccgcg gcctcacccg    120
agggtccccc cgcaccccctc ctcagaacg cgtgcagtat acatcggggc gctgtttccc    180
atgagcgggg gctggccggg gggccaggcc tgccagcccg cggtggagat ggcgctggag    240
gacgttaaca gccgcagaga catcctgccg gactacgagc tcaagcttat ccaccacgac    300
agcaagtgtg acccagggca agccaccaag tacttgtacg aactactcta caatgacccc    360
atcaagatca ttctcatgcc tggctgtagt tctgtctcca cacttgtagc tgaggctgcc    420
cggatgtgga accttattgt gctctcatat ggctccagtt caccagcctt gtcaaaccga    480
cagcggtttc ccacgttctt ccggacgcat ccatccgcca cactccacaa tcccacccgg    540
gtgaaactct tcgaaaagtg gggctggaag aagatcgcta ccatccaaca gaccaccgag    600
gtcttcacct caacgctgga tgacctggag gagcgagtga agaggctggg atcgagatc     660 actttccgac agagtttctt ctcggatcca gctgtgcctg ttaaaaacct gaagcgtcaa    720
gatgctcgaa tcatcgtggg acttttctat gagacggaag cccggaaagt tttttgtgag    780
gtctataagg aaaggctctt tggaagaag tacgtctggt tcctcatcgg tggtatgct     840 gacaactggt tcaagaccta tgacccgtca atcaattgta cagtggaaga atgaccgag     900 gcggtggagg ccacatcac cacggagatt gtcatgctga cctgccaa cacccgaagc      960 atttccaaca tgacgtcaca ggaatttgtg gagaaactaa ccaagcggct gaaaagacac    1020
cccgaggaga ctggaggctt ccaggaggca ccactggcct atgatgctat ctgggccttg    1080 gcttttggcct tgaacaagac gtctggagga ggtggtcgtt ccggcgtgcg cctggaggac    1140
tttaactaca caaccagac cattacagac cagatctacc gggccatgaa ctcctcctcc     1200
tttgagggcg tttctggcca tgtggtctt gatgccagcg gctcccggat ggcatggaca    1260
```

-continued

```
cttatcgagc agctacaggg cggcagctac aagaagatcg gctactacga cagcaccaag    1320
gatgatcttt cctggtccaa aacggacaag tggattggag ggtctccccc agctgaccag    1380
accttggtca tcaagacatt ccgtttcctg tctcagaaac tctttatctc cgtctcagtt    1440
ctctccagcc tgggcattgt tcttgctgtt gtctgtctgt cctttaacat ctacaactcc    1500
cacgttcgtt atatccagaa ctcccagccc aacctgaaca atctgactgc tgtgggctgc    1560
tcactggcac tggctgctgt cttccctctc gggctggatg gttaccacat agggagaagc    1620
cagttcccgt ttgtctgcca ggcccgcctt tggctcttgg gcttgggctt tagtctgggc    1680
tatggctcta tgttcaccaa gatctggtgg gtccacacag tcttcacgaa gaaggaggag    1740
aagaaggagt ggaggaagac cctagagccc tggaaactct atgccactgt gggcctgctg    1800
gtgggcatgg atgtcctgac tcttgccatc tggcagattg tggacccctt gcaccgaacc    1860
attgagactt ttgccaagga ggaaccaaag gaagacatcg atgtctccat tctgccccag    1920
ttggagcact gcagctccaa gaagatgaat acgtggcttg gcattttcta tggttacaag    1980
gggctgctgc tgctgctggg aatctttctt gcttacgaaa ccaagagcgt gtccactgaa    2040
aagatcaatg accacagggc cgtgggcatg gctatctaca atgtcgcggt cctgtgtctc    2100
atcactgctc ctgtgaccat gatccttttcc agtcagcagg acgcagcctt tgcctttgcc    2160
tctctggcca tcgtgttctc ttcctacatc actctggttg tgctctttgt gcccaagatg    2220
cgcaggctga tcacccgagg ggaatggcag tctgaaacgc aggacaccat gaaaacagga    2280
tcatccacca acaacaacga ggaagagaag tcccgactgt tggagaagga aaaccgagaa    2340
ctggaaaaga tcatcgctga gaaagaggag cgcgtctctg aactgcgcca tcagctccag    2400
tctcggcagc aactccgctc acggcgccac cccccaacac ccccagatcc ctctgggggc    2460
cttcccaggg gaccctctga gcccctgac cggcttagct gtgatgggag tcgagtacat    2520
ttgctttaca ag                                                        2532
```

<210> SEQ ID NO 24
<211> LENGTH: 960
<212> TYPE: PRT
<213> ORGANISM: Rat
<220> FEATURE:
<221> NAME/KEY: misc_feature
<223> OTHER INFORMATION: rat GABA-betaR1a

<400> SEQUENCE: 24

```
Met Leu Leu Leu Leu Val Pro Leu Phe Leu Arg Pro Leu Gly Ala
1               5                   10                  15

Gly Gly Ala Gln Thr Pro Asn Ala Thr Ser Glu Gly Cys Gln Ile Ile
            20                  25                  30

His Pro Pro Trp Glu Gly Gly Ile Arg Tyr Arg Gly Leu Thr Arg Asp
        35                  40                  45

Gln Val Lys Ala Ile Asn Phe Leu Pro Val Asp Tyr Glu Ile Glu Tyr
    50                  55                  60

Val Cys Arg Gly Glu Arg Glu Val Val Gly Pro Lys Val Arg Lys Cys
65                  70                  75                  80

Leu Ala Asn Gly Ser Trp Thr Asp Met Asp Thr Pro Ser Arg Cys Val
                85                  90                  95

Arg Ile Cys Ser Lys Ser Tyr Leu Thr Leu Glu Asn Gly Lys Val Phe
            100                 105                 110

Leu Thr Gly Gly Asp Leu Pro Ala Leu Asp Gly Ala Arg Val Glu Phe
        115                 120                 125
```

```
Arg Cys Asp Pro Asp Phe His Leu Val Gly Ser Ser Arg Ser Val Cys
    130                 135                 140

Ser Gln Gly Gln Trp Ser Thr Pro Lys Pro His Cys Gln Val Asn Arg
145                 150                 155                 160

Thr Pro His Ser Glu Arg Arg Ala Val Tyr Ile Gly Ala Leu Phe Pro
                165                 170                 175

Met Ser Gly Gly Trp Pro Gly Gly Gln Ala Cys Gln Pro Ala Val Glu
            180                 185                 190

Met Ala Leu Glu Asp Val Asn Ser Arg Arg Asp Ile Leu Pro Asp Tyr
            195                 200                 205

Glu Leu Lys Leu Ile His His Asp Ser Lys Cys Asp Pro Gly Gln Ala
        210                 215                 220

Thr Lys Tyr Leu Tyr Glu Leu Leu Tyr Asn Asp Pro Ile Lys Ile Ile
225                 230                 235                 240

Leu Met Pro Gly Cys Ser Ser Val Ser Thr Leu Val Ala Glu Ala Ala
                245                 250                 255

Arg Met Trp Asn Leu Ile Val Leu Ser Tyr Gly Ser Ser Ser Pro Ala
            260                 265                 270

Leu Ser Asn Arg Gln Arg Phe Pro Thr Phe Phe Arg Thr His Pro Ser
        275                 280                 285

Ala Thr Leu His Asn Pro Thr Arg Val Lys Leu Phe Glu Lys Trp Gly
    290                 295                 300

Trp Lys Lys Ile Ala Thr Ile Gln Gln Thr Thr Glu Val Phe Thr Ser
305                 310                 315                 320

Thr Leu Asp Asp Leu Glu Glu Arg Val Lys Glu Ala Gly Ile Glu Ile
                325                 330                 335

Thr Phe Arg Gln Ser Phe Phe Ser Asp Pro Ala Val Pro Val Lys Asn
            340                 345                 350

Leu Lys Arg Gln Asp Ala Arg Ile Ile Val Gly Leu Phe Tyr Glu Thr
        355                 360                 365

Glu Ala Arg Lys Val Phe Cys Glu Val Tyr Lys Glu Arg Leu Phe Gly
    370                 375                 380

Lys Lys Tyr Val Trp Phe Leu Ile Gly Trp Tyr Ala Asp Asn Trp Phe
385                 390                 395                 400

Lys Thr Tyr Asp Pro Ser Ile Asn Cys Thr Val Glu Glu Met Thr Glu
                405                 410                 415

Ala Val Glu Gly His Ile Thr Thr Glu Ile Val Met Leu Asn Pro Ala
            420                 425                 430

Asn Thr Arg Ser Ile Ser Asn Met Thr Ser Gln Glu Phe Val Glu Lys
        435                 440                 445

Leu Thr Lys Arg Leu Lys Arg His Pro Glu Glu Thr Gly Gly Phe Gln
    450                 455                 460

Glu Ala Pro Leu Ala Tyr Asp Ala Ile Trp Ala Leu Ala Leu Ala Leu
465                 470                 475                 480

Asn Lys Thr Ser Gly Gly Gly Arg Ser Gly Val Arg Leu Glu Asp
                485                 490                 495

Phe Asn Tyr Asn Asn Gln Thr Ile Thr Asp Gln Ile Tyr Arg Ala Met
            500                 505                 510

Asn Ser Ser Ser Phe Glu Gly Val Ser Gly His Val Val Phe Asp Ala
        515                 520                 525

Ser Gly Ser Arg Met Ala Trp Thr Leu Ile Glu Gln Leu Gln Gly Gly
    530                 535                 540
```

```
Ser Tyr Lys Lys Ile Gly Tyr Asp Ser Thr Lys Asp Asp Leu Ser
545                 550                 555                 560

Trp Ser Lys Thr Asp Lys Trp Ile Gly Gly Ser Pro Pro Ala Asp Gln
                565                 570                 575

Ile Leu Val Ile Lys Thr Phe Arg Phe Leu Ser Gln Lys Leu Phe Ile
                580                 585                 590

Ser Val Ser Val Leu Ser Ser Leu Gly Ile Val Leu Ala Val Val Cys
                595                 600                 605

Leu Ser Phe Asn Ile Tyr Asn Ser His Val Arg Tyr Ile Gln Asn Ser
                610                 615                 620

Gln Pro Asn Leu Asn Asn Leu Thr Ala Val Gly Cys Ser Leu Ala Leu
625                 630                 635                 640

Ala Ala Val Phe Pro Leu Gly Leu Asp Gly Tyr His Ile Gly Arg Ser
                645                 650                 655

Gln Phe Pro Phe Val Cys Gln Ala Arg Leu Trp Leu Leu Gly Leu Gly
                660                 665                 670

Phe Ser Leu Gly Tyr Gly Ser Met Phe Thr Lys Ile Trp Trp Val His
                675                 680                 685

Thr Val Phe Thr Lys Lys Glu Glu Lys Lys Glu Trp Arg Lys Thr Leu
                690                 695                 700

Glu Pro Trp Lys Leu Tyr Ala Thr Val Gly Leu Leu Val Gly Met Asp
705                 710                 715                 720

Val Leu Thr Leu Ala Ile Trp Gln Ile Val Asp Pro Leu His Arg Thr
                725                 730                 735

Ile Glu Thr Phe Ala Lys Glu Glu Pro Lys Glu Asp Ile Asp Val Ser
                740                 745                 750

Ile Leu Pro Gln Leu Glu His Cys Ser Ser Lys Lys Met Asn Thr Trp
                755                 760                 765

Leu Gly Ile Phe Tyr Gly Tyr Lys Gly Leu Leu Leu Leu Gly Ile
770                 775                 780

Phe Leu Ala Tyr Glu Thr Lys Ser Val Ser Thr Glu Lys Ile Asn Asp
785                 790                 795                 800

His Arg Ala Val Gly Met Ala Ile Tyr Asn Val Ala Val Leu Cys Leu
                805                 810                 815

Ile Thr Ala Pro Val Thr Met Ile Leu Ser Ser Gln Gln Asp Ala Ala
                820                 825                 830

Phe Ala Phe Ala Ser Leu Ala Ile Val Phe Ser Ser Tyr Ile Thr Leu
                835                 840                 845

Val Val Leu Phe Val Pro Lys Met Arg Arg Leu Ile Thr Arg Gly Glu
850                 855                 860

Trp Gln Ser Glu Thr Gln Asp Thr Met Lys Thr Gly Ser Ser Thr Asn
865                 870                 875                 880

Asn Asn Glu Glu Glu Lys Ser Arg Leu Leu Glu Lys Glu Asn Arg Glu
                885                 890                 895

Leu Glu Lys Ile Ile Ala Glu Lys Glu Glu Arg Val Ser Glu Leu Arg
                900                 905                 910

His Gln Leu Gln Ser Arg Gln Gln Leu Arg Ser Arg His Pro Pro
                915                 920                 925

Thr Pro Pro Asp Pro Ser Gly Gly Leu Pro Arg Gly Pro Ser Glu Pro
930                 935                 940

Pro Asp Arg Leu Ser Cys Asp Gly Ser Arg Val His Leu Leu Tyr Lys
945                 950                 955                 960
```

-continued

<210> SEQ ID NO 25
<211> LENGTH: 844
<212> TYPE: PRT
<213> ORGANISM: Rat
<220> FEATURE:
<221> NAME/KEY: misc_feature
<223> OTHER INFORMATION: rat GABA-betaR1b

<400> SEQUENCE: 25

| | | | | | | | | | | | | | | | |
|---|---|---|---|---|---|---|---|---|---|---|---|---|---|---|---|
| Met | Gly | Pro | Gly | Pro | Cys | Thr | Pro | Val | Gly | Trp | Pro | Leu | Pro | Leu | |
| 1 | | | | 5 | | | | | 10 | | | | | 15 | |
| Leu | Leu | Val | Met | Ala | Ala | Gly | Val | Ala | Pro | Val | Trp | Ala | Ser | His | Ser |
| | | | 20 | | | | | 25 | | | | | 30 | | |
| Pro | His | Leu | Pro | Arg | Pro | His | Pro | Arg | Val | Pro | Pro | His | Pro | Ser | Ser |
| | | | 35 | | | | | 40 | | | | | 45 | | |
| Glu | Arg | Arg | Ala | Val | Tyr | Ile | Gly | Ala | Leu | Phe | Pro | Met | Ser | Gly | Gly |
| | 50 | | | | | 55 | | | | | 60 | | | | |
| Trp | Pro | Gly | Gly | Gln | Ala | Cys | Gln | Pro | Ala | Val | Glu | Met | Ala | Leu | Glu |
| 65 | | | | | 70 | | | | | 75 | | | | | 80 |
| Asp | Val | Asn | Ser | Arg | Arg | Asp | Ile | Leu | Pro | Asp | Tyr | Glu | Leu | Lys | Leu |
| | | | | 85 | | | | | 90 | | | | | 95 | |
| Ile | His | His | Asp | Ser | Lys | Cys | Asp | Pro | Gly | Gln | Ala | Thr | Lys | Tyr | Leu |
| | | | 100 | | | | | 105 | | | | | 110 | | |
| Tyr | Glu | Leu | Leu | Tyr | Asn | Asp | Pro | Ile | Lys | Ile | Leu | Met | Pro | Gly | |
| | | | 115 | | | | | 120 | | | | | 125 | | |
| Cys | Ser | Ser | Val | Ser | Thr | Leu | Val | Ala | Glu | Ala | Ala | Arg | Met | Trp | Asn |
| 130 | | | | | 135 | | | | | 140 | | | | | |
| Leu | Ile | Val | Leu | Ser | Tyr | Gly | Ser | Ser | Pro | Ala | Leu | Ser | Asn | Arg | |
| 145 | | | | | 150 | | | | | 155 | | | | | 160 |
| Gln | Arg | Phe | Pro | Thr | Phe | Phe | Arg | Thr | His | Pro | Ser | Ala | Thr | Leu | His |
| | | | | 165 | | | | | 170 | | | | | 175 | |
| Asn | Pro | Thr | Arg | Val | Lys | Leu | Phe | Glu | Lys | Trp | Gly | Trp | Lys | Lys | Ile |
| | | | 180 | | | | | 185 | | | | | 190 | | |
| Ala | Thr | Ile | Gln | Gln | Thr | Thr | Glu | Val | Phe | Thr | Ser | Thr | Leu | Asp | Asp |
| | 195 | | | | | 200 | | | | | 205 | | | | |
| Leu | Glu | Glu | Arg | Val | Lys | Glu | Ala | Gly | Ile | Glu | Ile | Thr | Phe | Arg | Gln |
| 210 | | | | | 215 | | | | | 220 | | | | | |
| Ser | Phe | Phe | Ser | Asp | Pro | Ala | Val | Pro | Val | Lys | Asn | Leu | Lys | Arg | Gln |
| 225 | | | | | 230 | | | | | 235 | | | | | 240 |
| Asp | Ala | Arg | Ile | Ile | Val | Gly | Leu | Phe | Tyr | Glu | Thr | Glu | Ala | Arg | Lys |
| | | | | 245 | | | | | 250 | | | | | 255 | |
| Val | Phe | Cys | Glu | Val | Tyr | Lys | Glu | Arg | Leu | Phe | Gly | Lys | Lys | Tyr | Val |
| | | | 260 | | | | | 265 | | | | | 270 | | |
| Trp | Phe | Leu | Ile | Gly | Trp | Tyr | Ala | Asp | Asn | Trp | Phe | Lys | Thr | Tyr | Asp |
| | 275 | | | | | 280 | | | | | 285 | | | | |
| Pro | Ser | Ile | Asn | Cys | Thr | Val | Glu | Glu | Met | Thr | Glu | Ala | Val | Glu | Gly |
| | 290 | | | | | 295 | | | | | 300 | | | | |
| His | Ile | Thr | Thr | Glu | Ile | Val | Met | Leu | Asn | Pro | Ala | Asn | Thr | Arg | Ser |
| 305 | | | | | 310 | | | | | 315 | | | | | 320 |
| Ile | Ser | Asn | Met | Thr | Ser | Gln | Glu | Phe | Val | Glu | Lys | Leu | Thr | Lys | Arg |
| | | | | 325 | | | | | 330 | | | | | 335 | |
| Leu | Lys | Arg | His | Pro | Glu | Glu | Thr | Gly | Gly | Phe | Gln | Glu | Ala | Pro | Leu |
| | | | 340 | | | | | 345 | | | | | 350 | | |
| Ala | Tyr | Asp | Ala | Ile | Trp | Ala | Leu | Ala | Leu | Ala | Leu | Asn | Lys | Thr | Ser |
| | 355 | | | | | 360 | | | | | 365 | | | | |

-continued

```
Gly Gly Gly Gly Arg Ser Gly Val Arg Leu Glu Asp Phe Asn Tyr Asn
    370             375             380

Asn Gln Thr Ile Thr Asp Gln Ile Tyr Arg Ala Met Asn Ser Ser Ser
385             390             395                 400

Phe Glu Gly Val Ser Gly His Val Val Phe Asp Ala Ser Gly Ser Arg
            405             410             415

Met Ala Trp Thr Leu Ile Glu Gln Leu Gln Gly Gly Ser Tyr Lys Lys
            420             425             430

Ile Gly Tyr Tyr Asp Ser Thr Lys Asp Asp Leu Ser Trp Ser Lys Thr
        435             440             445

Asp Lys Trp Ile Gly Gly Ser Pro Pro Ala Asp Gln Ile Leu Val Ile
    450             455             460

Lys Thr Phe Arg Phe Leu Ser Gln Lys Leu Phe Ile Ser Val Ser Val
465             470             475             480

Leu Ser Ser Leu Gly Ile Val Leu Ala Val Cys Leu Ser Phe Asn
                485             490             495

Ile Tyr Asn Ser His Val Arg Tyr Ile Gln Asn Ser Gln Pro Asn Leu
            500             505             510

Asn Asn Leu Thr Ala Val Gly Cys Ser Leu Ala Leu Ala Ala Val Phe
            515             520             525

Pro Leu Gly Leu Asp Gly Tyr His Ile Gly Arg Ser Gln Phe Pro Phe
    530             535             540

Val Cys Gln Ala Arg Leu Trp Leu Leu Gly Leu Gly Phe Ser Leu Gly
545             550             555             560

Tyr Gly Ser Met Phe Thr Lys Ile Trp Trp Val His Thr Val Phe Thr
                565             570             575

Lys Lys Glu Glu Lys Glu Trp Arg Lys Thr Leu Glu Pro Trp Lys
            580             585             590

Leu Tyr Ala Thr Val Gly Leu Leu Val Gly Met Asp Val Leu Thr Leu
    595             600             605

Ala Ile Trp Gln Ile Val Asp Pro Leu His Arg Thr Ile Glu Thr Phe
    610             615             620

Ala Lys Glu Glu Pro Lys Glu Asp Ile Asp Val Ser Ile Leu Pro Gln
625             630             635             640

Leu Glu His Cys Ser Ser Lys Lys Met Asn Thr Trp Leu Gly Ile Phe
            645             650             655

Tyr Gly Tyr Lys Gly Leu Leu Leu Leu Gly Ile Phe Leu Ala Tyr
        660             665             670

Glu Thr Lys Ser Val Ser Thr Glu Lys Ile Asn Asp His Arg Ala Val
        675             680             685

Gly Met Ala Ile Tyr Asn Val Ala Val Leu Cys Leu Ile Thr Ala Pro
    690             695             700

Val Thr Met Ile Leu Ser Ser Gln Gln Asp Ala Ala Phe Ala Phe Ala
705             710             715             720

Ser Leu Ala Ile Val Phe Ser Ser Tyr Ile Thr Leu Val Val Leu Phe
            725             730             735

Val Pro Lys Met Arg Arg Leu Ile Thr Arg Gly Glu Trp Gln Ser Glu
            740             745             750

Thr Gln Asp Thr Met Lys Thr Gly Ser Ser Thr Asn Asn Asn Glu Glu
            755             760             765

Glu Lys Ser Arg Leu Leu Glu Lys Glu Asn Arg Glu Leu Glu Lys Ile
    770             775             780

Ile Ala Glu Lys Glu Glu Arg Val Ser Glu Leu Arg His Gln Leu Gln
```

-continued

```
                785                 790                 795                 800
Ser Arg Gln Gln Leu Arg Ser Arg Arg His Pro Pro Thr Pro Pro Asp
                    805                 810                 815
Pro Ser Gly Gly Leu Pro Arg Gly Pro Ser Glu Pro Pro Asp Arg Leu
            820                 825                 830
Ser Cys Asp Gly Ser Arg Val His Leu Leu Tyr Lys
        835                 840

<210> SEQ ID NO 26
<211> LENGTH: 2616
<212> TYPE: DNA
<213> ORGANISM: Human
<220> FEATURE:
<221> NAME/KEY: misc_feature
<223> OTHER INFORMATION: human mGluR2

<400> SEQUENCE: 26
atgggatcgc tgcttgcgct cctggcactg ctgccgctgt ggggtgctgt ggctgagggc      60
ccagccaaga aggtgctgac cctggaggga gacttggtgc tgggtgggct gttcccagtg     120
caccagaagg gcggcccagc agaggactgt ggtcctgtca atgagcaccg tggcatccag     180
cgcctggagg ccatgctttt tgcactggac cgcatcaacc gtgacccgca cctgctgcct     240
ggcgtgcgcc tggtgcaca catcctcgac agttgctcca aggacacaca tgcgctggag     300
caggcactgg actttgtgcg tgcctcactc agccgtggtg ctgatggatc acgccacatc     360
tgccccgacg gctcttatgc gacccatggt gatgctccca ctgccatcac tggtgtttatt     420
ggcggttcct acagtgatgt ctccatccag gtggccaacc tcttgaggct atttcagatc     480
ccacagatta gctacgcctc taccagtgcc aagctgagtg acaagtcccg ctatgactac     540
tttgcccgca cagtgcctcc tgacttcttc caagccaagg ccatggctga gattctccgc     600
ttcttcaact ggacctatgt gtccactgag gcctctgagg gcgactatgg cgagacaggc     660
attgaggcct ttgagctaga ggctcgtgcc cgcaacatct gtgtggccac ctcggagaaa     720
gtgggccgtg ccatgagccg cgcggccttt gagggtgtgg tgcgagccct gctgcagaag     780
cccagtgccc gcgtggctgt cctgttcacc cgttctgagg atgcccggga gctgcttgct     840
gccagccagc gcctcaatgc cagcttcacc tgggtggcca gtgatggttg ggggcctg      900
gagagtgtgg tggcaggcag tgagggggct gctgagggtg ctatcaccat cgagctggcc     960
tcctacccca tcagtgactt tgcctcctac ttccagagcc tggaccct tg aacaacagc    1020
cggaaccct  ggttccgtga attctgggag cagaggttcc gctgcagctt ccggcagcga    1080
gactgcgcag cccactctct ccgggctgtg ccctttgaac aggagtccaa gatcatgttt    1140
gtggtcaatg cagtgtacgc catggcccat gcgctccaca acatgcaccg tgccctctgc    1200
cccaacacca cccggctctg tgacgcgatg cggccagtta acgggcgccg cctctacaag    1260
gactttgtgc tcaacgtcaa gtttgatgcc ccctttcgcc agctgacac ccacaatgag    1320
gtccgctttg accgctttgg tgatggtatt ggccgctaca acatcttcac ctatctgcgt    1380
gcaggcagtg ggcgctatcg ctaccagaag gtgggctact gggcagaagg cttgactctg    1440
gacaccagcc tcatcccatg ggcctcaccg tcagccggcc ccctggccgc ctctcgctgc    1500
agtgagccct gcctccagaa tgaggtgaag agtgtgcagc cgggcgaagt ctgctgctgg    1560
ctctgcattc cgtgccagcc ctatgagtac cgattggacg aattcacttg cgctgattgt    1620
ggcctgggct actggcccaa tgccagcctg actggctgct cgaactgcc ccaggagtac    1680
atccgctggg gcgatgcctg gctgtgggga cctgtcacca tcgcctgcct cggtgccctg    1740
```

```
gccaccctgt tgtgctggg tgtctttgtg cggcacaatg ccacaccagt ggtcaaggcc      1800
tcaggtcggg agctctgcta catcctgctg gtggtgtct tcctctgcta ctgcatgacc      1860
ttcatcttca ttgccaagcc atccacggca gtgtgtacct tacggcgtct tggtttgggc      1920
actgccttct ctgtctgcta ctcagccctg ctcaccaaga ccaaccgcat tgcacgcatc      1980
ttcggtgggg cccgggaggg tgcccagcgg ccacgcttca tcagtcctgc ctcacaggtg      2040
gccatctgcc tggcacttat ctcgggccag ctgctcatcg tggtcgcctg gctggtggtg      2100
gaggcaccgg gcacaggcaa ggagacagcc cccgaacggc gggaggtggt gacactgcgc      2160
tgcaaccacc gcgatgcaag tatgttgggc tcgctggcct acaatgtgct cctcatcgcg      2220
ctctgcacgc tttatgcctt caatactcgc aagtgcccg aaaacttcaa cgaggccaag      2280
ttcattggct tcaccatgta caccacctgc atcatctggc tggcattgtt gcccatcttc      2340
tatgtcacct ccagtgacta ccgggtacag accaccacca tgtgcgtgtc agtcagcctc      2400
agcggctccg tggtgcttgg ctgcctcttt gcgcccaagc tgcacatcat cctcttccag      2460
ccgcagaaga acgtggttag ccaccgggca cccaccagcc gctttggcag tgctgctgcc      2520
agggccagct ccagccttgg ccaagggtct ggctcccagt ttgtccccac tgtttgcaat      2580
ggccgtgagg tggtggactc gacaacgtca tcgctt                               2616
```

<210> SEQ ID NO 27
<211> LENGTH: 824
<212> TYPE: PRT
<213> ORGANISM: Human
<220> FEATURE:
<221> NAME/KEY: misc_feature
<223> OTHER INFORMATION: human mGluR2

<400> SEQUENCE: 27

```
Met Gly Ser Leu Leu Ala Leu Leu Ala Leu Leu Pro Leu Trp Gly Ala
1               5                   10                  15

Val Ala Glu Gly Pro Ala Lys Lys Val Leu Thr Leu Glu Gly Asp Leu
                20                  25                  30

Val Leu Gly Gly Leu Phe Pro Val His Gln Lys Gly Gly Pro Ala Glu
            35                  40                  45

Asp Cys Gly Pro Val Asn Glu His Arg Gly Ile Gln Arg Leu Glu Ala
        50                  55                  60

Met Leu Phe Ala Leu Asp Arg Ile Asn Arg Asp Pro His Leu Leu Pro
65                  70                  75                  80

Gly Val Arg Leu Gly Ala His Ile Leu Asp Ser Cys Ser Lys Asp Thr
                85                  90                  95

His Ala Leu Glu Gln Ala Leu Asp Phe Val Arg Ala Ser Leu Ser Arg
            100                 105                 110

Gly Ala Asp Gly Ser Arg His Ile Cys Pro Asp Gly Ser Tyr Ala Thr
        115                 120                 125

His Gly Asp Ala Pro Thr Ala Ile Thr Gly Val Ile Gly Gly Ser Tyr
    130                 135                 140

Ser Asp Val Ser Ile Gln Val Ala Asn Leu Leu Arg Leu Phe Gln Ile
145                 150                 155                 160

Pro Gln Ile Ser Tyr Ala Ser Thr Ser Ala Lys Leu Ser Asp Lys Ser
                165                 170                 175

Arg Tyr Asp Tyr Phe Ala Arg Thr Val Pro Pro Asp Phe Phe Gln Ala
            180                 185                 190

Lys Ala Met Ala Glu Ile Leu Arg Phe Phe Asn Trp Thr Tyr Val Ser
```

-continued

```
              195                 200                 205
Thr Glu Ala Ser Glu Gly Asp Tyr Gly Glu Thr Gly Ile Glu Ala Phe
    210                 215                 220
Glu Leu Glu Ala Arg Ala Arg Asn Ile Cys Val Ala Thr Ser Glu Lys
225                 230                 235                 240
Val Gly Arg Ala Met Ser Arg Ala Ala Phe Glu Gly Val Val Arg Ala
                245                 250                 255
Leu Leu Gln Lys Pro Ser Ala Arg Val Ala Val Leu Phe Thr Arg Ser
                260                 265                 270
Glu Asp Ala Arg Glu Leu Leu Ala Ala Ser Gln Arg Leu Asn Ala Ser
            275                 280                 285
Phe Thr Trp Val Ala Ser Asp Gly Trp Gly Ala Leu Glu Ser Val Val
        290                 295                 300
Ala Gly Ser Glu Gly Ala Ala Glu Gly Ala Ile Thr Ile Glu Leu Ala
305                 310                 315                 320
Ser Tyr Pro Ile Ser Asp Phe Ala Ser Tyr Phe Gln Ser Leu Asp Pro
                325                 330                 335
Trp Asn Asn Ser Arg Asn Pro Trp Phe Arg Glu Phe Trp Glu Gln Arg
                340                 345                 350
Phe Arg Cys Ser Phe Arg Gln Arg Asp Cys Ala Ala His Ser Leu Arg
            355                 360                 365
Ala Val Pro Phe Glu Gln Glu Ser Lys Ile Met Phe Val Val Asn Ala
        370                 375                 380
Val Tyr Ala Met Ala His Ala Leu His Asn Met His Arg Ala Leu Cys
385                 390                 395                 400
Pro Asn Thr Thr Arg Leu Cys Asp Ala Met Arg Pro Val Asn Gly Arg
                405                 410                 415
Arg Leu Tyr Lys Asp Phe Val Leu Asn Val Lys Phe Asp Ala Pro Phe
                420                 425                 430
Arg Pro Ala Asp Thr His Asn Glu Val Arg Phe Asp Arg Phe Gly Asp
            435                 440                 445
Gly Ile Gly Arg Tyr Asn Ile Phe Thr Tyr Leu Arg Ala Gly Ser Gly
        450                 455                 460
Arg Tyr Arg Tyr Gln Lys Val Gly Tyr Trp Ala Glu Gly Leu Thr Leu
465                 470                 475                 480
Asp Thr Ser Leu Ile Pro Trp Ala Ser Pro Ser Ala Gly Pro Leu Ala
                485                 490                 495
Ala Ser Arg Cys Ser Glu Pro Cys Leu Gln Asn Glu Val Lys Ser Val
                500                 505                 510
Gln Pro Gly Glu Val Cys Cys Trp Leu Cys Ile Pro Cys Gln Pro Tyr
            515                 520                 525
Glu Tyr Arg Leu Asp Glu Phe Thr Cys Ala Asp Cys Gly Leu Gly Tyr
        530                 535                 540
Trp Pro Asn Ala Ser Leu Thr Gly Cys Phe Glu Leu Pro Gln Glu Tyr
545                 550                 555                 560
Ile Arg Trp Gly Asp Ala Trp Ala Val Gly Pro Val Thr Ile Ala Cys
                565                 570                 575
Leu Gly Ala Leu Ala Thr Leu Phe Val Leu Gly Val Phe Val Arg His
                580                 585                 590
Asn Ala Thr Pro Val Val Lys Ala Ser Gly Arg Glu Leu Cys Tyr Ile
            595                 600                 605
Leu Leu Gly Gly Val Phe Leu Cys Tyr Cys Met Thr Phe Ile Phe Ile
        610                 615                 620
```

```
Ala Lys Pro Ser Thr Ala Val Cys Thr Leu Arg Arg Leu Gly Leu Gly
625                 630                 635                 640

Thr Ala Phe Ser Val Cys Tyr Ser Ala Leu Leu Thr Lys Thr Asn Arg
            645                 650                 655

Ile Ala Arg Ile Phe Gly Gly Ala Arg Glu Gly Ala Gln Arg Pro Arg
        660                 665                 670

Phe Ile Ser Pro Ala Ser Gln Val Ala Ile Cys Leu Ala Leu Ile Ser
    675                 680                 685

Gly Gln Leu Leu Ile Val Val Ala Trp Leu Val Glu Ala Pro Gly
690                 695                 700

Thr Gly Lys Glu Thr Ala Pro Glu Arg Arg Glu Val Val Thr Leu Arg
705                 710                 715                 720

Cys Asn His Arg Asp Ala Ser Met Leu Gly Ser Leu Ala Tyr Asn Val
                725                 730                 735

Leu Leu Ile Ala Leu Cys Thr Leu Tyr Ala Phe Asn Thr Arg Lys Cys
            740                 745                 750

Pro Glu Asn Phe Asn Glu Ala Lys Phe Ile Gly Phe Thr Met Tyr Thr
        755                 760                 765

Thr Cys Ile Ile Trp Leu Ala Leu Leu Pro Ile Phe Tyr Val Thr Ser
    770                 775                 780

Ser Asp Tyr Arg Val Gln Thr Thr Thr Met Cys Val Ser Val Ser Leu
785                 790                 795                 800

Ser Gly Ser Val Val Leu Gly Cys Leu Phe Ala Pro Lys Leu His Ile
                805                 810                 815

Ile Leu Phe Gln Pro Gln Lys Asn
            820
```

<210> SEQ ID NO 28
<211> LENGTH: 1077
<212> TYPE: DNA
<213> ORGANISM: Artificial Sequence
<220> FEATURE:
<221> NAME/KEY: misc_feature
<223> OTHER INFORMATION: chimeric Gqi5

<400> SEQUENCE: 28

```
atgactctgg agtccatcat ggcgtgctgc ctgagcgagg aggccaagga agcccggcgg     60
atcaacgacg agatcgagcg gcagctccgc agggacaagc gggacgcccg ccgggagctc    120
aagctgctgc tgctcgggac aggagagagt ggcaagagta cgtttatcaa gcagatgaga    180
atcatccatg gtcaggata ctctgatgaa gataaaaggg gcttcaccaa gctggtgtat    240
cagaacatct tcacggccat gcaggccatg atcagagcca tggacacact caagatccca    300
tacaagtatg agcacaataa ggctcatgca caattagttc gagaagttga tgtggagaag    360
gtgtctgctt ttgagaatcc atatgtagat gcaataaaga gtttatggaa tgatcctgga    420
atccaggaat gctatgatag acgacgagaa tatcaattat ctgactctac caaatactat    480
cttaatgact tggaccgcgt agctgaccct gcctacctgc ctacgcaaca gatgtgctt    540 agagttcgag tccccaccac agggatcatc gaatacccct ttgacttaca aagtgtcatt    600
ttcagaatgg tcgatgtagg gggccaaagg tcagagagaa gaaatggat acactgcttt    660 gaaaatgtca cctctatcat gtttctagta gcgcttagtg aatatgatca gttctcgtg    720 gagtcagaca atgagaaccg aatggaggaa agcaaggctc tctttagaac aattatcaca    780 taccccctggt tccagaactc ctcggttatt ctgttcttaa acaagaaaga tcttctagag    840
```

-continued

```
gagaaaatca tgtattccca tctagtcgac tacttcccag aatatgatgg accccagaga      900
gatgcccagg cagcccgaga attcattctg aagatgttcg tggacctgaa cccagacagt      960
gacaaaatta tctactccca cttcacgtgc gccacagaca ccgagaatat ccgctttgtc     1020
tttgctgccg tcaaggacac catcctccag ttgaacctga aggactgcgg tctgttc        1077
```

<210> SEQ ID NO 29
<211> LENGTH: 359
<212> TYPE: PRT
<213> ORGANISM: Artificial Sequence
<220> FEATURE:
<221> NAME/KEY: misc_feature
<223> OTHER INFORMATION: chimeric Gci5

<400> SEQUENCE: 29

```
Met Thr Leu Glu Ser Ile Met Ala Cys Cys Leu Ser Glu Glu Ala Lys
1               5                   10                  15

Glu Ala Arg Arg Ile Asn Asp Glu Ile Glu Arg Gln Leu Arg Arg Asp
            20                  25                  30

Lys Arg Asp Ala Arg Arg Glu Leu Lys Leu Leu Leu Leu Gly Thr Gly
        35                  40                  45

Glu Ser Gly Lys Ser Thr Phe Ile Lys Gln Met Arg Ile Ile His Gly
    50                  55                  60

Ser Gly Tyr Ser Asp Glu Asp Lys Arg Gly Phe Thr Lys Leu Val Tyr
65                  70                  75                  80

Gln Asn Ile Phe Thr Ala Met Gln Ala Met Ile Arg Ala Met Asp Thr
                85                  90                  95

Leu Lys Ile Pro Tyr Lys Tyr Glu His Asn Lys Ala His Ala Gln Leu
            100                 105                 110

Val Arg Glu Val Asp Val Glu Lys Val Ser Ala Phe Glu Asn Pro Tyr
        115                 120                 125

Val Asp Ala Ile Lys Ser Leu Trp Asn Asp Pro Gly Ile Gln Glu Cys
    130                 135                 140

Tyr Asp Arg Arg Arg Glu Tyr Gln Leu Ser Asp Ser Thr Lys Tyr Tyr
145                 150                 155                 160

Leu Asn Asp Leu Asp Arg Val Ala Asp Pro Ala Tyr Leu Pro Thr Gln
                165                 170                 175

Gln Asp Val Leu Arg Val Arg Val Pro Thr Thr Gly Ile Ile Glu Tyr
            180                 185                 190

Pro Phe Asp Leu Gln Ser Val Ile Phe Arg Met Val Asp Val Gly Gly
        195                 200                 205

Gln Arg Ser Glu Arg Arg Lys Trp Ile His Cys Phe Glu Asn Val Thr
    210                 215                 220

Ser Ile Met Phe Leu Val Ala Leu Ser Glu Tyr Asp Gln Val Leu Val
225                 230                 235                 240

Glu Ser Asp Asn Glu Asn Arg Met Glu Glu Ser Lys Ala Leu Phe Arg
                245                 250                 255

Thr Ile Ile Thr Tyr Pro Trp Phe Gln Asn Ser Ser Val Ile Leu Phe
            260                 265                 270

Leu Asn Lys Lys Asp Leu Leu Glu Glu Lys Ile Met Tyr Ser His Leu
        275                 280                 285

Val Asp Tyr Phe Pro Glu Tyr Asp Gly Pro Gln Arg Asp Ala Gln Ala
    290                 295                 300

Ala Arg Glu Phe Ile Leu Lys Met Phe Val Asp Leu Asn Pro Asp Ser
305                 310                 315                 320
```

| Asp | Lys | Ile | Ile | Tyr | Ser | His | Phe | Thr | Cys | Ala | Thr | Asp | Thr | Glu | Asn |
|||||||||||||||||
|     |     |     |     | 325 |     |     |     | 330 |     |     |     |     | 335 |     |     |

| Ile | Arg | Phe | Val | Phe | Ala | Ala | Val | Lys | Asp | Thr | Ile | Leu | Gln | Leu | Asn |
|||||||||||||||||
|     |     |     | 340 |     |     |     |     | 345 |     |     |     |     | 350 |     |     |

| Leu | Lys | Asp | Cys | Gly | Leu | Phe |
|||||||||
|     |     |     | 355 |     |     |     |

<210> SEQ ID NO 30
<211> LENGTH: 2751
<212> TYPE: DNA
<213> ORGANISM: Artificial Sequence
<220> FEATURE:
<221> NAME/KEY: misc_feature
<223> OTHER INFORMATION: chimeric hCAR/hmGluR2

<400> SEQUENCE: 30

```
atggcatttt atagctgctg ctgggtcctc ttggcactca cctggcacac ctctgcctac      60
gggccagacc agcgagccca aaagaagggg gacattatcc ttgggggggct ctttcctatt    120
cattttggag tagcagctaa agatcaagat ctcaaatcaa ggccggagtc tgtggaatgt    180
atcaggtata atttccgtgg gtttcgctgg ttagaggcta tgatatttgc catagaggag    240
ataaacagca gcccagccct tcttcccaac ttgacgctgg gatacaggat atttgacact    300
tgcaacaccg tttctaaggc cttggaagcc accctgagtt tgttgctca aaacaaaatt    360
gattctttga accttgatga gttctgcaac tgctcagagc acattccctc tacgattgct    420
gtggtgggag caactggctc aggcgtctcc acggcagtgg caaatctgct ggggctcttc    480
tacattcccc aggtcagtta tgcctcctcc agcagactcc tcagcaacaa gaatcaattc    540
aagtctttcc tccgaaccat ccccaatgat gagcaccagg ccactgccat ggcagacatc    600
atcgagtatt tccgctggaa ctgggtgggc acaattgcag ctgatgacga ctatgggcgg    660
ccggggattg agaaattccg agaggaagct gaggaaaggg atatctgcat cgacttcagt    720
gaactcatct cccagtactc tgatgaggaa gagatccagc atgtggtaga ggtgattcaa    780
aattccacgg ccaaagtcat cgtggttttc tccagtggcc cagatcttga ccccctcatc    840
aaggagattg tccggcgcaa tatcacgggc aagatctggc tggccagcga ggcctgggcc    900
agctcctccc tgatcgccat gcctcagtac ttccacgtgg ttggcggcac cattggattc    960
gctctgaagg ctgggcagat cccaggcttc cgggaattcc tgaagaaggt ccatcccagg   1020
aagtctgtcc acaatggttt tgccaaggag ttttgggaag aaacatttaa ctgccacctc   1080
caagaaggtg caaaaggacc tttacctgtg acacccttc tgagaggtca cgaagaaagt   1140
ggcgacaggt ttagcaacag ctcgacagcc ttccgacccc tctgtacagg ggatgagaac   1200
atcagcagtg tcgagacccc ttacatagat tacacgcatt tacggatatc ctacaatgtg   1260
tacttagcag tctactccat gcccacgcc ttgcaagata tatacctg cttacctggg    1320
agagggctct tcaccaatgg ctcctgtgca gacatcaaga agttgaggc gtggcaggtc   1380
ctgaagcacc tacggcatct aaactttaca acaatatgg gggagcaggt gacctttgat   1440
gagtgtggtg acctggtggg gaactattcc atcatcaact ggcacctctc cccagaggat   1500
ggctccatcg tgtttaagga agtcgggtat acaacgtct atgccaagaa gggagaaaga   1560
ctcttcatca cgaggagaa aatcctgtgg agtgggttct ccagggaggt gcccttctcc   1620
aactgcagcc gagactgcct ggcagggacc aggaaaggga tcattgaggg ggagcccacc   1680
tgctgctttg agtgtgtgga gtgtcctgat ggggagtata gtgatgagac agatgccagt   1740
gcctgtaaca agtgcccaga tgacttctgg tccaatgaga accacaccct ctgcttcgaa   1800
```

-continued

```
ctgccccagg agtacatccg ctggggcgat gcctgggctg tgggacctgt caccatcgcc    1860
tgcctcggtg ccctggccac cctgtttgtg ctgggtgtct ttgtgcggca caatgccaca    1920
ccagtggtca aggcctcagg tcgggagctc tgctacatcc tgctgggtgg tgtcttcctc    1980
tgctactgca tgaccttcat cttcattgcc aagccatcca cggcagtgtg taccttacgg    2040
cgtcttggtt tgggcactgc cttctctgtc tgctactcag ccctgctcac caagaccaac    2100
cgcattgcac gcatcttcgg tggggcccgg gagggtgccc agcggccacg cttcatcagt    2160
cctgcctcac aggtggccat ctgcctggca cttatctcgg gccagctgct catcgtggtc    2220
gcctggctgg tggtggaggc accgggcaca ggcaaggaga cagcccccga acggcgggag    2280
gtggtgacac tgcgctgcaa ccaccgcgat gcaagtatgt tgggctcgct ggcctacaat    2340
gtgctcctca tcgcgctctg cacgctttat gccttcaata tcgcaagtg ccccgaaaac    2400 ttcaacgagg ccaagttcat tggcttcacc atgtacacca cctgcatcat ctggctggca    2460
ttgttgccca tcttctatgt cacctccagt gactaccggg tacagaccac caccatgtgc    2520
gtgtcagtca gcctcagcgg ctccgtggtg cttggctgcc tctttgcgcc caagctgcac    2580
atcatcctct tccagccgca gaagaacgtg gttagccacc gggcacccac cagccgcttt    2640
ggcagtgctg ctgccagggc cagctccagc cttggccaag gtctggctc ccagtttgtc     2700 cccactgttt gcaatggccg tgaggtggtg gactcgacaa cgtcatcgct t              2751
```

<210> SEQ ID NO 31
<211> LENGTH: 917
<212> TYPE: PRT
<213> ORGANISM: Artificial Sequence
<220> FEATURE:
<221> NAME/KEY: misc_feature
<223> OTHER INFORMATION: chimeric hCAR/hmGluR2

<400> SEQUENCE: 31

```
Met Ala Phe Tyr Ser Cys Cys Trp Val Leu Leu Ala Leu Thr Trp His
1               5                   10                  15

Thr Ser Ala Tyr Gly Pro Asp Gln Arg Ala Gln Lys Lys Gly Asp Ile
            20                  25                  30

Ile Leu Gly Gly Leu Phe Pro Ile His Phe Gly Val Ala Ala Lys Asp
        35                  40                  45

Gln Asp Leu Lys Ser Arg Pro Glu Ser Val Glu Cys Ile Arg Tyr Asn
    50                  55                  60

Phe Arg Gly Phe Arg Trp Leu Gln Ala Met Ile Phe Ala Ile Glu Glu
65                  70                  75                  80

Ile Asn Ser Ser Pro Ala Leu Leu Pro Asn Leu Thr Leu Gly Tyr Arg
                85                  90                  95

Ile Phe Asp Thr Cys Asn Thr Val Ser Lys Ala Leu Glu Ala Thr Leu
            100                 105                 110

Ser Phe Val Ala Gln Asn Lys Ile Asp Ser Leu Asn Leu Asp Glu Phe
        115                 120                 125

Cys Asn Cys Ser Glu His Ile Pro Ser Thr Ile Ala Val Val Gly Ala
    130                 135                 140

Thr Gly Ser Gly Val Ser Thr Ala Val Ala Asn Leu Leu Gly Leu Phe
145                 150                 155                 160

Tyr Ile Pro Gln Val Ser Tyr Ala Ser Ser Arg Leu Leu Ser Asn
                165                 170                 175

Lys Asn Gln Phe Lys Ser Phe Leu Arg Thr Ile Pro Asn Asp Glu His
            180                 185                 190
```

```
Gln Ala Thr Ala Met Ala Asp Ile Ile Glu Tyr Phe Arg Trp Asn Trp
            195                 200                 205

Val Gly Thr Ile Ala Ala Asp Asp Tyr Gly Arg Pro Gly Ile Glu
    210                 215                 220

Lys Phe Arg Glu Glu Ala Glu Glu Arg Asp Ile Cys Ile Asp Phe Ser
225                 230                 235                 240

Glu Leu Ile Ser Gln Tyr Ser Asp Glu Glu Ile Gln His Val Val
            245                 250                 255

Glu Val Ile Gln Asn Ser Thr Ala Lys Val Ile Val Phe Ser Ser
                260                 265                 270

Gly Pro Asp Leu Glu Pro Leu Ile Lys Glu Ile Val Arg Arg Asn Ile
    275                 280                 285

Thr Gly Lys Ile Trp Leu Ala Ser Glu Ala Trp Ala Ser Ser Ser Leu
    290                 295                 300

Ile Ala Met Pro Gln Tyr Phe His Val Val Gly Gly Thr Ile Gly Phe
305                 310                 315                 320

Ala Leu Lys Ala Gly Gln Ile Pro Gly Phe Arg Glu Phe Leu Lys Lys
                325                 330                 335

Val His Pro Arg Lys Ser Val His Asn Gly Phe Ala Lys Glu Phe Trp
            340                 345                 350

Glu Glu Thr Phe Asn Cys His Leu Gln Glu Gly Ala Lys Gly Pro Leu
            355                 360                 365

Pro Val Asp Thr Phe Leu Arg Gly His Glu Glu Ser Gly Asp Arg Phe
    370                 375                 380

Ser Asn Ser Ser Thr Ala Phe Arg Pro Leu Cys Thr Gly Asp Glu Asn
385                 390                 395                 400

Ile Ser Ser Val Glu Thr Pro Tyr Ile Asp Tyr Thr His Leu Arg Ile
                405                 410                 415

Ser Tyr Asn Val Tyr Leu Ala Val Tyr Ser Ile Ala His Ala Leu Gln
            420                 425                 430

Asp Ile Tyr Thr Cys Leu Pro Gly Arg Gly Leu Phe Thr Asn Gly Ser
            435                 440                 445

Cys Ala Asp Ile Lys Lys Val Glu Ala Trp Gln Val Leu Lys His Leu
450                 455                 460

Arg His Leu Asn Phe Thr Asn Asn Met Gly Glu Gln Val Thr Phe Asp
465                 470                 475                 480

Glu Cys Gly Asp Leu Val Gly Asn Tyr Ser Ile Ile Asn Trp His Leu
                485                 490                 495

Ser Pro Glu Asp Gly Ser Ile Val Phe Lys Glu Val Gly Tyr Tyr Asn
            500                 505                 510

Val Tyr Ala Lys Lys Gly Glu Arg Leu Phe Ile Asn Glu Glu Lys Ile
            515                 520                 525

Leu Trp Ser Gly Phe Ser Arg Glu Val Pro Phe Ser Asn Cys Ser Arg
    530                 535                 540

Asp Cys Leu Ala Gly Thr Arg Lys Gly Ile Ile Glu Gly Glu Pro Thr
545                 550                 555                 560

Cys Cys Phe Glu Cys Val Glu Cys Pro Asp Gly Glu Tyr Ser Asp Glu
                565                 570                 575

Thr Asp Ala Ser Ala Cys Asn Lys Cys Pro Asp Asp Phe Trp Ser Asn
            580                 585                 590

Glu Asn His Thr Ser Cys Phe Glu Leu Pro Gln Glu Tyr Ile Arg Trp
    595                 600                 605
```

Gly Asp Ala Trp Ala Val Gly Pro Val Thr Ile Ala Cys Leu Gly Ala
    610                 615                 620
Leu Ala Thr Leu Phe Val Leu Gly Val Phe Val Arg His Asn Ala Thr
625                 630                 635                 640
Pro Val Val Lys Ala Ser Gly Arg Glu Leu Cys Tyr Ile Leu Leu Gly
                645                 650                 655
Gly Val Phe Leu Cys Tyr Cys Met Thr Phe Ile Phe Ile Ala Lys Pro
                660                 665                 670
Ser Thr Ala Val Cys Thr Leu Arg Arg Leu Gly Leu Gly Thr Ala Phe
            675                 680                 685
Ser Val Cys Tyr Ser Ala Leu Leu Thr Lys Thr Asn Arg Ile Ala Arg
    690                 695                 700
Ile Phe Gly Gly Ala Arg Glu Gly Ala Gln Arg Pro Arg Phe Ile Ser
705                 710                 715                 720
Pro Ala Ser Gln Val Ala Ile Cys Leu Ala Leu Ile Ser Gly Gln Leu
                725                 730                 735
Leu Ile Val Val Ala Trp Leu Val Glu Ala Pro Gly Thr Gly Lys
                740                 745                 750
Glu Thr Ala Pro Glu Arg Arg Glu Val Val Thr Leu Arg Cys Asn His
            755                 760                 765
Arg Asp Ala Ser Met Leu Gly Ser Leu Ala Tyr Asn Val Leu Leu Ile
    770                 775                 780
Ala Leu Cys Thr Leu Tyr Ala Phe Asn Thr Arg Lys Cys Pro Glu Asn
785                 790                 795                 800
Phe Asn Glu Ala Lys Phe Ile Gly Phe Thr Met Tyr Thr Thr Cys Ile
                805                 810                 815
Ile Trp Leu Ala Leu Leu Pro Ile Phe Tyr Val Thr Ser Ser Asp Tyr
            820                 825                 830
Arg Val Gln Thr Thr Thr Met Cys Val Ser Val Ser Leu Ser Gly Ser
    835                 840                 845
Val Val Leu Gly Cys Leu Phe Ala Pro Lys Leu His Ile Ile Leu Phe
850                 855                 860
Gln Pro Gln Lys Asn Val Ser His Arg Ala Pro Thr Ser Arg Phe
865                 870                 875                 880
Gly Ser Ala Ala Ala Arg Ala Ser Ser Leu Gly Gln Gly Ser Gly
                885                 890                 895
Ser Gln Phe Val Pro Thr Val Cys Asn Gly Arg Glu Val Val Asp Ser
            900                 905                 910
Thr Thr Ser Ser Leu
        915

<210> SEQ ID NO 32
<211> LENGTH: 3831
<212> TYPE: DNA
<213> ORGANISM: Artificial Sequence
<220> FEATURE:
<221> NAME/KEY: misc_feature
<223> OTHER INFORMATION: chimeric phCaR/hmGluR2*Gqi5

<400> SEQUENCE: 32
atggcatttt tatagctgctg ctgggtcctc ttggcactca cctggcacac ctctgcctac    60
gggccagacc agcgagccca aaagaagggg gacattatcc ttgggggct ctttcctatt    120
cattttggag tagcagctaa agatcaagat ctcaaatcaa ggccggagtc tgtggaatgt    180
atcaggtata atttccgtgg gtttcgctgg ttacaggcta tgatatttgc catagaggag    240

```
ataaacagca gcccagccct tcttcccaac ttgacgctgg gatacaggat atttgacact    300
tgcaacaccg tttctaaggc cttggaagcc accctgagtt ttgttgctca aaacaaaatt    360
gattctttga accttgatga gttctgcaac tgctcagagc acattccctc tacgattgct    420
gtggtgggag caactggctc aggcgtctcc acggcagtgg caaatctgct ggggctcttc    480
tacattcccc aggtcagtta tgcctcctcc agcagactcc tcagcaacaa gaatcaattc    540
aagtctttcc tccgaaccat ccccaatgat gagcaccagg ccactgccat ggcagacatc    600
atcgagtatt tccgctggaa ctgggtgggc acaattgcag ctgatgacga ctatgggcgg    660
ccggggattg agaaattccg agaggaagct gaggaaaggg atatctgcat cgacttcagt    720
gaactcatct cccagtactc tgatgaggaa gagatccagc atgtggtaga ggtgattcaa    780
aattccacgg ccaaagtcat cgtggttttc tccagtggcc cagatcttga gcccctcatc    840
aaggagattg tccggcgcaa tatcacgggc aagatctggc tggccagcga ggcctgggcc    900
agctcctccc tgatcgccat gcctcagtac ttccacgtgg ttggcggcac cattggattc    960
gctctgaagg ctgggcagat cccaggcttc cgggaattcc tgaagaaggt ccatcccagg   1020
aagtctgtcc acaatggttt tgccaaggag ttttgggaag aaacatttaa ctgccacctc   1080
caagaaggtg caaaaggacc tttacctgtg dacacctttc tgagaggtca cgaagaaagt   1140
ggcgacaggt ttagcaacag ctcgacagcc ttccgacccc tctgtacagg ggatgagaac   1200
atcagcagtg tcgagacccc ttacatagat tacacgcatt tacggatatc ctacaatgtg   1260
tacttagcag tctactccat tgcccacgcc ttgcaagata tatacctg cttacctggg    1320 agagggctct tcaccaatgg ctcctgtgca gacatcaaga agttgaggc gtggcaggtc    1380 ctgaagcacc tacggcatct aaactttaca aacaatatgg gggagcaggt gacctttgat   1440
gagtgtggtg acctggtggg gaactattcc atcatcaact ggcacctctc cccagaggat   1500
ggctccatcg tgtttaagga agtcgggtat tacaacgtct atgccaagaa gggagaaaga   1560
ctcttcatca acgaggagaa aatcctgtgg agtgggttct ccagggaggt gcccttctcc   1620
aactgcagcc gagactgcct ggcagggacc aggaaaggga tcattgaggg ggagcccacc   1680
tgctgctttg agtgtgtgga gtgtcctgat ggggagtata gtgatgagac agatgccagt   1740
gcctgtaaca gtgcccagga tgacttctgg tccaatgaga accacacctc ctgcttcgaa   1800 ctgcccagg agtacatccg ctggggcgat gcctggctg tgggacctgt caccatcgcc   1860
tgcctcggtg ccctggccac cctgtttgtg ctgggtgtct ttgtgcggca caatgccaca   1920
ccagtggtca aggcctcagg tcgggagctc tgctacatcc tgctggtgg tgtcttcctc   1980 tgctactgca tgaccttcat cttcattgcc aagccatcca cggcagtgtg taccttacgg   2040
cgtcttggtt tgggcactgc cttctctgtc tgctactcag ccctgctcac caagaccaac   2100
cgcattgcac gcatcttcgg tggggcccgg gagggtgccc agcggccacg cttcatcagt   2160
cctgcctcac aggtggccat ctgcctggca cttatctcgg gccagctgct catcgtggtc   2220
gcctggctgg tggtggaggc accgggcaca ggcaaggaga cagcccccga acggcgggag   2280
gtggtgacac tgcgctgcaa ccaccgcgat gcaagtatgt tgggctcgct ggcctacaat   2340
gtgctcctca tcgcgctctg cacgctttat gccttcaata tcgcaagtg ccccgaaaac   2400 ttcaacgagg ccaagttcat tggcttcacc atgtacacca cctgcatcat ctggctggca   2460
ttgttgccca tcttctatgt cacctccagt gactaccggg tacagaccac caccatgtgc   2520
gtgtcagtca gcctcagcgg ctccgtggtg cttggctgcc tctttgcgcc caagctgcac   2580
atcatcctct tccagccgca gaagaacgtg gttagccacc gggcacccac cagccgcttt   2640
```

-continued

```
ggcagtgctg ctgccagggc cagctccagc cttggccaag ggtctggctc ccagtttgtc    2700
cccactgttt gcaatggccg tgaggtggtg gactcgacaa cgtcatcgct tatgactctg    2760
gagtccatca tggcgtgctg cctgagcgag gaggccaagg aagcccggcg gatcaacgac    2820
gagatcgagc ggcagctccg cagggacaag cgggacgccc gccgggagct caagctgctg    2880
ctgctcggga caggagagag tgcaagagt acgtttatca agcagatgag aatcatccat    2940
gggtcaggat actctgatga agataaaagg ggcttcacca agctggtgta tcagaacatc    3000
ttcacggcca tgcaggccat gatcagagcc atggacacac tcaagatccc atacaagtat    3060
gagcacaata aggctcatgc acaattagtt cgagaagttg atgtggagaa ggtgtctgct    3120
tttgagaatc catatgtaga tgcaataaag agtttatgga atgatcctgg aatccaggaa    3180
tgctatgata gacgacgaga atatcaatta tctgactcta ccaaatacta tcttaatgac    3240
ttggaccgcg tagctgaccc tgcctacctg cctacgcaac aagatgtgct tagagttcga    3300
gtccccacca cagggatcat cgaataccccc tttgacttac aaagtgtcat tttcagaatg    3360
gtcgatgtag ggggccaaag gtcagagaga agaaaatgga tacactgctt tgaaaatgtc    3420
acctctatca tgtttctagt agcgcttagt gaatatgatc aagttctcgt ggagtcagac    3480
aatgagaacc gaatggagga aagcaaggct ctctttagaa caattatcac ataccccctgg    3540 ttccagaact cctcggttat tctgttctta aacaagaaag atcttctaga ggagaaaatc    3600
atgtattccc atctagtcga ctacttccca gaatatgatg acccagag agatgcccag    3660 gcagcccgag aattcattct gaagatgttc gtggacctga acccagacag tgacaaaatt    3720
atctactccc acttcacgtg cgccacagac accgagaata tccgctttgt ctttgctgcc    3780
gtcaaggaca ccatcctcca gttgaacctg aaggactgcg gtctgttcta a            3831
```

<210> SEQ ID NO 33
<211> LENGTH: 1276
<212> TYPE: PRT
<213> ORGANISM: Artificial Sequence
<220> FEATURE:
<221> NAME/KEY: misc_feature
<223> OTHER INFORMATION: chimeric phCaR/hmGluR2*Gqi5

<400> SEQUENCE: 33

```
Met Ala Phe Tyr Ser Cys Cys Trp Val Leu Leu Ala Leu Thr Trp His
1               5                   10                  15

Thr Ser Ala Tyr Gly Pro Asp Gln Arg Ala Gln Lys Lys Gly Asp Ile
            20                  25                  30

Ile Leu Gly Gly Leu Phe Pro Ile His Phe Gly Val Ala Ala Lys Asp
        35                  40                  45

Gln Asp Leu Lys Ser Arg Pro Glu Ser Val Glu Cys Ile Arg Tyr Asn
    50                  55                  60

Phe Arg Gly Phe Arg Trp Leu Gln Ala Met Ile Phe Ala Ile Glu Glu
65                  70                  75                  80

Ile Asn Ser Ser Pro Ala Leu Leu Pro Asn Leu Thr Leu Gly Tyr Arg
                85                  90                  95

Ile Phe Asp Thr Cys Asn Thr Val Ser Lys Ala Leu Glu Ala Thr Leu
            100                 105                 110

Ser Phe Val Ala Gln Asn Lys Ile Asp Ser Leu Asn Leu Asp Glu Phe
        115                 120                 125

Cys Asn Cys Ser Glu His Ile Pro Ser Thr Ile Ala Val Val Gly Ala
    130                 135                 140
```

-continued

```
Thr Gly Ser Gly Val Ser Thr Ala Val Ala Asn Leu Leu Gly Leu Phe
145                 150                 155                 160

Tyr Ile Pro Gln Val Ser Tyr Ala Ser Ser Ser Arg Leu Leu Ser Asn
                165                 170                 175

Lys Asn Gln Phe Lys Ser Phe Leu Arg Thr Ile Pro Asn Asp Glu His
            180                 185                 190

Gln Ala Thr Ala Met Ala Asp Ile Ile Glu Tyr Phe Arg Trp Asn Trp
        195                 200                 205

Val Gly Thr Ile Ala Ala Asp Asp Tyr Gly Arg Pro Gly Ile Glu
    210                 215                 220

Lys Phe Arg Glu Glu Ala Glu Glu Arg Asp Ile Cys Ile Asp Phe Ser
225                 230                 235                 240

Glu Leu Ile Ser Gln Tyr Ser Asp Glu Glu Ile Gln His Val Val
                245                 250                 255

Glu Val Ile Gln Asn Ser Thr Ala Lys Val Ile Val Phe Ser Ser
            260                 265                 270

Gly Pro Asp Leu Glu Pro Leu Ile Lys Glu Ile Val Arg Arg Asn Ile
        275                 280                 285

Thr Gly Lys Ile Trp Leu Ala Ser Glu Ala Trp Ala Ser Ser Ser Leu
    290                 295                 300

Ile Ala Met Pro Gln Tyr Phe His Val Val Gly Gly Thr Ile Gly Phe
305                 310                 315                 320

Ala Leu Lys Ala Gly Gln Ile Pro Gly Phe Arg Glu Phe Leu Lys Lys
                325                 330                 335

Val His Pro Arg Lys Ser Val His Asn Gly Phe Ala Lys Glu Phe Trp
            340                 345                 350

Glu Glu Thr Phe Asn Cys His Leu Gln Glu Gly Ala Lys Gly Pro Leu
        355                 360                 365

Pro Val Asp Thr Phe Leu Arg Gly His Glu Glu Ser Gly Asp Arg Phe
    370                 375                 380

Ser Asn Ser Ser Thr Ala Phe Arg Pro Leu Cys Thr Gly Asp Glu Asn
385                 390                 395                 400

Ile Ser Ser Val Glu Thr Pro Tyr Ile Asp Tyr Thr His Leu Arg Ile
                405                 410                 415

Ser Tyr Asn Val Tyr Leu Ala Val Tyr Ser Ile Ala His Ala Leu Gln
            420                 425                 430

Asp Ile Tyr Thr Cys Leu Pro Gly Arg Gly Leu Phe Thr Asn Gly Ser
        435                 440                 445

Cys Ala Asp Ile Lys Lys Val Glu Ala Trp Gln Val Leu Lys His Leu
    450                 455                 460

Arg His Leu Asn Phe Thr Asn Asn Met Gly Glu Gln Val Thr Phe Asp
465                 470                 475                 480

Glu Cys Gly Asp Leu Val Gly Asn Tyr Ser Ile Ile Asn Trp His Leu
                485                 490                 495

Ser Pro Glu Asp Gly Ser Ile Val Phe Lys Glu Val Gly Tyr Tyr Asn
            500                 505                 510

Val Tyr Ala Lys Lys Gly Glu Arg Leu Phe Ile Asn Glu Lys Ile
        515                 520                 525

Leu Trp Ser Gly Phe Ser Arg Glu Val Pro Phe Ser Asn Cys Ser Arg
    530                 535                 540

Asp Cys Leu Ala Gly Thr Arg Lys Gly Ile Ile Glu Gly Glu Pro Thr
545                 550                 555                 560

Cys Cys Phe Glu Cys Val Glu Cys Pro Asp Gly Glu Tyr Ser Asp Glu
```

-continued

```
                565                 570                 575
Thr Asp Ala Ser Ala Cys Asn Lys Cys Pro Asp Asp Phe Trp Ser Asn
            580                 585                 590
Glu Asn His Thr Ser Cys Phe Glu Leu Pro Gln Glu Tyr Ile Arg Trp
            595                 600                 605
Gly Asp Ala Trp Ala Val Gly Pro Val Thr Ile Ala Cys Leu Gly Ala
610                 615                 620
Leu Ala Thr Leu Phe Val Leu Gly Val Phe Val Arg His Asn Ala Thr
625                 630                 635                 640
Pro Val Val Lys Ala Ser Gly Arg Glu Leu Cys Tyr Ile Leu Leu Gly
            645                 650                 655
Gly Val Phe Leu Cys Tyr Cys Met Thr Phe Ile Phe Ile Ala Lys Pro
            660                 665                 670
Ser Thr Ala Val Cys Thr Leu Arg Arg Leu Gly Leu Gly Thr Ala Phe
            675                 680                 685
Ser Val Cys Tyr Ser Ala Leu Leu Thr Lys Thr Asn Arg Ile Ala Arg
            690                 695                 700
Ile Phe Gly Gly Ala Arg Glu Gly Ala Gln Arg Pro Arg Phe Ile Ser
705                 710                 715                 720
Pro Ala Ser Gln Val Ala Ile Cys Leu Ala Leu Ile Ser Gly Gln Leu
            725                 730                 735
Leu Ile Val Val Ala Trp Leu Val Val Glu Ala Pro Gly Thr Gly Lys
            740                 745                 750
Glu Thr Ala Pro Glu Arg Arg Glu Val Val Thr Leu Arg Cys Asn His
            755                 760                 765
Arg Asp Ala Ser Met Leu Gly Ser Leu Ala Tyr Asn Val Leu Leu Ile
770                 775                 780
Ala Leu Cys Thr Leu Tyr Ala Phe Asn Thr Arg Lys Cys Pro Glu Asn
785                 790                 795                 800
Phe Asn Glu Ala Lys Phe Ile Gly Phe Thr Met Tyr Thr Thr Cys Ile
            805                 810                 815
Ile Trp Leu Ala Leu Leu Pro Ile Phe Tyr Val Thr Ser Ser Asp Tyr
            820                 825                 830
Arg Val Gln Thr Thr Thr Met Cys Val Ser Val Ser Leu Ser Gly Ser
            835                 840                 845
Val Val Leu Gly Cys Leu Phe Ala Pro Lys Leu His Ile Ile Leu Phe
850                 855                 860
Gln Pro Gln Lys Asn Val Val Ser His Arg Ala Pro Thr Ser Arg Phe
865                 870                 875                 880
Gly Ser Ala Ala Ala Arg Ala Ser Ser Leu Gly Gln Gly Ser Gly
            885                 890                 895
Ser Gln Phe Val Pro Thr Val Cys Asn Gly Arg Glu Val Val Asp Ser
            900                 905                 910
Thr Thr Ser Ser Leu Met Thr Leu Glu Ser Ile Met Ala Cys Cys Leu
            915                 920                 925
Ser Glu Glu Ala Lys Glu Ala Arg Arg Ile Asn Asp Glu Ile Glu Arg
            930                 935                 940
Gln Leu Arg Arg Asp Lys Arg Asp Ala Arg Arg Glu Leu Lys Leu Leu
945                 950                 955                 960
Leu Leu Gly Thr Gly Glu Ser Gly Lys Ser Thr Phe Ile Lys Gln Met
            965                 970                 975
Arg Ile Ile His Gly Ser Gly Tyr Ser Asp Glu Asp Lys Arg Gly Phe
            980                 985                 990
```

-continued

```
Thr Lys Leu Val Tyr Gln Asn Ile Phe Thr Ala Met Gln Ala Met Ile
        995                 1000                1005

Arg Ala Met Asp Thr Leu Lys Ile Pro Tyr Lys Tyr Glu His Asn
    1010                1015                1020

Lys Ala His Ala Gln Leu Val Arg Glu Val Asp Val Glu Lys Val
    1025                1030                1035

Ser Ala Phe Glu Asn Pro Tyr Val Asp Ala Ile Lys Ser Leu Trp
    1040                1045                1050

Asn Asp Pro Gly Ile Gln Glu Cys Tyr Asp Arg Arg Glu Tyr
    1055                1060                1065

Gln Leu Ser Asp Ser Thr Lys Tyr Tyr Leu Asn Asp Leu Asp Arg
    1070                1075                1080

Val Ala Asp Pro Ala Tyr Leu Pro Thr Gln Gln Asp Val Leu Arg
    1085                1090                1095

Val Arg Val Pro Thr Thr Gly Ile Ile Glu Tyr Pro Phe Asp Leu
    1100                1105                1110

Gln Ser Val Ile Phe Arg Met Val Asp Val Gly Gly Gln Arg Ser
    1115                1120                1125

Glu Arg Arg Lys Trp Ile His Cys Phe Glu Asn Val Thr Ser Ile
    1130                1135                1140

Met Phe Leu Val Ala Leu Ser Glu Tyr Asp Gln Val Leu Val Glu
    1145                1150                1155

Ser Asp Asn Glu Asn Arg Met Glu Glu Ser Lys Ala Leu Phe Arg
    1160                1165                1170

Thr Ile Ile Thr Tyr Pro Trp Phe Gln Asn Ser Ser Val Ile Leu
    1175                1180                1185

Phe Leu Asn Lys Lys Asp Leu Leu Glu Glu Lys Ile Met Tyr Ser
    1190                1195                1200

His Leu Val Asp Tyr Phe Pro Glu Tyr Asp Gly Pro Gln Arg Asp
    1205                1210                1215

Ala Gln Ala Ala Arg Glu Phe Ile Leu Lys Met Phe Val Asp Leu
    1220                1225                1230

Asn Pro Asp Ser Asp Lys Ile Ile Tyr Ser His Phe Thr Cys Ala
    1235                1240                1245

Thr Asp Thr Glu Asn Ile Arg Phe Val Phe Ala Ala Val Lys Asp
    1250                1255                1260

Thr Ile Leu Gln Leu Asn Leu Lys Asp Cys Gly Leu Phe
    1265                1270                1275
```

<210> SEQ ID NO 34
<211> LENGTH: 3105
<212> TYPE: DNA
<213> ORGANISM: Artificial Sequence
<220> FEATURE:
<221> NAME/KEY: misc_feature
<223> OTHER INFORMATION: chimeric hmGluR1/hCaR

<400> SEQUENCE: 34

```
atgggatcgc tgcttgcgct cccggcactg ctgctgctgt ggggtgctgt ggctgagggc      60
ccagccaaga aggtgctgac cctggaggga gacttggtgc tggtgggct gttcccagtg     120 caccagaagg gcggcccagc agaggactgt ggtcctgtca atgagcaccg tgcatccag     180 cgcctggagg ccatgctttt tgcactggac cgcatcaacc gtgacccgca cctgctgcct     240
ggcgtgcgcc tgggtgcaca catcctcgac agttgctcca aggacacaca tgcgctggag     300
```

-continued

| | |
|---|---|
| caggcactgg actttgtgcg tgcctcactc agccgtggtg ctgatggctc acgccacatc | 360 |
| tgccccgacg gctcttatgc gacccatggt gatgctccca ctgccatcac tggtgttatt | 420 |
| ggcggttcct acagtgatgt ctccatccag gtggccaacc tcttgaggct atttcagatc | 480 |
| ccacagatta gctacgcctc taccagtgcc aagctgagtg acaagtcccg ctatgactac | 540 |
| tttgcccgca cagtgcctcc tgacttcttc aagccaagg ccatggctga gattctccgc | 600 |
| ttcttcaact ggacctatgt gtccactgtg gcgtctgagg gcgactatgg cgagacaggc | 660 |
| attgaggcct ttgagctaga ggctcgtgcc cgcaacatct gtgtggccac ctcggagaaa | 720 |
| gtgggccgtg ccatgagccg cgcggccttt gagggtgtgg tgcgagccct gctgcagaag | 780 |
| cccagtgccc gcgtggctgt cctgttcacc cgttctgagg atgcccggga gctgcttgct | 840 |
| gccagccagc gcctcaatgc cagcttcacc tgggtggcca gtgatggttg ggggccctg | 900 |
| gagagtgtgg tggcaggcag tgagggggct gctgagggtg ctatcaccat cgagctggcc | 960 |
| tcctacccca tcagtgactt tgcctcctac ttccagagcc tggaccttg gaacaacagc | 1020 |
| cggaacccct ggttccgtga attctgggag cagaggttcc gctgcagctt ccggcagcga | 1080 |
| gactgcgcag cccactctct ccgggctgtg ccctttgagc aggagtccaa gatcatgttt | 1140 |
| gtggtcaatg cagtgtacgc catggcccat gcgctccaca acatgcaccg tgccctctgc | 1200 |
| cccaacacca cccggctctg tgacgcgatg cggccagtta acgggcgccg cctctacaag | 1260 |
| gactttgtgc tcaacgtcaa gtttgatgcc cccttcgcc cagctgacac ccacaatgag | 1320 |
| gtccgctttg accgctttgg tgatggtatt ggccgctaca acatcttcac ctatctgcgt | 1380 |
| gcaggcagtg ggcgctatcg ctaccagaag gtgggctact gggcagaagg cttgactctg | 1440 |
| gacaccagcc tcatcccatg ggcctcaccc tcagccggcc ccctgcccgc ctctcgctgc | 1500 |
| agtgagccct gcctccagaa tgaggtgaag agtgtgcagc cgggcgaagt ctgctgctgg | 1560 |
| ctctgcattc cgtgccagcc ctatgagtac cgattggacg aattcacttg cgctgattgt | 1620 |
| ggcctgggct actggcccaa tgccagcctg actggctgct cgaactgcc ccaggagtac | 1680 |
| atccgctggg gcgatgcctg ggctgtggga cctgtcacca tcgcctgcct cggtgccctg | 1740 |
| gccaccctct ttgtgctggg tgtctttgtg cggcacaatg ccacaccagt ggtcaaggcc | 1800 |
| tcaggtcggg agctctgcta catcctgctg gtggtgtctc tcctctgcta ctgcatgacc | 1860 |
| ttcatcttca ttgccaagcc atccacggca gtgtgtacct tacggcgtct tggtttgggc | 1920 |
| actgccttct ctgtctgcta ctcagccctc tcaccaaga ccaaccgcat tgcacgcatc | 1980 |
| ttcggtgggg cccgggaggg tgcccagcgg ccacgcttca tcagtcctgc ctcacaggtg | 2040 |
| gccatctgcc tggcacttat ctcgggccag ctgctcatcg tggtcgcctg gctggtggtg | 2100 |
| gaggcaccgg gcacaggcaa ggagacagcc cccgaacggc gggaggtggt gacactgcgc | 2160 |
| tgcaaccacc gcgatgcaag tatgttgggc tcgctggcct acaatgtgct cctcatcgcg | 2220 |
| ctctgcacgc tttatgcctt caagactcgc aagtgccccg aaaacttcaa cgaggccaag | 2280 |
| ttcattggct tcaccatgta caccacctgc atcatctggc tggcattcct gcccatcttc | 2340 |
| tatgtcacct ccagtgacta ccgggtacag accaccacca tgtgcgtgtc agtcagcctc | 2400 |
| agcggctccg tggtgcttgg ctgcctcttt gcgcccaagc tgcacatcat cctcttccag | 2460 |
| ccgcagaaga acaccatcga ggaggtgcgt tgcagcaccg cagctcacgc tttcaaggtg | 2520 |
| gctgcccggg ccacgctgcg ccgcagcaac gtctcccgca gcggtccag cagccttgga | 2580 |
| ggctccacgg gatccacccc ctcctcctcc atcagcagca gagcaacag cgaagaccca | 2640 |
| ttcccacagc ccgagaggca gaagcagcag cagccgctgg ccctaaccca gcaagagcag | 2700 |

-continued

```
cagcagcagc ccctgaccct cccacagcag caacgatctc agcagcagcc cagatgcaag    2760
cagaaggtca tctttggcag cggcacggtc accttctcac tgagctttga tgagcctcag    2820
aagaacgcca tggcccacgg gaattctacg caccagaact ccctggaggc ccagaaaagc    2880
agcgatacgc tgacccgaca ccagccatta ctcccgctgc agtgcgggga acggactta    2940 gatctgaccg tccaggaaac aggtctgcaa ggacctgtgg gtggagacca gcggccagag    3000
gtggaggacc ctgaagagtt gtccccagca cttgtagtgt ccagttcaca gagctttgtc    3060
atcagtggtg gaggcagcac tgttacagaa aacgtagtga attca                    3105
```

<210> SEQ ID NO 35
<211> LENGTH: 1035
<212> TYPE: PRT
<213> ORGANISM: Artificial Sequence
<220> FEATURE:
<221> NAME/KEY: misc_feature
<223> OTHER INFORMATION: chimeric hmGluR1/hCaR

<400> SEQUENCE: 35

```
Met Gly Ser Leu Leu Ala Leu Pro Ala Leu Leu Leu Trp Gly Ala
1               5                   10                  15

Val Ala Glu Gly Pro Ala Lys Lys Val Leu Thr Leu Glu Gly Asp Leu
            20                  25                  30

Val Leu Gly Gly Leu Phe Pro Val His Gln Lys Gly Gly Pro Ala Glu
        35                  40                  45

Asp Cys Gly Pro Val Asn Glu His Arg Gly Ile Gln Arg Leu Glu Ala
    50                  55                  60

Met Leu Phe Ala Leu Asp Arg Ile Asn Arg Asp Pro His Leu Leu Pro
65                  70                  75                  80

Gly Val Arg Leu Gly Ala His Ile Leu Asp Ser Cys Ser Lys Asp Thr
                85                  90                  95

His Ala Leu Glu Gln Ala Leu Asp Phe Val Arg Ala Ser Leu Ser Arg
            100                 105                 110

Gly Ala Asp Gly Ser Arg His Ile Cys Pro Asp Gly Ser Tyr Ala Thr
        115                 120                 125

His Gly Asp Ala Pro Thr Ala Ile Thr Gly Val Ile Gly Gly Ser Tyr
    130                 135                 140

Ser Asp Val Ser Ile Gln Val Ala Asn Leu Leu Arg Leu Phe Gln Ile
145                 150                 155                 160

Pro Gln Ile Ser Tyr Ala Ser Thr Ser Ala Lys Leu Ser Asp Lys Ser
                165                 170                 175

Arg Tyr Asp Tyr Phe Ala Arg Thr Val Pro Pro Asp Phe Phe Gln Ala
            180                 185                 190

Lys Ala Met Ala Glu Ile Leu Arg Phe Phe Asn Trp Thr Tyr Val Ser
        195                 200                 205

Thr Val Ala Ser Glu Gly Asp Tyr Gly Glu Thr Gly Ile Glu Ala Phe
    210                 215                 220

Glu Leu Glu Ala Arg Ala Arg Asn Ile Cys Val Ala Thr Ser Glu Lys
225                 230                 235                 240

Val Gly Arg Ala Met Ser Arg Ala Ala Phe Glu Gly Val Val Arg Ala
                245                 250                 255

Leu Leu Gln Lys Pro Ser Ala Arg Val Ala Val Leu Phe Thr Arg Ser
            260                 265                 270

Glu Asp Ala Arg Glu Leu Leu Ala Ala Ser Gln Arg Leu Asn Ala Ser
        275                 280                 285
```

-continued

```
Phe Thr Trp Val Ala Ser Asp Gly Trp Gly Ala Leu Glu Ser Val Val
    290                 295                 300
Ala Gly Ser Glu Gly Ala Ala Glu Gly Ala Ile Thr Ile Glu Leu Ala
305                 310                 315                 320
Ser Tyr Pro Ile Ser Asp Phe Ala Ser Tyr Phe Gln Ser Leu Asp Pro
                325                 330                 335
Trp Asn Asn Ser Arg Asn Pro Trp Phe Arg Glu Phe Trp Glu Gln Arg
            340                 345                 350
Phe Arg Cys Ser Phe Arg Gln Arg Asp Cys Ala Ala His Ser Leu Arg
        355                 360                 365
Ala Val Pro Phe Glu Gln Glu Ser Lys Ile Met Phe Val Asn Ala
370                 375                 380
Val Tyr Ala Met Ala His Ala Leu His Asn Met His Arg Ala Leu Cys
385                 390                 395                 400
Pro Asn Thr Thr Arg Leu Cys Asp Ala Met Arg Pro Val Asn Gly Arg
                405                 410                 415
Arg Leu Tyr Lys Asp Phe Val Leu Asn Val Lys Phe Asp Ala Pro Phe
            420                 425                 430
Arg Pro Ala Asp Thr His Asn Glu Val Arg Phe Asp Arg Phe Gly Asp
        435                 440                 445
Gly Ile Gly Arg Tyr Asn Ile Phe Thr Tyr Leu Arg Ala Gly Ser Gly
    450                 455                 460
Arg Tyr Arg Tyr Gln Lys Val Gly Tyr Trp Ala Glu Gly Leu Thr Leu
465                 470                 475                 480
Asp Thr Ser Leu Ile Pro Trp Ala Ser Pro Ser Ala Gly Pro Leu Pro
                485                 490                 495
Ala Ser Arg Cys Ser Glu Pro Cys Leu Gln Asn Glu Val Lys Ser Val
            500                 505                 510
Gln Pro Gly Glu Val Cys Cys Trp Leu Cys Ile Pro Cys Gln Pro Tyr
        515                 520                 525
Glu Tyr Arg Leu Asp Glu Phe Thr Cys Ala Asp Cys Gly Leu Gly Tyr
    530                 535                 540
Trp Pro Asn Ala Ser Leu Thr Gly Cys Phe Glu Leu Pro Gln Glu Tyr
545                 550                 555                 560
Ile Arg Trp Gly Asp Ala Trp Ala Val Gly Pro Val Thr Ile Ala Cys
                565                 570                 575
Leu Gly Ala Leu Ala Thr Leu Phe Val Leu Gly Val Phe Val Arg His
            580                 585                 590
Asn Ala Thr Pro Val Val Lys Ala Ser Gly Arg Glu Leu Cys Tyr Ile
        595                 600                 605
Leu Leu Gly Gly Val Phe Leu Cys Tyr Cys Met Thr Phe Ile Phe Ile
    610                 615                 620
Ala Lys Pro Ser Thr Ala Val Cys Thr Leu Arg Arg Leu Gly Leu Gly
625                 630                 635                 640
Thr Ala Phe Ser Val Cys Tyr Ser Ala Leu Leu Thr Lys Thr Asn Arg
                645                 650                 655
Ile Ala Arg Ile Phe Gly Gly Ala Arg Glu Gly Ala Gln Arg Pro Arg
            660                 665                 670
Phe Ile Ser Pro Ala Ser Gln Val Ala Ile Cys Leu Ala Leu Ile Ser
        675                 680                 685
Gly Gln Leu Leu Ile Val Val Ala Trp Leu Val Val Glu Ala Pro Gly
    690                 695                 700
```

-continued

```
Thr Gly Lys Glu Thr Ala Pro Glu Arg Arg Glu Val Val Thr Leu Arg
705                 710                 715                 720

Cys Asn His Arg Asp Ala Ser Met Leu Gly Ser Leu Ala Tyr Asn Val
            725                 730                 735

Leu Leu Ile Ala Leu Cys Thr Leu Tyr Ala Phe Lys Thr Arg Lys Cys
        740                 745                 750

Pro Glu Asn Phe Asn Glu Ala Lys Phe Ile Gly Phe Thr Met Tyr Thr
    755                 760                 765

Thr Cys Ile Ile Trp Leu Ala Phe Leu Pro Ile Phe Tyr Val Thr Ser
770                 775                 780

Ser Asp Tyr Arg Val Gln Thr Thr Met Cys Val Ser Val Ser Leu
785                 790                 795                 800

Ser Gly Ser Val Val Leu Gly Cys Leu Phe Ala Pro Lys Leu His Ile
                805                 810                 815

Ile Leu Phe Gln Pro Gln Lys Asn Thr Ile Glu Glu Val Arg Cys Ser
            820                 825                 830

Thr Ala Ala His Ala Phe Lys Val Ala Ala Arg Ala Thr Leu Arg Arg
        835                 840                 845

Ser Asn Val Ser Arg Lys Arg Ser Ser Ser Leu Gly Gly Ser Thr Gly
850                 855                 860

Ser Thr Pro Ser Ser Ser Ile Ser Ser Lys Ser Asn Ser Glu Asp Pro
865                 870                 875                 880

Phe Pro Gln Pro Glu Arg Gln Lys Gln Gln Pro Leu Ala Leu Thr
                885                 890                 895

Gln Gln Glu Gln Gln Gln Pro Leu Thr Leu Pro Gln Gln Gln Arg
            900                 905                 910

Ser Gln Gln Gln Pro Arg Cys Lys Gln Lys Val Ile Phe Gly Ser Gly
        915                 920                 925

Thr Val Thr Phe Ser Leu Ser Phe Asp Glu Pro Gln Lys Asn Ala Met
930                 935                 940

Ala His Gly Asn Ser Thr His Gln Asn Ser Leu Glu Ala Gln Lys Ser
945                 950                 955                 960

Ser Asp Thr Leu Thr Arg His Gln Pro Leu Leu Pro Leu Gln Cys Gly
                965                 970                 975

Glu Thr Asp Leu Asp Leu Thr Val Gln Glu Thr Gly Leu Gln Gly Pro
            980                 985                 990

Val Gly Gly Asp Gln Arg Pro Glu  Val Glu Asp Pro Glu  Glu Leu Ser
        995                 1000                1005

Pro Ala  Leu Val Val Ser Ser  Ser Gln Ser Phe Val  Ile Ser Gly
    1010                1015                1020

Gly Gly  Ser Thr Val Thr Glu  Asn Val Val Asn Ser
    1025                1030                1035
```

<210> SEQ ID NO 36
<211> LENGTH: 4185
<212> TYPE: DNA
<213> ORGANISM: Artificial Sequence
<220> FEATURE:
<221> NAME/KEY: misc_feature
<223> OTHER INFORMATION: pmGluR2//CaR*G qi5 fusion construct

<400> SEQUENCE: 36

```
atgggatcgc tgcttgcgct cccggcactg ctgctgctgt ggggtgctgt ggctgagggc      60
ccagccaaga aggtgctgac cctggaggga gacttggtgc tgggtgggct gttcccagtg     120
caccagaagg gcggcccagc agaggactgt ggtcctgtca atgagcaccg tggcatccag     180
```

-continued

```
cgcctggagg ccatgctttt tgcactggac cgcatcaacc gtgacccgca cctgctgcct      240
ggcgtgcgcc tgggtgcaca catcctcgac agttgctcca aggacacaca tgcgctggag      300
caggcactgg actttgtgcg tgcctcactc agccgtggtg ctgatggctc acgccacatc      360
tgccccgacg gctcttatgc gacccatggt gatgctccca ctgccatcac tggtgttatt      420
ggcggttcct acagtgatgt ctccatccag gtggccaacc tcttgaggct atttcagatc      480
ccacagatta gctacgcctc taccagtgcc aagctgagtg acaagtcccg ctatgactac      540
tttgcccgca cagtgcctcc tgacttcttc caagccaagg ccatggctga gattctccgc      600
ttcttcaact ggacctatgt gtccactgtg gcgtctgagg gcgactatgg cgagacaggc      660
attgaggcct ttgagctaga ggctcgtgcc cgcaacatct gtgtggccac ctcggagaaa      720
gtgggccgtg ccatgagccg cgcggccttt gagggtgtgg tgcgagccct gctgcagaag      780
cccagtgccc gcgtggctgt cctgttcacc cgttctgagg atgcccggga gctgcttgct      840
gccagccagc gcctcaatgc cagcttcacc tgggtggcca gtgatggttg gggggccctg      900
gagagtgtgg tggcaggcag tgaggggggct gctgagggtg ctatcaccat cgagctggcc      960
tcctacccca tcagtgactt tgcctcctac ttccagagcc tggacccttg aacaacagc     1020 cggaacccct ggttccgtga attctgggag cagaggttcc gctgcagctt ccggcagcga     1080
gactgcgcag cccactctct ccgggctgtg cccttgagc aggagtccaa gatcatgttt     1140
gtggtcaatg cagtgtacgc catggcccat gcgctccaca acatgcaccg tgccctctgc     1200
cccaacacca cccggctctg tgacgcgatg cggccagtta acgggcgccg cctctacaag     1260
gactttgtgc tcaacgtcaa gtttgatgcc ccctttcgcc cagctgacac ccacaatgag     1320
gtccgctttg accgctttgg tgatggtatt ggccgctaca acatcttcac ctatctgcgt     1380
gcaggcagtg ggcgctatcg ctaccagaag gtgggctact gggcagaagg cttgactctg     1440
gacaccagcc tcatcccatg ggcctcaccc tcagccggcc cctgcccgc ctctcgctgc     1500 agtgagccct gcctccagaa tgaggtgaag agtgtgcagc cgggcgaagt ctgctgctgg     1560
ctctgcattc cgtgccagcc ctatgagtac cgattggacg aattcacttg cgctgattgt     1620
ggcctgggct actggcccaa tgccagcctg actggctgct tcgaactgcc ccaggagtac     1680
atccgctggg gcgatgcctg ggctgtggga cctgtcacca tcgcctgcct cggtgccctg     1740
gccaccctct ttgtgctggg tgtctttgtg cggcacaatg ccacaccagt ggtcaaggcc     1800
tcaggtcgga gctctgctca catcctgctg ggtggtgtct tcctctgcta ctgcatgacc     1860
ttcatcttca ttgccaagcc atccacggca gtgtgtacct acggcgtct tggtttgggc     1920 actgccttct ctgtctgcta ctcagccctg ctcaccaaga ccaaccgcat gcacgcatc     1980 ttcggtgggg cccgggaggg tgcccagcgg ccacgcttca tcagtcctgc ctcacaggtg     2040
gccatctgcc tggcacttat ctcgggccag ctgctcatcg tggtcgcctg ctggtggtg     2100 gaggcaccgg gcacaggcaa ggagacagcc cccgaacggc gggaggtggt gacactgcgc     2160
tgcaaccacc gcgatgcaag tatgttgggc tcgctggcct acaatgtgct cctcatcgcg     2220
ctctgcacgc tttatgcctt caagactcgc aagtgccccg aaaacttcaa cgaggccaag     2280
ttcattggct tcaccatgta caccacctgc atcatctggc tggcattcct gcccatcttc     2340
tatgtcacct ccagtgacta ccgggtacag accaccacca tgtgcgtgtc agtcagcctc     2400
agcggctccg tggtgcttgg ctgcctcttt gcgcccaagc tgcacatcat cctcttccag     2460
ccgcagaaga acaccatcga ggaggtgcgt tgcagcaccg cagctcacgc tttcaaggtg     2520
```

-continued

```
gctgcccggg ccacgctgcg ccgcagcaac gtctcccgca agcggtccag cagccttgga    2580
ggctccacgg gatccacccc ctcctcctcc atcagcagca gagcaacag cgaagaccca     2640 ttcccacagc ccgagaggca gaagcagcag cagccgctgg ccctaaccca gcaagagcag    2700
cagcagcagc ccctgaccct cccacagcag caacgatctc agcagcagcc cagatgcaag    2760
cagaaggtca tctttggcag cggcacggtc accttctcac tgagctttga tgagcctcag    2820
aagaacgcca tgcccacgg gaattctacg caccagaact ccctggaggc ccagaaaagc     2880
agcgatacgc tgacccgaca ccagccatta ctcccgctgc agtgcgggga aacggactta    2940
gatctgaccg tccaggaaac aggtctgcaa ggacctgtgg gtggagacca gcggccagag    3000
gtggaggacc ctgaagagtt gtccccagca cttgtagtgt ccagttcaca gagctttgtc    3060
atcagtggtg gaggcagcac tgttacagaa acgtagtga attcaatgac tctggagtcc     3120
atcatggcgt gctgcctgag cgaggaggcc aaggaagccc ggcggatcaa cgacgagatc    3180
gagcggcagc tccgcaggga caagcgggac gcccgccggg agctcaagct gctgctgctc    3240
gggacaggag agagtggcaa gagtacgttt atcaagcaga tgagaatcat ccatgggtca    3300
ggatactctg atgaagataa aaggggcttc accaagctgg tgtatcagaa catcttcacg    3360
gccatgcagg ccatgatcag agccatggac acactcaaga tcccatacaa gtatgagcac    3420
aataaggctc atgcacaatt agttcgagaa gttgatgtgg agaaggtgtc tgcttttgag    3480
aatccatatg tagatgcaat aaagagttta tggaatgatc ctggaatcca ggaatgctat    3540
gatagacgac gagaatatca attatctgac tctaccaaat actatcttaa tgacttggac    3600
cgcgtagctg accctgccta cctgcctacg caacaagatg tgcttagagt tcgagtcccc    3660
accacaggga tcatcgaata ccccctttgac ttacaaagtg tcatttttcag aatggtcgat    3720 gtaggggggcc aaaggtcaga gagaagaaaa tggatacact gctttgaaaa tgtcacctct    3780
atcatgtttc tagtagcgct tagtgaatat gatcaagttc tcgtggagtc agacaatgag    3840
aaccgaatgg aggaaagcaa ggctctcttt agaacaatta tcacataccc ctggttccag    3900
aactcctcgg ttattctgtt cttaaacaag aaagatcttc tagaggagaa atcatgtat    3960 tcccatctag tcgactactt cccagaatat gatggacccc agagagatgc ccaggcagcc    4020
cgagaattca ttctgaagat gttcgtggac ctgaacccag acagtgacaa aattatctac    4080
tcccacttca cgtgcgccac agacaccgag aatatccgct ttgtctttgc tgccgtcaag    4140
gacaccatcc tccagttgaa cctgaaggac tgcggtctgt tctaa                    4185
```

<210> SEQ ID NO 37
<211> LENGTH: 1394
<212> TYPE: PRT
<213> ORGANISM: Artificial Sequence
<220> FEATURE:
<221> NAME/KEY: misc_feature
<223> OTHER INFORMATION: pmGluR2//CaR*G qi5 fusion construct

<400> SEQUENCE: 37

```
Met Gly Ser Leu Leu Ala Leu Pro Ala Leu Leu Leu Trp Gly Ala
1               5                   10                  15

Val Ala Glu Gly Pro Ala Lys Lys Val Leu Thr Leu Glu Gly Asp Leu
            20                  25                  30

Val Leu Gly Gly Leu Phe Pro Val His Gln Lys Gly Gly Pro Ala Glu
        35                  40                  45

Asp Cys Gly Pro Val Asn Glu His Arg Gly Ile Gln Arg Leu Glu Ala
    50                  55                  60
```

```
Met Leu Phe Ala Leu Asp Arg Ile Asn Arg Asp Pro His Leu Leu Pro
 65                  70                  75                  80

Gly Val Arg Leu Gly Ala His Ile Leu Asp Ser Cys Ser Lys Asp Thr
                 85                  90                  95

His Ala Leu Glu Gln Ala Leu Asp Phe Val Arg Ala Ser Leu Ser Arg
            100                 105                 110

Gly Ala Asp Gly Ser Arg His Ile Cys Pro Asp Gly Ser Tyr Ala Thr
            115                 120                 125

His Gly Asp Ala Pro Thr Ala Ile Thr Gly Val Ile Gly Gly Ser Tyr
        130                 135                 140

Ser Asp Val Ser Ile Gln Val Ala Asn Leu Leu Arg Leu Phe Gln Ile
145                 150                 155                 160

Pro Gln Ile Ser Tyr Ala Ser Thr Ser Ala Lys Leu Ser Asp Lys Ser
                165                 170                 175

Arg Tyr Asp Tyr Phe Ala Arg Thr Val Pro Pro Asp Phe Phe Gln Ala
                180                 185                 190

Lys Ala Met Ala Glu Ile Leu Arg Phe Phe Asn Trp Thr Tyr Val Ser
            195                 200                 205

Thr Val Ala Ser Glu Gly Asp Tyr Gly Glu Thr Gly Ile Glu Ala Phe
210                 215                 220

Glu Leu Glu Ala Arg Ala Arg Asn Ile Cys Val Ala Thr Ser Glu Lys
225                 230                 235                 240

Val Gly Arg Ala Met Ser Arg Ala Ala Phe Glu Gly Val Val Arg Ala
                245                 250                 255

Leu Leu Gln Lys Pro Ser Ala Arg Val Ala Val Leu Phe Thr Arg Ser
                260                 265                 270

Glu Asp Ala Arg Glu Leu Leu Ala Ala Ser Gln Arg Leu Asn Ala Ser
            275                 280                 285

Phe Thr Trp Val Ala Ser Asp Gly Trp Gly Ala Leu Glu Ser Val Val
        290                 295                 300

Ala Gly Ser Glu Gly Ala Ala Glu Gly Ala Ile Thr Ile Glu Leu Ala
305                 310                 315                 320

Ser Tyr Pro Ile Ser Asp Phe Ala Ser Tyr Phe Gln Ser Leu Asp Pro
                325                 330                 335

Trp Asn Asn Ser Arg Asn Pro Trp Phe Arg Glu Phe Trp Glu Gln Arg
                340                 345                 350

Phe Arg Cys Ser Phe Arg Gln Arg Asp Cys Ala Ala His Ser Leu Arg
            355                 360                 365

Ala Val Pro Phe Glu Gln Glu Ser Lys Ile Met Phe Val Val Asn Ala
        370                 375                 380

Val Tyr Ala Met Ala His Ala Leu His Asn Met His Arg Ala Leu Cys
385                 390                 395                 400

Pro Asn Thr Thr Arg Leu Cys Asp Ala Met Arg Pro Val Asn Gly Arg
                405                 410                 415

Arg Leu Tyr Lys Asp Phe Val Leu Asn Val Lys Phe Asp Ala Pro Phe
                420                 425                 430

Arg Pro Ala Asp Thr His Asn Glu Val Arg Phe Asp Arg Phe Gly Asp
            435                 440                 445

Gly Ile Gly Arg Tyr Asn Ile Phe Thr Tyr Leu Arg Ala Gly Ser Gly
        450                 455                 460

Arg Tyr Arg Tyr Gln Lys Val Gly Tyr Trp Ala Glu Gly Leu Thr Leu
465                 470                 475                 480

Asp Thr Ser Leu Ile Pro Trp Ala Ser Pro Ser Ala Gly Pro Leu Pro
```

-continued

```
                485                 490                 495
Ala Ser Arg Cys Ser Glu Pro Cys Leu Gln Asn Glu Val Lys Ser Val
            500                 505                 510
Gln Pro Gly Glu Val Cys Cys Trp Leu Cys Ile Pro Cys Gln Pro Tyr
            515                 520                 525
Glu Tyr Arg Leu Asp Glu Phe Thr Cys Ala Asp Cys Gly Leu Gly Tyr
            530                 535                 540
Trp Pro Asn Ala Ser Leu Thr Gly Cys Phe Glu Leu Pro Gln Glu Tyr
545                 550                 555                 560
Ile Arg Trp Gly Asp Ala Trp Ala Val Gly Pro Val Thr Ile Ala Cys
            565                 570                 575
Leu Gly Ala Leu Ala Thr Leu Phe Val Leu Gly Val Phe Val Arg His
            580                 585                 590
Asn Ala Thr Pro Val Val Lys Ala Ser Gly Arg Glu Leu Cys Tyr Ile
            595                 600                 605
Leu Leu Gly Gly Val Phe Leu Cys Tyr Cys Met Thr Phe Ile Phe Ile
            610                 615                 620
Ala Lys Pro Ser Thr Ala Val Cys Thr Leu Arg Arg Leu Gly Leu Gly
625                 630                 635                 640
Thr Ala Phe Ser Val Cys Tyr Ser Ala Leu Leu Thr Lys Thr Asn Arg
            645                 650                 655
Ile Ala Arg Ile Phe Gly Gly Ala Arg Glu Gly Ala Gln Arg Pro Arg
            660                 665                 670
Phe Ile Ser Pro Ala Ser Gln Val Ala Ile Cys Leu Ala Leu Ile Ser
            675                 680                 685
Gly Gln Leu Leu Ile Val Val Ala Trp Leu Val Val Glu Ala Pro Gly
            690                 695                 700
Thr Gly Lys Glu Thr Ala Pro Glu Arg Arg Glu Val Val Thr Leu Arg
705                 710                 715                 720
Cys Asn His Arg Asp Ala Ser Met Leu Gly Ser Leu Ala Tyr Asn Val
            725                 730                 735
Leu Leu Ile Ala Leu Cys Thr Leu Tyr Ala Phe Lys Thr Arg Lys Cys
            740                 745                 750
Pro Glu Asn Phe Asn Glu Ala Lys Phe Ile Gly Phe Thr Met Tyr Thr
            755                 760                 765
Thr Cys Ile Ile Trp Leu Ala Phe Leu Pro Ile Phe Tyr Val Thr Ser
            770                 775                 780
Ser Asp Tyr Arg Val Gln Thr Thr Thr Met Cys Val Ser Val Ser Leu
785                 790                 795                 800
Ser Gly Ser Val Val Leu Gly Cys Leu Phe Ala Pro Lys Leu His Ile
            805                 810                 815
Ile Leu Phe Gln Pro Gln Lys Asn Thr Ile Glu Glu Val Arg Cys Ser
            820                 825                 830
Thr Ala His Ala Phe Lys Val Ala Ala Arg Ala Thr Leu Arg Arg
            835                 840                 845
Ser Asn Val Ser Arg Lys Arg Ser Ser Ser Leu Gly Gly Ser Thr Gly
850                 855                 860
Ser Thr Pro Ser Ser Ser Ile Ser Ser Lys Ser Asn Ser Glu Asp Pro
865                 870                 875                 880
Phe Pro Gln Pro Glu Arg Gln Lys Gln Gln Gln Pro Leu Ala Leu Thr
            885                 890                 895
Gln Gln Glu Gln Gln Gln Pro Leu Thr Leu Pro Gln Gln Arg
            900                 905                 910
```

```
Ser Gln Gln Gln Pro Arg Cys Lys Gln Lys Val Ile Phe Gly Ser Gly
        915                 920                 925
Thr Val Thr Phe Ser Leu Ser Phe Asp Glu Pro Gln Lys Asn Ala Met
        930                 935                 940
Ala His Gly Asn Ser Thr His Gln Asn Ser Leu Glu Ala Gln Lys Ser
945                 950                 955                 960
Ser Asp Thr Leu Thr Arg His Gln Pro Leu Pro Leu Gln Cys Gly
            965                 970                 975
Glu Thr Asp Leu Asp Leu Thr Val Gln Glu Thr Gly Leu Gln Gly Pro
                980                 985                 990
Val Gly Gly Asp Gln Arg Pro Glu Val Glu Asp Pro Glu Glu Leu Ser
        995                 1000                1005
Pro Ala Leu Val Val Ser Ser Gln Ser Phe Val Ile Ser Gly
        1010                1015                1020
Gly Gly Ser Thr Val Thr Glu Asn Val Val Asn Ser Met Thr Leu
        1025                1030                1035
Glu Ser Ile Met Ala Cys Cys Leu Ser Glu Glu Ala Lys Glu Ala
        1040                1045                1050
Arg Arg Ile Asn Asp Glu Ile Glu Arg Gln Leu Arg Arg Asp Lys
        1055                1060                1065
Arg Asp Ala Arg Arg Glu Leu Lys Leu Leu Leu Leu Gly Thr Gly
        1070                1075                1080
Glu Ser Gly Lys Ser Thr Phe Ile Lys Gln Met Arg Ile Ile His
        1085                1090                1095
Gly Ser Gly Tyr Ser Asp Glu Asp Lys Arg Gly Phe Thr Lys Leu
        1100                1105                1110
Val Tyr Gln Asn Ile Phe Thr Ala Met Gln Ala Met Ile Arg Ala
        1115                1120                1125
Met Asp Thr Leu Lys Ile Pro Tyr Lys Tyr Glu His Asn Lys Ala
        1130                1135                1140
His Ala Gln Leu Val Arg Glu Val Asp Val Glu Lys Val Ser Ala
        1145                1150                1155
Phe Glu Asn Pro Tyr Val Asp Ala Ile Lys Ser Leu Trp Asn Asp
        1160                1165                1170
Pro Gly Ile Gln Glu Cys Tyr Asp Arg Arg Arg Glu Tyr Gln Leu
        1175                1180                1185
Ser Asp Ser Thr Lys Tyr Tyr Leu Asn Asp Leu Asp Arg Val Ala
        1190                1195                1200
Asp Pro Ala Tyr Leu Pro Thr Gln Gln Asp Val Leu Arg Val Arg
        1205                1210                1215
Val Pro Thr Thr Gly Ile Ile Glu Tyr Pro Phe Asp Leu Gln Ser
        1220                1225                1230
Val Ile Phe Arg Met Val Asp Val Gly Gly Gln Arg Ser Glu Arg
        1235                1240                1245
Arg Lys Trp Ile His Cys Phe Glu Asn Val Thr Ser Ile Met Phe
        1250                1255                1260
Leu Val Ala Leu Ser Glu Tyr Asp Gln Val Leu Val Glu Ser Asp
        1265                1270                1275
Asn Glu Asn Arg Met Glu Glu Ser Lys Ala Leu Phe Arg Thr Ile
        1280                1285                1290
Ile Thr Tyr Pro Trp Phe Gln Asn Ser Ser Val Ile Leu Phe Leu
        1295                1300                1305
```

| | | | | | | | | | | |
|---|---|---|---|---|---|---|---|---|---|---|
| Asn | Lys | Lys | Asp | Leu | Leu | Glu | Glu | Lys | Ile | Met | Tyr | Ser | His | Leu |
| | 1310 | | | | 1315 | | | | 1320 | |

Val Asp Tyr Phe Pro Glu Tyr Asp Gly Pro Gln Arg Asp Ala Gln
    1325                1330                1335

Ala Ala Arg Glu Phe Ile Leu Lys Met Phe Val Asp Leu Asn Pro
    1340                1345                1350

Asp Ser Asp Lys Ile Ile Tyr Ser His Phe Thr Cys Ala Thr Asp
    1355                1360                1365

Thr Glu Asn Ile Arg Phe Val Phe Ala Ala Val Lys Asp Thr Ile
    1370                1375                1380

Leu Gln Leu Asn Leu Lys Asp Cys Gly Leu Phe
    1385                1390

```
<210> SEQ ID NO 38
<211> LENGTH: 3177
<212> TYPE: DNA
<213> ORGANISM: Artificial Sequence
<220> FEATURE:
<221> NAME/KEY: misc_feature
<223> OTHER INFORMATION: chimeric hmGluR8/hCaR

<400> SEQUENCE: 38
atggtatgcg agggaaagcg atcagcctct tgcccttgtt tcttcctctt gaccgccaag      60
ttctactgga tcctcacaat gatgcaaaga actcacagcc aggagtatgc ccattccata     120
cgggtggatg gggacattat tttggggggt ctcttccctg ccacgcaaa gggagagaga     180 ggggtgcctt gtggggagct gaagaaggaa aaggggattc acagactgga ggccatgctt     240
tatgcaattg accagattaa caaggaccct gatctccttt ccaacatcac tctgggtgtc     300
cgcatcctcg acacgtgctc tagggacacc tatgctttgg agcagtctct aacattcgtg     360
caggcattaa tagagaaaga tgcttcggat gtgaagtgtg ctaatggaga tccacccatt     420
ttcaccaagc ccgacaagat ttctggcgtc ataggtgctg cagcaagctc cgtgtccatc     480
atggttgcta acattttaag acttttttaag atacctcaaa tcagctatgc atccacagcc     540
ccagagctaa gtgataacac caggtatgac ttttttctctc gagtggttcc gcctgactcc     600
taccaagccc aagccatggt ggacatcgtg acagcactgg gatggaatta tgtttcgaca     660
ctggcttctg aggggaacta tggtgagagc ggtgtggagg ccttcaccca gatctcgagg     720
gagattggtg tgtttgcat tgctcagtca cagaaaatcc cacgtgaacc aagacctgga     780
gaatttgaaa aaattatcaa acgcctgcta gaaacaccta atgctcgagc agtgattatg     840
tttgccaatg aggatgacat caggaggata ttggaagcag caaaaaaact aaaccaaagt     900
gggcattttc tctggattgg ctcagatagt tggggatcca aaatagcacc tgtctatcag     960
caagaggaga ttgcagaagg ggctgtgaca atttgccca acgagcatc aattgatgga    1020 tttgatcgat actttagaag ccgaactctt gccaataatc gaagaaatgt gtggtttgca    1080
gaattctggg aggagaattt tggctgcaag ttaggatcac atgggaaaag gaacagtcat    1140
ataaagaaat gcacagggct ggagcgaatt gctcgggatt catcttatga acaggaagga    1200
aaggtccaat tgtaattga tgctgtatat tccatggctt acgccctgca caatatgcac    1260
aaagatctct gccctggata cattggcctt gtccacgaa tgagtaccat tgatgggaaa    1320
gagctacttg gttatattcg ggctgtaaat tttaatggca gtgctggcac tcctgtcact    1380
tttaatgaaa acgagatgc tcctggacgt tatgatatct ccagtatca ataaccaac    1440 aaaagcacag agtacaaagt catcggccac tggaccaatc agcttcatct aaaagtggaa    1500
```

-continued

```
gacatgcagt gggctcatag agaacatact cacccggcgt ctgtctgcag cctgccgtgt    1560
aagccagggg agaggaagaa aacggtgaaa ggggtccctt gctgctggca ctgtgaacgc    1620
tgtgaaggtt acaactacca ggtggatgag ctgtcctgtg aactttgccc tctggatcag    1680
agacccaaca tgaaccgcac aggctgccag cttatcccca tcatcaaatt ggagtggcat    1740
tctccctggg ctgtggtgcc tgtgtttgtt gcaatattgg gaatcatcgc caccaccttt    1800
gtgatcgtga cctttgtccg ctataatgac acacctatcg tgagggcttc aggacgcgaa    1860
cttagttacg tgctcctaac ggggattttt ctctgttatt caatcacgtt tttaatgatt    1920
gcagcaccag atacaatcat atgctccttc cgacgggtct tcctaggact tggcatgtgt    1980
ttcagctatg cagcccttct gaccaaaaca aaccgtatcc accgaatatt tgagcagggg    2040
aagaaatctg tcacagcgcc caagttcatt agtccagcat ctcagctggt gatcaccttc    2100
agcctcatct ccgtccagct ccttggagtg tttgtctggt tgttgtgga tccccccac     2160 atcatcattg actatggaga gcagcggaca ctagatccag agaaggccag gggagtgctc    2220
aagtgtgaca tttctgatct ctcactcatt tgttcacttg gatacagtat cctcttgatg    2280
gtcacttgta ctgtttatgc cattaaaacg agaggtgtcc cagagacttt caatgaagcc    2340
aaacctattg gatttaccat gtataccacc tgcatcattt ggttagcttt catccccatc    2400 tttttttggta cagcccagtc agcagaaaag atgtacatcc agacaacaac acttactgtc    2460
tccatgagtt taagtgcttc agtatctctg ggcatgctct atatgcccaa ggtttatatt    2520
ataatttttc atccagaaca gaataccatc gaggaggtgc gttgcagcac cgcagctcac    2580
gctttcaagg tggctgcccg ggccacgctg cgccgcagca acgtctcccg caagcggtcc    2640
agcagccttg gaggctccac gggatccacc ccctcctcct ccatcagcag caagagcaac    2700
agcgaagacc cattcccaca gcccgagagg cagaagcagc agcagccgct ggccctaacc    2760
cagcaagagc agcagcagca gcccctgacc ctcccacagc agcaacgatc tcagcagcag    2820
cccagatgca agcagaaggt catctttggc agcggcacgg tcaccttctc actgagcttt    2880
gatgagcctc agaagaacgc catggcccac gggaattcta cgcaccagaa ctccctggag    2940
gcccagaaaa gcagcgatac gctgacccga caccagccat tactcccgct gcagtgcggg    3000
gaaacggact tagatctgac cgtccaggaa acaggtctgc aaggacctgt gggtggagac    3060
cagcggccag aggtggagga ccctgaagag ttgtccccag cacttgtagt gtccagttca    3120
cagagctttg tcatcagtgg tggaggcagc actgttacag aaaacgtagt gaattca      3177
```

<210> SEQ ID NO 39
<211> LENGTH: 1059
<212> TYPE: PRT
<213> ORGANISM: Artificial Sequence
<220> FEATURE:
<221> NAME/KEY: misc_feature
<223> OTHER INFORMATION: chimeric hmGluR8/hCaR

<400> SEQUENCE: 39

```
Met Val Cys Glu Gly Lys Arg Ser Ala Ser Cys Pro Cys Phe Phe Leu
1               5                   10                  15

Leu Thr Ala Lys Phe Tyr Trp Ile Leu Thr Met Met Gln Arg Thr His
            20                  25                  30

Ser Gln Glu Tyr Ala His Ser Ile Arg Val Asp Gly Asp Ile Ile Leu
        35                  40                  45

Gly Gly Leu Phe Pro Val His Ala Lys Gly Glu Arg Gly Val Pro Cys
    50                  55                  60
```

-continued

```
Gly Glu Leu Lys Lys Glu Lys Gly Ile His Arg Leu Glu Ala Met Leu
 65                  70                  75                  80

Tyr Ala Ile Asp Gln Ile Asn Lys Asp Pro Asp Leu Leu Ser Asn Ile
                 85                  90                  95

Thr Leu Gly Val Arg Ile Leu Asp Thr Cys Ser Arg Asp Thr Tyr Ala
            100                 105                 110

Leu Glu Gln Ser Leu Thr Phe Val Gln Ala Leu Ile Glu Lys Asp Ala
            115                 120                 125

Ser Asp Val Lys Cys Ala Asn Gly Asp Pro Ile Phe Thr Lys Pro
130                 135                 140

Asp Lys Ile Ser Gly Val Ile Gly Ala Ala Ser Ser Val Ser Ile
145                 150                 155                 160

Met Val Ala Asn Ile Leu Arg Leu Phe Lys Ile Pro Gln Ile Ser Tyr
                165                 170                 175

Ala Ser Thr Ala Pro Glu Leu Ser Asp Asn Thr Arg Tyr Asp Phe Phe
            180                 185                 190

Ser Arg Val Val Pro Pro Asp Ser Tyr Gln Ala Gln Ala Met Val Asp
            195                 200                 205

Ile Val Thr Ala Leu Gly Trp Asn Tyr Val Ser Thr Leu Ala Ser Glu
            210                 215                 220

Gly Asn Tyr Gly Glu Ser Gly Val Glu Ala Phe Thr Gln Ile Ser Arg
225                 230                 235                 240

Glu Ile Gly Gly Val Cys Ile Ala Gln Ser Gln Lys Ile Pro Arg Glu
                245                 250                 255

Pro Arg Pro Gly Glu Phe Glu Lys Ile Ile Lys Arg Leu Leu Glu Thr
            260                 265                 270

Pro Asn Ala Arg Ala Val Ile Met Phe Ala Asn Glu Asp Asp Ile Arg
            275                 280                 285

Arg Ile Leu Glu Ala Ala Lys Lys Leu Asn Gln Ser Gly His Phe Leu
290                 295                 300

Trp Ile Gly Ser Asp Ser Trp Gly Ser Lys Ile Ala Pro Val Tyr Gln
305                 310                 315                 320

Gln Glu Glu Ile Ala Glu Gly Ala Val Thr Ile Leu Pro Lys Arg Ala
                325                 330                 335

Ser Ile Asp Gly Phe Asp Arg Tyr Phe Arg Ser Arg Thr Leu Ala Asn
            340                 345                 350

Asn Arg Arg Asn Val Trp Phe Ala Glu Phe Trp Glu Glu Asn Phe Gly
            355                 360                 365

Cys Lys Leu Gly Ser His Gly Lys Arg Asn Ser His Ile Lys Lys Cys
370                 375                 380

Thr Gly Leu Glu Arg Ile Ala Arg Asp Ser Ser Tyr Glu Gln Glu Gly
385                 390                 395                 400

Lys Val Gln Phe Val Ile Asp Ala Val Tyr Ser Met Ala Tyr Ala Leu
                405                 410                 415

His Asn Met His Lys Asp Leu Cys Pro Gly Tyr Ile Gly Leu Cys Pro
            420                 425                 430

Arg Met Ser Thr Ile Asp Gly Lys Glu Leu Leu Gly Tyr Ile Arg Ala
            435                 440                 445

Val Asn Phe Asn Gly Ser Ala Gly Thr Pro Val Thr Phe Asn Glu Asn
            450                 455                 460

Gly Asp Ala Pro Gly Arg Tyr Asp Ile Phe Gln Tyr Gln Ile Thr Asn
465                 470                 475                 480

Lys Ser Thr Glu Tyr Lys Val Ile Gly His Trp Thr Asn Gln Leu His
```

```
                  485                 490                 495
Leu Lys Val Glu Asp Met Gln Trp Ala His Arg Glu His Thr His Pro
                500                 505                 510
Ala Ser Val Cys Ser Leu Pro Cys Lys Pro Gly Glu Arg Lys Lys Thr
                515                 520                 525
Val Lys Gly Val Pro Cys Cys Trp His Cys Glu Arg Cys Glu Gly Tyr
            530                 535                 540
Asn Tyr Gln Val Asp Glu Leu Ser Cys Glu Leu Cys Pro Leu Asp Gln
545                 550                 555                 560
Arg Pro Asn Met Asn Arg Thr Gly Cys Gln Leu Ile Pro Ile Ile Lys
                565                 570                 575
Leu Glu Trp His Ser Pro Trp Ala Val Val Pro Val Phe Val Ala Ile
                580                 585                 590
Leu Gly Ile Ile Ala Thr Thr Phe Val Ile Val Thr Phe Val Arg Tyr
            595                 600                 605
Asn Asp Thr Pro Ile Val Arg Ala Ser Gly Arg Glu Leu Ser Tyr Val
        610                 615                 620
Leu Leu Thr Gly Ile Phe Leu Cys Tyr Ser Ile Thr Phe Leu Met Ile
625                 630                 635                 640
Ala Ala Pro Asp Thr Ile Ile Cys Ser Phe Arg Arg Val Phe Leu Gly
                645                 650                 655
Leu Gly Met Cys Phe Ser Tyr Ala Ala Leu Leu Thr Lys Thr Asn Arg
                660                 665                 670
Ile His Arg Ile Phe Glu Gln Gly Lys Lys Ser Val Thr Ala Pro Lys
            675                 680                 685
Phe Ile Ser Pro Ala Ser Gln Leu Val Ile Thr Phe Ser Leu Ile Ser
690                 695                 700
Val Gln Leu Leu Gly Val Phe Val Trp Phe Val Val Asp Pro Pro His
705                 710                 715                 720
Ile Ile Ile Asp Tyr Gly Glu Gln Arg Thr Leu Asp Pro Glu Lys Ala
                725                 730                 735
Arg Gly Val Leu Lys Cys Asp Ile Ser Asp Leu Ser Leu Ile Cys Ser
                740                 745                 750
Leu Gly Tyr Ser Ile Leu Leu Met Val Thr Cys Thr Val Tyr Ala Ile
            755                 760                 765
Lys Thr Arg Gly Val Pro Glu Thr Phe Asn Glu Ala Lys Pro Ile Gly
            770                 775                 780
Phe Thr Met Tyr Thr Thr Cys Ile Ile Trp Leu Ala Phe Ile Pro Ile
785                 790                 795                 800
Phe Phe Gly Thr Ala Gln Ser Ala Glu Lys Met Tyr Ile Gln Thr Thr
                805                 810                 815
Thr Leu Thr Val Ser Met Ser Leu Ser Ala Ser Val Ser Leu Gly Met
                820                 825                 830
Leu Tyr Met Pro Lys Val Tyr Ile Ile Phe His Pro Glu Gln Asn
                835                 840                 845
Thr Ile Glu Glu Val Arg Cys Ser Thr Ala Ala His Ala Phe Lys Val
        850                 855                 860
Ala Ala Arg Ala Thr Leu Arg Arg Ser Asn Val Ser Arg Lys Arg Ser
865                 870                 875                 880
Ser Ser Leu Gly Gly Ser Thr Gly Ser Thr Pro Ser Ser Ile Ser
                885                 890                 895
Ser Lys Ser Asn Ser Glu Asp Pro Phe Pro Gln Pro Glu Arg Gln Lys
                900                 905                 910
```

```
Gln Gln Gln Pro Leu Ala Leu Thr Gln Gln Glu Gln Gln Gln Pro
        915                 920                 925
Leu Thr Leu Pro Gln Gln Gln Arg Ser Gln Gln Pro Arg Cys Lys
        930                 935                 940
Gln Lys Val Ile Phe Gly Ser Gly Thr Val Thr Phe Ser Leu Ser Phe
945                 950                 955                 960
Asp Glu Pro Gln Lys Asn Ala Met Ala His Gly Asn Ser Thr His Gln
                965                 970                 975
Asn Ser Leu Glu Ala Gln Lys Ser Ser Asp Thr Leu Thr Arg His Gln
            980                 985                 990
Pro Leu Leu Pro Leu Gln Cys Gly  Glu Thr Asp Leu Asp  Leu Thr Val
        995                 1000                 1005
Gln Glu  Thr Gly Leu Gln Gly  Pro Val Gly Gly Asp  Gln Arg Pro
    1010                 1015                 1020
Glu Val  Glu Asp Pro Glu Glu  Leu Ser Pro Ala Leu  Val Val Ser
    1025                 1030                 1035
Ser Ser  Gln Ser Phe Val Ile  Ser Gly Gly Gly Ser  Thr Val Thr
    1040                 1045                 1050
Glu Asn  Val Val Asn Ser
    1055
```

<210> SEQ ID NO 40
<211> LENGTH: 4320
<212> TYPE: DNA
<213> ORGANISM: Artificial Sequence
<220> FEATURE:
<221> NAME/KEY: misc_feature
<223> OTHER INFORMATION: mGluR8//CaR*G qi5 fusion construct
<221> NAME/KEY: MOD_RES
<222> LOCATION: (3178)..(3240)
<223> OTHER INFORMATION: n is a or g or c or t/u, unknown, or other

<400> SEQUENCE: 40

```
atggtatgcg agggaaagcg atcagcctct tgcccttgtt tcttcctctt gaccgccaag      60
ttctactgga tcctcacaat gatgcaaaga actcacagcc aggagtatgc ccattccata    120
cgggtggatg gggacattat tttgggggt ctcttccctg tccacgcaaa gggagagaga     180
ggggtgcctt gtgggagct gaagaaggaa aaggggattc acagactgga ggccatgctt     240
tatgcaattg accagattaa caaggaccct gatctccttt ccaacatcac tctgggtgtc    300
cgcatcctcg acacgtgctc tagggacacc tatgctttgg agcagtctct aacattcgtg    360
caggcattaa tagagaaaga tgcttcggat gtgaagtgtg ctaatggaga tccacccatt    420
ttcaccaagc ccgacaagat ttctggcgtc ataggtgctg cagcaagctc cgtgtccatc    480
atggttgcta acattttaag acttttttaag ataccctcaaa tcagctatgc atccacagcc    540
ccagagctaa gtgataacac caggtatgac tttttctctc gagtggttcc gcctgactcc    600
taccaagccc aagccatggt ggacatcgtg acagcactgg gatggaatta tgtttcgaca    660
ctggcttctg aggggaacta tggtgagagc ggtgtggagg ccttcaccca gatctcgagg    720
gagattggtg gtgtttgcat tgctcagtca cagaaaatcc cacgtgaacc aagacctgga    780
gaatttgaaa aaattatcaa acgcctgcta gaaacaccta tgctcgagc agtgattatg    840
tttgccaatg aggatgacat caggaggata ttggaagcag caaaaaaact aaaccaaagt    900
gggcattttc tctggattgg ctcagatagt tgggggatcca aaatagcacc tgtctatcag    960
caagaggaga ttgcagaagg ggctgtgaca attttgccca acgagcatc aattgatgga   1020
```

-continued

```
tttgatcgat actttagaag ccgaactctt gccaataatc gaagaaatgt gtggtttgca    1080
gaattctggg aggagaattt tggctgcaag ttaggatcac atgggaaaag gaacagtcat    1140
ataaagaaat gcacagggct ggagcgaatt gctcgggatt catcttatga acaggaagga    1200
aaggtccaat ttgtaattga tgctgtatat tccatggctt acgccctgca caatatgcac    1260
aaagatctct gccctggata cattggcctt tgtccacgaa tgagtaccat tgatgggaaa    1320
gagctacttg gttatattcg ggctgtaaat tttaatggca gtgctggcac tcctgtcact    1380
tttaatgaaa acggagatgc tcctggacgt tatgatatct tccagtatca aataaccaac    1440
aaaagcacac agtacaaagt catcggccac tggaccaatc agcttcatct aaaagtggaa    1500
gacatgcagt gggctcatag agaacatact cacccggcgt ctgtctgcag cctgccgtgt    1560
aagccagggg agaggaagaa aacggtgaaa ggggtcccctt gctgctggca ctgtgaacgc    1620
tgtgaaggtt acaactacca ggtggatgag ctgtcctgtg aactttgccc tctggatcag    1680
agacccaaca tgaaccgcac aggctgccag cttatcccca tcatcaaatt ggagtggcat    1740
tctccctggg ctgtggtgcc tgtgtttgtt gcaatattgg gaatcatcgc caccaccttt    1800
gtgatcgtga cctttgtccg ctataatgac acacctatcg tgagggcttc aggacgcgaa    1860
cttagttacg tgctcctaac ggggattttt ctctgttatt caatcacgtt tttaatgatt    1920
gcagcaccag atacaatcat atgctccttc cgacgggtct tcctaggact tggcatgtgt    1980
ttcagctatg cagcccttct gaccaaaaca aaccgtatcc accgaatatt tgagcagggg    2040
aagaaatctg tcacagcgcc caagttcatt agtccagcat ctcagctggt gatcaccttc    2100
agcctcatct ccgtccagct ccttggagtg tttgtctggt tgttgtgga tccccccac    2160 atcatcattg actatggaga gcagcggaca ctagatccag agaaggccag gggagtgctc    2220
aagtgtgaca tttctgatct ctcactcatt tgttcacttg gatacagtat cctcttgatg    2280
gtcacttgta ctgtttatgc cattaaaacg agaggtgtcc cagagacttt caatgaagcc    2340
aaacctattg gatttaccat gtataccacc tgcatcattt ggttagcttt catccccatc    2400
ttttttggta cagcccagtc agcagaaaag atgtacatcc agacaacaac acttactgtc    2460
tccatgagtt taagtgcttc agtatctctg ggcatgctct atatgcccaa ggtttatatt    2520
ataatttttc atccagaaca gaataccatc gaggaggtgc gttgcagcac cgcagctcac    2580
gctttcaagg tggctgcccg ggccacgctg cgccgcagca acgtctcccg caagcggtcc    2640
agcagccttg gaggctccac gggatccacc ccctcctcct ccatcagcag caagagcaac    2700
agcgaagacc cattcccaca gcccgagagg cagaagcagc agcagccgct ggccctaacc    2760
cagcaagagc agcagcagca gccccctgacc ctcccacagc agcaacgatc tcagcagcag    2820
cccagatgca agcagaaggt catctttggc agcggcacgg tcaccttctc actgagcttt    2880
gatgagcctc agaagaacgc catggccac gggaattcta cgcaccagaa ctccctggag    2940
gcccagaaaa gcagcgatac gctgacccga caccagccat tactcccgct gcagtgcggg    3000
gaaacggact tagatctgac cgtccaggaa acaggtctgc aaggacctgt gggtggagac    3060
cagcggccag aggtggagga ccctgaagag ttgtccccag cacttgtagt gtccagttca    3120
cagagctttg tcatcagtgg tggaggcagc actgttacag aaaacgtagt gaattcannn    3180
nnnnnnnnnn nnnnnnnnnn nnnnnnnnnn nnnnnnnnnn nnnnnnnnnn nnnnnnnnnn    3240
atgactctgg agtccatcat ggcgtgctgc ctgagcgagg aggccaagga agcccggcgg    3300
atcaacgacg agatcgagcg gcagctccgc agggacaagc gggacgcccg ccggagctc    3360 aagctgctgc tgctcgggac aggagagagt ggcaagagta cgtttatcaa gcagatgaga    3420
```

```
atcatccatg ggtcaggata ctctgatgaa gataaaaggg gcttcaccaa gctggtgtat    3480
cagaacatct tcacggccat gcaggccatg atcagagcca tggacacact caagatccca    3540
tacaagtatg agcacaataa ggctcatgca caattagttc gagaagttga tgtggagaag    3600
gtgtctgctt ttgagaatcc atatgtagat gcaataaaga gtttatggaa tgatcctgga    3660
atccaggaat gctatgatag acgacgagaa tatcaattat ctgactctac caaatactat    3720
cttaatgact tggaccgcgt agctgaccct gcctacctgc ctacgcaaca agatgtgctt    3780
agagttcgag tccccaccac agggatcatc gaatacccct ttgacttaca aagtgtcatt    3840
ttcagaatgg tcgatgtagg gggccaaagg tcagagagaa gaaaatggat acactgcttt    3900
gaaaatgtca cctctatcat gtttctagta gcgcttagtg aatatgatca agttctcgtg    3960
gagtcagaca atgagaaccg aatggaggaa agcaaggctc tctttagaac aattatcaca    4020 taccctggt tccagaactc ctcggttatt ctgttcttaa acaagaaaga tcttctagag    4080
gagaaaatca tgtattccca tctagtcgac tacttcccag aatatgatgg accccagaga    4140
gatgcccagg cagcccgaga attcattctg aagatgttcg tggacctgaa cccagacagt    4200
gacaaaatta tctactccca cttcacgtgc gccacagaca ccgagaatat ccgctttgtc    4260
tttgctgccg tcaaggacac catcctccag ttgaacctga aggactgcgg tctgttctaa    4320
```

<210> SEQ ID NO 41
<211> LENGTH: 1418
<212> TYPE: PRT
<213> ORGANISM: Artificial Sequence
<220> FEATURE:
<221> NAME/KEY: misc_feature
<223> OTHER INFORMATION: mGluR8//CaR*G qi5 fusion construct

<400> SEQUENCE: 41

```
Met Val Cys Glu Gly Lys Arg Ser Ala Ser Cys Pro Cys Phe Phe Leu
1               5                   10                  15

Leu Thr Ala Lys Phe Tyr Trp Ile Leu Thr Met Met Gln Arg Thr His
            20                  25                  30

Ser Gln Glu Tyr Ala His Ser Ile Arg Val Asp Gly Asp Ile Ile Leu
        35                  40                  45

Gly Gly Leu Phe Pro Val His Ala Lys Gly Glu Arg Gly Val Pro Cys
    50                  55                  60

Gly Glu Leu Lys Lys Glu Lys Gly Ile His Arg Leu Glu Ala Met Leu
65                  70                  75                  80

Tyr Ala Ile Asp Gln Ile Asn Lys Asp Pro Asp Leu Leu Ser Asn Ile
                85                  90                  95

Thr Leu Gly Val Arg Ile Leu Asp Thr Cys Ser Arg Asp Thr Tyr Ala
            100                 105                 110

Leu Glu Gln Ser Leu Thr Phe Val Gln Ala Leu Ile Glu Lys Asp Ala
        115                 120                 125

Ser Asp Val Lys Cys Ala Asn Gly Asp Pro Pro Ile Phe Thr Lys Pro
    130                 135                 140

Asp Lys Ile Ser Gly Val Ile Gly Ala Ala Ser Ser Val Ser Ile
145                 150                 155                 160

Met Val Ala Asn Ile Leu Arg Leu Phe Lys Ile Pro Gln Ile Ser Tyr
                165                 170                 175

Ala Ser Thr Ala Pro Glu Leu Ser Asp Asn Thr Arg Tyr Asp Phe Phe
            180                 185                 190

Ser Arg Val Val Pro Pro Asp Ser Tyr Gln Ala Gln Ala Met Val Asp
```

-continued

```
                195                 200                 205
Ile Val Thr Ala Leu Gly Trp Asn Tyr Val Ser Thr Leu Ala Ser Glu
            210                 215                 220
Gly Asn Tyr Gly Glu Ser Gly Val Glu Ala Phe Thr Gln Ile Ser Arg
225                 230                 235                 240
Glu Ile Gly Gly Val Cys Ile Ala Gln Ser Gln Lys Ile Pro Arg Glu
                245                 250                 255
Pro Arg Pro Gly Glu Phe Glu Lys Ile Ile Lys Arg Leu Leu Glu Thr
            260                 265                 270
Pro Asn Ala Arg Ala Val Ile Met Phe Ala Asn Glu Asp Asp Ile Arg
            275                 280                 285
Arg Ile Leu Glu Ala Ala Lys Lys Leu Asn Gln Ser Gly His Phe Leu
            290                 295                 300
Trp Ile Gly Ser Asp Ser Trp Gly Ser Lys Ile Ala Pro Val Tyr Gln
305                 310                 315                 320
Gln Glu Glu Ile Ala Glu Gly Ala Val Thr Ile Leu Pro Lys Arg Ala
                325                 330                 335
Ser Ile Asp Gly Phe Asp Arg Tyr Phe Arg Ser Arg Thr Leu Ala Asn
            340                 345                 350
Asn Arg Arg Asn Val Trp Phe Ala Glu Phe Trp Glu Glu Asn Phe Gly
            355                 360                 365
Cys Lys Leu Gly Ser His Gly Lys Arg Asn Ser His Ile Lys Lys Cys
            370                 375                 380
Thr Gly Leu Glu Arg Ile Ala Arg Asp Ser Ser Tyr Glu Gln Glu Gly
385                 390                 395                 400
Lys Val Gln Phe Val Ile Asp Ala Val Tyr Ser Met Ala Tyr Ala Leu
                405                 410                 415
His Asn Met His Lys Asp Leu Cys Pro Gly Tyr Ile Gly Leu Cys Pro
            420                 425                 430
Arg Met Ser Thr Ile Asp Gly Lys Glu Leu Leu Gly Tyr Ile Arg Ala
            435                 440                 445
Val Asn Phe Asn Gly Ser Ala Gly Thr Pro Val Thr Phe Asn Glu Asn
            450                 455                 460
Gly Asp Ala Pro Gly Arg Tyr Asp Ile Phe Gln Tyr Gln Ile Thr Asn
465                 470                 475                 480
Lys Ser Thr Glu Tyr Lys Val Ile Gly His Trp Thr Asn Gln Leu His
                485                 490                 495
Leu Lys Val Glu Asp Met Gln Trp Ala His Arg Glu His Thr His Pro
            500                 505                 510
Ala Ser Val Cys Ser Leu Pro Cys Lys Pro Gly Glu Arg Lys Lys Thr
            515                 520                 525
Val Lys Gly Val Pro Cys Cys Trp His Cys Glu Arg Cys Glu Gly Tyr
            530                 535                 540
Asn Tyr Gln Val Asp Glu Leu Ser Cys Glu Leu Cys Pro Leu Asp Gln
545                 550                 555                 560
Arg Pro Asn Met Asn Arg Thr Gly Cys Gln Leu Ile Pro Ile Ile Lys
                565                 570                 575
Leu Glu Trp His Ser Pro Trp Ala Val Val Pro Val Phe Val Ala Ile
            580                 585                 590
Leu Gly Ile Ile Ala Thr Thr Phe Val Ile Val Thr Phe Val Arg Tyr
            595                 600                 605
Asn Asp Thr Pro Ile Val Arg Ala Ser Gly Arg Glu Leu Ser Tyr Val
610                 615                 620
```

-continued

```
Leu Leu Thr Gly Ile Phe Leu Cys Tyr Ser Ile Thr Phe Leu Met Ile
625                 630                 635                 640

Ala Ala Pro Asp Thr Ile Ile Cys Ser Phe Arg Arg Val Phe Leu Gly
                645                 650                 655

Leu Gly Met Cys Phe Ser Tyr Ala Ala Leu Leu Thr Lys Thr Asn Arg
                660                 665                 670

Ile His Arg Ile Phe Glu Gln Gly Lys Lys Ser Val Thr Ala Pro Lys
                675                 680                 685

Phe Ile Ser Pro Ala Ser Gln Leu Val Ile Thr Phe Ser Leu Ile Ser
690                 695                 700

Val Gln Leu Leu Gly Val Phe Val Trp Phe Val Val Asp Pro Pro His
705                 710                 715                 720

Ile Ile Ile Asp Tyr Gly Glu Gln Arg Thr Leu Asp Pro Glu Lys Ala
                725                 730                 735

Arg Gly Val Leu Lys Cys Asp Ile Ser Asp Leu Ser Leu Ile Cys Ser
                740                 745                 750

Leu Gly Tyr Ser Ile Leu Leu Met Val Thr Cys Thr Val Tyr Ala Ile
                755                 760                 765

Lys Thr Arg Gly Val Pro Glu Thr Phe Asn Glu Ala Lys Pro Ile Gly
770                 775                 780

Phe Thr Met Tyr Thr Thr Cys Ile Ile Trp Leu Ala Phe Ile Pro Ile
785                 790                 795                 800

Phe Phe Gly Thr Ala Gln Ser Ala Glu Lys Met Tyr Ile Gln Thr Thr
                805                 810                 815

Thr Leu Thr Val Ser Met Ser Leu Ser Ala Ser Val Ser Leu Gly Met
                820                 825                 830

Leu Tyr Met Pro Lys Val Tyr Ile Ile Phe His Pro Glu Gln Asn
                835                 840                 845

Thr Ile Glu Glu Val Arg Cys Ser Thr Ala Ala His Ala Phe Lys Val
                850                 855                 860

Ala Ala Arg Ala Thr Leu Arg Arg Ser Asn Val Ser Arg Lys Arg Ser
865                 870                 875                 880

Ser Ser Leu Gly Gly Ser Thr Gly Ser Thr Pro Ser Ser Ile Ser
                885                 890                 895

Ser Lys Ser Asn Ser Glu Asp Pro Phe Pro Gln Pro Glu Arg Gln Lys
                900                 905                 910

Gln Gln Gln Pro Leu Ala Leu Thr Gln Gln Glu Gln Gln Gln Gln Pro
                915                 920                 925

Leu Thr Leu Pro Gln Gln Gln Arg Ser Gln Gln Gln Pro Arg Cys Lys
930                 935                 940

Gln Lys Val Ile Phe Gly Ser Gly Thr Val Thr Phe Ser Leu Ser Phe
945                 950                 955                 960

Asp Glu Pro Gln Lys Asn Ala Met Ala His Gly Asn Ser Thr His Gln
                965                 970                 975

Asn Ser Leu Glu Ala Gln Lys Ser Ser Asp Thr Leu Thr Arg His Gln
                980                 985                 990

Pro Leu Leu Pro Leu Gln Cys Gly Glu Thr Asp Leu Asp Leu Thr Val
                995                 1000                1005

Gln Glu Thr Gly Leu Gln Gly Pro Val Gly Gly Asp Gln Arg Pro
        1010                1015                1020

Glu Val Glu Asp Pro Glu Glu Leu Ser Pro Ala Leu Val Val Ser
        1025                1030                1035
```

```
Ser Ser Gln Ser Phe Val Ile Ser Gly Gly Ser Thr Val Thr
1040                1045            1050
Glu Asn Val Val Asn Ser Met Thr Leu Glu Ser Ile Met Ala Cys
1055                1060            1065
Cys Leu Ser Glu Glu Ala Lys Glu Ala Arg Arg Ile Asn Asp Glu
1070                1075            1080
Ile Glu Arg Gln Leu Arg Arg Asp Lys Arg Asp Ala Arg Arg Glu
1085                1090            1095
Leu Lys Leu Leu Leu Leu Gly Thr Gly Glu Ser Gly Lys Ser Thr
1100                1105            1110
Phe Ile Lys Gln Met Arg Ile Ile His Gly Ser Gly Tyr Ser Asp
1115                1120            1125
Glu Asp Lys Arg Gly Phe Thr Lys Leu Val Tyr Gln Asn Ile Phe
1130                1135            1140
Thr Ala Met Gln Ala Met Ile Arg Ala Met Asp Thr Leu Lys Ile
1145                1150            1155
Pro Tyr Lys Tyr Glu His Asn Lys Ala His Ala Gln Leu Val Arg
1160                1165            1170
Glu Val Asp Val Glu Lys Val Ser Ala Phe Glu Asn Pro Tyr Val
1175                1180            1185
Asp Ala Ile Lys Ser Leu Trp Asn Asp Pro Gly Ile Gln Glu Cys
1190                1195            1200
Tyr Asp Arg Arg Arg Glu Tyr Gln Leu Ser Asp Ser Thr Lys Tyr
1205                1210            1215
Tyr Leu Asn Asp Leu Asp Arg Val Ala Asp Pro Ala Tyr Leu Pro
1220                1225            1230
Thr Gln Gln Asp Val Leu Arg Val Arg Val Pro Thr Thr Gly Ile
1235                1240            1245
Ile Glu Tyr Pro Phe Asp Leu Gln Ser Val Ile Phe Arg Met Val
1250                1255            1260
Asp Val Gly Gly Gln Arg Ser Glu Arg Arg Lys Trp Ile His Cys
1265                1270            1275
Phe Glu Asn Val Thr Ser Ile Met Phe Leu Val Ala Leu Ser Glu
1280                1285            1290
Tyr Asp Gln Val Leu Val Glu Ser Asp Asn Glu Asn Arg Met Glu
1295                1300            1305
Glu Ser Lys Ala Leu Phe Arg Thr Ile Ile Thr Tyr Pro Trp Phe
1310                1315            1320
Gln Asn Ser Ser Val Ile Leu Phe Leu Asn Lys Lys Asp Leu Leu
1325                1330            1335
Glu Glu Lys Ile Met Tyr Ser His Leu Val Asp Tyr Phe Pro Glu
1340                1345            1350
Tyr Asp Gly Pro Gln Arg Asp Ala Gln Ala Ala Arg Glu Phe Ile
1355                1360            1365
Leu Lys Met Phe Val Asp Leu Asn Pro Asp Ser Asp Lys Ile Ile
1370                1375            1380
Tyr Ser His Phe Thr Cys Ala Thr Asp Thr Glu Asn Ile Arg Phe
1385                1390            1395
Val Phe Ala Ala Val Lys Asp Thr Ile Leu Gln Leu Asn Leu Lys
1400                1405            1410
Asp Cys Gly Leu Phe
1415
```

```
<210> SEQ ID NO 42
<211> LENGTH: 3909
<212> TYPE: DNA
<213> ORGANISM: Artificial Sequence
<220> FEATURE:
<221> NAME/KEY: misc_feature
<223> OTHER INFORMATION: GABA-R2*Gqo5 fusion construct

<400> SEQUENCE: 42
atggcttccc cgcggagctc cgggcagccc gggccgccgc cgccgccgcc accgccgccc      60
gcgcgcctgc tactgctact gctgctgccg ctgctgctgc tctggcgcc cggggcctgg     120 ggctgggcg ggggcgcccc ccggccgccg cccagcagcc cgccgctctc catcatgggc     180
ctcatgccgc tcaccaagga ggtggccaag ggcagcatcg gcgcggtgt gctccccgcc     240 gtggaactgg ccatcgagca gatccgcaac gagtcactcc tgcgcccta cttcctcgac     300 ctgcggctct atgacacgga gtgcgacaac gcaaaggggt tgaaagcctt ctacgatgca     360
ataaaatacg gccgaaacca cttgatggtg tttggaggcg tctgtccatc cgtcacatcc     420
atcattgcag agtccctcca aggctggaat ctggtgcagc tttcttttgc tgcaaccacg     480
cctgttctag ccgataagaa aaatacccct tatttctttc ggaccgtccc atcagacaat     540
gcggtgaatc cagccattct gaagttgctc aagcactacc agtggaagcg cgtgggcacg     600
ctgacgcaag acgttcagag gttctctgag gtgcggaatg acctgactgg agttctgtat     660
ggcgaggaca ttgagatttc agacaccgag agcttctcca cgatccctg taccagtgtc     720 aaaaagctga ggggaatga tgtgcggatc atccttggcc agtttgacca gaatatggca     780
gcaaaagtgt ctgttgtgc atacgaggag aacatgtatg gtagtaaata tcagtggatc     840
attccgggct ggtacgagcc ttcttggtgg gagcaggtgc acacggaagc caactcatcc     900
cgctgcctcc ggaagaatct gcttgctgcc atggagggct acattggcgt ggatttcgag     960
cccctgagct ccaagcagat caagaccatc tcaggaaaga ctccacagca gtatgagaga    1020
gagtacaaca caagcggtc aggcgtgggg cccagcaagt tccacgggta cgcctacgat    1080
ggcatctggg tcatcgccaa gacactgcag agggccatgg agacactgca tgccagcagc    1140
cggcaccagc ggatccagga cttcaactac acggaccaca cgctgggcag gatcatcctc    1200
aatgccatga cgagaccaa cttcttcggg gtcacgggtc aagttgtatt ccggaatggg    1260
gagagaatgg ggaccattaa atttactcaa tttcaagaca gcagggaggt gaaggtggga    1320
gagtacaacg ctgtggccga cactggag atcatcaatg acaccatcag gttccaagga    1380
tccgaaccac caaagacaa gaccatcatc ctggagcagc tgcggaagat ctccctacct    1440
ctctacagca tcctctctgc cctcaccatc ctcgggatga tcatggccag tgcttttctc    1500
ttcttcaaca tcaagaaccg gaatcagaag ctcataaaga tgtcgagtcc atacatgaac    1560
aaccttatca tccttggagg gatgctctcc tatgcttcca tatttctctt tggccttgat    1620
ggatcctttg tctctgaaaa gacctttgaa acactttgca ccgtcaggac ctggattctc    1680
accgtgggct acacgaccgc ttttgggcc atgtttgcaa agacctggag agtccacgcc    1740
atcttcaaaa atgtgaaaat gaagaagaag atcatcaagg accagaaact gcttgtgatc    1800
gtggggggca tgctgctgat cgacctgtgt atcctgatct gctggcaggc tgtggaccc    1860 ctgcgaagga cagtggagaa gtacagcatg gagccggacc agcaggacgg gatatctcc    1920 atccgccctc tcctggagca ctgtgagaac acccatatga ccatctggct tggcatcgtc    1980
tatgcctaca agggacttct catgttgttc ggttgtttct tagcttggga gacccgcaac    2040
gtcagcatcc ccgcactcaa cgacagcaag tacatcggga tgagtgtcta caacgtgggg    2100
```

-continued

```
atcatgtgca tcatcggggc cgctgtctcc ttcctgaccc gggaccagcc caatgtgcag    2160
ttctgcatcg tggctctggt catcatcttc tgcagcacca tcaccctctg cctggtattc    2220
gtgccgaagc tcatcaccct gagaacaaac ccagatgcag caacgcagaa caggcgattc    2280
cagttcactc agaatcagaa gaaagaagat tctaaaacgt ccacctcggt caccagtgtg    2340
aaccaagcca gcacatcccg cctggagggc ctacagtcag aaaaccatcg cctgcgaatg    2400
aagatcacag agctggataa agacttggaa gaggtcacca tgcagctgca ggacacacca    2460
gaaaagacca cctacattaa acagaaccac taccaagagc tcaatgacat cctcaacctg    2520
ggaaacttca ctgagagcac agatggagga aaggccattt taaaaaatca cctcgatcaa    2580
aatccccagc tacagtggaa cacaacagag ccctctcgaa catgcaaaga tcctatagaa    2640
gatataaact ctccagaaca catccagcgt cggctgtccc tccagctccc catcctccac    2700
cacgcctacc tccatccat cggaggcgtg gacgccagct gtgtcagccc ctgcgtcagc    2760
cccaccgcca gcccccgcca cagacatgtg ccaccctcct tccgagtcat ggtctcgggc    2820
ctggcggccg ccatgactct ggagtccatc atggcgtgct gcctgagcga ggaggccaag    2880
gaagcccggc ggatcaacga cgagatcgag cggcagctcc gcagggacaa gcgggacgcc    2940
cgccgggagc tcaagctgct gctgctcggg acaggagaga gtggcaagag tacgtttatc    3000
aagcagatga gaatcatcca tgggtcagga tactctgatg aagataaaag gggcttcacc    3060
aagctggtgt atcagaacat cttcacggcc atgcaggcca tgatcagagc catggacaca    3120
ctcaagatcc catacaagta tgagcacaat aaggctcatg cacaattagt tcgagaagtt    3180
gatgtggaga aggtgtctgc ttttgagaat ccatatgtag atgcaataaa gagtttatgg    3240
aatgatcctg gaatccagga atgctatgat agacgacgag aatatcaatt atctgactct    3300
accaaatact atcttaatga cttggaccgc gtagctgacc ctgcctacct gcctacgcaa    3360
caagatgtgc ttagagttcg agtccccacc acagggatca tcgaataccc ctttgactta    3420
caaagtgtca ttttcagaat ggtcgatgta gggggccaaa ggtcagagag aagaaaatgg    3480
atacactgct ttgaaaatgt cacctctatc atgtttctag tagcgcttag tgaatatgat    3540
caagttctgg tggagtcaga caatgagaac cgaatggagg aaagcaaggc tctctttaga    3600
acaattatca cataccctg gttccagaac tcctcggtta ttctgttctt aaacaagaaa    3660
gatcttctag aggagaaaat catgtattcc catctagtcg actacttccc agaatatgat    3720 ggacccaga gagatgccca ggcagcccga gaattcattc tgaagatgtt cgtggacctg    3780
aacccagaca gtgacaaaat taactactcc cacttcacgt gcgccacaga caccgagaat    3840
atccgctttg tctttgctgc cgtcaaggac accatcctcc agttgaacct gaagggctgc    3900
ggtctgtac                                                           3909
```

<210> SEQ ID NO 43
<211> LENGTH: 1303
<212> TYPE: PRT
<213> ORGANISM: Artificial Sequence
<220> FEATURE:
<221> NAME/KEY: misc_feature
<223> OTHER INFORMATION: GABA-R2*Gqo5 fusion construct

<400> SEQUENCE: 43

```
Met Ala Ser Pro Arg Ser Ser Gly Gln Pro Gly Pro Pro Pro Pro Pro
1               5                   10                  15

Pro Pro Pro Ala Arg Leu Leu Leu Leu Leu Leu Leu Pro Leu Leu
            20                  25                  30
```

```
Leu Pro Leu Ala Pro Gly Ala Trp Gly Trp Ala Arg Gly Ala Pro Arg
        35                  40                  45

Pro Pro Pro Ser Ser Pro Leu Ser Ile Met Gly Leu Met Pro Leu
        50                  55                  60

Thr Lys Glu Val Ala Lys Gly Ser Ile Gly Arg Gly Val Leu Pro Ala
65                      70                  75                  80

Val Glu Leu Ala Ile Glu Gln Ile Arg Asn Glu Ser Leu Leu Arg Pro
                85                  90                  95

Tyr Phe Leu Asp Leu Arg Leu Tyr Asp Thr Glu Cys Asp Asn Ala Lys
                100                 105                 110

Gly Leu Lys Ala Phe Tyr Asp Ala Ile Lys Tyr Gly Pro Asn His Leu
                115                 120                 125

Met Val Phe Gly Gly Val Cys Pro Ser Val Thr Ser Ile Ile Ala Glu
                130                 135                 140

Ser Leu Gln Gly Trp Asn Leu Val Gln Leu Ser Phe Ala Ala Thr Thr
145                     150                 155                 160

Pro Val Leu Ala Asp Lys Lys Tyr Pro Tyr Phe Phe Arg Thr Val
                165                 170                 175

Pro Ser Asp Asn Ala Val Asn Pro Ala Ile Leu Lys Leu Leu Lys His
                180                 185                 190

Tyr Gln Trp Lys Arg Val Gly Thr Leu Thr Gln Asp Val Gln Arg Phe
                195                 200                 205

Ser Glu Val Arg Asn Asp Leu Thr Gly Val Leu Tyr Gly Glu Asp Ile
                210                 215                 220

Glu Ile Ser Asp Thr Glu Ser Phe Ser Asn Asp Pro Cys Thr Ser Val
225                     230                 235                 240

Lys Lys Leu Lys Gly Asn Asp Val Arg Ile Ile Leu Gly Gln Phe Asp
                245                 250                 255

Gln Asn Met Ala Ala Lys Val Phe Cys Cys Ala Tyr Glu Glu Asn Met
                260                 265                 270

Tyr Gly Ser Lys Tyr Gln Trp Ile Ile Pro Gly Trp Tyr Glu Pro Ser
                275                 280                 285

Trp Trp Glu Gln Val His Thr Glu Ala Asn Ser Ser Arg Cys Leu Arg
                290                 295                 300

Lys Asn Leu Leu Ala Ala Met Glu Gly Tyr Ile Gly Val Asp Phe Glu
305                     310                 315                 320

Pro Leu Ser Ser Lys Gln Ile Lys Thr Ile Ser Gly Lys Thr Pro Gln
                325                 330                 335

Gln Tyr Glu Arg Glu Tyr Asn Asn Lys Arg Ser Gly Val Gly Pro Ser
                340                 345                 350

Lys Phe His Gly Tyr Ala Tyr Asp Gly Ile Trp Val Ile Ala Lys Thr
                355                 360                 365

Leu Gln Arg Ala Met Glu Thr Leu His Ala Ser Arg His Gln Arg
                370                 375                 380

Ile Gln Asp Phe Asn Tyr Thr Asp His Thr Leu Gly Arg Ile Ile Leu
385                     390                 395                 400

Asn Ala Met Asn Glu Thr Asn Phe Phe Gly Val Thr Gly Gln Val Val
                405                 410                 415

Phe Arg Asn Gly Glu Arg Met Gly Thr Ile Lys Phe Thr Gln Phe Gln
                420                 425                 430

Asp Ser Arg Glu Val Lys Val Gly Glu Tyr Asn Ala Val Ala Asp Thr
                435                 440                 445
```

```
Leu Glu Ile Ile Asn Asp Thr Ile Arg Phe Gln Gly Ser Glu Pro Pro
    450                 455                 460

Lys Asp Lys Thr Ile Ile Leu Glu Gln Leu Arg Lys Ile Ser Leu Pro
465                 470                 475                 480

Leu Tyr Ser Ile Leu Ser Ala Leu Thr Ile Leu Gly Met Ile Met Ala
                485                 490                 495

Ser Ala Phe Leu Phe Phe Asn Ile Lys Asn Arg Asn Gln Lys Leu Ile
            500                 505                 510

Lys Met Ser Ser Pro Tyr Met Asn Asn Leu Ile Ile Leu Gly Gly Met
        515                 520                 525

Leu Ser Tyr Ala Ser Ile Phe Leu Phe Gly Leu Asp Gly Ser Phe Val
    530                 535                 540

Ser Glu Lys Thr Phe Glu Thr Leu Cys Thr Val Arg Thr Trp Ile Leu
545                 550                 555                 560

Thr Val Gly Tyr Thr Thr Ala Phe Gly Ala Met Phe Ala Lys Thr Trp
                565                 570                 575

Arg Val His Ala Ile Phe Lys Asn Val Lys Met Lys Lys Lys Ile Ile
            580                 585                 590

Lys Asp Gln Lys Leu Leu Val Ile Val Gly Gly Met Leu Leu Ile Asp
        595                 600                 605

Leu Cys Ile Leu Ile Cys Trp Gln Ala Val Asp Pro Leu Arg Arg Thr
    610                 615                 620

Val Glu Lys Tyr Ser Met Glu Pro Asp Pro Ala Gly Arg Asp Ile Ser
625                 630                 635                 640

Ile Arg Pro Leu Leu Glu His Cys Glu Asn Thr His Met Thr Ile Trp
                645                 650                 655

Leu Gly Ile Val Tyr Ala Tyr Lys Gly Leu Leu Met Leu Phe Gly Cys
            660                 665                 670

Phe Leu Ala Trp Glu Thr Arg Asn Val Ser Ile Pro Ala Leu Asn Asp
    675                 680                 685

Ser Lys Tyr Ile Gly Met Ser Val Tyr Asn Val Gly Ile Met Cys Ile
690                 695                 700

Ile Gly Ala Ala Val Ser Phe Leu Thr Arg Asp Gln Pro Asn Val Gln
705                 710                 715                 720

Phe Cys Ile Val Ala Leu Val Ile Ile Phe Cys Ser Thr Ile Thr Leu
                725                 730                 735

Cys Leu Val Phe Val Pro Lys Leu Ile Thr Leu Arg Thr Asn Pro Asp
            740                 745                 750

Ala Ala Thr Gln Asn Arg Arg Phe Gln Phe Thr Gln Asn Gln Lys Lys
        755                 760                 765

Glu Asp Ser Lys Thr Ser Thr Ser Val Thr Ser Val Asn Gln Ala Ser
    770                 775                 780

Thr Ser Arg Leu Glu Gly Leu Gln Ser Glu Asn His Arg Leu Arg Met
785                 790                 795                 800

Lys Ile Thr Glu Leu Asp Lys Asp Leu Glu Glu Val Thr Met Gln Leu
                805                 810                 815

Gln Asp Thr Pro Glu Lys Thr Thr Tyr Ile Lys Gln Asn His Tyr Gln
            820                 825                 830

Glu Leu Asn Asp Ile Leu Asn Leu Gly Asn Phe Thr Glu Ser Thr Asp
        835                 840                 845

Gly Gly Lys Ala Ile Leu Lys Asn His Leu Asp Gln Asn Pro Gln Leu
    850                 855                 860

Gln Trp Asn Thr Thr Glu Pro Ser Arg Thr Cys Lys Asp Pro Ile Glu
```

-continued

```
              865                 870                 875                 880
        Asp Ile Asn Ser Pro Glu His Ile Gln Arg Arg Leu Ser Leu Gln Leu
                        885                 890                 895
        Pro Ile Leu His His Ala Tyr Leu Pro Ser Ile Gly Gly Val Asp Ala
                        900                 905                 910
        Ser Cys Val Ser Pro Cys Val Ser Pro Thr Ala Ser Pro Arg His Arg
                        915                 920                 925
        His Val Pro Pro Ser Phe Arg Val Met Val Ser Gly Leu Ala Ala Ala
                        930                 935                 940
        Met Thr Leu Glu Ser Ile Met Ala Cys Cys Leu Ser Glu Glu Ala Lys
        945                 950                 955                 960
        Glu Ala Arg Arg Ile Asn Asp Glu Ile Glu Arg Gln Leu Arg Arg Asp
                        965                 970                 975
        Lys Arg Asp Ala Arg Arg Glu Leu Lys Leu Leu Leu Leu Gly Thr Gly
                        980                 985                 990
        Glu Ser Gly Lys Ser Thr Phe Ile Lys Gln Met Arg Ile Ile His Gly
                        995                 1000                1005
        Ser Gly Tyr Ser Asp Glu Asp Lys Arg Gly Phe Thr Lys Leu Val
            1010                1015                1020
        Tyr Gln Asn Ile Phe Thr Ala Met Gln Ala Met Ile Arg Ala Met
            1025                1030                1035
        Asp Thr Leu Lys Ile Pro Tyr Lys Tyr Glu His Asn Lys Ala His
            1040                1045                1050
        Ala Gln Leu Val Arg Glu Val Asp Val Glu Lys Val Ser Ala Phe
            1055                1060                1065
        Glu Asn Pro Tyr Val Asp Ala Ile Lys Ser Leu Trp Asn Asp Pro
            1070                1075                1080
        Gly Ile Gln Glu Cys Tyr Asp Arg Arg Arg Glu Tyr Gln Leu Ser
            1085                1090                1095
        Asp Ser Thr Lys Tyr Tyr Leu Asn Asp Leu Asp Arg Val Ala Asp
            1100                1105                1110
        Pro Ala Tyr Leu Pro Thr Gln Gln Asp Val Leu Arg Val Arg Val
            1115                1120                1125
        Pro Thr Thr Gly Ile Ile Glu Tyr Pro Phe Asp Leu Gln Ser Val
            1130                1135                1140
        Ile Phe Arg Met Val Asp Val Gly Gly Gln Arg Ser Glu Arg Arg
            1145                1150                1155
        Lys Trp Ile His Cys Phe Glu Asn Val Thr Ser Ile Met Phe Leu
            1160                1165                1170
        Val Ala Leu Ser Glu Tyr Asp Gln Val Leu Val Glu Ser Asp Asn
            1175                1180                1185
        Glu Asn Arg Met Glu Glu Ser Lys Ala Leu Phe Arg Thr Ile Ile
            1190                1195                1200
        Thr Tyr Pro Trp Phe Gln Asn Ser Ser Val Ile Leu Phe Leu Asn
            1205                1210                1215
        Lys Lys Asp Leu Leu Glu Glu Lys Ile Met Tyr Ser His Leu Val
            1220                1225                1230
        Asp Tyr Phe Pro Glu Tyr Asp Gly Pro Gln Arg Asp Ala Gln Ala
            1235                1240                1245
        Ala Arg Glu Phe Ile Leu Lys Met Phe Val Asp Leu Asn Pro Asp
            1250                1255                1260
        Ser Asp Lys Ile Asn Tyr Ser His Phe Thr Cys Ala Thr Asp Thr
            1265                1270                1275
```

```
Glu Asn Ile Arg Phe Val Phe Ala Ala Val Lys Asp Thr Ile Leu
    1280            1285                1290
Gln Leu Asn Leu Lys Gly Cys Gly Leu Tyr
    1295            1300
```

<210> SEQ ID NO 44
<211> LENGTH: 3969
<212> TYPE: DNA
<213> ORGANISM: Artificial Sequence
<220> FEATURE:
<221> NAME/KEY: misc_feature
<223> OTHER INFORMATION: GABA-BR1a*Gqo5 fusion construct

<400> SEQUENCE: 44

| | | | | | |
|---|---|---|---|---|---|
| atgttgctgc | tgctgctact | ggcgccactc | ttcctccgcc | ccccgggcgc | gggcggggcg | 60 |
| cagaccccca | acgccacctc | agaaggttgc | cagatcatac | acccgccctg | ggaaggggc | 120 |
| atcaggtacc | ggggcctgac | tcgggaccag | gtgaaggcta | tcaacttcct | gccagtggac | 180 |
| tatgagattg | agtatgtgtg | ccggggggag | cgcgaggtgg | tggggcccaa | ggtccgcaag | 240 |
| tgcctggcca | acggctcctg | gacagatatg | gacacaccca | gccgctgtgt | ccgaatctgc | 300 |
| tccaagtctt | atttgaccct | ggaaaatggg | aaggttttcc | tgacgggtgg | ggacctccca | 360 |
| gctctggacg | gagcccgggt | ggatttccgg | tgtgaccccg | acttccatct | ggtgggcagc | 420 |
| tcccggagca | tctgtagtca | gggccagtgg | agcaccccca | gccccactg | ccaggtgaat | 480 |
| cgaacgccac | actcagaacg | gcgcgcagtg | tacatcgggg | cactgttttcc | catgagcggg | 540 |
| ggctggccag | ggggccaggc | ctgccagccc | gcggtggaga | tggcgctgga | ggacgtgaat | 600 |
| agccgcaggg | acatcctgcc | ggactatgag | ctcaagctca | tccaccacga | cagcaagtgt | 660 |
| gatccaggcc | aagccaccaa | gtacctatat | gagctgctct | acaacgaccc | tatcaagatc | 720 |
| atccttatgc | ctggctgcag | ctctgtctcc | acgctggtgg | ctgaggctgc | taggatgtgg | 780 |
| aacctcattg | tgcttttccta | tggctccagc | tcaccagccc | tgtcaaaccg | gcagcgtttc | 840 |
| cccactttct | tccgaacgca | cccatcagcc | cactccaca | ccctacccg | cgtgaaactc | 900 |
| tttgaaaagt | ggggctggaa | gaagattgct | accatccagc | agaccactga | ggtcttcact | 960 |
| tcgactctgg | acgacctgga | ggaacgagtg | aaggaggctg | gaattgagat | tactttccgc | 1020 |
| cagagtttct | tctcagatcc | agctgtgccc | gtcaaaaacc | tgaagcgcca | ggatgcccga | 1080 |
| atcatcgtgg | gacttttcta | tgagactgaa | gcccggaaag | ttttttgtga | ggtgtacaag | 1140 |
| gagcgtctct | tgggaagaa | gtacgtctgg | ttcctcattg | gtggtatgc | tgacaattgg | 1200 |
| ttcaagatct | acgacccttc | tatcaactgc | acagtggatg | agatgactga | ggcggtggag | 1260 |
| ggccacatca | caactgagat | tgtcatgctg | aatcctgcca | tacccgcag | catttccaac | 1320 |
| atgacatccc | aggaatttgt | ggagaaacta | accaagcgac | tgaaaagaca | ccctgaggag | 1380 |
| acaggaggct | tccaggaggc | accgctggcc | tatgatgcca | tctgggcctt | ggcactggcc | 1440 |
| ctgaacaaga | catctggagg | aggcggccgt | tctggtgtgc | gcctggagga | cttcaactac | 1500 |
| aacaaccaga | ccattaccga | ccaaatctac | cgggcaatga | actcttcgtc | ctttgagggt | 1560 |
| gtctctggcc | atgtggtgtt | tgatgccagc | ggctctcgga | tggcatggac | gcttatcgag | 1620 |
| cagcttcagg | gtggcagcta | caagaagatt | ggctactatg | acagcaccaa | ggatgatctt | 1680 |
| tcctggtcca | aaacagataa | atggattgga | gggtccccc | cagctgacca | gaccctggtc | 1740 |
| atcaagacat | tccgcttcct | gtcacagaaa | ctctttatct | ccgtctcagt | tctctccagc | 1800 |
| ctgggcattg | tcctagctgt | tgtctgtctg | tcctttaaca | tctacaactc | acatgtccgt | 1860 |

-continued

```
tatatccaga actcacagcc caacctgaac aacctgactg ctgtgggctg ctcactggct    1920
ttagctgctg tcttccccct ggggctcgat ggttaccaca ttgggaggaa ccagtttcct    1980
ttcgtctgcc aggcccgcct ctggctcctg ggcctgggct ttagtctggg ctacggttcc    2040
atgttcacca agatttggtg ggtccacacg gtcttcacaa agaaggaaga aagaaggag     2100 tggaggaaga ctctggaacc ctggaagctg tatgccacag tgggcctgct ggtgggcatg    2160
gatgtcctca ctctcgccat ctggcagatc gtggaccctc tgcaccggac cattgagaca    2220
tttgccaagg aggaacctaa ggaagatatt gacgtctcta ttctgcccca gctgagcat     2280 tgcagctcca ggaagatgaa tacatggctt ggcattttct atggttacaa ggggctgctg    2340
ctgctgctgg gaatcttcct tgcttatgag accaagagtg tgtccactga aagatcaat    2400 gatcaccggg ctgtgggcat ggctatctac aatgtggcag tcctgtgcct catcactgct    2460
cctgtcacca tgattctgtc cagccagcag gatgcagcct ttgcctttgc ctctcttgcc    2520
atagttttct cctcctatat cactcttgtt gtgctctttg tgcccaagat gcgcaggctg    2580
atcacccgag gggaatggca gtcggaggcg caggacacca tgaagacagg gtcatcgacc    2640
aacaacaacg aggaggagaa gtcccggctg ttggagaagg agaaccgtga actggaaaag    2700
atcattgctg agaaagagga gcgtgtctct gaactgcgcc atcaactcca gtctcggcag    2760
cagctccgct cccggcgcca cccaccgaca cccccagaac cctctggggg cctgcccagg    2820
ggaccccctg agccccccga ccggcttagc tgtgatggga gtcgagtgca tttgctttat    2880
aaggcggccg ccatgactct ggagtccatc atggcgtgct gcctgagcga ggaggccaag    2940
gaagcccggc ggatcaacga cgagatcgag cggcagctcc gcaggggacaa gcgggacgcc    3000 cgccgggagc tcaagctgct gctgctcggg acaggagaga gtggcaagag tacgtttatc    3060
aagcagatga gaatcatcca tgggtcagga tactctgatg aagataaaag gggcttcacc    3120
aagctggtgt atcagaacat cttcacggcc atgcaggcca tgatcagagc catggacaca    3180
ctcaagatcc catacaagta tgagcacaat aaggctcatg cacaattagt tcgagaagtt    3240
gatgtggaga aggtgtctgc ttttgagaat ccatatgtag atgcaataaa gagtttatgg    3300
aatgatcctg gaatccagga atgctatgat agacgacgag aatatcaatt atctgactct    3360
accaaatact atcttaatga cttggaccgc gtagctgacc ctgcctacct gcctacgcaa    3420
caagatgtgc ttagagttcg agtccccacc acagggatca tcgaataccc ctttgactta    3480
caaagtgtca ttttcagaat ggtcgatgta gggggccaaa ggtcagagag aagaaaatgg    3540
atacactgct ttgaaaatgt cacctctatc atgtttctag tagcgcttag tgaatatgat    3600
caagttctcg tggagtcaga caatgagaac cgaatggagg aaagcaaggc tctctttaga    3660
acaattatca catacccctg gttccagaac tcctcggtta ttctgttctt aaacaagaaa    3720
gatcttctag aggagaaaat catgtattcc catctagtcg actacttccc agaatatgat    3780
ggaccccaga gagatgccca ggcagcccga gaattcattc tgaagatgtt cgtggacctg    3840
aacccagaca gtgacaaaat tatctactcc cacttcacgt gcgccacaga caccgagaat    3900
atccgctttg tctttgctgc cgtcaaggac accatcctcc agttgaacct gaagggctgc    3960
ggtctgtac                                                           3969
```

<210> SEQ ID NO 45
<211> LENGTH: 1324
<212> TYPE: PRT
<213> ORGANISM: Artificial Sequence
<220> FEATURE:

```
<221> NAME/KEY: misc_feature
<223> OTHER INFORMATION: GABA-BR1a*Gqo5 fusion construct
<221> NAME/KEY: MOD_RES
<222> LOCATION: (464)..(464)
<223> OTHER INFORMATION: Xaa is unknown or other

<400> SEQUENCE: 45
```

| | | | | | | | | | | | | | | |
|---|---|---|---|---|---|---|---|---|---|---|---|---|---|---|
| Met | Leu | Leu | Leu | Leu | Leu | Ala | Pro | Leu | Phe | Leu | Arg | Pro | Pro | Gly |
| 1 | | | | 5 | | | | | 10 | | | | | 15 |
| Ala | Gly | Gly | Ala | Gln | Thr | Pro | Asn | Ala | Thr | Ser | Glu | Gly | Cys | Gln | Ile |
| | | | 20 | | | | | 25 | | | | | 30 | | |
| Ile | His | Pro | Pro | Trp | Glu | Gly | Gly | Ile | Arg | Tyr | Arg | Gly | Leu | Thr | Arg |
| | | 35 | | | | | 40 | | | | | 45 | | | |
| Asp | Gln | Val | Lys | Ala | Ile | Asn | Phe | Leu | Pro | Val | Asp | Tyr | Glu | Ile | Glu |
| | 50 | | | | | 55 | | | | | 60 | | | | |
| Tyr | Val | Cys | Arg | Gly | Glu | Arg | Glu | Val | Val | Gly | Pro | Lys | Val | Arg | Lys |
| 65 | | | | | 70 | | | | | 75 | | | | | 80 |
| Cys | Leu | Ala | Asn | Gly | Ser | Trp | Thr | Asp | Met | Asp | Thr | Pro | Ser | Arg | Cys |
| | | | | 85 | | | | | 90 | | | | | 95 | |
| Val | Arg | Ile | Cys | Ser | Lys | Ser | Tyr | Leu | Thr | Leu | Glu | Asn | Gly | Lys | Val |
| | | | 100 | | | | | 105 | | | | | 110 | | |
| Phe | Leu | Thr | Gly | Gly | Asp | Leu | Pro | Ala | Leu | Asp | Gly | Ala | Arg | Val | Asp |
| | | 115 | | | | | 120 | | | | | 125 | | | |
| Phe | Arg | Cys | Asp | Pro | Asp | Phe | His | Leu | Val | Gly | Ser | Ser | Arg | Ser | Ile |
| | 130 | | | | | 135 | | | | | 140 | | | | |
| Cys | Ser | Gln | Gly | Gln | Trp | Ser | Thr | Pro | Lys | Pro | His | Cys | Gln | Val | Asn |
| 145 | | | | | 150 | | | | | 155 | | | | | 160 |
| Arg | Thr | Pro | His | Ser | Glu | Arg | Arg | Ala | Val | Tyr | Ile | Gly | Ala | Leu | Phe |
| | | | | 165 | | | | | 170 | | | | | 175 | |
| Pro | Met | Ser | Gly | Gly | Trp | Pro | Gly | Gly | Gln | Ala | Cys | Gln | Pro | Ala | Val |
| | | | 180 | | | | | 185 | | | | | 190 | | |
| Glu | Met | Ala | Leu | Glu | Asp | Val | Asn | Ser | Arg | Arg | Asp | Ile | Leu | Pro | Asp |
| | | 195 | | | | | 200 | | | | | 205 | | | |
| Tyr | Glu | Leu | Lys | Leu | Ile | His | His | Asp | Ser | Lys | Cys | Asp | Pro | Gly | Gln |
| | 210 | | | | | 215 | | | | | 220 | | | | |
| Ala | Thr | Lys | Tyr | Leu | Tyr | Glu | Leu | Leu | Tyr | Asn | Asp | Pro | Ile | Lys | Ile |
| 225 | | | | | 230 | | | | | 235 | | | | | 240 |
| Ile | Leu | Met | Pro | Gly | Cys | Ser | Ser | Val | Ser | Thr | Leu | Val | Ala | Glu | Ala |
| | | | | 245 | | | | | 250 | | | | | 255 | |
| Ala | Arg | Met | Trp | Asn | Leu | Ile | Val | Leu | Ser | Tyr | Gly | Ser | Ser | Ser | Pro |
| | | | 260 | | | | | 265 | | | | | 270 | | |
| Ala | Leu | Ser | Asn | Arg | Gln | Arg | Phe | Pro | Thr | Phe | Phe | Arg | Thr | His | Pro |
| | 275 | | | | | 280 | | | | | 285 | | | | |
| Ser | Ala | Thr | Leu | His | Asn | Pro | Thr | Arg | Val | Lys | Leu | Phe | Glu | Lys | Trp |
| 290 | | | | | 295 | | | | | 300 | | | | | |
| Gly | Trp | Lys | Lys | Ile | Ala | Thr | Ile | Gln | Gln | Thr | Thr | Glu | Val | Phe | Thr |
| 305 | | | | | 310 | | | | | 315 | | | | | 320 |
| Ser | Thr | Leu | Asp | Asp | Leu | Glu | Glu | Arg | Val | Lys | Glu | Ala | Gly | Ile | Glu |
| | | | | 325 | | | | | 330 | | | | | 335 | |
| Ile | Thr | Phe | Arg | Gln | Ser | Phe | Phe | Ser | Asp | Pro | Ala | Val | Pro | Val | Lys |
| | | | 340 | | | | | 345 | | | | | 350 | | |
| Asn | Leu | Lys | Arg | Gln | Asp | Ala | Arg | Ile | Ile | Val | Gly | Leu | Phe | Tyr | Glu |
| | 355 | | | | | 360 | | | | | 365 | | | | |
| Thr | Glu | Ala | Arg | Lys | Val | Phe | Cys | Glu | Val | Tyr | Lys | Glu | Arg | Leu | Phe |
| 370 | | | | | 375 | | | | | 380 | | | | | |

-continued

```
Gly Lys Lys Tyr Val Trp Phe Leu Ile Gly Trp Tyr Ala Asp Asn Trp
385                 390                 395                 400

Phe Lys Ile Tyr Asp Pro Ser Ile Asn Cys Thr Val Asp Glu Met Thr
                405                 410                 415

Glu Ala Val Glu Gly His Ile Thr Thr Glu Ile Val Met Leu Asn Pro
                420                 425                 430

Ala Asn Thr Arg Ser Ile Ser Asn Met Thr Ser Gln Glu Phe Val Glu
                435                 440                 445

Lys Leu Thr Lys Arg Leu Lys Arg His Pro Glu Glu Thr Gly Gly Xaa
450                 455                 460

Phe Gln Glu Ala Pro Leu Ala Tyr Asp Ala Ile Trp Ala Leu Ala Leu
465                 470                 475                 480

Ala Leu Asn Lys Thr Ser Gly Gly Gly Arg Ser Gly Val Arg Leu
                485                 490                 495

Glu Asp Phe Asn Tyr Asn Asn Gln Thr Ile Thr Asp Gln Ile Tyr Arg
                500                 505                 510

Ala Met Asn Ser Ser Ser Phe Glu Gly Val Ser Gly His Val Val Phe
                515                 520                 525

Asp Ala Ser Gly Ser Arg Met Ala Trp Thr Leu Ile Glu Gln Leu Gln
                530                 535                 540

Gly Gly Ser Tyr Lys Lys Ile Gly Tyr Tyr Asp Ser Thr Lys Asp Asp
545                 550                 555                 560

Leu Ser Trp Ser Lys Thr Asp Lys Trp Ile Gly Gly Ser Pro Pro Ala
                565                 570                 575

Asp Gln Thr Leu Val Ile Lys Thr Phe Arg Phe Leu Ser Gln Lys Leu
                580                 585                 590

Phe Ile Ser Val Ser Val Leu Ser Ser Leu Gly Ile Val Leu Ala Val
                595                 600                 605

Val Cys Leu Ser Phe Asn Ile Tyr Asn Ser His Val Arg Tyr Ile Gln
610                 615                 620

Asn Ser Gln Pro Asn Leu Asn Asn Leu Thr Ala Val Gly Cys Ser Leu
625                 630                 635                 640

Ala Leu Ala Ala Val Phe Pro Leu Gly Leu Asp Gly Tyr His Ile Gly
                645                 650                 655

Arg Asn Gln Phe Pro Phe Val Cys Gln Ala Arg Leu Trp Leu Leu Gly
                660                 665                 670

Leu Gly Phe Ser Leu Gly Tyr Gly Ser Met Phe Thr Lys Ile Trp Trp
                675                 680                 685

Val His Thr Val Phe Thr Lys Lys Glu Glu Lys Lys Glu Trp Arg Lys
690                 695                 700

Thr Leu Glu Pro Trp Lys Leu Tyr Ala Thr Val Gly Leu Leu Val Gly
705                 710                 715                 720

Met Asp Val Leu Thr Leu Ala Ile Trp Gln Ile Val Asp Pro Leu His
                725                 730                 735

Arg Thr Ile Glu Thr Phe Ala Lys Glu Pro Lys Glu Asp Ile Asp
                740                 745                 750

Val Ser Ile Leu Pro Gln Leu Glu His Cys Ser Ser Arg Lys Met Asn
755                 760                 765

Thr Trp Leu Gly Ile Phe Tyr Gly Tyr Lys Gly Leu Leu Leu Leu
770                 775                 780

Gly Ile Phe Leu Ala Tyr Glu Thr Lys Ser Val Ser Thr Glu Lys Ile
785                 790                 795                 800
```

```
Asn Asp His Arg Ala Val Gly Met Ala Ile Tyr Asn Val Ala Val Leu
            805                 810                 815

Cys Leu Ile Thr Ala Pro Val Thr Met Ile Leu Ser Ser Gln Gln Asp
            820                 825                 830

Ala Ala Phe Ala Phe Ala Ser Leu Ala Ile Val Phe Ser Ser Tyr Ile
            835                 840                 845

Thr Leu Val Val Leu Phe Val Pro Lys Met Arg Arg Leu Ile Thr Arg
            850                 855                 860

Gly Glu Trp Gln Ser Glu Ala Gln Asp Thr Met Lys Thr Gly Ser Ser
865                 870                 875                 880

Thr Asn Asn Asn Glu Glu Lys Ser Arg Leu Leu Glu Lys Glu Asn
            885                 890                 895

Arg Glu Leu Glu Lys Ile Ile Ala Glu Lys Glu Arg Val Ser Glu
            900                 905                 910

Leu Arg His Gln Leu Gln Ser Arg Gln Gln Leu Arg Ser Arg Arg His
            915                 920                 925

Pro Pro Thr Pro Pro Glu Pro Ser Gly Gly Leu Pro Arg Gly Pro Pro
930                 935                 940

Glu Pro Pro Asp Arg Leu Ser Cys Asp Gly Ser Arg Val His Leu Leu
945                 950                 955                 960

Tyr Lys Ala Ala Ala Met Thr Leu Glu Ser Ile Met Ala Cys Cys Leu
            965                 970                 975

Ser Glu Glu Ala Lys Glu Ala Arg Arg Ile Asn Asp Glu Ile Glu Arg
            980                 985                 990

Gln Leu Arg Arg Asp Lys Arg Asp  Ala Arg Arg Glu Leu  Lys Leu Leu
            995                 1000                1005

Leu Leu Gly Thr Gly Glu Ser  Gly Lys Ser Thr Phe  Ile Lys Gln
            1010                1015                1020

Met Arg Ile Ile His Gly Ser  Gly Tyr Ser Asp Glu  Asp Lys Arg
            1025                1030                1035

Gly Phe Thr Lys Leu Val Tyr  Gln Asn Ile Phe Thr  Ala Met Gln
            1040                1045                1050

Ala Met Ile Arg Ala Met Asp  Thr Leu Lys Ile Pro  Tyr Lys Tyr
            1055                1060                1065

Glu His Asn Lys Ala His Ala  Gln Leu Val Arg Glu  Val Asp Val
            1070                1075                1080

Glu Lys Val Ser Ala Phe Glu  Asn Pro Tyr Val Asp  Ala Ile Lys
            1085                1090                1095

Ser Leu Trp Asn Asp Pro Gly  Ile Gln Glu Cys Tyr  Asp Arg Arg
            1100                1105                1110

Arg Glu Tyr Gln Leu Ser Asp  Ser Thr Lys Tyr Tyr  Leu Asn Asp
            1115                1120                1125

Leu Asp Arg Val Ala Asp Pro  Ala Tyr Leu Pro Thr  Gln Gln Asp
            1130                1135                1140

Val Leu Arg Val Arg Val Pro  Thr Thr Gly Ile Ile  Glu Tyr Pro
            1145                1150                1155

Phe Asp Leu Gln Ser Val Ile  Phe Arg Met Val Asp  Val Gly Gly
            1160                1165                1170

Gln Arg Ser Glu Arg Arg Lys  Trp Ile His Cys Phe  Glu Asn Val
            1175                1180                1185

Thr Ser Ile Met Phe Leu Val  Ala Leu Ser Glu Tyr  Asp Gln Val
            1190                1195                1200

Leu Val Glu Ser Asp Asn Glu  Asn Arg Met Glu Glu  Ser Lys Ala
```

-continued

```
              1205                  1210                  1215
Leu Phe Arg Thr Ile Ile Thr Tyr Pro Trp Phe Gln Asn Ser Ser
    1220                  1225                  1230

Val Ile Leu Phe Leu Asn Lys Lys Asp Leu Leu Glu Glu Lys Ile
    1235                  1240                  1245

Met Tyr Ser His Leu Val Asp Tyr Phe Pro Glu Tyr Asp Gly Pro
    1250                  1255                  1260

Gln Arg Asp Ala Gln Ala Ala Arg Glu Phe Ile Leu Lys Met Phe
    1265                  1270                  1275

Val Asp Leu Asn Pro Asp Ser Asp Lys Ile Ile Tyr Ser His Phe
    1280                  1285                  1290

Thr Cys Ala Thr Asp Thr Glu Asn Ile Arg Phe Val Phe Ala Ala
    1295                  1300                  1305

Val Lys Asp Thr Ile Leu Gln Leu Asn Leu Lys Gly Cys Gly Leu
    1310                  1315                  1320

Tyr
```

<210> SEQ ID NO 46
<211> LENGTH: 4231
<212> TYPE: DNA
<213> ORGANISM: Artificial Sequence
<220> FEATURE:
<221> NAME/KEY: misc_feature
<223> OTHER INFORMATION: pmGluR2//CaR*G qi5+Ala linker fusion construct

<400> SEQUENCE: 46

| | | |
|---|---|---|
| atgggatcgc tgcttgcgct cccggcactg ctgctgctgt ggggtgctgt ggctgagggc | 60 |
| ccagccaaga aggtgctgac cctggaggga gacttggtgc tgggtgggct gttcccagtg | 120 |
| caccagaagg gcggcccagc agaggactgt ggtcctgtca atgagcaccg tggcatccag | 180 |
| cgcctggagg ccatgctttt tgcactggac cgcatcaacc gtgacccgca cctgctgcct | 240 |
| ggcgtgcgcc tgggtgcaca catcctcgac agttgctcca aggacacaca tgcgctggag | 300 |
| caggcactgg actttgtgcg tgcctcactc agccgtggtg ctgatggctc acgccacatc | 360 |
| tgccccgacg gctcttatgc gacccatggt gatgctccca ctgccatcac tggtgttatt | 420 |
| ggcggttcct acagtgatgt ctccatccag gtggccaacc tcttgaggct atttcagatc | 480 |
| ccacagatta gctacgcctc taccagtgcc aagctgagtg acaagtcccg ctatgactac | 540 |
| tttgcccgca cagtgcctcc tgacttcttc aagccaaggg ccatggctga gattctccgc | 600 |
| ttcttcaact ggacctatgt gtccactgtg gcgtctgagg gcgactatgg cgagacaggc | 660 |
| attgaggcct tgagctaga ggctcgtgcc cgcaacatct gtgtggccac ctcggagaaa | 720 |
| gtgggccgtg ccatgagccg gcggcctttt gagggtgtgg tgcgagccct gctgcagaag | 780 |
| cccagtgccc gcgtggctgt cctgttcacc cgttctgagc atgcccggga gctgcttgct | 840 |
| gccagccagc gcctcaatgc cagcttcacc tgggtggcca gtgatggttg gggggccctg | 900 |
| gagagtgtgg tggcaggcag tgagggggct gctgagggtg ctatcaccat cgagctggcc | 960 |
| tcctacccca tcagtgactt tgcctcctac ttccagagcc tggaccctg gaacaacagc | 1020 |
| cggaacccct ggttccgtga attctgggag cagaggttcc gctgcagctt ccggcagcga | 1080 |
| gactgcgcag cccactctct ccgggctgtg ccctttgagc aggagtccaa gatcatgttt | 1140 |
| gtggtcaatg cagtgtacgc catggcccat gcgctccaca acatgcaccg tgccctctgc | 1200 |
| cccaacacca cccggctctg tgacgcgatg cggccagtta acgggcgccg cctctacaag | 1260 |
| gactttgtgc tcaacgtcaa gtttgatgcc ccctttcgcc cagctgacac ccacaatgag | 1320 |

-continued

```
gtccgctttg accgctttgg tgatggtatt ggccgctaca acatcttcac ctatctgcgt    1380
gcaggcagtg ggcgctatcg ctaccagaag gtgggctact gggcagaagg cttgactctg    1440
gacaccagcc tcatcccatg ggcctcaccc tcagccggcc cctgcccgc ctctcgctgc     1500 agtgagccct gcctccagaa tgaggtgaag agtgtgcagc cgggcgaagt ctgctgctgg    1560
ctctgcattc cgtgccagcc ctatgagtac cgattggacg aattcacttg cgctgattgt    1620
ggcctgggct actggcccaa tgccagcctg actggctgct cgaactgcc ccaggagtac     1680 atccgctggg gcgatgcctg ggctgtggga cctgtcacca tcgcctgcct cggtgccctg    1740
gccaccctct ttgtgctggg tgtctttgtg cggcacaatg ccacaccagt ggtcaaggcc    1800
tcaggtcggg agctctgcta catcctgctg ggtggtgtct tcctctgcta ctgcatgacc    1860
ttcatcttca ttgccaagcc atccacggca gtgtgtacct acggcgtct tggtttgggc    1920 actgccttct ctgtctgcta ctcagccctg ctcaccaaga ccaaccgcat tgcacgcatc    1980
ttcggtgggg cccgggaggg tgcccagcgg ccacgcttca tcagtcctgc ctcacaggtg    2040
gccatctgcc tggcacttat ctcgggccag ctgctcatcg tggtcgcctg gctggtggtg    2100
gaggcaccgg gcacaggcaa ggagacagcc cccgaacggc gggaggtggt gacactgcgc    2160
tgcaaccacc gcgatgcaag tatgttgggc tcgctggcct acaatgtgct cctcatcgcg    2220
ctctgcacgc tttatgcctt caagactcgc aagtgccccg aaaacttcaa cgaggccaag    2280
ttcattggct tcaccatgta caccacctgc atcatctggc tggcattcct gcccatcttc    2340
tatgtcacct ccagtgacta ccgggtacag accaccacca tgtgcgtgtc agtcagcctc    2400
agcggctccg tggtgcttgg ctgcctcttt gcgcccaagc tgcacatcat cctcttccag    2460
ccgcagaaga acaccatcga ggaggtgcgt tgcagcaccg cagctcacgc tttcaaggtg    2520
gctgcccggg ccacgctgcg ccgcagcaac gtctcccgca agcggtccag cagccttgga    2580
ggctccacgg gatccacccc ctcctcctcc atcagcagca agagcaacag cgaagaccca    2640
ttcccacagc ccgagaggca gaagcagcag cagccgctgg ccctaaccca gcaagagcag    2700
cagcagcagc ccctgaccct cccacagcag caacgatctc agcagcagcc cagatgcaag    2760
cagaaggtca tctttggcag cggcacggtc accttctcac tgagctttga tgagcctcag    2820
aagaacgcca tggcccacgg gaattctacg caccagaact ccctggaggc cagaaaagc    2880 agcgatacgc tgacccgaca ccagccatta ctcccgctgc agtgcgggga aacggactta    2940
gatctgaccg tccaggaaac aggtctgcaa ggacctgtgg gtggagacca gcggccagag    3000
gtggaggacc ctgaagagtt gtccccagca cttgtagtgt ccagttcaca gagctttgtc    3060
atcagtggtg gaggcagcac tgttacagaa aacgtagtga attcagcggc cgccatgact    3120
ctggagtcca tcatggcgtg ctgcctgagc gaggaggcca aggaagcccg gcggatcaac    3180
gacgagatcg agcggcagct ccgcagggac aagcgggacg cccgccggga gctcaagctg    3240
ctgctgctcg ggacaggaga gagtggcaag agtacgttta tcaagcagat gagaatcatc    3300
catgggtcag atactctga tgaagataaa aggggcttca ccaagctggt gtatcagaac    3360
atcttcacgg ccatgcaggc catgatcaga gccatggaca cactcaagat cccatacaag    3420
tatgagcaca ataaggctca tgcacaatta gttcgagaag ttgatgtgga aaggtgtct    3480 gcttttgaga atccatatgt agatgcaata aagagtttat ggaatgatcc tggaatccag    3540
gaatgctatg atagcgacg agaatatcaa ttatctgact ctaccaaata ctatcttaat    3600
gacttggacc gcgtagctga ccctgcctac ctgcctacgc aacaagatgt gcttagagtt    3660
```

-continued

| | |
|---|---|
| cgagtcccca ccacagggat catcgaatac cccttttgact tacaaagtgt cattttcaga | 3720 |
| atggtcgatg taggggggcca aaggtcagag agaagaaaat ggatacactg ctttgaaaat | 3780 |
| gtcacctcta tcatgtttct agtagcgctt agtgaatatg atcaagttct cgtggagtca | 3840 |
| gacaatgaga accgaatgga ggaaagcaag gctctcttta gaacaattat cacatacccc | 3900 |
| tggttccaga actcctcggt tattctgttc ttaaacaaga aagatcttct agaggagaaa | 3960 |
| atcatgtatt cccatctagt cgactacttc ccagaatatg atggaccccca gagagatgcc | 4020 |
| caggcagccc gagaattcat tctgaagatg ttcgtggacc tgaacccaga cagtgacaaa | 4080 |
| attatctact cccacttcac gtgcgccaca gacaccgaga atatccgctt tgtctttgct | 4140 |
| gccgtcaagg acaccatcct ccagttgaac ctgaaggact gcggtctgtt ctaattgtgc | 4200 |
| ctcctagaca cccgccctgc ccttccctgg t | 4231 |

<210> SEQ ID NO 47
<211> LENGTH: 1397
<212> TYPE: PRT
<213> ORGANISM: Artificial Sequence
<220> FEATURE:
<221> NAME/KEY: misc_feature
<223> OTHER INFORMATION: pmGluR2//CaR*G qi5+Ala linker fusion construct

<400> SEQUENCE: 47

```
Met Gly Ser Leu Leu Ala Leu Pro Ala Leu Leu Leu Trp Gly Ala
1               5                   10                  15

Val Ala Glu Gly Pro Ala Lys Lys Val Leu Thr Leu Glu Gly Asp Leu
            20                  25                  30

Val Leu Gly Gly Leu Phe Pro Val His Gln Lys Gly Gly Pro Ala Glu
        35                  40                  45

Asp Cys Gly Pro Val Asn Glu His Arg Gly Ile Gln Arg Leu Glu Ala
    50                  55                  60

Met Leu Phe Ala Leu Asp Arg Ile Asn Arg Asp Pro His Leu Leu Pro
65                  70                  75                  80

Gly Val Arg Leu Gly Ala His Ile Leu Asp Ser Cys Ser Lys Asp Thr
                85                  90                  95

His Ala Leu Glu Gln Ala Leu Asp Phe Val Arg Ala Ser Leu Ser Arg
            100                 105                 110

Gly Ala Asp Gly Ser Arg His Ile Cys Pro Asp Gly Ser Tyr Ala Thr
        115                 120                 125

His Gly Asp Ala Pro Thr Ala Ile Thr Gly Val Ile Gly Gly Ser Tyr
    130                 135                 140

Ser Asp Val Ser Ile Gln Val Ala Asn Leu Leu Arg Leu Phe Gln Ile
145                 150                 155                 160

Pro Gln Ile Ser Tyr Ala Ser Thr Ser Ala Lys Leu Ser Asp Lys Ser
                165                 170                 175

Arg Tyr Asp Tyr Phe Ala Arg Thr Val Pro Pro Asp Phe Phe Gln Ala
            180                 185                 190

Lys Ala Met Ala Glu Ile Leu Arg Phe Phe Asn Trp Thr Tyr Val Ser
        195                 200                 205

Thr Val Ala Ser Glu Gly Asp Tyr Gly Glu Thr Gly Ile Glu Ala Phe
    210                 215                 220

Glu Leu Glu Ala Arg Ala Arg Asn Ile Cys Val Ala Thr Ser Glu Lys
225                 230                 235                 240

Val Gly Arg Ala Met Ser Arg Ala Ala Phe Glu Gly Val Val Arg Ala
                245                 250                 255
```

-continued

Leu Leu Gln Lys Pro Ser Ala Arg Val Ala Val Leu Phe Thr Arg Ser
            260                 265                 270

Glu Asp Ala Arg Glu Leu Leu Ala Ala Ser Gln Arg Leu Asn Ala Ser
        275                 280                 285

Phe Thr Trp Val Ala Ser Asp Gly Trp Gly Ala Leu Glu Ser Val Val
    290                 295                 300

Ala Gly Ser Glu Gly Ala Ala Glu Gly Ala Ile Thr Ile Glu Leu Ala
305                 310                 315                 320

Ser Tyr Pro Ile Ser Asp Phe Ala Ser Tyr Phe Gln Ser Leu Asp Pro
                325                 330                 335

Trp Asn Asn Ser Arg Asn Pro Trp Phe Arg Glu Phe Trp Glu Gln Arg
            340                 345                 350

Phe Arg Cys Ser Phe Arg Gln Arg Asp Cys Ala Ala His Ser Leu Arg
        355                 360                 365

Ala Val Pro Phe Glu Gln Glu Ser Lys Ile Met Phe Val Val Asn Ala
    370                 375                 380

Val Tyr Ala Met Ala His Ala Leu His Asn Met His Arg Ala Leu Cys
385                 390                 395                 400

Pro Asn Thr Thr Arg Leu Cys Asp Ala Met Arg Pro Val Asn Gly Arg
                405                 410                 415

Arg Leu Tyr Lys Asp Phe Val Leu Asn Val Lys Phe Asp Ala Pro Phe
            420                 425                 430

Arg Pro Ala Asp Thr His Asn Glu Val Arg Phe Asp Arg Phe Gly Asp
        435                 440                 445

Gly Ile Gly Arg Tyr Asn Ile Phe Thr Tyr Leu Arg Ala Gly Ser Gly
    450                 455                 460

Arg Tyr Arg Tyr Gln Lys Val Gly Tyr Trp Ala Glu Gly Leu Thr Leu
465                 470                 475                 480

Asp Thr Ser Leu Ile Pro Trp Ala Ser Pro Ser Ala Gly Pro Leu Pro
                485                 490                 495

Ala Ser Arg Cys Ser Glu Pro Cys Leu Gln Asn Glu Val Lys Ser Val
            500                 505                 510

Gln Pro Gly Glu Val Cys Cys Trp Leu Cys Ile Pro Cys Gln Pro Tyr
        515                 520                 525

Glu Tyr Arg Leu Asp Glu Phe Thr Cys Ala Asp Cys Gly Leu Gly Tyr
    530                 535                 540

Trp Pro Asn Ala Ser Leu Thr Gly Cys Phe Glu Leu Pro Gln Glu Tyr
545                 550                 555                 560

Ile Arg Trp Gly Asp Ala Trp Ala Val Gly Pro Val Thr Ile Ala Cys
                565                 570                 575

Leu Gly Ala Leu Ala Thr Leu Phe Val Leu Gly Val Phe Val Arg His
            580                 585                 590

Asn Ala Thr Pro Val Val Lys Ala Ser Gly Arg Glu Leu Cys Tyr Ile
        595                 600                 605

Leu Leu Gly Gly Val Phe Leu Cys Tyr Cys Met Thr Phe Ile Phe Ile
    610                 615                 620

Ala Lys Pro Ser Thr Ala Val Cys Thr Leu Arg Arg Leu Gly Leu Gly
625                 630                 635                 640

Thr Ala Phe Ser Val Cys Tyr Ser Ala Leu Leu Thr Lys Thr Asn Arg
                645                 650                 655

Ile Ala Arg Ile Phe Gly Gly Ala Arg Glu Gly Ala Gln Arg Pro Arg
            660                 665                 670

Phe Ile Ser Pro Ala Ser Gln Val Ala Ile Cys Leu Ala Leu Ile Ser

-continued

```
              675                 680                 685
Gly Gln Leu Leu Ile Val Val Ala Trp Leu Val Glu Ala Pro Gly
        690                 695                 700
Thr Gly Lys Glu Thr Ala Pro Glu Arg Arg Glu Val Val Thr Leu Arg
705                 710                 715                 720
Cys Asn His Arg Asp Ala Ser Met Leu Gly Ser Leu Ala Tyr Asn Val
                725                 730                 735
Leu Leu Ile Ala Leu Cys Thr Leu Tyr Ala Phe Lys Thr Arg Lys Cys
            740                 745                 750
Pro Glu Asn Phe Asn Glu Ala Lys Phe Ile Gly Phe Thr Met Tyr Thr
            755                 760                 765
Thr Cys Ile Ile Trp Leu Ala Phe Leu Pro Ile Phe Tyr Val Thr Ser
    770                 775                 780
Ser Asp Tyr Arg Val Gln Thr Thr Thr Met Cys Val Ser Val Ser Leu
785                 790                 795                 800
Ser Gly Ser Val Val Leu Gly Cys Leu Phe Ala Pro Lys Leu His Ile
                805                 810                 815
Ile Leu Phe Gln Pro Gln Lys Asn Thr Ile Glu Glu Val Arg Cys Ser
            820                 825                 830
Thr Ala Ala His Ala Phe Lys Val Ala Ala Arg Ala Thr Leu Arg Arg
            835                 840                 845
Ser Asn Val Ser Arg Lys Arg Ser Ser Ser Leu Gly Gly Ser Thr Gly
    850                 855                 860
Ser Thr Pro Ser Ser Ser Ile Ser Ser Lys Ser Asn Ser Glu Asp Pro
865                 870                 875                 880
Phe Pro Gln Pro Glu Arg Gln Lys Gln Gln Gln Pro Leu Ala Leu Thr
                885                 890                 895
Gln Gln Glu Gln Gln Gln Gln Pro Leu Thr Leu Pro Gln Gln Gln Arg
            900                 905                 910
Ser Gln Gln Gln Pro Arg Cys Lys Gln Lys Val Ile Phe Gly Ser Gly
            915                 920                 925
Thr Val Thr Phe Ser Leu Ser Phe Asp Glu Pro Gln Lys Asn Ala Met
    930                 935                 940
Ala His Gly Asn Ser Thr His Gln Asn Ser Leu Glu Ala Gln Lys Ser
945                 950                 955                 960
Ser Asp Thr Leu Thr Arg His Gln Pro Leu Leu Pro Leu Gln Cys Gly
                965                 970                 975
Glu Thr Asp Leu Asp Leu Thr Val Gln Glu Thr Gly Leu Gln Gly Pro
            980                 985                 990
Val Gly Gly Asp Gln Arg Pro Glu Val Glu Asp Pro Glu Glu Leu Ser
        995                 1000                1005
Pro Ala Leu Val Val Ser Ser Ser Gln Ser Phe Val Ile Ser Gly
    1010                1015                1020
Gly Gly Ser Thr Val Thr Glu Asn Val Val Asn Ser Ala Ala Ala
    1025                1030                1035
Met Thr Leu Glu Ser Ile Met Ala Cys Cys Leu Ser Glu Glu Ala
    1040                1045                1050
Lys Glu Ala Arg Arg Ile Asn Asp Glu Ile Glu Arg Gln Leu Arg
    1055                1060                1065
Arg Asp Lys Arg Asp Ala Arg Arg Glu Leu Lys Leu Leu Leu Leu
    1070                1075                1080
Gly Thr Gly Glu Ser Gly Lys Ser Thr Phe Ile Lys Gln Met Arg
    1085                1090                1095
```

Ile Ile His Gly Ser Gly Tyr Ser Asp Glu Asp Lys Arg Gly Phe
1100                1105                1110

Thr Lys Leu Val Tyr Gln Asn Ile Phe Thr Ala Met Gln Ala Met
     1115                1120                1125

Ile Arg Ala Met Asp Thr Leu Lys Ile Pro Tyr Lys Tyr Glu His
     1130                1135                1140

Asn Lys Ala His Ala Gln Leu Val Arg Glu Val Asp Val Glu Lys
     1145                1150                1155

Val Ser Ala Phe Glu Asn Pro Tyr Val Asp Ala Ile Lys Ser Leu
     1160                1165                1170

Trp Asn Asp Pro Gly Ile Gln Glu Cys Tyr Asp Arg Arg Arg Glu
     1175                1180                1185

Tyr Gln Leu Ser Asp Ser Thr Lys Tyr Tyr Leu Asn Asp Leu Asp
     1190                1195                1200

Arg Val Ala Asp Pro Ala Tyr Leu Pro Thr Gln Gln Asp Val Leu
     1205                1210                1215

Arg Val Arg Val Pro Thr Thr Gly Ile Ile Glu Tyr Pro Phe Asp
     1220                1225                1230

Leu Gln Ser Val Ile Phe Arg Met Val Asp Val Gly Gly Gln Arg
     1235                1240                1245

Ser Glu Arg Arg Lys Trp Ile His Cys Phe Glu Asn Val Thr Ser
     1250                1255                1260

Ile Met Phe Leu Val Ala Leu Ser Glu Tyr Asp Gln Val Leu Val
     1265                1270                1275

Glu Ser Asp Asn Glu Asn Arg Met Glu Glu Ser Lys Ala Leu Phe
     1280                1285                1290

Arg Thr Ile Ile Thr Tyr Pro Trp Phe Gln Asn Ser Ser Val Ile
     1295                1300                1305

Leu Phe Leu Asn Lys Lys Asp Leu Leu Glu Glu Lys Ile Met Tyr
     1310                1315                1320

Ser His Leu Val Asp Tyr Phe Pro Glu Tyr Asp Gly Pro Gln Arg
     1325                1330                1335

Asp Ala Gln Ala Ala Arg Glu Phe Ile Leu Lys Met Phe Val Asp
     1340                1345                1350

Leu Asn Pro Asp Ser Asp Lys Ile Ile Tyr Ser His Phe Thr Cys
     1355                1360                1365

Ala Thr Asp Thr Glu Asn Ile Arg Phe Val Phe Ala Ala Val Lys
     1370                1375                1380

Asp Thr Ile Leu Gln Leu Asn Leu Lys Asp Cys Gly Leu Phe
     1385                1390                1395

<210> SEQ ID NO 48
<211> LENGTH: 909
<212> TYPE: PRT
<213> ORGANISM: Artificial Sequence
<220> FEATURE:
<221> NAME/KEY: misc_feature
<223> OTHER INFORMATION: chimeric ph8SPmGluR4

<400> SEQUENCE: 48

Met Val Cys Glu Gly Lys Arg Ser Ala Ser Cys Pro Cys Phe Phe Leu
1               5                   10                  15

Leu Thr Ala Lys Phe Tyr Trp Ile Leu Thr Met Met Gln Arg Thr His
            20                  25                  30

Ser Gln Glu Tyr Ala His Ser Ile Arg Ile Asp Gly Asp Ile Thr Leu

-continued

```
                35                  40                  45
Gly Gly Leu Phe Pro Val His Gly Arg Gly Ser Glu Gly Lys Pro Cys
 50                  55                  60
Gly Glu Leu Lys Lys Glu Lys Gly Ile His Arg Leu Glu Ala Met Leu
 65                  70                  75                  80
Phe Ala Leu Asp Arg Ile Asn Asn Asp Pro Asp Leu Leu Pro Asn Ile
                 85                  90                  95
Thr Leu Gly Ala Arg Ile Leu Asp Thr Cys Ser Arg Asp Thr His Ala
                100                 105                 110
Leu Glu Gln Ser Leu Thr Phe Val Gln Ala Leu Ile Glu Lys Asp Gly
                115                 120                 125
Thr Glu Val Arg Cys Gly Ser Gly Pro Pro Ile Ile Thr Lys Pro
130                 135                 140
Glu Arg Val Val Gly Val Ile Gly Ala Ser Gly Ser Ser Val Ser Ile
145                 150                 155                 160
Met Val Ala Asn Ile Leu Arg Leu Phe Lys Ile Pro Gln Ile Ser Tyr
                165                 170                 175
Ala Ser Thr Ala Pro Asp Leu Ser Asp Asn Ser Arg Tyr Asp Phe Phe
                180                 185                 190
Ser Arg Val Val Pro Ser Asp Thr Tyr Gln Ala Gln Ala Met Val Asp
                195                 200                 205
Ile Val Arg Ala Leu Lys Trp Asn Tyr Val Ser Thr Val Ala Ser Glu
210                 215                 220
Gly Ser Tyr Gly Glu Ser Gly Val Glu Ala Phe Ile Gln Lys Ser Arg
225                 230                 235                 240
Glu Asp Gly Gly Val Cys Ile Ala Gln Ser Val Lys Ile Pro Arg Glu
                245                 250                 255
Pro Lys Ala Gly Glu Phe Asp Lys Ile Ile Arg Arg Leu Leu Glu Thr
                260                 265                 270
Ser Asn Ala Arg Ala Val Ile Ile Phe Ala Asn Glu Asp Asp Ile Arg
                275                 280                 285
Arg Val Leu Glu Ala Ala Arg Arg Ala Asn Gln Thr Gly His Phe Phe
                290                 295                 300
Trp Met Gly Ser Asp Ser Trp Gly Ser Lys Ile Ala Pro Val Leu His
305                 310                 315                 320
Leu Glu Glu Val Ala Glu Gly Ala Val Thr Ile Leu Pro Lys Arg Met
                325                 330                 335
Ser Val Arg Gly Phe Asp Arg Tyr Phe Ser Ser Arg Thr Leu Asp Asn
                340                 345                 350
Asn Arg Arg Asn Ile Trp Phe Ala Glu Phe Trp Glu Asp Asn Phe His
                355                 360                 365
Cys Lys Leu Ser Arg His Ala Leu Lys Lys Gly Ser His Val Lys Lys
                370                 375                 380
Cys Thr Asn Arg Glu Arg Ile Gly Gln Asp Ser Ala Tyr Glu Gln Glu
385                 390                 395                 400
Gly Lys Val Gln Phe Val Ile Asp Ala Val Tyr Ala Met Gly His Ala
                405                 410                 415
Leu His Ala Met His Arg Asp Leu Cys Pro Gly Arg Val Gly Leu Cys
                420                 425                 430
Pro Arg Met Asp Pro Val Asp Gly Thr Gln Leu Leu Lys Tyr Ile Arg
                435                 440                 445
Asn Val Asn Phe Ser Gly Ile Ala Gly Asn Pro Val Thr Phe Asn Glu
450                 455                 460
```

```
Asn Gly Asp Ala Pro Gly Arg Tyr Asp Ile Tyr Gln Tyr Gln Leu Arg
465                 470                 475                 480

Asn Asp Ser Ala Glu Tyr Lys Val Ile Gly Ser Trp Thr Asp His Leu
            485                 490                 495

His Leu Arg Ile Glu Arg Met His Trp Pro Gly Ser Gly Gln Gln Leu
            500                 505                 510

Pro Arg Ser Ile Cys Ser Leu Pro Cys Gln Pro Gly Glu Arg Lys Lys
            515                 520                 525

Thr Val Lys Gly Met Pro Cys Cys Trp His Cys Glu Pro Cys Thr Gly
            530                 535                 540

Tyr Gln Tyr Gln Val Asp Arg Tyr Thr Cys Lys Thr Cys Pro Tyr Asp
545                 550                 555                 560

Met Arg Pro Thr Glu Asn Arg Thr Gly Cys Arg Pro Ile Pro Ile Ile
            565                 570                 575

Lys Leu Glu Trp Gly Ser Pro Trp Ala Val Leu Pro Leu Phe Leu Ala
            580                 585                 590

Val Val Gly Ile Ala Ala Thr Leu Phe Val Val Ile Thr Phe Val Arg
            595                 600                 605

Tyr Asn Asp Thr Pro Ile Val Lys Ala Ser Gly Arg Glu Leu Ser Tyr
            610                 615                 620

Val Leu Leu Ala Gly Ile Phe Leu Cys Tyr Ala Thr Thr Phe Leu Met
625                 630                 635                 640

Ile Ala Glu Pro Asp Leu Gly Thr Cys Ser Leu Arg Arg Ile Phe Leu
            645                 650                 655

Gly Leu Gly Met Ser Ile Ser Tyr Ala Ala Leu Leu Thr Lys Thr Asn
            660                 665                 670

Arg Ile Tyr Arg Ile Phe Glu Gln Gly Lys Arg Ser Val Ser Ala Pro
            675                 680                 685

Arg Phe Ile Ser Pro Ala Ser Gln Leu Ala Ile Thr Phe Ser Leu Ile
            690                 695                 700

Ser Leu Gln Leu Leu Gly Ile Cys Val Trp Phe Val Val Asp Pro Ser
705                 710                 715                 720

His Ser Val Val Asp Phe Gln Asp Gln Arg Thr Leu Asp Pro Arg Phe
            725                 730                 735

Ala Arg Gly Val Leu Lys Cys Asp Ile Ser Asp Leu Ser Leu Ile Cys
            740                 745                 750

Leu Leu Gly Tyr Ser Met Leu Leu Met Val Thr Cys Thr Val Tyr Ala
            755                 760                 765

Ile Lys Thr Arg Gly Val Pro Glu Thr Phe Asn Glu Ala Lys Pro Ile
770                 775                 780

Gly Phe Thr Met Tyr Thr Thr Cys Ile Val Trp Leu Ala Phe Ile Pro
785                 790                 795                 800

Ile Phe Phe Gly Thr Ser Gln Ser Ala Asp Lys Leu Tyr Ile Gln Thr
            805                 810                 815

Thr Thr Leu Thr Val Ser Val Ser Leu Ser Ala Ser Val Ser Leu Gly
            820                 825                 830

Met Leu Tyr Met Pro Lys Val Tyr Ile Ile Leu Phe His Pro Glu Gln
            835                 840                 845

Asn Val Pro Lys Arg Lys Arg Ser Leu Lys Ala Val Val Thr Ala Ala
            850                 855                 860

Thr Met Ser Asn Lys Phe Thr Gln Lys Gly Asn Phe Arg Pro Asn Gly
865                 870                 875                 880
```

```
Glu Ala Lys Ser Glu Leu Cys Glu Asn Leu Glu Ala Pro Ala Leu Ala
                885                 890                 895

Thr Lys Gln Thr Tyr Val Thr Tyr Thr Asn His Ala Ile
            900                 905

<210> SEQ ID NO 49
<211> LENGTH: 1422
<212> TYPE: PRT
<213> ORGANISM: Artificial Sequence
<220> FEATURE:
<221> NAME/KEY: misc_feature
<223> OTHER INFORMATION: phmGluR4//CaR*AAA*G-alpha qi5 fusion construct

<400> SEQUENCE: 49

Met Val Cys Glu Gly Lys Arg Ser Ala Ser Cys Pro Cys Phe Phe Leu
1               5                   10                  15

Leu Thr Ala Lys Phe Tyr Trp Ile Leu Thr Met Met Gln Arg Thr His
                20                  25                  30

Ser Gln Glu Tyr Ala His Ser Ile Arg Ile Asp Gly Asp Ile Thr Leu
            35                  40                  45

Gly Gly Leu Phe Pro Val His Gly Arg Gly Ser Glu Gly Lys Pro Cys
50                  55                  60

Gly Glu Leu Lys Lys Glu Lys Gly Ile His Arg Leu Glu Ala Met Leu
65                  70                  75                  80

Phe Ala Leu Asp Arg Ile Asn Asn Asp Pro Asp Leu Leu Pro Asn Ile
                85                  90                  95

Thr Leu Gly Ala Arg Ile Leu Asp Thr Cys Ser Arg Asp Thr His Ala
            100                 105                 110

Leu Glu Gln Ser Leu Thr Phe Val Gln Ala Leu Ile Glu Lys Asp Gly
        115                 120                 125

Thr Glu Val Arg Cys Gly Ser Gly Pro Pro Ile Ile Thr Lys Pro
130                 135                 140

Glu Arg Val Val Gly Val Ile Gly Ala Ser Gly Ser Ser Val Ser Ile
145                 150                 155                 160

Met Val Ala Asn Ile Leu Arg Leu Phe Lys Ile Pro Gln Ile Ser Tyr
                165                 170                 175

Ala Ser Thr Ala Pro Asp Leu Ser Asp Asn Ser Arg Tyr Asp Phe Phe
            180                 185                 190

Ser Arg Val Val Pro Ser Asp Thr Tyr Gln Ala Gln Ala Met Val Asp
        195                 200                 205

Ile Val Arg Ala Leu Lys Trp Asn Tyr Val Ser Thr Val Ala Ser Glu
    210                 215                 220

Gly Ser Tyr Gly Glu Ser Gly Val Glu Ala Phe Ile Gln Lys Ser Arg
225                 230                 235                 240

Glu Asp Gly Gly Val Cys Ile Ala Gln Ser Val Lys Ile Pro Arg Glu
                245                 250                 255

Pro Lys Ala Gly Glu Phe Asp Lys Ile Ile Arg Arg Leu Leu Glu Thr
            260                 265                 270

Ser Asn Ala Arg Ala Val Ile Ile Phe Ala Asn Glu Asp Asp Ile Arg
        275                 280                 285

Arg Val Leu Glu Ala Ala Arg Arg Ala Asn Gln Thr Gly His Phe Phe
    290                 295                 300

Trp Met Gly Ser Asp Ser Trp Gly Ser Lys Ile Ala Pro Val Leu His
305                 310                 315                 320

Leu Glu Glu Val Ala Glu Gly Ala Val Thr Ile Leu Pro Lys Arg Met
                325                 330                 335
```

-continued

```
Ser Val Arg Gly Phe Asp Arg Tyr Phe Ser Ser Arg Thr Leu Asp Asn
            340                 345                 350

Asn Arg Arg Asn Ile Trp Phe Ala Glu Phe Trp Glu Asp Asn Phe His
            355                 360                 365

Cys Lys Leu Ser Arg His Ala Leu Lys Lys Gly Ser His Val Lys Lys
            370                 375                 380

Cys Thr Asn Arg Glu Arg Ile Gly Gln Asp Ser Ala Tyr Glu Gln Glu
385                 390                 395                 400

Gly Lys Val Gln Phe Val Ile Asp Ala Val Tyr Ala Met Gly His Ala
                    405                 410                 415

Leu His Ala Met His Arg Asp Leu Cys Pro Gly Arg Val Gly Leu Cys
                420                 425                 430

Pro Arg Met Asp Pro Val Asp Gly Thr Gln Leu Leu Lys Tyr Ile Arg
            435                 440                 445

Asn Val Asn Phe Ser Gly Ile Ala Gly Asn Pro Val Thr Phe Asn Glu
450                 455                 460

Asn Gly Asp Ala Pro Gly Arg Tyr Asp Ile Tyr Gln Tyr Gln Leu Arg
465                 470                 475                 480

Asn Asp Ser Ala Glu Tyr Lys Val Ile Gly Ser Trp Thr Asp His Leu
                485                 490                 495

His Leu Arg Ile Glu Arg Met His Trp Pro Gly Ser Gly Gln Gln Leu
                500                 505                 510

Pro Arg Ser Ile Cys Ser Leu Pro Cys Gln Pro Gly Glu Arg Lys Lys
            515                 520                 525

Thr Val Lys Gly Met Pro Cys Cys Trp His Cys Glu Pro Cys Thr Gly
            530                 535                 540

Tyr Gln Tyr Gln Val Asp Arg Tyr Thr Cys Lys Thr Cys Pro Tyr Asp
545                 550                 555                 560

Met Arg Pro Thr Glu Asn Arg Thr Gly Cys Arg Pro Ile Pro Ile Ile
                565                 570                 575

Lys Leu Glu Trp Gly Ser Pro Trp Ala Val Leu Pro Leu Phe Leu Ala
            580                 585                 590

Val Val Gly Ile Ala Ala Thr Leu Phe Val Val Ile Thr Phe Val Arg
            595                 600                 605

Tyr Asn Asp Thr Pro Ile Val Lys Ala Ser Gly Arg Glu Leu Ser Tyr
            610                 615                 620

Val Leu Leu Ala Gly Ile Phe Leu Cys Tyr Ala Thr Thr Phe Leu Met
625                 630                 635                 640

Ile Ala Glu Pro Asp Leu Gly Thr Cys Ser Leu Arg Arg Ile Phe Leu
                645                 650                 655

Gly Leu Gly Met Ser Ile Ser Tyr Ala Ala Leu Leu Thr Lys Thr Asn
                660                 665                 670

Arg Ile Tyr Arg Ile Phe Glu Gln Gly Lys Arg Ser Val Ser Ala Pro
            675                 680                 685

Arg Phe Ile Ser Pro Ala Ser Gln Leu Ala Ile Thr Phe Ser Leu Ile
            690                 695                 700

Ser Leu Gln Leu Leu Gly Ile Cys Val Trp Phe Val Val Asp Pro Ser
705                 710                 715                 720

His Ser Val Val Asp Phe Gln Asp Gln Arg Thr Leu Asp Pro Arg Phe
                    725                 730                 735

Ala Arg Gly Val Leu Lys Cys Asp Ile Ser Asp Leu Ser Leu Ile Cys
            740                 745                 750
```

-continued

```
Leu Leu Gly Tyr Ser Met Leu Met Val Thr Cys Thr Val Tyr Ala
        755                 760                 765
Ile Lys Thr Arg Gly Val Pro Glu Thr Phe Asn Glu Ala Lys Pro Ile
    770                 775                 780
Gly Phe Thr Met Tyr Thr Thr Cys Ile Val Trp Leu Ala Phe Ile Pro
785                 790                 795                 800
Ile Phe Phe Gly Thr Ser Gln Ser Ala Asp Lys Leu Tyr Ile Gln Thr
                805                 810                 815
Thr Thr Leu Thr Val Ser Val Ser Leu Ser Ala Ser Val Ser Leu Gly
                820                 825                 830
Met Leu Tyr Met Pro Lys Val Tyr Ile Ile Leu Phe His Pro Glu Gln
            835                 840                 845
Asn Thr Ile Glu Glu Val Arg Cys Ser Thr Ala Ala His Ala Phe Lys
850                 855                 860
Val Ala Ala Arg Ala Thr Leu Arg Arg Ser Asn Val Ser Arg Lys Arg
865                 870                 875                 880
Ser Ser Ser Leu Gly Gly Ser Thr Gly Ser Thr Pro Ser Ser Ser Ile
                885                 890                 895
Ser Ser Lys Ser Asn Ser Glu Asp Pro Phe Pro Gln Pro Glu Arg Gln
            900                 905                 910
Lys Gln Gln Gln Pro Leu Ala Leu Thr Gln Gln Glu Gln Gln Gln Gln
        915                 920                 925
Pro Leu Thr Leu Pro Gln Gln Arg Ser Gln Gln Pro Arg Cys
    930                 935                 940
Lys Gln Lys Val Ile Phe Gly Ser Gly Thr Val Thr Phe Ser Leu Ser
945                 950                 955                 960
Phe Asp Glu Pro Gln Lys Asn Ala Met Ala His Gly Asn Ser Thr His
                965                 970                 975
Gln Asn Ser Leu Glu Ala Gln Lys Ser Ser Asp Thr Leu Thr Arg His
            980                 985                 990
Gln Pro Leu Leu Pro Leu Gln Cys  Gly Glu Thr Asp Leu  Asp Leu Thr
        995                 1000                1005
Val Gln  Glu Thr Gly Leu Gln  Gly Pro Val Gly Gly  Asp Gln Arg
    1010                1015                1020
Pro Glu  Val Glu Asp Pro Glu  Glu Leu Ser Pro Ala  Leu Val Val
    1025                1030                1035
Ser Ser  Ser Gln Ser Phe Val  Ile Ser Gly Gly Gly  Ser Thr Val
    1040                1045                1050
Thr Glu  Asn Val Val Asn Ser  Ala Ala Ala Met Thr  Leu Glu Ser
    1055                1060                1065
Ile Met  Ala Cys Cys Leu Ser  Glu Glu Ala Lys Glu  Ala Arg Arg
    1070                1075                1080
Ile Asn  Asp Glu Ile Glu Arg  Gln Leu Arg Arg Asp  Lys Arg Asp
    1085                1090                1095
Ala Arg  Arg Glu Leu Lys Leu  Leu Leu Leu Gly Thr  Gly Glu Ser
    1100                1105                1110
Gly Lys  Ser Thr Phe Ile Lys  Gln Met Arg Ile Ile  His Gly Ser
    1115                1120                1125
Gly Tyr  Ser Asp Glu Asp Lys  Arg Gly Phe Thr Lys  Leu Val Tyr
    1130                1135                1140
Gln Asn  Ile Phe Thr Ala Met  Gln Ala Met Ile Arg  Ala Met Asp
    1145                1150                1155
Thr Leu  Lys Ile Pro Tyr Lys  Tyr Glu His Asn Lys  Ala His Ala
```

```
              1160                1165                1170
      Gln Leu Val Arg Glu Val Asp Val Glu Lys Val Ser Ala Phe Glu
          1175                1180                1185

Asn Pro Tyr Val Asp Ala Ile Lys Ser Leu Trp Asn Asp Pro Gly
          1190                1195                1200

Ile Gln Glu Cys Tyr Asp Arg Arg Arg Glu Tyr Gln Leu Ser Asp
          1205                1210                1215

Ser Thr Lys Tyr Tyr Leu Asn Asp Leu Asp Arg Val Ala Asp Pro
          1220                1225                1230

Ala Tyr Leu Pro Thr Gln Gln Asp Val Leu Arg Val Arg Val Pro
          1235                1240                1245

Thr Thr Gly Ile Ile Glu Tyr Pro Phe Asp Leu Gln Ser Val Ile
          1250                1255                1260

Phe Arg Met Val Asp Val Gly Gly Gln Arg Ser Glu Arg Arg Lys
          1265                1270                1275

Trp Ile His Cys Phe Glu Asn Val Thr Ser Ile Met Phe Leu Val
          1280                1285                1290

Ala Leu Ser Glu Tyr Asp Gln Val Leu Val Glu Ser Asp Asn Glu
          1295                1300                1305

Asn Arg Met Glu Glu Ser Lys Ala Leu Phe Arg Thr Ile Ile Thr
          1310                1315                1320

Tyr Pro Trp Phe Gln Asn Ser Ser Val Ile Leu Phe Leu Asn Lys
          1325                1330                1335

Lys Asp Leu Leu Glu Glu Lys Ile Met Tyr Ser His Leu Val Asp
          1340                1345                1350

Tyr Phe Pro Glu Tyr Asp Gly Pro Gln Arg Asp Ala Gln Ala Ala
          1355                1360                1365

Arg Glu Phe Ile Leu Lys Met Phe Val Asp Leu Asn Pro Asp Ser
          1370                1375                1380

Asp Lys Ile Ile Tyr Ser His Phe Thr Cys Ala Thr Asp Thr Glu
          1385                1390                1395

Asn Ile Arg Phe Val Phe Ala Ala Val Lys Asp Thr Ile Leu Gln
          1400                1405                1410

Leu Asn Leu Lys Asp Cys Gly Leu Phe
          1415                1420

<210> SEQ ID NO 50
<211> LENGTH: 1422
<212> TYPE: PRT
<213> ORGANISM: Artificial Sequence
<220> FEATURE:
<221> NAME/KEY: misc_feature
<223> OTHER INFORMATION: phmGluR8//CaR*AAA*G-alpha qi5 fusion construct
<221> NAME/KEY: MOD_RES
<222> LOCATION: (379)..(379)
<223> OTHER INFORMATION: Xaa is unknown or other

<400> SEQUENCE: 50

Met Val Cys Glu Gly Lys Arg Ser Ala Ser Cys Pro Cys Phe Phe Leu
1               5                   10                  15

Leu Thr Ala Lys Phe Tyr Trp Ile Leu Thr Met Met Gln Arg Thr His
            20                  25                  30

Ser Gln Glu Tyr Ala His Ser Ile Arg Val Asp Gly Asp Ile Ile Leu
        35                  40                  45

Gly Gly Leu Phe Pro Val His Ala Lys Gly Glu Arg Gly Val Pro Cys
    50                  55                  60
```

-continued

```
Gly Glu Leu Lys Lys Glu Lys Gly Ile His Arg Leu Glu Ala Met Leu
 65                  70                  75                  80

Tyr Ala Ile Asp Gln Ile Asn Lys Asp Pro Asp Leu Leu Ser Asn Ile
                 85                  90                  95

Thr Leu Gly Val Arg Ile Leu Asp Thr Cys Ser Arg Asp Thr Tyr Ala
            100                 105                 110

Leu Glu Gln Ser Leu Thr Phe Val Gln Ala Leu Ile Glu Lys Asp Ala
        115                 120                 125

Ser Asp Val Lys Cys Ala Asn Gly Asp Pro Pro Ile Phe Thr Lys Pro
    130                 135                 140

Asp Lys Ile Ser Gly Val Ile Gly Ala Ala Ser Ser Val Ser Ile
145                 150                 155                 160

Met Val Ala Asn Ile Leu Arg Leu Phe Lys Ile Pro Gln Ile Ser Tyr
                165                 170                 175

Ala Ser Thr Ala Pro Glu Leu Ser Asp Asn Thr Arg Tyr Asp Phe Phe
            180                 185                 190

Ser Arg Val Val Pro Pro Asp Ser Tyr Gln Ala Gln Ala Met Val Asp
        195                 200                 205

Ile Val Thr Ala Leu Gly Trp Asn Tyr Val Ser Thr Leu Ala Ser Glu
    210                 215                 220

Gly Asn Tyr Gly Glu Ser Gly Val Glu Ala Phe Thr Gln Ile Ser Arg
225                 230                 235                 240

Glu Ile Gly Gly Val Cys Ile Ala Gln Ser Gln Lys Ile Pro Arg Glu
                245                 250                 255

Pro Arg Pro Gly Glu Phe Glu Lys Ile Ile Lys Arg Leu Leu Glu Thr
            260                 265                 270

Pro Asn Ala Arg Ala Val Ile Met Phe Ala Asn Glu Asp Asp Ile Arg
        275                 280                 285

Arg Ile Leu Glu Ala Ala Lys Lys Leu Asn Gln Ser Gly His Phe Leu
    290                 295                 300

Trp Ile Gly Ser Asp Ser Trp Gly Ser Lys Ile Ala Pro Val Tyr Gln
305                 310                 315                 320

Gln Glu Glu Ile Ala Glu Gly Ala Val Thr Ile Leu Pro Lys Arg Ala
                325                 330                 335

Ser Ile Asp Gly Phe Asp Arg Tyr Phe Arg Ser Arg Thr Leu Ala Asn
            340                 345                 350

Asn Arg Arg Asn Val Trp Phe Ala Glu Phe Trp Glu Glu Asn Phe Gly
        355                 360                 365

Cys Lys Leu Gly Ser His Gly Lys Arg Asn Xaa Ser His Ile Lys Lys
    370                 375                 380

Cys Thr Gly Leu Glu Arg Ile Ala Arg Asp Ser Ser Tyr Glu Gln Glu
385                 390                 395                 400

Gly Lys Val Gln Phe Val Ile Asp Ala Val Tyr Ser Met Ala Tyr Ala
                405                 410                 415

Leu His Asn Met His Lys Asp Leu Cys Pro Gly Tyr Ile Gly Leu Cys
            420                 425                 430

Pro Arg Met Ser Thr Ile Asp Gly Lys Glu Leu Leu Gly Tyr Ile Arg
        435                 440                 445

Ala Val Asn Phe Asn Gly Ser Ala Gly Thr Pro Val Thr Phe Asn Glu
    450                 455                 460

Asn Gly Asp Ala Pro Gly Arg Tyr Asp Ile Phe Gln Tyr Gln Ile Thr
465                 470                 475                 480

Asn Lys Ser Thr Glu Tyr Lys Val Ile Gly His Trp Thr Asn Gln Leu
```

-continued

```
                485                 490                 495
His Leu Lys Val Glu Asp Met Gln Trp Ala His Arg Glu His Thr His
                500                 505                 510

Pro Ala Ser Val Cys Ser Leu Pro Cys Lys Pro Gly Glu Arg Lys Lys
                515                 520                 525

Thr Val Lys Gly Val Pro Cys Cys Trp His Cys Glu Arg Cys Glu Gly
                530                 535                 540

Tyr Asn Tyr Gln Val Asp Glu Leu Ser Cys Glu Leu Cys Pro Leu Asp
545                 550                 555                 560

Gln Arg Pro Asn Met Asn Arg Thr Gly Cys Gln Leu Ile Pro Ile Ile
                565                 570                 575

Lys Leu Glu Trp His Ser Pro Trp Ala Val Pro Val Phe Val Ala
                580                 585                 590

Ile Leu Gly Ile Ile Ala Thr Thr Phe Val Ile Val Thr Phe Val Arg
                595                 600                 605

Tyr Asn Asp Thr Pro Ile Val Arg Ala Ser Gly Arg Glu Leu Ser Tyr
                610                 615                 620

Val Leu Leu Thr Gly Ile Phe Leu Cys Tyr Ser Ile Thr Phe Leu Met
625                 630                 635                 640

Ile Ala Ala Pro Asp Thr Ile Ile Cys Ser Phe Arg Arg Val Phe Leu
                645                 650                 655

Gly Leu Gly Met Cys Phe Ser Tyr Ala Ala Leu Leu Thr Lys Thr Asn
                660                 665                 670

Arg Ile His Arg Ile Phe Glu Gln Gly Lys Lys Ser Val Thr Ala Pro
                675                 680                 685

Lys Phe Ile Ser Pro Ala Ser Gln Leu Val Ile Thr Phe Ser Leu Ile
                690                 695                 700

Ser Val Gln Leu Leu Gly Val Phe Val Trp Phe Val Val Asp Pro Pro
705                 710                 715                 720

His Ile Ile Ile Asp Tyr Gly Glu Gln Arg Thr Leu Asp Pro Glu Lys
                725                 730                 735

Ala Arg Gly Val Leu Lys Cys Asp Ile Ser Asp Leu Ser Leu Ile Cys
                740                 745                 750

Ser Leu Gly Tyr Ser Ile Leu Leu Met Val Thr Cys Thr Val Tyr Ala
                755                 760                 765

Ile Lys Thr Arg Gly Val Pro Glu Thr Phe Asn Glu Ala Lys Pro Ile
                770                 775                 780

Gly Phe Thr Met Tyr Thr Thr Cys Ile Ile Trp Leu Ala Phe Ile Pro
785                 790                 795                 800

Ile Phe Phe Gly Thr Ala Gln Ser Ala Glu Lys Met Tyr Ile Gln Thr
                805                 810                 815

Thr Thr Leu Thr Val Ser Met Ser Leu Ser Ala Ser Val Ser Leu Gly
                820                 825                 830

Met Leu Tyr Met Pro Lys Val Tyr Ile Ile Phe His Pro Glu Gln
                835                 840                 845

Asn Thr Ile Glu Glu Val Arg Cys Ser Thr Ala Ala His Ala Phe Lys
850                 855                 860

Val Ala Ala Arg Ala Thr Leu Arg Arg Ser Asn Val Ser Arg Lys Arg
865                 870                 875                 880

Ser Ser Ser Leu Gly Gly Ser Thr Gly Ser Thr Pro Ser Ser Ser Ile
                885                 890                 895

Ser Ser Lys Ser Asn Ser Glu Asp Pro Phe Pro Gln Pro Glu Arg Gln
                900                 905                 910
```

-continued

```
Lys Gln Gln Gln Pro Leu Ala Leu Thr Gln Gln Gln Gln Gln
        915                 920                 925

Pro Leu Thr Leu Pro Gln Gln Arg Ser Gln Gln Pro Arg Cys
        930                 935             940

Lys Gln Lys Val Ile Phe Gly Ser Gly Thr Val Thr Phe Ser Leu Ser
945             950                 955                     960

Phe Asp Glu Pro Gln Lys Asn Ala Met Ala His Gly Asn Ser Thr His
                965                 970                 975

Gln Asn Ser Leu Glu Ala Gln Lys Ser Ser Asp Thr Leu Thr Arg His
            980                 985                 990

Gln Pro Leu Leu Pro Leu Gln Cys Gly Glu Thr Asp Leu Asp Leu Thr
        995                 1000                1005

Val Gln Glu Thr Gly Leu Gln Gly Pro Val Gly Gly Asp Gln Arg
    1010                1015                1020

Pro Glu Val Glu Asp Pro Glu Leu Ser Pro Ala Leu Val Val
    1025                1030                1035

Ser Ser Ser Gln Ser Phe Val Ile Ser Gly Gly Gly Ser Thr Val
    1040                1045                1050

Thr Glu Asn Val Val Asn Ser Ala Ala Ala Met Thr Leu Glu Ser
    1055                1060                1065

Ile Met Ala Cys Cys Leu Ser Glu Glu Ala Lys Glu Ala Arg Arg
    1070                1075                1080

Ile Asn Asp Glu Ile Glu Arg Gln Leu Arg Arg Asp Lys Arg Asp
    1085                1090                1095

Ala Arg Arg Glu Leu Lys Leu Leu Leu Leu Gly Thr Gly Glu Ser
    1100                1105                1110

Gly Lys Ser Thr Phe Ile Lys Gln Met Arg Ile Ile His Gly Ser
    1115                1120                1125

Gly Tyr Ser Asp Glu Asp Lys Arg Gly Phe Thr Lys Leu Val Tyr
    1130                1135                1140

Gln Asn Ile Phe Thr Ala Met Gln Ala Met Ile Arg Ala Met Asp
    1145                1150                1155

Thr Leu Lys Ile Pro Tyr Lys Tyr Glu His Asn Lys Ala His Ala
    1160                1165                1170

Gln Leu Val Arg Glu Val Asp Val Glu Lys Val Ser Ala Phe Glu
    1175                1180                1185

Asn Pro Tyr Val Asp Ala Ile Lys Ser Leu Trp Asn Asp Pro Gly
    1190                1195                1200

Ile Gln Glu Cys Tyr Asp Arg Arg Arg Glu Tyr Gln Leu Ser Asp
    1205                1210                1215

Ser Thr Lys Tyr Tyr Leu Asn Asp Leu Asp Arg Val Ala Asp Pro
    1220                1225                1230

Ala Tyr Leu Pro Thr Gln Gln Asp Val Leu Arg Val Arg Val Pro
    1235                1240                1245

Thr Thr Gly Ile Ile Glu Tyr Pro Phe Asp Leu Gln Ser Val Ile
    1250                1255                1260

Phe Arg Met Val Asp Val Gly Gly Gln Arg Ser Glu Arg Arg Lys
    1265                1270                1275

Trp Ile His Cys Phe Glu Asn Val Thr Ser Ile Met Phe Leu Val
    1280                1285                1290

Ala Leu Ser Glu Tyr Asp Gln Val Leu Val Glu Ser Asp Asn Glu
    1295                1300                1305
```

```
Asn Arg Met Glu Glu Ser Lys Ala Leu Phe Arg Thr Ile Ile Thr
    1310            1315                1320

Tyr Pro Trp Phe Gln Asn Ser Ser Val Ile Leu Phe Leu Asn Lys
    1325            1330                1335

Lys Asp Leu Leu Glu Glu Lys Ile Met Tyr Ser His Leu Val Asp
    1340            1345                1350

Tyr Phe Pro Glu Tyr Asp Gly Pro Gln Arg Asp Ala Gln Ala Ala
    1355            1360                1365

Arg Glu Phe Ile Leu Lys Met Phe Val Asp Leu Asn Pro Asp Ser
    1370            1375                1380

Asp Lys Ile Ile Tyr Ser His Phe Thr Cys Ala Thr Asp Thr Glu
    1385            1390                1395

Asn Ile Arg Phe Val Phe Ala Ala Val Lys Asp Thr Ile Leu Gln
    1400            1405                1410

Leu Asn Leu Lys Asp Cys Gly Leu Phe
    1415            1420

<210> SEQ ID NO 51
<211> LENGTH: 21
<212> TYPE: DNA
<213> ORGANISM: Oligonucleotide
<220> FEATURE:
<221> NAME/KEY: misc_feature
<223> OTHER INFORMATION: Primer 3.1-535F

<400> SEQUENCE: 51
ggcattatgc ccagtacatg a                                             21

<210> SEQ ID NO 52
<211> LENGTH: 42
<212> TYPE: DNA
<213> ORGANISM: Oligonucleotide
<220> FEATURE:
<221> NAME/KEY: misc_feature
<223> OTHER INFORMATION: Hybrid primer 8/4RP

<400> SEQUENCE: 52
caagcctctc ttcccaggca ttttctccac aggtggtatt gc                      42

<210> SEQ ID NO 53
<211> LENGTH: 18
<212> TYPE: DNA
<213> ORGANISM: Oligonucleotide
<220> FEATURE:
<221> NAME/KEY: misc_feature
<223> OTHER INFORMATION: human mGluR4 cDNA

<400> SEQUENCE: 53
ctgaagcacc gatgacac                                                 18

<210> SEQ ID NO 54
<211> LENGTH: 39
<212> TYPE: DNA
<213> ORGANISM: Oligonucleotide
<220> FEATURE:
<221> NAME/KEY: misc_feature
<223> OTHER INFORMATION: NtI hGBR1 primer

<400> SEQUENCE: 54
cagagtcatg gcggccgcct tataaagcaa atgcactcg                          39

<210> SEQ ID NO 55
<211> LENGTH: 19
```

-continued

```
<212> TYPE: DNA
<213> ORGANISM: Oligonucleotide
<220> FEATURE:
<221> NAME/KEY: misc_feature
<223> OTHER INFORMATION: mG4-2028R primer

<400> SEQUENCE: 55
catctaccgc atcttcgag                                                    19

<210> SEQ ID NO 56
<211> LENGTH: 42
<212> TYPE: DNA
<213> ORGANISM: Oligonucleotide
<220> FEATURE:
<221> NAME/KEY: misc_feature
<223> OTHER INFORMATION: hybrid primer 4CT

<400> SEQUENCE: 56
acgcacctcc tcgatggtgt tctgctccgg gtggaagagg at                          42

<210> SEQ ID NO 57
<211> LENGTH: 21
<212> TYPE: DNA
<213> ORGANISM: Oligonucleotide
<220> FEATURE:
<221> NAME/KEY: misc_feature
<223> OTHER INFORMATION: Gaqi58R

<400> SEQUENCE: 57
ctcgatctcg tcgttgatcc g                                                 21
```